(12) United States Patent
Zhang et al.

(10) Patent No.: US 7,777,035 B2
(45) Date of Patent: Aug. 17, 2010

(54) AZAINDAZOLE COMPOUNDS AND METHODS OF USE

(75) Inventors: Penglie Zhang, Foster City, CA (US); Andrew M. K. Pennell, San Francisco, CA (US); John J. Kim Wright, Redwood City, CA (US); Wei Chen, Fremont, CA (US); Manmohan R. Leleti, Sunnyvale, CA (US); Yandong Li, San Jose, CA (US); Lianfa Li, Palo Alto, CA (US); Yuan Xu, Fremont, CA (US); Mark M. Gleason, Redwood City, CA (US); Yibin Zeng, San Mateo, CA (US); Kevin Lloyd Greenman, Burlingame, CA (US)

(73) Assignee: Chemocentryx, Inc., Mountain View, CA (US)

( * ) Notice: Subject to any disclaimer, the term of this patent is extended or adjusted under 35 U.S.C. 154(b) by 433 days.

(21) Appl. No.: 11/752,201

(22) Filed: May 22, 2007

(65) Prior Publication Data

US 2008/0058341 A1    Mar. 6, 2008

Related U.S. Application Data

(63) Continuation-in-part of application No. 11/474,132, filed on Jun. 22, 2006, now Pat. No. 7,524,845.

(60) Provisional application No. 60/693,525, filed on Jun. 22, 2005.

(51) Int. Cl.
    *C07D 471/04* (2006.01)
(52) U.S. Cl. .................. 544/362; 544/236; 544/262; 544/350; 514/249; 514/262.1; 514/284; 514/253.04
(58) Field of Classification Search .................. None
    See application file for complete search history.

(56) References Cited

U.S. PATENT DOCUMENTS

| | | | |
|---|---|---|---|
| 3,818,035 A * | 6/1974 | Binon et al. ............. 548/311.4 |
| 4,238,497 A | 12/1980 | Black et al. | |
| 4,443,466 A | 4/1984 | Karjalainen et al. | |
| 4,927,942 A | 5/1990 | Speranza et al. | |
| 7,157,464 B2 | 1/2007 | Pennell | |
| 2004/0082571 A1 | 4/2004 | Pennell et al. | |
| 2004/0162282 A1 | 8/2004 | Pennell | |
| 2005/0234034 A1 | 10/2005 | Pennell | |
| 2005/0256130 A1 | 11/2005 | Pennell | |
| 2006/0074121 A1 | 4/2006 | Chen | |
| 2006/0106218 A1 | 5/2006 | Pennell | |
| 2007/0010523 A1 | 1/2007 | Zhang et al. | |
| 2007/0010524 A1 | 1/2007 | Zhang et al. | |
| 2008/0300257 A1* | 12/2008 | Li et al. .................. 514/253.04 |

FOREIGN PATENT DOCUMENTS

| WO | WO 03/105853 | 12/2004 |
|---|---|---|
| WO | WO 2005/056015 | 1/2005 |
| WO | WO 2005/084667 | 9/2005 |
| WO | WO 2007/027734 | 3/2007 |

OTHER PUBLICATIONS

International Search Report mailed on Aug. 15, 2008, for PCT Application No. PCT/US08/64394 filed on May 21, 2008, 2 pages.
Bendele, et al., "Animal Models of Arthritis: Relevance to Human Disease," Toxicologic Pathology, 1999, vol. 27, pp. 134-142.
Bendele, et al., "Efficacy of Sustained Blood Levels of Interleukin-1 Receptor Antagonist in Animal Models of Arthritis," Arthritis & Rheumatism, 1999, vol. 42, No. 3, pp. 498-506.
Dairaghi, et al., "Chemokine Receptor CCR3 Function is Highly Dependent on Local pH and Ionic Strength," J. Biol. Chem., 1997, vol. 272, pp. 28206-28209.
Dairaghi, et al., "HHV8-encoded vMIP-1 Selectively Engages Chemokine Receptor CCR8," J. Biol. Chem., 1999, vol. 274, No. 31, pp. 21569-21574.
Hesselgesser, et al. "Identification and Characterization of Small Molecule Functional Antagonists of the CCR1 Chemokine Receptor," J. Biol. Chem., 1998, vol. 273, No. 25, pp. 15687-15692.
Jones, J et al., "British Society of Gastroenterology guidelines for the management of the irritable bowel syndrome," Division of Gastroenterology, University Hospital, Nottingham, UK, 19 pp.
Liang, et al., "Identification and Characterization of a Potent, Selective, and Orally Active Antagonist of the CC Chemokine Receptor-1," 2000, J. Biol. Chem. vol. 275, No. 25, pp. 19000-19008.
Liang, et al., "Species Selectivity of a small molecule antagonist for the CCR1 chemokine receptor," European Journal of Pharmacology, 2000, vol. 389, No. 1, pp. 41-49.
Ng, et al., "Discovery of Novel Non-Peptide CCR1 Receptor Antagonists," *J. Med. Chem.*, 1999, vol. 42, No. 22, pp. 4680-4694.
Palmer, Alan M. "Pharmacotherapy for Alzheimer's disease: progress and prospects," Trends in Pharmacological Sciences, 2002, vol. 23, No. 9, pp. 426-433.
Penfold, et al., "Cytomegalovirus encodes a potent α chemokine," Proc. Natl. Acad. Sci. USA, 1999, vol. 96, pp. 9839-9844.
Podolin, et al. "A Potent and Selective Nonpeptide Antagonist of CXCR2 Inhibits Acute and Chronic Models of Arthritis in the Rabbit," The Journal of Immunology, 2002, vol. 169, No. 11 pp. 6435-6444.
Trentham, et al., "Autoimmunity to Type II Collagen: An Experimental Model of Arthritis," J. Exp. Med, 1977. vol. 146, No. 3, pp. 857-868.

* cited by examiner

*Primary Examiner*—Emily Bernhardt
(74) *Attorney, Agent, or Firm*—Townsend and Townsend and Crew LLP

(57) ABSTRACT

Methods are provided for the synthesis of 1-[4-(substituted phenyl)-piperazin-1-yl]-2-[3-(1H-imidazol-2-yl)-pyrazolo[3,4-b]pyridin-1-yl]-ethanone compounds via construction of the imidazole portion onto the corresponding aldehyde or nitrile compounds.

10 Claims, No Drawings

US 7,777,035 B2

AZAINDAZOLE COMPOUNDS AND METHODS OF USE

CROSS-REFERENCES TO RELATED APPLICATIONS

This application is a continuation-in-part application of U.S. application Ser. No. 11/474,132, filed Jun. 22, 2006 which claims priority to U.S. Provisional Application No. 60/693,525 filed on Jun. 22, 2005, the contents of each are incorporated herein in their entirety for all purposes.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

The present invention provides compounds, pharmaceutical compositions containing one or more of those compounds or their pharmaceutically acceptable salts, which are effective in inhibiting the binding of various chemokines, such as MIP-1α, leukotactin, MPIF-1 and RANTES, to the CCR1 receptor. As antagonists or modulators for the CCR1 receptor, the compounds and compositions have utility in treating inflammatory and immune disorder conditions and diseases.

Human health depends on the body's ability to detect and destroy foreign pathogens that might otherwise take valuable resources from the individual and/or induce illness. The immune system, which comprises leukocytes (white blood cells (WBCs): T and B lymphocytes, monocytes, macrophages granulocytes, NK cell, mast cells, dendritic cell, and immune derived cells (for example, osteoclasts)), lymphoid tissues and lymphoid vessels, is the body's defense system. To combat infection, white blood cells circulate throughout the body to detect pathogens. Once a pathogen is detected, innate immune cells and cytotoxic T cells in particular are recruited to the infection site to destroy the pathogen. Chemokines act as molecular beacons for the recruitment and activation of immune cells, such as lymphocytes, monocytes and granulocytes, identifying sites where pathogens exist.

Despite the immune system's regulation of pathogens, certain inappropriate chemokine signaling can develop and has been attributed to triggering or sustaining inflammatory disorders, such as rheumatoid arthritis, multiple sclerosis and others. For example, in rheumatoid arthritis, unregulated chemokine accumulation in bone joints attracts and activates infiltrating macrophages and T-cells. The activities of these cells induce synovial cell proliferation that leads, at least in part, to inflammation and eventual bone and cartilage loss (see, DeVries, M. E., et al., *Semin Immunol* 11(2):95-104 (1999)). A hallmark of some demyelinating diseases such as multiple sclerosis is the chemokine-mediated monocyte/macrophage and T cell recruitment to the central nervous system (see, Kennedy, et al., *J. Clin. Immunol.* 19(5):273-279 (1999)). Chemokine recruitment of destructive WBCs to transplants has been implicated in their subsequent rejection. See, DeVries, M. E., et al., *ibid*. Because chemokines play pivotal roles in inflammation and lymphocyte development, the ability to specifically manipulate their activity has enormous impact on ameliorating and halting diseases that currently have no satisfactory treatment. In addition, transplant rejection may be minimized without the generalized and complicating effects of costly immunosuppressive pharmaceuticals.

Chemokines, a group of greater than 40 small peptides (7-10 kD), ligate receptors expressed primarily on WBCs or immune derived cells, and signal through G-protein-coupled signaling cascades to mediate their chemoattractant and chemostimulant functions. Receptors may bind more than one ligand; for example, the receptor CCR1 ligates RANTES (regulated on activation normal T cell expressed), MIP-1α (macrophage inflammatory protein), MPIF-1/CKβ8, and Leukotactin chemokines (among others with lesser affinities). To date, 24 chemokine receptors are known. The sheer number of chemokines, multiple ligand binding receptors, and different receptor profiles on immune cells allow for tightly controlled and specific immune responses. See, Rossi, et al., *Ann. Rev. Immunol.* 18(1):217-242 (2000). Chemokine activity can be controlled through the modulation of their corresponding receptors, treating related inflammatory and immunological diseases and enabling organ and tissue transplants.

The receptor CCR1 and its chemokine ligands, including, for example MIP-1α, MPIF-1/CKβ8, leukotactin and RANTES, represent significant therapeutic targets (see Saeki, et al., *Current Pharmaceutical Design* 9:1201-1208 (2003)) since they have been implicated in rheumatoid arthritis, transplant rejection (see, DeVries, M. E., et al., *ibid.*), and multiple sclerosis (see, Fischer, et al., *J Neuroimmunol.* 110 (1-2):195-208 (2000); Izikson, et al., *J. Exp. Med.* 192(7): 1075-1080 (2000); and Rottman, et al., *Eur. J. Immunol.* 30(8):2372-2377 (2000). In fact, function-blocking antibodies, modified chemokine receptor ligands and small organic compounds have been discovered, some of which have been successfully demonstrated to prevent or treat some chemokine-mediated diseases (reviewed in Rossi, et al., *ibid.*). Notably, in an experimental model of rheumatoid arthritis, disease development is diminished when a signaling-blocking, modified-RANTES ligand is administered (see Plater-Zyberk, et al., *Immunol Lett.* 57(1-3): 117-120 (1997)). While function-blocking antibody and small peptide therapies are promising, they suffer from the perils of degradation, extremely short half-lives once administered, and prohibitive expense to develop and manufacture, characteristic of most proteins. Small organic compounds are preferable since they often have longer half lives in vivo, require fewer doses to be effective, can often be administered orally, and are consequently less expensive. Some organic antagonists of CCR1 have been previously described (see, Hesselgesser, et al., *J. Biol. Chem.* 273(25):15687-15692 (1998); Ng, et al., *J. Med. Chem.* 42(22):4680-4694 (1999); Liang, et al., *J. Biol. Chem.* 275(25):19000-19008 (2000); and Liang, et al., *Eur. J. Pharmacol.* 389(1):41-49 (2000)). In view of the effectiveness demonstrated for treatment of disease in animal models (see, Liang, et al., *J. Biol. Chem.* 275(25):19000-19008 (2000)), the search has continued to identify additional compounds that can be used in the treatment of diseases mediated by CCR1 signaling.

BRIEF SUMMARY OF THE INVENTION

The present invention provides compounds having a formula selected from the group consisting of:

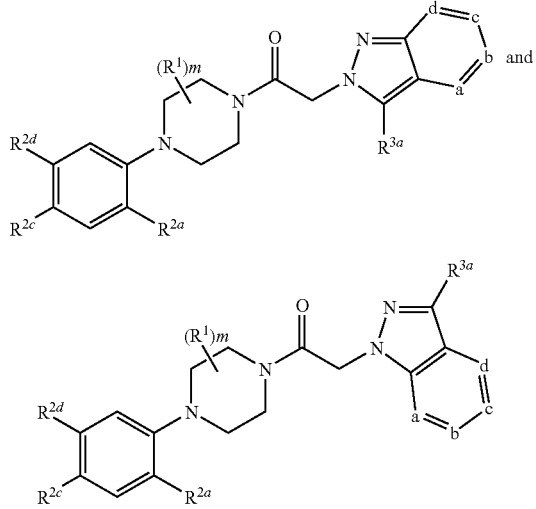

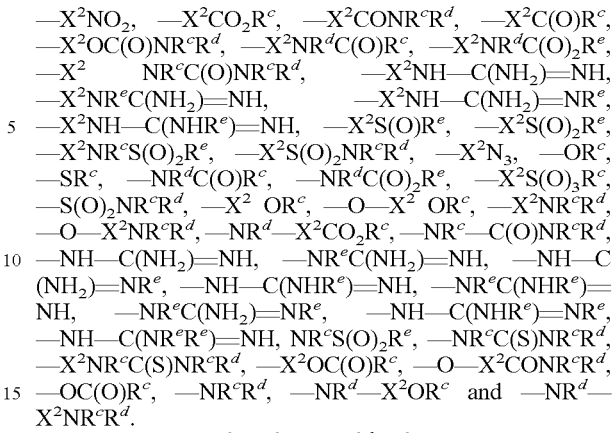

or a pharmaceutically acceptable salt, hydrate or N-oxide thereof. In the formulae above, the subscript m is an integer of from 0 to 4.

The symbol $R^1$ is a substituent independently selected from the group consisting of $C_{1-8}$ alkyl, $C_{1-8}$ haloalkyl, $C_{3-6}$ cycloalkyl, $-CO_2R^a$, $-S(O)_3R^a$, $-X^1CO_2R^a$, $-X^1SO_2R^a$, $-X^1S(O)_3R^a$, $-X^1OR^a$, $-COR^a$, $-CONR^aR^b$, $-X^1NR^aR^b$, $-X^1NR^aCOR^b$, $-X^1CONR^aR^b$, $X^1S(O)_2NR^aR^b$, $X^1S(O)_2R^a$, $-OR^a$, $-NR^aR^b$, $-NR^aCOR^b$, $-CONR^aR^b$, $-NR^aS(O)_2R^b$, $-S(O)_2NR^aR^b$, $-S(O)_2R^a$, $-X^1COR^a$, $X^1CONR^aR^b$, and $-X^1NR^aS(O)_2R^b$, wherein $X^1$ is $C_{1-4}$ alkylene and each $R^a$ and $R^b$ is independently selected from the group consisting of hydrogen, $C_{1-8}$ alkyl, $C_{1-8}$ haloalkyl and $C_{3-6}$ cycloalkyl, or optionally $R^a$ and $R^b$ when attached to the same nitrogen atom are combined to form a 3- to 7-membered ring having from 0-2 additional heteroatoms as ring members; and wherein the aliphatic portions of each of said $R^1$ substituents is optionally substituted with from one to three members selected from the group consisting of $-OH$, $-OR^m$, $-OC(O)NHR^m$, $-OC(O)N(R^m)_2$, $-SH$, $-SR^m$, $-S(O)R^m$, $-S(O)_2R^m$, $-SO_2NH_2$, $-S(O)_2NHR^m$, $-S(O)_2N(R^m)_2$, $-NHS(O)_2R^m$, $-NR^mS(O)_2R^m$, $-C(O)NH_2$, $-C(O)NHR^m$, $-C(O)N(R^m)_2$, $-C(O)R^m$, $-NHC(O)R^m$, $-NR^mC(O)R^m$, $-NHC(O)NH_2$, $-NR^mC(O)NH_2$, $-NR^mC(O)NHR^m$, $-NHC(=NH)NH_2$, $-NHC(=NR^m)NH_2$, $-NR^mC(=NR^m)N(R^m)_2$, $-NR^mC(=NR^m)NH(R^m)$, $-NHC(=NR^m)NH(R^m)$, $-NHC(=NR^m)N(R^m)_2$, $-NHC(=NH)N(R^m)_2$, $-NHC(=NH)NH(R^m)$, $-C(=NH)NH_2$, $-C(=NR^m)NH_2$, $-C(=NR^m)N(R^m)_2$, $-C(=NR^m)NH(R^m)$, $-NHC(O)NHR^m$, $-NR^mC(O)N(R^m)_2$, $-NHC(O)N(R^m)_2$, $-CO_2H$, $-CO_2R^m$, $-NHCO_2R^m$, $-NR^mCO_2R^m$, $-CN$, $-NO_2$, $-NH_2$, $-NHR^m$, $-N(R^m)_2$, $-NR^mS(O)NH_2$ and $-NR^mS(O)_2NHR^m$, wherein each $R^m$ is independently an unsubstituted $C_{1-6}$ alkyl.

The symbols $R^{2a}$, $R^{2c}$ and $R^{2d}$ in formulae Ia and Ib are each substituents independently selected from the group consisting of hydrogen, halogen, cyano, aryl, heteroaryl, $-NO_2$, $-CO_2R^c$, $-CONR^cR^d$, $-C(O)R^c$, $-S(O)R^e$, $-S(O)_2R^e$, $-S(O)_3R^c$, $-R^e$, $-C(NOR^c)R^d$, $-C(NR^cV)=NV$, $-N(V)C(R^c)=NV$, $-X^2C(NOR^c)R^d$, $-X^2C(NR^cV)=NV$, $-X^2N(V)C(R^c)=NV$, $-X^2NR^cR^d$, $-X^2SR^c$, $-X^2CN$, $-X^2NO_2$, $-X^2CO_2R^c$, $-X^2CONR^cR^d$, $-X^2C(O)R^c$, $-X^2OC(O)NR^cR^d$, $-X^2NR^dC(O)R^c$, $-X^2NR^dC(O)_2R^e$, $-X^2$ $NR^cC(O)NR^cR^d$, $-X^2NH-C(NH_2)=NH$, $-X^2NR^eC(NH_2)=NH$, $-X^2NH-C(NH_2)=NR^e$, $-X^2NH-C(NHR^e)=NH$, $-X^2S(O)R^e$, $-X^2S(O)_2R^e$, $-X^2NR^cS(O)_2R^e$, $-X^2S(O)_2NR^cR^d$, $-X^2N_3$, $-OR^c$, $-SR^c$, $-NR^dC(O)R^c$, $-NR^dC(O)_2R^e$, $-X^2S(O)_3R^c$, $-S(O)_2NR^cR^d$, $-X^2$ $OR^c$, $-O-X^2$ $OR^c$, $-X^2NR^cR^d$, $-O-X^2NR^cR^d$, $-NR^d-X^2CO_2R^c$, $-NR^c-C(O)NR^cR^d$, $-NH-C(NH_2)=NH$, $-NR^eC(NH_2)=NH$, $-NH-C(NH_2)=NR^e$, $-NH-C(NHR^e)=NH$, $-NR^eC(NHR^e)=NH$, $-NR^eC(NH_2)=NR^e$, $-NH-C(NHR^e)=NR^e$, $-NH-C(NR^eR^e)=NH$, $NR^cS(O)_2R^e$, $-NR^cC(S)NR^cR^d$, $-X^2NR^cC(S)NR^cR^d$, $-X^2OC(O)R^c$, $-O-X^2CONR^cR^d$, $-OC(O)R^c$, $-NR^cR^d$, $-NR^d-X^2OR^c$ and $-NR^d-X^2NR^cR^d$.

Within each of $R^{2a}$, $R^{2c}$ and $R^{2d}$, $X^2$ is $C_{1-4}$ alkylene and each $R^c$ and $R^d$ is independently selected from hydrogen, $C_{1-8}$ alkyl, $C_{1-8}$ haloalkyl, and $C_{3-6}$ cycloalkyl. Optionally, $R^c$ and $R^d$ when attached to the same nitrogen atom can be combined with the nitrogen atom to form a five or six-membered ring having from 0 to 2 additional heteroatoms as ring members. The symbol $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl, and each of $R^c$, $R^d$ and $R^e$ is optionally further substituted with from one to three members selected from the group consisting of $-OH$, $-OR''$, $-OC(O)NHR''$, $-OC(O)N(R'')_2$, $-SH$, $-SR''$, $-S(O)R''$, $-S(O)_2R''$, $-SO_2NH_2$, $-S(O)_2NHR''$, $-S(O)_2N(R'')_2$, $-NHS(O)_2R''$, $-NR''S(O)_2R''$, $-C(O)NH_2$, $-C(O)NHR''$, $-C(O)N(R'')_2$, $-C(O)R''$, $-NHC(O)R''$, $-NR''C(O)R''$, $-NHC(O)NH_2$, $-NR''C(O)NH_2$, $-NR''C(O)NHR''$, $-NHC(O)NHR''$, $-NR''C(O)N(R'')_2$, $-NHC(O)N(R'')_2$, $-CO_2H$, $-CO_2R''$, $-NHCO_2R''$, $-NR''CO_2R''$, $-CN$, $-NO_2$, $-NH_2$, $-NHR''$, $-N(R'')_2$, $-NR''S(O)NH_2$ and $-NR''S(O)_2NHR''$, wherein each $R''$ is independently an unsubstituted $C_{1-6}$ alkyl; and wherein V is independently selected from the group consisting of $-R^c$, $-CN$, $-CO_2R^e$ and $-NO_2$.

Each of ring vertices a, b, c and d in formulae Ia and Ib is independently selected from N and $C(R^{3a})$, and from one to two of said ring vertices is N. The symbol $R^{3a}$ in formulae Ia and Ib is independently selected from the group consisting of hydrogen, halogen, $-OR^f$, $-OC(O)R^f$, $-NR^fR^g$, $-SR^f$, $-R^h$, $-CN$, $-NO_2$, $-CO_2R^f$, $-CONR^fR^g$, $-C(O)R^f$, $-OC(O)NR^fR^g$, $-NR^gC(O)R^f$, $-NR^gC(O)_2R^h$, $-NR^f-C(O)NR^fR^g$, $-NH-C(NH_2)=NH$, $-NR^hC(NH_2)=NH$, $-NH-C(NH_2)=NR^h$, $-NH-C(NHR^h)=NH$, $-C(=NR^f)NR^gR^h$, $-S(O)_3R^f$, $-S(O)R^h$, $-S(O)_2R^h$, $-S(O)_3R^h$, $-NR^fS(O)_2R^h$, $-S(O)_2NR^fR^g$, $-NR^fS(O)_2R^h$, $-NR^fS(O)_2NR^fR^g$, $-N_3$, $-C(C=NOR^f)NR^fR^g$, $-X_3SO_3R^f$, $-X_3C(=NR^f)NR^gR^h$, $-X^3OR^f$, $-X^3OC(O)R^f$, $-X^3NR^fR^g$, $-X^3SR^f$, $-X^3CN$, $-X^3NO_2$, $-X^3CO_2R^f$, $-X^3CONR^fR^g$, $-X^3C(O)R^f$, $-X^3OC(O)NR^fR^g$, $-X^3NR^gC(O)R^f$, $-X^3NR^gC(O)_2R^h$, $-X^3NR^f-C(O)NR^fR^g$, $-X^3NH-C(NH_2)=NH$, $-X^3NR^hC(NH_2)=NH$, $-X^3NH-C(NH_2)=NR^h$, $-X^3NH-C(NHR^h)=NH$, $-X^3S(O)R^h$, $-X^3S(O)_2R^h$, $-X^3NR^fS(O)_2R^h$, $-X^3S(O)_2NR^fR^g$, $-Y$, $-X^3Y$, $-X^3N_3$, $-C(O)NR^fS(O)R^h$, $-P=O(OR^f)(OR^g)$, $-X^3C(O)NR^fS(O)_2R^h$, $-X^3C(O)NR^fS(O)R^h$ and $-X^3P=O(OR^f)(OR^g)$. The symbol Y is a five to ten-membered aryl, heteroaryl or heterocycloalkyl ring, optionally substituted with from one to three substitutents selected from the group consisting of halogen, $-OR^f$, $-NR^fR^g$, $-R^h$, $-SR^f$, $-CN$, $-NO_2$, $-CO_2R^f$, $-CONR^fR^g$, $-C(O)R^f$, $-NR^gC(O)R^f$, $-S(O)R^h$, $-S(O)_2R^h$, $-NR^fS(O)_2R^h$, $-S(O)_2NR^fR^g$, $-X^3OR^f$, $-X^3NR^fR^g$, $-X^3NR^fS(O)_2R^h$ and —X³S(O)₂NR^f R^g, and wherein each X³ is independently selected from the group consisting of $C_{1-4}$ alkylene, $C_{2-4}$ alkenylene and $C_{2-4}$ alkynylene; each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members; and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —OH, —OR°, —OC(O)NHR°, —OC(O)N(R°)₂, —SH, —SR°, —S(O)R°, —S(O)₂R°, —SO₂NH₂, —S(O)₂NHR°, —S(O)₂N(R°)₂, —NHS(O)₂R°, —NR°S(O)₂R°, —C(O)NH₂, —C(O)NHR°, —C(O)N(R°)₂, —C(O)R°, —NHC(O)R°, —NR°C(O)R°, —NHC(O)NH₂, —NR°C(O)NH₂, —NR°C(O)NHR°, —NHC(O)NHR°, —NR°C(O)N(R°)₂, —NHC(O)N(R°)₂, —CO₂H, —CO₂R°, —NHCO₂R°, —NR°CO₂R°, —CN, —NO₂, —NH₂, —NHR°, —N(R°)₂, —NR°S(O)NH₂ and —NR°S(O)₂NHR°, wherein R° is unsubstituted $C_{1-6}$ alkyl.

In addition to the compounds provided herein, the present invention further provides pharmaceutical compositions containing one or more of these compounds, as well as methods for the use of these compounds in therapeutic methods, primarily to treat diseases associated with CCR1 signaling activity.

BRIEF DESCRIPTION OF THE DRAWINGS

None

DETAILED DESCRIPTION OF THE INVENTION

I. Abbreviation and Definitions

The term "alkyl", by itself or as part of another substituent, means, unless otherwise stated, a straight or branched chain hydrocarbon radical, having the number of carbon atoms designated (i.e. $C_{1-8}$ Means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. The term "alkenyl" refers to an unsaturated alkyl group having one or more double bonds. Similarly, the term "alkynyl" refers to an unsaturated alkyl group having one or more triple bonds. Examples of such unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "cycloalkyl" refers to hydrocarbon rings having the indicated number of ring atoms (e.g., $C_{3-6}$cycloalkyl) and being fully saturated or having no more than one double bond between ring vertices. "Cycloalkyl" is also meant to refer to bicyclic and polycyclic hydrocarbon rings such as, for example, bicyclo[2.2.1]heptane, bicyclo[2.2.2]octane, etc. The term "heterocycloalkyl" refers to a cycloalkyl group that contain from one to five heteroatoms selected from N, O, and S, wherein the nitrogen and sulfur atoms are optionally oxidized, and the nitrogen atom(s) are optionally quaternized. The heterocycloalkyl may be a monocyclic, a bicyclic or a polycyclic ring system. Non limiting examples of heterocycloalkyl groups include pyrrolidine, piperidinyl, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "alkylene" by itself or as part of another substituent means a divalent radical derived from an alkane, as exemplified by —CH₂CH₂CH₂CH₂—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms. Similarly, "alkenylene" and "alkynylene" refer to the unsaturated forms of "alkylene" having double or triple bonds, respectively.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 Membered ring with the nitrogen atom to which each is attached. Accordingly, a group represented as —NR^a R^b is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon group which can be a single ring or multiple rings (up to three rings) which are fused together or linked covalently. The term "heteroaryl" refers to aryl groups (or rings) that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like).

The above terms (e.g., "alkyl," "aryl" and "heteroaryl"), in some embodiments, will include both substituted and unsubstituted forms of the indicated radical. Preferred substituents for each type of radical are provided below. For brevity, the terms aryl and heteroaryl will refer to substituted or unsubstituted versions as provided below, while the term "alkyl" and related aliphatic radicals is meant to refer to unsubstituted version, unless indicated to be substituted.

Substituents for the alkyl radicals (including those groups often referred to as alkylene, alkenyl, alkynyl and cycloalkyl) can be a variety of groups selected from: -halogen, —OR', —NR'R", —SR', —SiR'R"R"', —OC(O)R', —C(O)', —CO$_2$R', —CONR'R", —OC(O)NR'R", —NR"C(O)R', —NR'—C(O)NR"R"', —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —CN and —NO$_2$ in a number ranging from zero to (2 M'+1), where m' is the total number of carbon atoms in such radical. R', R" and R"' each independently refer to hydrogen, unsubstituted C$_{1-8}$ alkyl, unsubstituted heteroalkyl, unsubstituted aryl, aryl substituted with 1-3 halogens, unsubstituted C$_{1-8}$ alkyl, C$_{1-8}$ alkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl.

Similarly, substituents for the aryl and heteroaryl groups are varied and are generally selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R"', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —N$_3$, perfluoro(C$_1$-C$_4$)alkoxy, and perfluoro(C$_1$-C$_4$)alkyl, in a number ranging from zero to the total number of open valences on the aromatic ring system; and where R', R" and R"' are independently selected from hydrogen, C$_{1-8}$ alkyl, C$_{3-6}$ cycloalkyl, C$_{2-8}$ alkenyl, C$_{2-5}$ alkynyl, unsubstituted aryl and heteroaryl, (unsubstituted aryl)-C$_{1-4}$ alkyl, and unsubstituted aryloxy-C$_{1-4}$ alkyl. Other suitable substituents include each of the above aryl substituents attached to a ring atom by an alkylene tether of from 1-4 carbon atoms.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

II. General

The present invention derives from the discovery that compounds of formula Ia or Ib (as well as the subgeneric formulae Ia$^{1-4}$ and Ib$^{1-4}$) act as potent antagonists of the CCR1 receptor. The compounds have in vivo anti-inflammatory activity. Accordingly, the compounds provided herein are useful in pharmaceutical compositions, methods for the treatment of CCR1-mediated diseases, and as controls in assays for the identification of competitive CCR1 antagonists.

III. Compounds

In one aspect, the present invention provides compounds having a formula selected from the group consisting of:

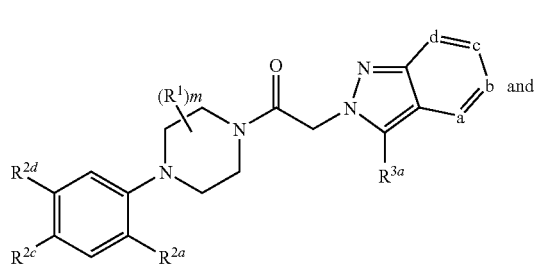

Ia and

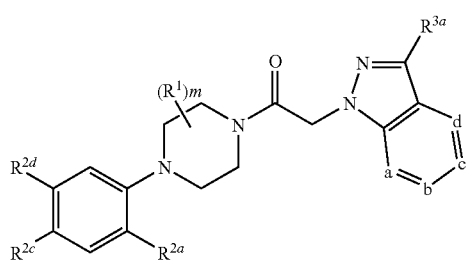

Ib or a pharmaceutically acceptable salt, hydrate or N-oxide thereof. In the formulae above, the subscript m is an integer of from 0 to 4. In certain embodiments, in formulae Ia and Ib the subscript m is an integer from 0 to 2. In yet another embodiment, the subscript m in formulae Ia and Ib is an integer of from 0 to 1.

The symbol $R^1$ in formulae Ia and Ib is a substituent independently selected from the group consisting of $C_{1-8}$ alkyl, $C_{1-8}$ haloalkyl, $C_{3-6}$ cycloalkyl, —$CO_2R^a$, —$S(O)_3R^a$, —$X^1CO_2R^a$, —$X^1SO_2R^a$, —$X^1S(O)_3R^a$, —$X^1OR^a$, —$COR^a$, —$CONR^aR^b$, —$X^1NR^aR^b$, —$X^1NR^aCOR^b$, —$X^1CONR^aR^b$, —$X^1S(O)_2NR^aR^b$, —$X^1S(O)_2R^a$, —$OR^a$, —$NR^aR^b$, —$NR^aCOR^b$, —$CONR^aR^b$, —$NR^aS(O)_2R^b$, —$S(O)_2NR^aR^b$, —$S(O)_2R^a$, —$X^1COR^a$, $X^1CONR^aR^b$, and —$X^1NR^aS(O)_2R^b$. The symbol $X^1$ is $C_{1-4}$ alkylene and each $R^a$ and $R^b$ substituent is independently selected from the group consisting of hydrogen, $C_{1-8}$ alkyl, $C_{1-8}$ haloalkyl and $C_{3-6}$ cycloalkyl, or optionally $R^a$ and $R^b$ when attached to the same nitrogen atom are combined to form a 3- to 7-membered ring having from 0-2 additional heteroatoms as ring members; and wherein the aliphatic portions of each of said $R^1$ substituents is optionally substituted with from one to three members selected from the group consisting of —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(=NH)NH_2$, —$NHC(=NR^m)NH_2$, —$NR^mC(=NR^m)N(R^m)_2$, —$NR^mC(=NR^m)NH(R^m)$, —$NHC(=NR^m)NH(R^m)$, —$NHC(=NR^m)N(R^m)_2$, —$NHC(=NH)N(R^m)_2$, —$NHC(=NH)NH(R^m)$, —$C(=NH)NH_2$, —$C(=NR^m)NH_2$, —$C(=NR^m)N(R^m)_2$, —$C(=NR^m)NH(R^m)$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl.

In another embodiment, $R^1$ in formulae Ia and Ib is a substituent independently selected from the group consisting of $C_{1-8}$ alkyl, $C_{1-8}$ haloalkyl, $C_{3-6}$ cycloalkyl, —$CO_2R^a$, —$X^1CO_2R^a$, —$X^1SO_2R^a$ and —$X^1OR^a$, wherein the aliphatic portions of each of said $R^1$ substituents is optionally substituted with from one to three members selected from the group consisting of —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl.

In another embodiment, $R^1$ in formulae Ia and Ib is a substituent independently selected from the group consisting of $C_{1-8}$ alkyl, $C_{1-8}$ haloalkyl and $C_{3-6}$ cycloalkyl, wherein the aliphatic portions of each of said $R^1$ substituents is optionally substituted with from one to three members selected from the group consisting of —OH, —$OR^m$, —$OC(O)NHR^m$, —$OC(O)N(R^m)_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl.

In one embodiment of the invention, $R^1$ in formulae Ia and Ib, if present, is selected from the group consisting of —$CO_2H$ or $C_{1-4}$ alkyl, optionally substituted with —OH, —$OR^m$, —$S(O)_2R^m$, —$CO_2H$ and —$CO_2R^m$. In another embodiment of the invention, $R^1$ is methyl; and m is 0-2.

The symbols $R^{2a}$, $R^{2c}$ and $R^{2d}$ in formulae Ia and Ib are each substituents independently selected from the group consisting of hydrogen, halogen, cyano, aryl, heteroaryl, —$NO_2$, —CO$_2$R$^c$, —CONR$^c$R$^d$, —C(O)R$^c$, —S(O)R$^e$, —S(O)$_2$R$^e$, —S(O)$_3$R$^c$, —R$^e$, —C(NOR$^c$)R$^d$, —C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$)=NV, —X$^2$NR$^c$R$^d$, —X$^2$SR$^c$, —X$^2$CN, —X$^2$NO$_2$, —X$^2$CO$_2$R$^c$, —X$^2$CONR$^c$R$^d$, —X$^2$C(O)R$^c$, —X$^2$C(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$, —X$^2$N$_3$, —OR$^c$, —SR$^c$, —NR$^d$C(O)R$^c$, —NR$^d$C(O)$_2$R$^e$, —X$^2$S(O)$_3$R$^c$, —S(O)$_2$NR$^c$R$^d$, —X$^2$OR$^c$, —O—X$^2$ OR$^c$, —X$^2$NR$^c$R$^d$, —O—X$^2$NR$^c$R$^d$, —NR$^d$—X$^2$CO$_2$R$^c$, —NR$^c$—C(O)NR$^c$R$^d$, —NH—C(NH$_2$)=NH, —NR$^e$C(NH$_2$)=NH, —NH—C(NH$_2$)=NR$^e$, —NH—C(NHR$^e$)=NH, —NR$^e$C(NHR$^e$)=NH, —NR$^e$C(NH$_2$)=NR$^e$, —NH—C(NHR$^e$)=NR$^e$, —NH—C(NR$^e$R$^e$)=NH, NR$^c$S(O)$_2$R$^e$, —NR$^c$C(S)NR$^c$R$^d$, —X$^2$NR$^c$C(S)NR$^c$R$^d$, —X$^2$OC(O)R$^c$, —O—X$^2$CONR$^c$R$^d$, —OC(O)R$^c$, —NR$^c$R$^d$, —NR$^d$—X$^2$ OR$^c$ and —NR$^d$—X$^2$NR$^c$R$^d$.

In one embodiment, the symbol R$^{2a}$ in formulae Ia and Ib is independently selected from the group consisting of hydrogen, halogen, cyano, heteroaryl, —NO$_2$, —CO$_2$R$^c$, —CONR$^c$R$^d$, —C(O)R$^c$, —S(O)R$^e$, —S(O)$_2$R$^e$, —R$^e$, —C(NOR$^c$)R$^d$, —C(NR$^c$V)=NV, —N(V)C(R$^c$)=NV, —X$^2$C(NOR$^c$)R$^d$, —X$^2$C(NR$^c$V)=NV, —X$^2$N(V)C(R$^c$)=NV, —X$^2$NR$^c$R$^d$, —X$^2$SR$^c$, —X$^2$ CN, —X$^2$NO$_2$, —X$^2$CO$_2$R$^c$, —X$^2$CONR$^c$R$^d$, —X$^2$C(O)R$^c$, —X$^2$OC(O)NR$^c$R$^d$, —X$^2$NR$^d$C(O)R$^c$, —X$^2$NR$^d$C(O)$_2$R$^e$, —X$^2$NR$^c$C(O)NR$^c$R$^d$, —X$^2$NH—C(NH$_2$)=NH, —X$^2$NR$^e$C(NH$_2$)=NH, —X$^2$NH—C(NH$_2$)=NR$^e$, —X$^2$NH—C(NHR$^e$)=NH, —X$^2$S(O)R$^e$, —X$^2$S(O)$_2$R$^e$, —X$^2$NR$^c$S(O)$_2$R$^e$, —X$^2$S(O)$_2$NR$^c$R$^d$ and —X$^2$N$_3$.

In another embodiment, the R$^{2a}$ substituent in formulae Ia and Ib is selected from the group consisting of hydrogen, F, Cl, Br, I, —CO$_2$R$^c$, —CONR$^c$R$^d$, —CN, a 5- to 6-membered heteroaryl, —X$_2$NR$^c$R$^d$, —C(NOR$^c$)R$^d$. In yet another embodiment, R$^{2a}$ is hydrogen. In yet another embodiment, the R$^{2a}$ substituent in formulae Ia and Ib is selected from the group consisting of F, Cl, Br, I, —CO$_2$ Me, —CONH$_2$, CN, oxazolyl, —CH$_2$NH$_2$, —CH$_2$NHMe, —CH$_2$NMe$_2$ and —CH=N—OH. In yet another embodiment, in compounds having formulae Ia and Ib, the R$^{2a}$ substituent is selected from the group consisting of hydrogen, F, Cl, Br and I.

In another embodiment, the symbols R$^{2c}$ and R$^{2d}$ in formulae Ia and Ib are each substituents independently selected from the group consisting of halogen, —OR$^c$, —SR$^c$, —OC(O)R$^c$, —NR$^c$R$^d$, —R$^e$, —CN, —NO$_2$, —CO$_2$R$^c$, —C(O)R$^c$, —NR$^d$C(O)R$^c$, —NR$^d$C(O)$_2$R$^e$, —S(O)$_2$R$^e$, —S(O)$_2$NR$^c$R$^d$, —X$^2$OR$^c$, —O—X$^2$OR$^c$, —X$^2$NR$^c$R$^d$, —O—X$^2$NR$^c$R$^d$ and —NR$^d$—X$^2$CO$_2$R$^c$. In certain aspects of this embodiment, R$^{2c}$ and R$^{2d}$ are each independently selected from the group consisting of hydrogen, halogen, F, Cl, Br, I and OR$^c$.

Within each of R$^{2a}$, R$^{2c}$ and R$^{2d}$, X$^2$ is C$_{1-4}$ alkylene and each R$^c$ and R$^d$ is independently selected from hydrogen, C$_{1-8}$ alkyl, C$_{1-8}$ haloalkyl, and C$_{3-6}$ cycloalkyl. Optionally, R$^c$ and R$^d$ when attached to the same nitrogen atom can be combined with the nitrogen atom to form a five or six-membered ring having from 0 to 2 additional heteroatoms as ring members. The symbol R$^e$ is independently selected from the group consisting of C$_{1-8}$ alkyl, C$_{1-8}$ haloalkyl, C$_{3-6}$ cycloalkyl, C$_{2-8}$ alkenyl, C$_{2-8}$ alkynyl, aryl and heteroaryl, and each of R$^c$, R$^d$ and R$^e$ is optionally further substituted with from one to three members selected from the group consisting of —OH, —OR'', —OC(O)NHR'', —OC(O)N(R'')$_2$, —SH, —SR'', —S(O)R'', —S(O)$_2$R'', —SO$_2$NH$_2$, —S(O)$_2$NHR'', —S(O)$_2$N(R'')$_2$, —NHS(O)$_2$R'', —NR''S(O)$_2$R'', —C(O)NH$_2$, —C(O)NHR'', —C(O)N(R'')$_2$, —C(O)R'', —NHC(O)R'', —NR''C(O)R'', —NHC(O)NH$_2$, —NR''C(O)NH$_2$, —NR''C(O)NHR'', —NHC(O)NHR'', —NR''C(O)N(R'')$_2$, —NHC(O)N(R'')$_2$, —CO$_2$H, —CO$_2$R'', —NHCO$_2$R'', —NR''CO$_2$R'', —CN, —NO$_2$, —NH$_2$, —NHR'', —N(R'')$_2$, —NR''S(O)NH$_2$ and —NR''S(O)$_2$NHR'', wherein each R'' is independently an unsubstituted C$_{1-6}$ alkyl; and wherein V is independently selected from the group consisting of —R$^c$, —CN, —CO$_2$R$^e$ and —NO$_2$.

In a certain embodiment of a compound having formulae Ia and Ib, the subscript m is 0 or 1; and the symbol R$^{2a}$ is hydrogen. In another embodiment, the subscript m is 0-1; and R$^{2a}$ is F or Cl.

In another embodiment of the invention, R$^{2c}$ in formulae Ia and Ib is selected from the group consisting of halogen, —CN, —NO$_2$, —CO$_2$R$^c$, —COR$^c$, —S(O)$_2$R$^e$. In another embodiments of the invention, the symbol R$^{2c}$ is selected from the group consisting of F, Cl, Br, CN, NO$_2$, —CO$_2$CH$_3$, —C(O)CH$_3$ and —S(O)$_2$CH$_3$.

In yet another embodiment of the invention, the symbol R$^{2d}$ in formulae Ia and Ib is selected from the group consisting of —SR$^c$, —O—X$^2$—OR$^c$, —X$^2$—OR$^c$, —OC(O)R$^c$, —NR$^c$R$^d$, —R$^e$ and —OR$^c$. In another embodiment, R$^{2d}$ is selected from the group consisting of —SMe, —OCH$_2$OMe, —CH$_2$OMe, —CH$_2$OEt, methyl, ethyl, methoxy and ethoxy.

In formulae Ia and Ib, each of the ring vertices a, b, c and d is independently selected from N and C(R$^{3a}$), and from one to two of said ring vertices is N. In one embodiment of the invention, the fused six membered ring having vertices a, b, c and d is a fused pyridine ring or a fused pyrimidine ring. In yet another embodiment of the invention, the fused six membered ring having vertices a, b, c and d is a fused pyrazine ring. In yet another embodiment of the invention, the fused six membered ring having vertices a, b, c and d is a fused pyridazine ring.

Turning to the R$^{3a}$ substituent in formulae Ia and Ib, at each occurrence, the symbol R$^{3a}$ is independently selected from the group consisting of hydrogen, halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —NH—C(NH$_2$)=NH, —NR$^h$C(NH$_2$)=NH, —NH—C(NH$_2$)=NR$^h$, —NH—C(NHR$^h$)=NH, —C(=NR$^f$)NR$^g$R$^h$, —S(O)$_3$R$^f$, —S(O)R$^h$, —S(O)$_2$R$^h$, —S(O)$_3$R$^h$, —NR$^f$S(O)$_2$R$^h$, —S(O)$_2$ NR$^g$R$^g$, —NR$^f$S(O)$_2$R$^h$, —NR$^f$S(O)$_2$NR$^f$R$^g$, —N$_3$, —C(=NOR$^f$)NR$^f$R$^g$, —X$_3$SO$_3$R$^f$, —X$^3$C(=NR$^f$)NR$^g$R$^h$, —X$^3$OR$^f$, —X$^3$OC(O)R$^f$, —X$^3$NR$^f$R$^g$, —X$^3$SR$^f$, —X$^3$CN, —X$^3$NO$_2$, —X$^3$CO$_2$R$^f$, —X$^3$CONR$^f$R$^g$, —X$^3$C(O)R$^f$, —X$^3$OC(O)NR$^f$R$^g$, —X$^3$NR$^g$C(O)R$^f$, —X$^3$NR$^g$C(O)$_2$R$^h$, —X$^3$NR$^f$—C(O)NR$^f$R$^g$, —X$^3$NH—C(NH$_2$)=NH, —X$^3$NR$^h$C(NH$_2$)=NH, —X$^3$NH—C(NH$_2$)=NR$^h$, —X$^3$NH—C(NHR$^h$)=NH, —X$^3$S(O)R$^h$, —X$^3$S(O)$_2$R$^h$, —X$^3$NR$^f$S(O)$_2$R$^h$, —X$^3$S(O)$_2$NR$^f$R$^g$, —Y, —X$^3$Y, —X$^3$N$_3$, —C(O)NR$^f$S(O)R$^h$, —P=O(OR$^f$)(OR$^g$), —X$^3$C(O)NR$^f$S(O)$_2$R$^h$, —X$^3$C(O)NR$^f$S(O)R$^h$ and —X$^3$P=O(OR$^f$)(OR$^g$). The symbol Y is a five to ten-membered aryl, heteroaryl or heterocycloalkyl ring, optionally substituted with from one to three substitutents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$, —S(O)$_2$NR$^f$R$^g$, —X$^3$OR$^f$, —X$^3$NR$^f$R$^g$, —X$^3$NR$^f$S(O)$_2$R$^h$ and —X$^3$S(O)$_2$NR$^f$R$^g$, and wherein each X$^3$ is independently selected from the group consisting of C$_{1-4}$ alkylene, C$_{2-4}$ alkenylene and C$_{2-4}$ alkynylene; each R$^f$ and R$^g$ is independently selected from hydrogen, C$_{1-8}$ alkyl, C$_{1-8}$ haloalkyl, C$_{3-6}$ cycloalkyl, C$_{2-8}$ alkenyl, C$_{2-8}$ alkynyl, aryl, heteroaryl, aryl-C$_{1-4}$ alkyl, and aryloxy-C$_{1-4}$ alkyl, or when attached to the same nitrogen atom can be combined with the nitrogen atom to form a five or six-membered ring having from 0 to 2 additional heteroatoms as ring members; and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$ R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$ NHR°, wherein R° is unsubstituted $C_{1-6}$ alkyl.

In one embodiment of formulae Ia and Ib, the symbol $R^{3a}$, at each occurrence, is independently selected from the group consisting of hydrogen, halogen, —OR$^f$, —OC(O)R$^f$, —NR$^f$R$^g$, —SR$^f$, —R$^h$, —CN, —NO$_2$, —CO$_2$R$^f$, —CONR$^f$R$^g$, —C(O)R$^f$, —OC(O)NR$^f$R$^g$, —NR$^g$C(O)R$^f$, —NR$^g$C(O)$_2$R$^h$, —NR$^f$—C(O)NR$^f$R$^g$, —S(O)R$^h$, —S(O)$_2$R$^h$, —NR$^f$S(O)$_2$R$^h$, —S(O)$_2$NR$^f$R$^g$, —NR$^f$S(O)$_2$NR$^f$R$^g$, —X$^3$OR$^f$, —X$^3$NR$^f$R$^g$, —X$^3$SR$^f$, —X$^3$CN, —X$^3$CO$_2$R$^f$, —X$^3$CONR$^f$R$^g$, —X$^3$C(O)R$^f$, —X$^3$NR$^g$C(O)R$^f$, —X$^3$NR$^g$C(O)$_2$R$^h$, —Y, —X$^3$Y and —X$^3$N$_3$. The symbol Y is a five or six-membered aryl, a five or six membered heteroaryl, or a three to eight membered heterocycloalkyl ring, optionally substituted with from one to three substituents selected from the group consisting of halogen, —OR$^f$, —NR$^f$R$^g$, —R$^h$, —SR$^f$, —CN, —NO$_2$, —CO$_2$R$^f$, —CONR$^f$R$^g$, —C(O)R$^f$, —NR$^g$C(O)R$^f$, —S(O)R$^h$, —S(O)$_2$R$^h$, —NR$^f$S(O)$_2$R$^h$ and —S(O)$_2$NR$^f$R$^g$. X$^3$ is independently $C_{1-4}$ alkylene. The symbols R$^f$ and R$^g$ are independently selected from hydrogen, $C_{1-8}$ alkyl, $C_{1-8}$ haloalkyl and $C_{3-6}$ cycloalkyl, and each R$^h$ is independently selected from the group consisting of $C_{1-8}$ alkyl, $C_{1-8}$ haloalkyl and $C_{3-6}$ cycloalkyl. The aliphatic portions of X$^3$, R$^f$, R$^g$ and R$^h$ is optionally further substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein each R° is independently an unsubstituted $C_{1-6}$ alkyl.

In another embodiment of the invention, the symbol $R^{3a}$ of formulae Ia and Ib is a member independently selected from the group consisting of hydrogen, halogen, —OR$^f$, —NR$^f$R$^g$, —R$^h$, —CN, and —Y, wherein Y is a five to six-membered aryl ring, a five to six-membered heteroaryl ring, or a three to eight-membered heterocycloalkyl ring selected from the group consisting of homopiperidinyl, morpholinyl, thiomorpholinyl, pyrrolidinyl, piperidinyl, azetidinyl, pyranyl, tetrahydrofuranyl, piperazinyl, phenyl, pyridyl, pyrimidinyl, oxadiazolyl, oxazolyl and thiazolyl, optionally substituted with from one to three substituents selected from the group consisting of halogen, —OR$^f$, —NR$^f$R$^g$, —R$^h$, —CN, wherein each R$^f$ and R$^g$ is independently selected from hydrogen, $C_{1-6}$ alkyl, $C_{1-6}$ haloalkyl and $C_{3-6}$ cycloalkyl, and each R$^h$ is independently selected from the group consisting of $C_{1-6}$ alkyl, $C_{1-6}$ haloalkyl and $C_{3-6}$ cycloalkyl, wherein the aliphatic portions of R$^f$, R$^g$ and R$^h$ are optionally further substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein R° is unsubstituted $C_{1-6}$ alkyl.

In another embodiment of the invention, the $R^{3a}$ groups in formulae Ia and Ib is selected from the group consisting of —Y and —X$^3$—Y, wherein Y is selected from the group consisting of homopiperidinyl, morpholinyl, thiomorpholinyl, pyrrolidinyl, piperidinyl, azetidinyl, pyranyl, tetrahydrofuranyl, piperazinyl, phenyl, thienyl, furanyl, pyridyl, pyrimidinyl, pyrazinyl, pyrrolyl, pyridizinyl, pyrazolyl, imidazolyl, thiazolyl, oxazolyl, isoxazolyl, isothiazolyl, triazolyl, tetrazolyl and oxadiazolyl, which is optionally substituted with from one to three substituents independently selected from the group consisting of halogen, —OR$^f$, —NR$^f$R$^g$, —COR$^f$, —CO$_2$R$^f$, —CONR$^f$R$^g$, —NO$_2$, —R$^h$ and —CN, wherein R$^f$ and R$^g$ are each independently selected from the group consisting of H, $C_{1-8}$ alkyl, $C_{3-6}$ cycloalkyl and $C_{1-8}$ haloalkyl, and each R$^h$ is independently selected from the group consisting of $C_{1-8}$ alkyl, $C_{3-6}$ cycloalkyl and $C_{1-8}$ haloalkyl. In certain embodiments of the invention, the symbol Y is selected from the group consisting of imidazolyl, phenyl, pyridyl, oxazolyl, pyrimidinyl, oxadiazolyl, and thiazolyl, each of which is optionally substituted with from one to three substituents independently selected from the group consisting of halogen, —OR$^f$, —NR$^f$R$^g$, —COR$^f$, —CO$_2$R$^f$, —CONR$^f$R$^g$, —NO$_2$, —R$^h$ and —CN, wherein R$^f$ and R$^g$ are each independently selected from the group consisting of H, $C_{1-8}$ alkyl, $C_{3-6}$ cycloalkyl and $C_{1-8}$ haloalkyl, and each R$^h$ is independently selected from the group consisting of $C_{1-8}$ alkyl, $C_{3-6}$ cycloalkyl and $C_{1-8}$ haloalkyl. In certain other embodiments of the invention, the symbol Y is selected from the group consisting of phenyl, pyridyl, oxazolyl, pyrimidinyl, oxadiazolyl, and thiazolyl, each of which is optionally substituted with from one to three substituents independently selected from the group consisting of halogen, —OR$^f$, NR$^f$R$^g$, —COR$^f$, —CO$_2$R$^f$, —CONR$^f$R$^g$, —NO$_2$, —R$^h$ and —CN, wherein R$^f$ and R$^g$ are each independently selected from the group consisting of H, $C_{1-8}$ alkyl, $C_{3-6}$ cycloalkyl and $C_{1-8}$ haloalkyl, and each R$^h$ is independently selected from the group consisting of $C_{1-8}$ alkyl, $C_{3-6}$ cycloalkyl and $C_{1-8}$ haloalkyl. Within this embodiment, in certain aspects of the invention, m is an integer from 0-2. In other aspect, m is an integer from 0-1.

In yet another embodiment of the invention, the $R^{3a}$ substituent in formulae Ia and Ib is selected from the group consisting of hydrogen, halogen, $C_{1-4}$ alkyl and $C_{1-4}$ haloalkyl, wherein the aliphatic portions are optionally substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein each R° is independently an unsubstituted $C_{1-6}$ alkyl. In certain instances of this embodiment, m is 0 or 1; $R^{2a}$ is preferably hydrogen; and additionally in other instances, $R^{2c}$ is preferably selected from the group consisting of F, Cl, Br, CN, $NO_2$, —$CO_2CH_3$, —$C(O)CH_3$ and —$S(O)_2CH_3$.

In yet another embodiment, the $R^{3a}$ substituent in formulae Ia and Ib is halogen, $C_{1-4}$ alkyl or $C_{1-4}$ haloalkyl.

In yet another embodiment, the $R^{3a}$ Moiety on the pyrazole ring in formulae Ia and Ib is hydrogen, halogen, chloro, fluoro, bromo, oxazolyl, pyridyl, pyrimidinyl, imidazolyl, oxadiazolyl, thiazolyl, $C_{1-8}$ alkyl, $C_{3-6}$ cycloalkyl or $C_{1-8}$ haloalkyl or cyano.

In yet another embodiment, the $R^{3a}$ Moiety on the pyrazole ring in formulae Ia and Ib is hydrogen, halogen, chloro, fluoro, bromo, oxazolyl, pyridyl, pyrimidinyl, oxadiazolyl, thiazolyl, $C_{1-8}$ alkyl, $C_{3-6}$ cycloalkyl or $C_{1-8}$ haloalkyl or cyano.

In a certain embodiment of the invention, in the compounds having formulae Ia and Ib, $R^{3a}$ is a member independently selected from the group consisting of hydrogen, halogen, —$OR^f$, —$NR^fR^g$, —$C(O)R^f$, —$C(O)OR^f$, —$S(O)R^f$, —$S(O)_2 R^f$, —$S(O)_3R^f$, —$S(O)_3R^h$, —$X^3C(O)_2R^f$, $X^3S(O)_3 R^f$, —$S(O)_2NR^fR^g$, —$X^3S(O)_2NR^fR^g$, —$R^h$, —CN, $X^3NR^fR^g$, $NR^gC(O)R^f$, $X^3N_3$ and Y. The symbol Y is a five to six-membered aryl, a five or six-membered heteroaryl ring or a three to eight-membered heterocycloalkyl ring selected from the group consisting of homopiperidinyl, morpholinyl, thiomorpholinyl, pyrrolidinyl, piperidinyl, azetidinyl, pyranyl, tetrahydrofuranyl, piperazinzyl, phenyl, pyridyl, oxazolyl, pyrimidinyl, oxadiazolyl, imidazolyl, pyrazolyl, triazolyl and thiazolyl, optionally substituted with from one to three substitutents selected from the group consisting of halogen, —$OR^f$, —$NR^fR^g$, —$R^h$, —CN. Each $R^f$ and $R^g$ is independently selected from hydrogen, $C_{1-6}$ alkyl, $C_{1-6}$ haloalkyl and $C_{3-6}$ cycloalkyl, and each $R^h$ is independently selected from the group consisting of $C_{1-6}$ alkyl, $C_{1-6}$ haloalkyl and $C_{3-6}$ cycloalkyl, wherein the aliphatic portions of $R^f$, $R^g$ and $R^h$ are optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein $R^o$ is unsubstituted $C_{1-6}$ alkyl.

In a certain embodiment of the invention, in the compounds having formulae Ia and Ib, $R^{3a}$ is a member independently selected from the group consisting of hydrogen, halogen, —$OR^f$, —$NR^fR^g$, —$C(O)R^f$, —$C(O)OR^f$, —$S(O)R^f$, —$S(O)_2 R^f$, —$S(O)_2NR^fR^g$, —$R^h$, —CN, $X^3 NR^fR^g$, $NR^gC(O)R^f$, $X^3N_3$ and —Y, wherein Y is a five to six-membered aryl, a five or six-membered heteroaryl ring or a three to eight-membered heterocycloalkyl ring selected from the group consisting of homopiperidinyl, morpholinyl, thiomorpholinyl, pyrrolidinyl, piperidinyl, azetidinyl, pyranyl, tetrahydrofuranyl, piperazinzyl, phenyl, pyridyl, oxazolyl, pyrimidinyl, oxadiazolyl and thiazolyl, optionally substituted with from one to three substitutents selected from the group consisting of halogen, —$OR^f$, —$NR^fR^g$, —$R^h$, —CN, wherein each $R^f$ and $R^g$ is independently selected from hydrogen, $C_{1-6}$ alkyl, $C_{1-6}$ haloalkyl and $C_{3-6}$ cycloalkyl, and each $R^h$ is independently selected from the group consisting of $C_{1-6}$ alkyl, $C_{1-6}$ haloalkyl and $C_{3-6}$ cycloalkyl, wherein the aliphatic portions of $R^f$, $R^g$ and $R^h$ are optionally further substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein $R^o$ is unsubstituted $C_{1-6}$ alkyl. The subscript m may be from 0 to 2; or alternatively from 0-1.

In another embodiment of the invention, in the compounds having formulae Ia or Ib, the symbol $R^{3a}$ Moiety on the pyrazole ring is hydrogen, halogen, chloro, fluoro, bromo, oxazolyl, pyridyl, oxadiazolyl thiazolyl, —$R^h$ or cyano; and optionally the symbol $R^1$, when present, is selected from the group consisting of —$CO_2H$ or $C_{1-4}$ alkyl, optionally substituted with —OH, —$OR^m$, —$S(O)_2R^m$, —$CO_2H$ and —$CO_2R^m$. In yet another embodiment, $R^1$, when present, is hydrogen or $C_{1-6}$ alkyl. m is an integer from 0-2.

In another embodiment of the invention, in compounds of formulae Ia and Ib, the $R^{3a}$ substituent is selected from the group consisting of hydrogen, halogen, —$OR^f$, $NR^fR^g$, —$R^h$, —Y, —CN, $X^3N_3$, —$SO_2R^h$, $X^3NR^fR^g$, $X^3Y$, —$S(O)_3R^f$, —$C(C=NOR^f)NR^fR^g$, —$NO_2$, and —$NR^gC(O)R^f$, wherein Y is an optionally substituted group selected from the group consisting of phenyl, pyridyl, pyrimidinyl, oxazolyl, thiazolyl, oxadiazolyl and morpholinyl, and $R^h$ is an optionally substituted group selected from the group consisting of $C_{1-8}$ alkyl, $C_{1-8}$ haloalkyl and $C_{3-8}$ cycloalkyl, and $R^f$ and $R^g$ are each independently an optionally substituted group selected from the group consisting of hydrogen, $C_{1-8}$ alkyl, $C_{1-8}$ haloalkyl and $C_{3-8}$ cycloalkyl. In certain aspects of this embodiment, the $R^{3a}$ substituent is selected from the group consisting of hydrogen, fluoro, chloro, bromo, iodo, amino, —$CH_3$, oxazolyl, thiazolyl, pyridyl, pyrimidinyl, morpholinyl, oxdiazolyl, —$NHC(O)CH_3$, —CN, $CH_2N_3$, $CH_2SO_3H$, $NO_2$, —(C=NOH)$NH_2$, —$S(O)_2CH_3$ and $CH_2NH_2$.

In yet another embodiment of the invention, in the compounds having formulae Ia or Ib, the subscript m is 0 or 1; $R^{2a}$ is hydrogen, halogen or —CN; $R^{2a}$ is selected from the group consisting of F, Cl, Br, CN, $NO_2$, —$CO_2CH_3$, —$C(O)CH_3$ and —$S(O)_2CH_3$; $R^{2d}$ is selected from the group consisting of —$SR^c$, —O—$X^2$—$OR^c$, —$X^2$—$OR^c$, —$R^e$ and —$OR^c$; and $R^{3a}$ substituents is selected from the group consisting of halogen, $C_{1-4}$ alkyl and $C_{1-4}$ haloalkyl, wherein the aliphatic portions of $R^{3a}$ are optionally substituted with from one to three members selected from the group consisting of —OH, —$OR^o$, —$OC(O)NHR^o$, —$OC(O)N(R^o)_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein each $R^o$ is independently an unsubstituted $C_{1-6}$ alkyl.

In one preferred embodiment, in the compounds of the invention having the formula Ib, when $R^{2a}$, is H, $R^{2c}$ is chloro, $R^{2d}$ is methoxy, m is 0, a is N, c is N, and b and d are CH, then $R^{3a}$ is other than hydrogen, methyl, unsubstituted 2-pyridyl, unsubstituted 2-pyrimidinyl or unsubstituted 2-oxazolyl.

In one specific embodiment, the present invention provides compounds having formula Ia and Ib wherein the subscript m is an integer of from 0 to 4. The symbol $R^1$ is a substituent independently selected from the group consisting of $C_{1-8}$ alkyl, $C_{1-8}$ haloalkyl, $C_{3-6}$ cycloalkyl, —$CO_2R^a$, —$X^1CO_2R^a$, —$X^1SO_2R^a$ and —$X^1OR^a$, —$COR^a$, —$CONR^aR^b$, —$X^1NR^aR^b$, —$X^1NR^aCOR^b$, —$X^1CONR^aR^b$, $X^1S(O)_2$ $NR^aR^b$ and $X^1S(O)_2R^a$, wherein $X^1$ is $C_{1-4}$ alkylene and each $R^a$ and $R^b$ is independently selected from the group consisting of hydrogen, $C_{1-8}$ alkyl, $C_{1-8}$ haloalkyl and $C_{3-6}$ cycloalkyl; and wherein the aliphatic portions of each of said $R^1$ substituents is optionally substituted with from one to three members selected from the group consisting of —OH, —$OR^m$, —OC(O)$NHR^m$, —OC(O)N($R^m$)$_2$, —SH, —$SR^m$, —S(O)$R^m$, —S(O)$_2R^m$, —$SO_2NH_2$, —S(O)$_2NHR^m$, —S(O)$_2$ N($R^m$)$_2$, —NHS(O)$_2R^m$, —$NR^mS(O)_2R^m$, —C(O)$NH_2$, —C(O)$NHR^m$, —C(O)N($R^m$)$_2$, —C(O)$R^m$, —NHC(O)$R^m$, —$NR^mC(O)R^m$, —NHC(O)$NH_2$, —$NR^mC(O)NH_2$, —$NR^mC(O)NHR^m$, —NHC(O)$NHR^m$, —$NR^mC(O)N(R^m)_2$, —NHC(O)N($R^m$)$_2$, —$CO_2H$, —$CO_2R^m$, —$NHCO_2R^m$, —$NR^mCO_2R^m$, —CN, —$NO_2$, —$NH_2$, —$NHR^m$, —N($R^m$)$_2$, —$NR^mS(O)NH_2$ and —$NR^mS(O)_2NHR^m$, wherein each $R^m$ is independently an unsubstituted $C_{1-6}$ alkyl. The symbols $R^{2a}$, $R^{2c}$ and $R^{2d}$ are each substituents independently selected from the group consisting of hydrogen, halogen, cyano, heteroaryl, —$NO_2$, —$CO_2R^c$, —$CONR^cR^d$, —C(O)$R^c$, —S(O)$R^e$, —S(O)$_2R^e$, —$R^e$, —C(NOR$^c$)$R^d$, —C(NR$^c$V)=NV, —N(V)C($R^c$)=NV, —$X^2$C(NOR$^c$)$R^d$, —$X^2$C(NR$^c$V)=NV, —$X^2$N(V)C($R^c$)=NV, —$X^2NR^cR^d$, —$X^2 SR^c$, —$X^2$ CN, —$X^2NO_2$, —$X^2CO_2R^c$, —$X^2CONR^cR^d$, —$X^2$C(O)$R^c$, —$X^2$OC(O)$NR^cR^d$, —$X^2NR^cC(O)R^c$, —$X^2NR^dC(O)_2R^e$, —$X^2NR^cC(O)NR^cR^d$, —$X^2$NH—C($NH_2$)=NH, —$X^2NR^cC(NH_2)$=NH, —$X^2$NH—C($NH_2$)=$NR^e$, —$X^2$NH—C($NHR^e$)=NH, —$X^2$S(O)$R^e$, —$X^2S(O)_2R^e$, —$X^2NR^cS(O)_2R^e$, —$X^2S(O)_2NR^cR^d$, —$X^2N_3$, —$OR^c$, —$SR^c$, —$NR^dC(O)R^c$, —$NR^dC(O)_2R^e$, —S(O)$_2R^e$, —S(O)$_2$ $NR^cR^d$, —$X^2$ $OR^c$, —O—$X^2$ $OR^c$, —$X^2NR^cR^d$, —O—$X^2NR^cR^d$ and —$NR^d$—$X^2CO_2R^e$. Within each of $R^{2a}$, $R^{2c}$ and $R^{2d}$, $X^2$ is $C_{1-4}$ alkylene and each $R^c$ and $R^d$ is independently selected from hydrogen, $C_{1-8}$ alkyl, $C_{1-8}$ haloalkyl, and $C_{3-6}$ cycloalkyl. Optionally, $R^c$ and $R^d$ when attached to the same nitrogen atom can be combined with the nitrogen atom to form a five or six-membered ring having from 0 to 2 additional heteroatoms as ring members. The symbol $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl, and each of $R^c$, $R^d$ and $R^e$ is optionally further substituted with from one to three members selected from the group consisting of —OH, —$OR^n$, —OC(O)$NHR^n$, —OC(O)N($R^n$)$_2$, —SH, —$SR^n$, —S(O)$R^n$, —S(O)$_2R^n$, —$SO_2NH_2$, —S(O)$_2NHR^n$, —S(O)$_2N(R^n)_2$, —NHS(O)$_2R^n$, —$NR^nS(O)_2R^n$, —C(O)$NH_2$, —C(O)$NHR^n$, —C(O)N($R^n$)$_2$, —C(O)$R^n$, —NHC(O)$R^n$, —$NR^nC(O)R^n$, —NHC(O)$NH_2$, —$NR^nC(O)NH_2$, —$NR^nC(O)NHR^n$, —NHC(O)$NHR^n$, —$NR^nC(O)N(R^n)_2$, —NHC(O)N($R^n$)$_2$, —$CO_2H$, —$CO_2R^n$, —$NHCO_2R^n$, —$NR^nCO_2R^n$, —CN, —$NO_2$, —$NH_2$, —$NHR^n$, —N($R^n$)$_2$, —$NR^nS(O)NH_2$ and —$NR^nS(O)_2NHR^n$, wherein each $R^n$ is independently an unsubstituted $C_{1-6}$ alkyl; and wherein V is independently selected from the group consisting of —$R^c$, —CN, —$CO_2R^e$ and —$NO_2$. Each of ring vertices a, b, c and d in formulae Ia and Ib is independently selected from N and C($R^{3a}$), and from one to two of said ring vertices is N. The symbol $R^{3a}$ in formulae Ia and Ib is independently selected from the group consisting of hydrogen, halogen, —$OR^f$, —OC(O)$R^f$, —$NR^fR^g$, —$SR^f$, —$R^h$, —CN, —$NO_2$, —$CO_2R^f$, —$CONR^fR^g$, —C(O)$R^f$, —OC(O)$NR^fR^g$, —$NR^gC(O)R^f$, —$NR^gC(O)_2R^h$, —$NR^f$—C(O)$NR^fR^g$, —NH—C($NH_2$)=NH, —$NR^hC(NH_2)$=NH, —NH—C($NH_2$)=$NR^h$, —NH—C($NHR^h$)=NH, —S(O)$R^h$, —S(O)$_2R^h$, —$NR^fS(O)_2R^h$, —S(O)$_2NR^fR^g$, —$NR^fS(O)_2R^h$, —$NR^fS(O)_2NR^fR^g$, —$N_3$, —$X^3OR^f$, —$X^3$OC(O)$R^f$, —$X^3NR^fR^g$, —$X^3SR^f$, —$X^3$CN, —$X^3NO_2$, —$X^3CO_2R^f$, —$X^3CONR^fR^g$, —$X^3$C(O)$R^f$, —$X^3$OC(O)$NR^f$ $R^g$, —$X^3NR^gC(O)R^f$, —$X^3NR^gC(O)_2R^h$, —$X^3NR^f$—C(O) $NR^fR^g$, —$X^3$NH—C($NH_2$)=NH, —$X^3NR^hC(NH_2)$=NH, —$X^3$NH—C($NH_2$)=$NR^h$, —$X^3$NH—C($NHR^h$)=NH, —$X^3$S(O)$R^h$, —$X^3S(O)_2R^h$, —$X^3NR^fS(O)_2R^h$, —$X^3S(O)_2$ $NR^fR^g$, —Y, —$X^3$Y and —$X^3N_3$. The symbol Y is a five to ten-membered aryl, heteroaryl or heterocycloalkyl ring, optionally substituted with from one to three substituents selected from the group consisting of halogen, —$OR^f$, —$NR^f$ $R^g$, —$R^h$, —$SR^f$, —CN, —$NO_2$, —$CO_2R^f$, —$CONR^fR^g$, —C(O)$R^f$, —$NR^gC(O)R^f$, —S(O)$R^h$, —S(O)$_2R^h$, —$NR^fS$(O)$_2R^h$, —S(O)$_2NR^fR^g$, —$X^3OR^f$, —$X^3NR^fR^g$, —$X^3NR^fS$(O)$_2R^h$ and —$X^3S(O)_2NR^fR^g$, and wherein each $X^3$ is independently selected from the group consisting of $C_{1-4}$ alkylene, $C_{2-4}$ alkenylene and $C_{2-4}$ alkynylene; each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members; and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —OH, —$OR^o$, —OC(O)$NHR^o$, —OC(O)N($R^o$)$_2$, —SH, —$SR^o$, —S(O)$R^o$, —S(O)$_2R^o$, —$SO_2NH_2$, —S(O)$_2NHR^o$, —S(O)$_2N(R^o)_2$, —NHS(O)$_2R^o$, —$NR^oS(O)_2R^o$, —C(O)$NH_2$, —C(O)$NHR^o$, —C(O)N($R^o$)$_2$, —C(O)$R^o$, —NHC(O)$R^o$, —$NR^oC(O)R^o$, —NHC(O)$NH_2$, —$NR^oC(O)NH_2$, —$NR^oC(O)NHR^o$, —NHC(O)$NHR^o$, —$NR^oC(O)N(R^o)_2$, —NHC(O)N($R^o$)$_2$, —$CO_2H$, —$CO_2R^o$, —$NHCO_2R^o$, —$NR^oCO_2R^o$, —CN, —$NO_2$, —$NH_2$, —$NHR^o$, —N($R^o$)$_2$, —$NR^oS(O)NH_2$ and —$NR^oS(O)_2NHR^o$, wherein $R^o$ is unsubstituted $C_{1-6}$ alkyl.

In another specific embodiment, in compounds having formula Ia and Ib, $R^1$ is independently selected from the group consisting of $C_{1-8}$ alkyl, $C_{1-8}$ haloalkyl, $C_{3-6}$ cycloalkyl, —$CO_2R^a$, —$X^1CO_2R^a$, —$X^1SO_2R^a$, —$X_1OR^a$, —$COR^a$, —$CONR^aR^b$, —$X^1NR^aR^b$, —$X^1NR^aCOR^b$, —$X^1CONR^aR^b$, $X^1S(O)_2NR^aR^b$ and $X^1S(O)_2R^a$, wherein $X^1$ is $C_{1-4}$ alkylene and each $R^a$ and $R^b$ is independently selected from the group consisting of hydrogen, $C_{1-8}$ alkyl, $C_{1-8}$ haloalkyl and $C_{3-6}$ cycloalkyl. The aliphatic portions of each of said $R^1$ substituents is optionally substituted with from one to three members selected from the group consisting of —OH, —$OR^m$, —OC(O)$NHR^m$, —OC(O)N($R^m$)$_2$, —SH, —$SR^m$, —S(O)$R^m$, —S(O)$_2R^m$, —$SO_2NH_2$, —S(O)$_2NHR^m$, —S(O)$_2N(R^m)_2$, —NHS(O)$_2R^m$, —$NR^mS(O)_2R^m$, —C(O)$NH_2$, —C(O)$NHR^m$, —C(O)N($R^m$)$_2$, —C(O)$R^m$, —NHC(O)$R^m$, —$NR^mC(O)R^m$, —NHC(O)$NH_2$, —$NR^mC(O)NH_2$, —$NR^mC(O)NHR^m$, —NHC(O)$NHR^m$, —$NR^mC(O)N(R^m)_2$, —NHC(O)N($R^m$)$_2$, —$CO_2H$, —$CO_2R^m$, —$NHCO_2R^m$, —$NR^mCO_2R^m$, —CN, —$NO_2$, —$NH_2$, —$NHR^m$, —N($R^m$)$_2$, —$NR^mS(O)NH_2$ and —$NR^mS(O)_2NHR^m$, wherein each $R^m$ is independently an unsubstituted $C_{1-6}$ alkyl. The substituents $R^{2a}$, $R^{2c}$ and $R^{2d}$ are each independently selected from the group consisting of hydrogen, halogen, cyano, heteroaryl, —$NO_2$, —$CO_2R^c$, —$CONR^cR^d$, —C(O)$R^c$, —S(O)$R^e$, —S(O)$_2R^e$, —$R^e$, —C(NOR$^c$)$R^d$, —C(NR$^c$V)=NV, —N(V)C($R^c$)=NV, —$X^2$C(NOR$^c$)$R^d$, —$X^2$C(NR$^c$V)=NV, —$X^2$N(V)C($R^c$)=NV, —$X^2NR^cR^d$, —$X^2 SR^c$, —$X^2$CN, —$X^2NO_2$, —$X^2CO_2R^c$, —$X^2CONR^cR^d$, —$X^2$C(O)$R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=$NH$, —$X^2NR^eC(NH_2)$=$NH$, —$X^2NH$—$C(NH_2)$=$NR^e$, —$X^2NH$—$C(NHR^e)$=$NH$, —$X^2S(O)R^e$, —$X^2S(O)_2R^e$, —$X^2NR^cS(O)_2R^e$, —$X^2S(O)_2NR^cR^d$, —$X^2N_3$, —$OR^c$, —$SR^c$, —$R^e$, —$NR^dC(O)R^c$, —$NR^dC(O)_2R^e$, —$S(O)_2R^e$, —$S(O)_2NR^cR^d$, —$X^2OR^c$, —O—$X^2OR^c$, —$X^2NR^cR^d$, —O—$X^2NR^cR^d$ and —$NR^d$—$X^2CO_2R^c$; in which within each of $R^{2a}$, $R^{2c}$ and $R^{2d}$, $X^2$ is $C_{1-4}$ alkylene and each $R^c$ and $R^d$ is independently selected from hydrogen, $C_{1-8}$ alkyl, $C_{1-8}$ haloalkyl, $C_{3-6}$ cycloalkyl, or optionally, $R^c$ and $R^d$ when attached to the same nitrogen atom can be combined with the nitrogen atom to form a five or six-membered ring having from 0 to 2 additional heteroatoms as ring members; and each $R^e$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl and heteroaryl, and each of $R^c$, $R^d$ and $R^e$ is optionally further substituted with from one to three members selected from the group consisting of —OH, —$OR''$, —OC(O)$NHR''$, —OC(O)N($R''$)$_2$, —SH, —$SR^{n1}$, —$S(O)R''$, —$S(O)_2R''$, —$SO_2NH_2$, —$S(O)_2NHR''$, —$S(O)_2N(R'')_2$, —$NHS(O)_2R''$, —$NR''S(O)_2R''$, —$C(O)NH_2$, —$C(O)NHR''$, —$C(O)N(R'')_2$, —$C(O)R''$, —$NHC(O)R''$, —$NR''C(O)R''$, —$NHC(O)NH_2$, —$NR''C(O)NH_2$, —$NR''C(O)NHR''$, —$NHC(O)NHR''$, —$NR''C(O)N(R'')_2$, —$NHC(O)N(R'')_2$, —$CO_2H$, —$CO_2R''$, —$NHCO_2R''$, —$NR''CO_2R''$, —CN, —$NO_2$, —$NH_2$, —$NHR''$, —$N(R'')_2$, —$NR''S(O)NH_2$ and —$NR''S(O)_2NHR''$. Each $R''$ is independently an unsubstituted $C_{1-6}$ alkyl; and wherein V is independently selected from the group consisting of —$R^c$, —CN, —$CO_2R^e$ and —$NO_2$. Each of ring vertices a, b, c and d in formulae Ia and Ib is independently selected from N and $C(R^{3a})$, and from one to two of said ring vertices is N. The substituent $R^{3a}$ is independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^f$, —$NR^f$—$C(O)NR^fR^g$, —NH—$C(NH_2)$=NH, —$NR^hC(NH_2)$=NH, —NH—$C(NH_2)$=$NR^h$, —NH—$C(NHR^h)$=NH, —$S(O)R^h$, —$S(O)_2R^h$, —$NR^fS(O)_2R^h$, —$S(O)_2NR^fR^g$, —$NR^fS(O)_2R^h$, —$NR^fS(O)_2NR^fR^g$, —$N_3$, —$X^3OR^f$, —$X^3OC(O)R^f$, —$X^3NR^fR^g$, —$X^3SR^f$, —$X^3CN$, —$X^3NO_2$, —$X^3CO_2R^f$, —$X^3CONR^fR^g$, —$X^3C(O)R^f$, —$X^3OC(O)NR^fR^g$, —$X^3NR^gC(O)R^f$, —$X^3NR^gC(O)_2R^f$, —$X^3NR^fC(O)NR^fR^g$, —$X^3NH$—$C(NH_2)$=NH, —$X^3NR^hC(NH_2)$=NH, —$X^3NH$—$C(NH_2)$=$NR^h$, —$X^3NH$—$C(NHR^h)$=NH, —$X^3S(O)R^h$, —$X^1S(O)_2R^h$, —$X^3NR^fS(O)_2R^h$, —$X^3S(O)_2 NR^fR^g$, —Y, —$X^3Y$ and —$X^3N_3$. The symbol Y is a five to ten-membered aryl, heteroaryl or heterocycloalkyl ring, optionally substituted with from one to three substitutents selected from the group consisting of halogen, —$OR^f$, $NR^fR^g$, —$R^h$, —$SR^f$, —CN, —$NO_2$, —$CO_2R^f$, —$CONR^fR^g$, —$C(O)R^f$, —$NR^gC(O)R^f$, —$S(O)R^h$, —$S(O)_2R^h$, —$NR^fS(O)_2R^h$, —$S(O)_2NR^fR^g$, —$X^3OR^f$, —$X^3NR^fR^g$, —$X^3NR^fS(O)_2R^h$ and —$X^3S(O)_2NR^fR^g$, and wherein each $X^3$ is independently selected from the group consisting of $C_{1-4}$ alkylene, $C_{2-4}$ alkenylene and $C_{2-4}$ alkynylene and each $R^f$ and $R^g$ is independently selected from hydrogen, $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, or when attached to the same nitrogen atom can be combined with the nitrogen atom to form a five or six-membered ring having from 0 to 2 additional heteroatoms as ring members, and each $R^h$ is independently selected from the group consisting of $C_{1-8}$ alkyl, $C_{1-8}$ haloalkyl, $C_{3-6}$ cycloalkyl, $C_{2-8}$ alkenyl, $C_{2-8}$ alkynyl, aryl, heteroaryl, aryl-$C_{1-4}$ alkyl, and aryloxy-$C_{1-4}$ alkyl, wherein the aliphatic portions of $X^3$, $R^f$, $R^g$ and $R^h$ are optionally further substituted with from one to three members selected from the group consisting of —OH, —$OR^o$, —OC(O)$NHR^o$, —OC(O)N($R^o$)$_2$, —SH, —$SR^o$, —$S(O)R^o$, —$S(O)_2R^o$, —$SO_2NH_2$, —$S(O)_2NHR^o$, —$S(O)_2N(R^o)_2$, —$NHS(O)_2R^o$, —$NR^oS(O)_2R^o$, —$C(O)NH_2$, —$C(O)NHR^o$, —$C(O)N(R^o)_2$, —$C(O)R^o$, —$NHC(O)R^o$, —$NR^oC(O)R^o$, —$NHC(O)NH_2$, —$NR^oC(O)NH_2$, —$NR^oC(O)NHR^o$, —$NHC(O)NHR^o$, —$NR^oC(O)N(R^o)_2$, —$NHC(O)N(R^o)_2$, —$CO_2H$, —$CO_2R^o$, —$NHCO_2R^o$, —$NR^oCO_2R^o$, —CN, —$NO_2$, —$NH_2$, —$NHR^o$, —$N(R^o)_2$, —$NR^oS(O)NH_2$ and —$NR^oS(O)_2NHR^o$, wherein $R^o$ is unsubstituted $C_{1-6}$ alkyl.

In another specific embodiment of the invention, in compounds having formula Ia or Ib, each $R^1$ is a substituent independently selected from the group consisting of $C_{1-8}$ alkyl, $C_{1-8}$ haloalkyl, $C_{3-6}$ cycloalkyl, —$CO_2R^a$, —$X^1CO_2R^a$, —$X^1SO_2R^a$ and —$X^1OR^a$, wherein the aliphatic portions of each of said $R^1$ substituents is optionally substituted with from one to three members selected from the group consisting of —OH, —$OR^m$, —OC(O)$NHR^m$, —OC(O)N($R^m$)$_2$, —SH, —$SR^m$, —$S(O)R^m$, —$S(O)_2R^m$, —$SO_2NH_2$, —$S(O)_2NHR^m$, —$S(O)_2N(R^m)_2$, —$NHS(O)_2R^m$, —$NR^mS(O)_2R^m$, —$C(O)NH_2$, —$C(O)NHR^m$, —$C(O)N(R^m)_2$, —$C(O)R^m$, —$NHC(O)R^m$, —$NR^mC(O)R^m$, —$NHC(O)NH_2$, —$NR^mC(O)NH_2$, —$NR^mC(O)NHR^m$, —$NHC(O)NHR^m$, —$NR^mC(O)N(R^m)_2$, —$NHC(O)N(R^m)_2$, —$CO_2H$, —$CO_2R^m$, —$NHCO_2R^m$, —$NR^mCO_2R^m$, —CN, —$NO_2$, —$NH_2$, —$NHR^m$, —$N(R^m)_2$, —$NR^mS(O)NH_2$ and —$NR^mS(O)_2NHR^m$, wherein each $R^m$ is independently an unsubstituted $C_{1-6}$ alkyl. The $R^{2a}$ substituent is selected from the group consisting of hydrogen, halogen, cyano, heteroaryl, —$NO_2$, —$CO_2R^c$, —$CONR^cR^d$, —$C(O)R^c$, —$S(O)R^e$, —$S(O)_2R^e$, —$R^e$, —$C(NOR^c)R^d$, —$C(NR^cV)$=NV, —N(V)$C(R^c)$=NV, —$X^2C(NOR^c)R^d$, —$X^2C(NR^cV)$=NV, —$X^2N(V)C(R^c)$=NV, —$X^2NR^cR^d$, —$X^2 SR^c$, —$X^2$ CN, —$X^2NO_2$, —$X^2CO_2R^c$, —$X^2CONR^cR^d$, —$X^2C(O)R^c$, —$X^2OC(O)NR^cR^d$, —$X^2NR^dC(O)R^c$, —$X^2NR^dC(O)_2R^e$, —$X^2NR^cC(O)NR^cR^d$, —$X^2NH$—$C(NH_2)$=NH, —$X^2NR^eC(NH_2)$=NH, —$X^2NH$—$C(NH_2)$=$NR^e$, —$X^2NH$—$C(NHR^e)$=NH, —$X^2S(O)R^e$, —$X^2S(O)_2R^e$, —$X^2NR^cS(O)_2R^e$, —$X^2S(O)_2NR^cR^d$ and —$X^2N_3$. The $R^{2c}$ and $R^{2d}$ substituents are each independently selected from the group consisting of halogen, —$OR^c$, —$SR^c$, —$R^e$, —CN, —$NO_2$, —$CO_2R^c$, —$C(O)R^c$, —$NR^dC(O)R^c$, —$NR^dC(O)_2R^e$, —$S(O)_2R^e$, —$S(O)_2NR^cR^d$, —$X^2OR^c$, —O—$X^2OR^c$, —$X^2NR^cR^d$, —O—$X^2NR^cR^d$ and —$NR^d$—$X^2CO_2R^c$. Each $R^{3a}$ substituent is independently selected from the group consisting of hydrogen, halogen, —$OR^f$, —$OC(O)R^f$, —$NR^fR^g$, —$SR^f$, —$R^h$, —CN, —$NO_2$, —$CO_2R^f$, —$CONR^fR^g$, —$C(O)R^f$, —$OC(O)NR^fR^g$, —$NR^gC(O)R^f$, —$NR^gC(O)_2R^h$, —$NR^f$—$C(O)NR^fR^g$, —$S(O)R^h$, —$S(O)_2R^h$, —$NR^fS(O)_2R^h$, —$S(O)_2NR^fR^g$, —$NR^fS(O)_2NR^fR^g$, —$X^3OR^f$, —$X^3NR^fR^g$, —$X^3SR^f$, —$X^3$ CN, —$C(C$=$NOR^f)NR^fR^g$, $X^3SO_2R^f$, —$X^3CO_2R^f$, —$X^3CONR^fR^g$, —$X^3C(O)R^f$, —$X^3NR^gC(O)R^f$, —$X^3NR^gC(O)_2R^h$, —Y, —$X^3Y$, —$X^3N_3$, wherein Y is selected from the group consisting of a five or six-membered aryl ring, a five or six-membered heteroaryl ring and three to eight membered heterocycloalkyl ring, wherein said Y group is optionally substituted with from one to three substitutents selected from the group consisting of halogen, —$OR^f$, —$NR^fR^g$, —$R^h$, —$SR^f$, —CN, —$NO_2$, —$CO_2R^f$, —$CONR^fR^g$, —$C(O)R^f$, —$S(O)R^h$, —$S(O)_2R^h$, —$NR^fS(O)_2R^h$ and —$S(O)_2NR^fR^g$, and wherein each $X^3$ is independently $C_{1-4}$ alkylene, and each $R^f$ and $R^g$ is independently selected from hydrogen, $C_{1-8}$ alkyl, $C_{1-8}$ haloalkyl and $C_{3-6}$ cycloalkyl, and each $R^h$ is independently selected from the group consisting of $C_{1-8}$ alkyl, $C_{1-8}$ haloalkyl and $C_{3-6}$ cycloalkyl, wherein the aliphatic portions of $X^3$, $R^f$, $R^g$ and $R^h$ is optionally further substituted with from one to three members selected from the group consisting of —OH, —OR°, —OC(O)NHR°, —OC(O)N(R°)$_2$, —SH, —SR°, —S(O)R°, —S(O)$_2$R°, —SO$_2$NH$_2$, —S(O)$_2$NHR°, —S(O)$_2$N(R°)$_2$, —NHS(O)$_2$R°, —NR°S(O)$_2$R°, —C(O)NH$_2$, —C(O)NHR°, —C(O)N(R°)$_2$, —C(O)R°, —NHC(O)R°, —NR°C(O)R°, —NHC(O)NH$_2$, —NR°C(O)NH$_2$, —NR°C(O)NHR°, —NHC(O)NHR°, —NR°C(O)N(R°)$_2$, —NHC(O)N(R°)$_2$, —CO$_2$H, —CO$_2$R°, —NHCO$_2$R°, —NR°CO$_2$R°, —CN, —NO$_2$, —NH$_2$, —NHR°, —N(R°)$_2$, —NR°S(O)NH$_2$ and —NR°S(O)$_2$NHR°, wherein each R° is independently an unsubstituted C$_{1-6}$ alkyl.

In another embodiment of the invention, the compounds of the invention having formula Ib is represented by formulae Ib$^1$ and Ib$^2$:

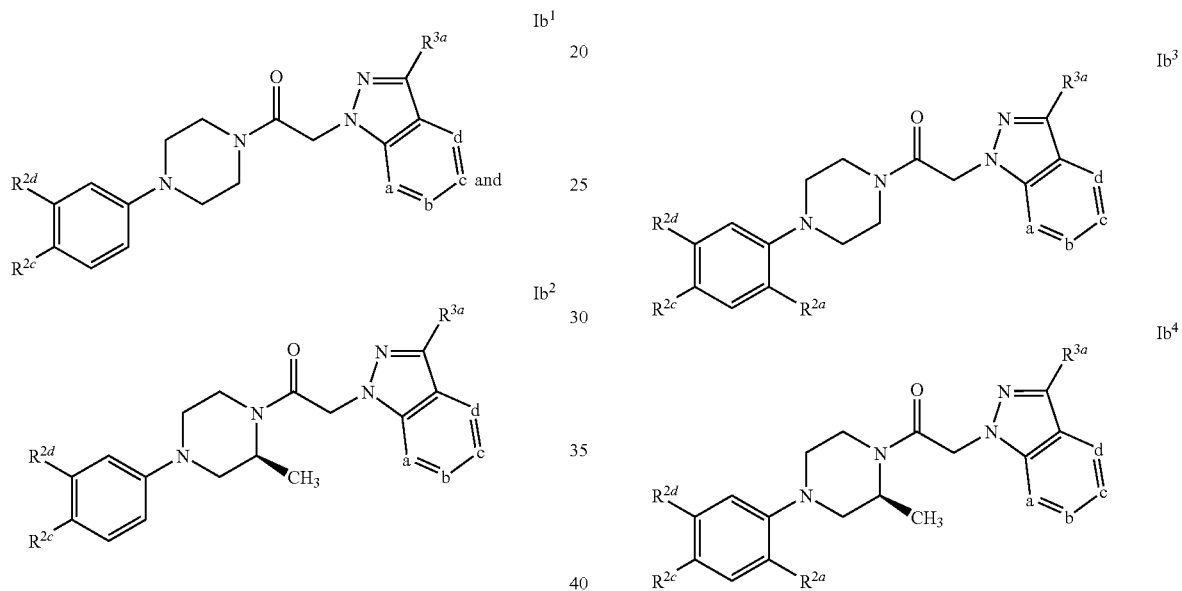

or a pharmaceutically acceptable salt, hydrate or N-oxide thereof. In one embodiment, in formulae Ib$^1$ and Ib$^2$, R$^{2c}$ is halogen, cyano or nitro; the symbol R$^{2d}$ is selected from —SR$^c$, —O—X$^2$—OR$^c$, —X$^2$—OR$^c$, —R$^e$, —OR$^c$ and —NR$^d$C(O)R$^c$; each of ring vertices a, b, c and d is independently selected from N and C(R$^{3a}$), and from one to two of said ring vertices is N; and each R$^{3a}$ is independently selected from the group consisting of hydrogen, halogen, C$_{1-6}$ alkyl, C$_{1-6}$ haloalkyl, C$_{3-6}$ cycloalkyl, C$_{3-6}$ heterocycloalkyl, —S(O)$_2$R$^h$, amino, phenyl, pyridyl, pyrimidinyl, oxazolyl, oxadiazolyl, isoxazolyl imiazolyl and thiazolyl. In one embodiment, the ring vertex a is N. In another embodiment, the ring vertex b is N. In another embodiment, the ring vertex c is N. In another embodiment, the ring vertex d is N. In yet another embodiment, the ring vertices a and c are each N; b is hydrogen; and d is C(R$^{3a}$), wherein R$^{3a}$ on ring vertex d is other than hydrogen. In another embodiment, the ring vertex a is N; b is C(R$^{3a}$) wherein R$^{3a}$ on ring vertex b is other than hydrogen; and c and d are each hydrogen. In another embodiment, the ring vertex a is N; b and c are each hydrogen; and d is C(R$^{3a}$), wherein R$^{3a}$ on ring vertex d is other than hydrogen. In another embodiment, the ring vertex a is C(R$^{3a}$), wherein R$^{3a}$ on ring vertex a is other than hydrogen; b is N; c and d are each hydrogen. In another embodiment, the ring vertex a is N; b and d are each hydrogen; and c is C(R$^{3a}$); wherein R$^{3a}$ on ring vertex c is other than hydrogen. In another embodiment, the ring vertices a and c are each N; b is hydrogen; and d is C(R$^{3a}$), wherein R$^{3a}$ on ring vertex d is other than hydrogen.

In yet another embodiment of the invention, in formulae Ib$^1$ and Ib$^2$, R$^{2c}$ and R$^{2d}$ are each a member independently selected from the group consisting of halogen, C$_{1-4}$ alkoxy, C$_{1-4}$ alkyl and C$_{1-4}$ haloalkyl; R$^{3a}$ on the pyrazole ring is an imidazolyl group optionally substituted with C$_{1-4}$ alkyl; and the ring vertex a is nitrogen and the ring vertices b, c, and d are each C(H). Within certain aspects of this embodiment, R$^{2c}$ is selected from the group consisting of fluoro, chloro, bromo and iodo; and R$^{2d}$ is selected from the group consisting of methoxy, ethoxy, trifluoromethoxy, methyl, ethyl, trifluoromethyl and 2-fluoroethoxy.

In yet another embodiment of the invention, the compounds of the invention having formula Ib is represented by formulae Ib$^3$ and Ib$^4$:

or a pharmaceutically acceptable salt, hydrate and an N-oxide thereof. In one embodiment, in formulae Ib$^3$ and Ib$^4$, R$^{2c}$ is independently halogen, cyano or nitro; R$^{2d}$ is selected from —SR$^c$, —O—X$^2$—OR$^c$, —X$^2$—OR$^c$, —R$^e$, —OR$^c$, —NR$^c$R$^d$, —NR$^c$S(O)$_2$R$^e$ and —NR$^d$C(O)R$^c$; R$^{2a}$ is selected from the group consisting of F, Cl, Br, I, —CO$_2$Me, —CONH$_2$, CN, oxazolyl, —CH$_2$NH$_2$, —CH$_2$NHMe, —CH$_2$NMe$_2$ and —CH═N—OH; each of ring vertices a, b, c and d is independently selected from N and C(R$^{3a}$), and from one to two of said ring vertices is N; and each R$^{3a}$ is independently selected from the group consisting of hydrogen, halogen, C$_{1-6}$ alkyl, C$_{1-6}$ haloalkyl, C$_{3-6}$ cycloalkyl, C$_{3-6}$ heterocycloalkyl, —S(O)$_2$R$^h$, amino, phenyl, pyridyl, pyrimidinyl, oxazolyl, oxadiazolyl, isoxazolyl and thiazolyl. In one embodiment the ring vertex a is N. In another embodiment the ring vertex b is N. In another embodiment the ring vertex c is N. In another embodiment the ring vertex d is N. In yet another embodiment, the ring vertices a and c are each N; b is hydrogen; and d is C(R$^{3a}$), wherein R$^{3a}$ on ring vertex d is other than hydrogen. In another embodiment, the ring vertex a is N; b is C(R$^{3a}$) wherein R$^{3a}$ on ring vertex b is other than hydrogen; and c and d are each hydrogen. In another embodiment, the ring vertex a is N; b and c are each hydrogen; and d is C(R$^{3a}$), wherein R$^{3a}$ on ring vertex d is other than hydrogen. In another embodiment, the ring vertex a is C(R$^{3a}$), wherein R$^{3a}$ on ring vertex a is other than hydrogen; b is N; c and d are each hydrogen. In another embodiment, the ring vertex a is N; b and d are each hydrogen; and c is $C(R^{3a})$; wherein $R^{3a}$ on ring vertex c is other than hydrogen. In another embodiment, the ring vertices a and c are each N; b is hydrogen; and d is $C(R^{3a})$, wherein $R^{3a}$ on ring vertex d is other than hydrogen.

In yet another embodiment of the invention, in formulae $Ib^3$ and $Ib^4$, $R^{2a}$, $R^{2c}$ and $R^{2d}$ are each a member independently selected from the group consisting of hydrogen, halogen, $C_{1-4}$ alkoxy, $C_{1-4}$ alkyl and $C_{1-4}$ haloalkyl; $R^{3a}$ on the pyrazole ring is an imidazolyl group optionally substituted with $C_{1-4}$ alkyl; and the ring vertex a is nitrogen and the ring vertices b, c, and d are each C(H). Within certain aspects of this embodiment, $R^{2a}$ and $R^{2c}$ in are each independently selected from the group consisting of fluoro, chloro, bromo and iodo; and $R^{2d}$ is selected from the group consisting of methoxy, ethoxy, trifluoromethoxy, methyl, ethyl, trifluoromethyl and 2-fluoroethoxy.

In yet another embodiment, the compounds of the invention having formula Ia is represented by formulae $Ia^1$ or $Ia^2$:

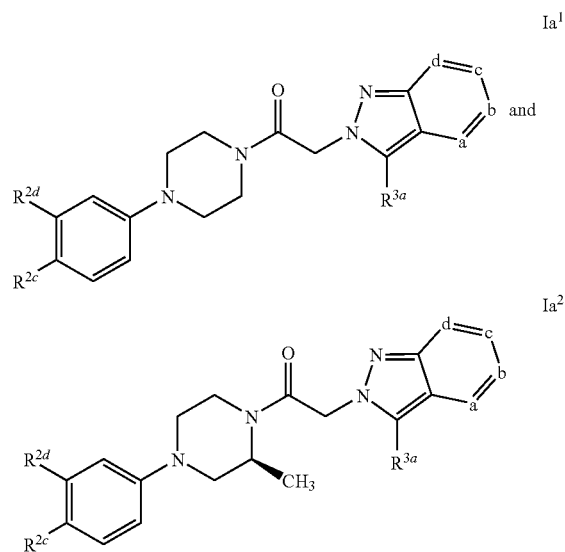

or a pharmaceutically acceptable salt, hydrate or N-oxide thereof; wherein the symbol $R^{2c}$ is halogen, cyano or nitro; the symbol $R^{2d}$ is selected from —$SR^c$, —O—$X^2$—$OR^c$, —$X^2$—$OR^c$, —$R^e$, —$OR^c$ and —$NR^dC(O)R^c$; each of ring vertices a, b, c and d is independently selected from N and $C(R^{3a})$, and from one to two of said ring vertices is N; and each $R^{3a}$ is independently selected from the group consisting of hydrogen, halogen, $C_{1-6}$ alkyl, $C_{1-6}$ haloalkyl, $C_{3-6}$ cycloalkyl, $C_{3-6}$ heterocycloalkyl, —$S(O)_2R^h$, amino, phenyl, pyridyl, pyrimidinyl, oxazoylyl, oxadiazolyl, isoxazolyl and thiazolyl. In one embodiment, the ring vertex d is N. In another embodiment the ring vertex b is N. In another embodiment the ring vertex c is N. In another embodiment the ring vertex d is N. In another embodiment, the ring vertex a is N; b and d are each hydrogen; and c is $C(R^{3a})$ wherein $R^{3a}$ is other than hydrogen. In another embodiment, the ring vertex a is $C(R^{3a})$, wherein $R^{3a}$ on ring vertex a is other than hydrogen; b is N; and c and d are each hydrogen. In another embodiment, the ring vertex a is N; b and c are each hydrogen; and d is $C(R^{3a})$ wherein $R^{3a}$ on ring vertex d is other than hydrogen. In another embodiment, the ring vertex a is $C(R^{3a})$, wherein $R^{3a}$ on ring vertex a is other than hydrogen; b and c are each hydrogen; and d is N. In another embodiment, the ring vertex a is $C(R^{3a})$, wherein $R^{3a}$ on ring vertex a is other than hydrogen; b and d are each N; and c is hydrogen. In another embodiment, the ring vertices a and b are each hydrogen; c is $C(R^{3a})$, wherein $R^{3a}$ on ring vertex c is other than hydrogen; and d is N.

In yet another embodiment, the compounds of the invention having formula Ia is represented by formula $Ia^3$ and $Ia^4$:

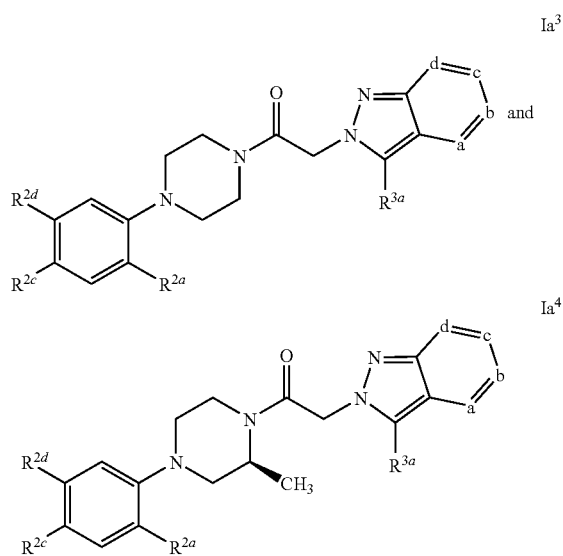

or pharmaceutically acceptable salt, hydrate or N-oxide thereof; wherein $R^{2c}$ is halogen, cyano or nitro; $R^{2d}$ is selected from —$SR^c$, —O—$X^2$—$OR^c$, —$X^2$—$OR^c$, —$R^e$, —$OR^c$ and —$NR^dC(O)R^c$; $R^{2a}$ is selected from the group consisting of F, Cl, Br, I, —$CO_2$Me, —$CONH_2$, CN, oxazolyl, —$CH_2NH_2$, —$CH_2NHMe$, and —$CH_2NMe_2$; each of ring vertices a, b, c and d is independently selected from N and $C(R^{3a})$, and from one to two of said ring vertices is N; and each $R^{3a}$ is independently selected from the group consisting of hydrogen, halogen, $C_{1-6}$ alkyl, $C_{1-6}$ haloalkyl, $C_{3-6}$ cycloalkyl, $C_{3-6}$ heterocycloalkyl, —$S(O)_2R^h$, amino, phenyl, pyridyl, pyrimidinyl, oxazolyl, oxadiazolyl, isoxazolyl and thiazolyl. In one embodiment, the ring vertex a is N. In another embodiment the ring vertex b is N. In another embodiment the ring vertex c is N. In another embodiment, the ring vertex d is N. In another embodiment, the ring vertex a is $C(R^{3a})$, wherein $R^{3a}$ on ring vertex a is other than hydrogen; b is N; and c and d are each hydrogen. In another embodiment, the ring vertex a is N; b and c are each hydrogen; and d is $C(R^{3a})$ wherein $R^{3a}$ on ring vertex d is other than hydrogen. In another embodiment, the ring vertex a is $C(R^{3a})$, wherein $R^{3a}$ on ring vertex a is other than hydrogen; b and c are each hydrogen; and d is N. In another embodiment, the ring vertex a is $C(R^{3a})$, wherein $R^{3a}$ on ring vertex a is other than hydrogen; b and d are each N; and c is hydrogen. In another embodiment, the ring vertices a and b are each hydrogen; c is $C(R^{3a})$, wherein $R^{3a}$ on ring vertex c is other than hydrogen; and d is N.

A family of specific compound of particular interest having formulae Ia and Ib consists of compounds, pharmaceutically acceptable salts, hydrates or N-oxides thereof, as set forth in Table 1.

TABLE 1

1. 1-[4-(4-Chloro-3-methoxy-phenyl)-piperazin-1-yl]-2-pyrazolo[4,3-b]pyridin-1-yl-ethanone
2. 1-[4-(4-Chloro-3-methoxy-phenyl)-piperazin-1-yl]-2-pyrazolo[4,3-b]pyridin-2-yl-ethanone
3. 1-[4-(4-Chloro-3-methoxy-phenyl)-piperazin-1-yl]-2-(3-chloro-pyrazolo[3,4-b]pyridin-2-yl)-ethanone
4. 1-[4-(4-Chloro-3-methoxy-phenyl)-piperazin-1-yl]-2-(pyrazolo[3,4-b]pyrazin-1-yl-7-oxide)-ethanone
5. 1-[4-(4-Chloro-3-methoxy-phenyl)-piperazin-1-yl]-2-(pyrazolo[3,4-b]pyrazin-1-yl-7-oxide)-ethanone
6. 1-[4-(4-Chloro-2-fluoro-5-methoxy-phenyl)-2-methyl-piperazin-1-yl]-2-pyrazolo[3,4-b]pyridin-1-yl-ethanone.
7. 1-[4-(4-Chloro-2-fluoro-5-methoxy-phenyl)-2-methyl-piperazin-1-yl]-2-pyrazolo[3,4-b]pyridin-2-yl-ethanone.
8. 2-(3-Amino-pyrazolo[3,4-b]pyridin-1-yl)-1-[4-(4-chloro-2-fluoro-5-methoxy-phenyl)-2-methyl-piperazin-1-yl]-ethanone.
9. 1-[4-(4-Chloro-3-methoxy-phenyl)-piperazin-1-yl]-2-(3-chloro-pyrazolo[3,4-b]pyridin-1-yl)-ethanone.
10. 1-[4-(4-Chloro-2-fluoro-5-methoxy-phenyl)-2-methyl-piperazin-1-yl]-2-(3-methyl-pyrazolo[3,4-b]pyridin-1-yl)-ethanone.
11. 1-[4-(4-Chloro-3-methoxy-phenyl)-piperazin-1-yl]-2-pyrazolo[3,4-b]pyridin-2-yl-ethanone.
12. 1-[4-(4-Chloro-3-methoxy-phenyl)-piperazin-1-yl]-2-pyrazolo[3,4-b]pyridin-1-yl-ethanone.
13. 1-[4-(4-Chloro-2-fluoro-5-methoxy-phenyl)-2-methylpiperazin-1-yl]-2-pyrazolo[4,3-c]pyridin-1-yl-ethanone.
14. 1-[4-(4-Chloro-2-fluoro-5-methoxy-phenyl)-2-methyl-piperazin-1-yl]-2-pyrazolo[3,4-c]pyridin-2-yl-ethanone.
15. 1-[4-(4-Chloro-3-methoxy-phenyl)-piperazin-1-yl]-2-(3-pyridin-2-yl-pyrazolo[3,4-b]pyridin-1-yl)-ethanone.
16. 1-[4-(4-Chloro-3-methoxy-phenyl)-piperazin-1-yl]-2-(3-thiazol-2-yl-pyrazolo[3,4-b]pyridin-1-yl)-ethanone.
17. 1-[4-(4-Chloro-2-fluoro-5-methoxy-phenyl)-piperazin-1-yl]-2-pyrazolo[3,4-b]pyridin-1-yl-ethanone.
18. 1-[4-(4-Chloro-2-fluoro-5-methoxy-phenyl)-piperazin-1-yl]-2-pyrazolo[3,4-b]pyridin-2-yl-ethanone.
19. 1-[4-(4-Chloro-3-methoxy-phenyl)-piperazin-1-yl]-2-(3-methyl-pyrazolo[3,4-b]pyridin-1-yl)-ethanone.
20. 1-[4-(4-Chloro-3-methoxy-phenyl)-piperazin-1-yl]-2-(3-oxazol-2-yl-pyrazolo[3,4-b]pyridin-1-yl)-ethanone.
21. 1-[4-(4-Chloro-3-methoxy-phenyl)-piperazin-1-yl]-2-(3-fluoro-pyrazolo[3,4-b]pyridin-1-yl)-ethanone.
22. 1-[4-(4-Chloro-2-fluoro-5-methoxy-phenyl)-2-methyl-piperazin-1-yl]-2-(3-oxazol-2-yl-pyrazolo[3,4-b]pyridin-1-yl)-ethanone
23. 1-[4-(4-Chloro-3-methoxy-phenyl)-piperazin-1-yl]-2-pyrazolo[3,4-c]pyridin-2-yl-ethanone
24. 1-[4-(4-Chloro-3-methoxy-phenyl)-piperazin-1-yl]-2-pyrazolo[3,4-c]pyridin-1-yl-ethanone
25. 1-[4-(4-Chloro-2-fluoro-5-methoxy-phenyl)-piperazin-1-yl]-2-pyrazolo[3,4-b]pyridin-1-yl-ethanone
26. 1-[4-(4-Chloro-2-fluoro-5-methoxy-phenyl)-2-methyl-piperazin-1-yl]-2-(3-thiazol-2-yl-pyrazolo[3,4-b]pyridin-1-yl)-ethanone
27. 1-[4-(4-Chloro-2-fluoro-5-methoxy-phenyl)-2-methyl-piperazin-1-yl]-2-(3-pyridin-2-yl-pyrazolo[3,4-b]pyridin-1-yl)-ethanone
28. 1-[4-(4-Chloro-3-methoxy-phenyl)-piperazin-1-yl]-2-(3-methyl-pyrazolo[3,4-b]pyridin-1-yl)-ethanone
29. 1-[4-(4-Chloro-2-fluoro-5-methoxy-phenyl)-2-methyl-piperazin-1-yl]-2-(3-methyl-pyrazolo[3,4-b]pyridin-1-yl)-ethanone
30. 1-[4-(4-Chloro-3-methoxy-phenyl)-piperazin-1-yl]-2-(3-thiazol-2-yl-pyrazolo[3,4-b]pyridin-1-yl)-ethanone
31. 1-{2-[4-(4-Chloro-3-methoxy-phenyl)-piperazin-1-yl]-2-oxo-ethyl}-1H-pyrazolo[3,4-b]pyridine-3-carbonitrile
32. 1-[4-(4-Chloro-3-methoxy-phenyl)-piperazin-1-yl]-2-(pyrazolo[3,4-b]pyridin-1-yl-2-oxide)-ethanone
33. 1-[4-(4-Chloro-3-methoxy-phenyl)-piperazin-1-yl]-2-(6-methyl-pyrazolo[3,4-b]pyridin-1-yl)-ethanone
34. 1-[4-(4-Chloro-3-methoxy-phenyl)-piperazin-1-yl]-2-(6-methyl-pyrazolo[3,4-b]pyridin-2-yl)-ethanone
35. 1-[4-(4-Chloro-3-methoxy-phenyl)-piperazin-1-yl]-2-(3-morpholin-4-yl-pyrazolo[3,4-b]pyridin-1-yl)-ethanone
36. 1-[4-(4-Chloro-2-fluoro-5-methoxy-phenyl)-2-methyl-piperazin-1-yl]-2-pyrazolo[3,4-c]pyridin-1-yl-ethanone
37. 1-[4-(4-Chloro-3-methoxy-phenyl)-piperazin-1-yl]-2-(pyrazolo[3,4-c]pyridin-1-yl-6-oxide)-ethanone
38. 1-[4-(4-Chloro-3-methoxy-phenyl)-piperazin-1-yl]-2-(4-chloro-pyrazolo[4,3-c]pyridin-2-yl)-ethanone
39. 1-[4-(4-Chloro-3-methoxy-phenyl)-piperazin-1-yl]-2-(4-iodo-pyrazolo[3,4-b]pyridin-2-yl)-ethanone
40. 1-[4-(4-Chloro-3-methoxy-phenyl)-piperazin-1-yl]-2-(4-iodo-pyrazolo[3,4-b]pyridin-1-yl)-ethanone TABLE 1-continued

| | |
|---|---|
| 41. | 1-[4-(4-Chloro-3-methoxy-phenyl)-piperazin-1-yl]-2-(4-methanesulfonyl-pyrazolo[3,4-b]pyridin-1-yl)-ethanone |
| 42. | 2-(3-Azidomethyl-pyrazolo[3,4-b]pyridin-1-yl)-1-[4-(4-chloro-3-methoxy-phenyl)-piperazin-1-yl]-ethanone |
| 43. | (1-{2-[4-(4-Chloro-3-methoxy-phenyl)-piperazin-1-yl]-2-oxo-ethyl}-1H-pyrazolo[3,4-b]pyridin-3-yl)-methanesulfonic acid |
| 44. | 1-[4-(4-Chloro-3-methoxy-phenyl)-piperazin-1-yl]-2-(5-chloro-pyrazolo[3,4-b]pyridin-1-yl)-ethanone |
| 45. | 1-[4-(4-Chloro-3-methoxy-phenyl)-piperazin-1-yl]-2-(4-chloro-pyrazolo[3,4-d]pyrimidin-2-yl)-ethanone |
| 46. | 1-[4-(4-Chloro-3-methoxy-phenyl)-piperazin-1-yl]-2-(4-chloro-pyrazolo[3,4-d]pyrimidin-1-yl)-ethanone |
| 47. | 1-[4-(4-Chloro-3-methoxy-phenyl)-piperazin-1-yl]-2-(4-methoxy-pyrazolo[3,4-d]pyrimidin-1-yl)-ethanone |
| 48. | 1-[4-(4-Chloro-3-methoxy-phenyl)-piperazin-1-yl]-2-(6-chloro-pyrazolo[3,4-b]pyridin-2-yl)-ethanone |
| 49. | 1-[4-(4-Chloro-3-methoxy-phenyl)-piperazin-1-yl]-2-(6-chloro-pyrazolo[3,4-b]pyridin-1-yl)-ethanone |
| 50. | 2-(6-Azido-pyrazolo[3,4-b]pyridin-1-yl)-1-[4-(4-chloro-3-methoxy-phenyl)-piperazin-1-yl]-ethanone |
| 51. | 2-(6-Amino-pyrazolo[3,4-b]pyridin-1-yl)-1-[4-(4-chloro-3-methoxy-phenyl)-piperazin-1-yl]-ethanone |
| 52. | 2-(7-Azido-pyrazolo[3,4-c]pyridin-1-yl)-1-[4-(4-chloro-3-methoxy-phenyl)-piperazin-1-yl]-ethanone |
| 53. | 2-(7-Amino-pyrazolo[3,4-c]pyridin-1-yl)-1-[4-(4-chloro-3-methoxy-phenyl)-piperazin-1-yl]-ethanone |
| 54. | 1-[4-(4-Chloro-3-methoxy-phenyl)-piperazin-1-yl]-2-(3-oxazol-2-yl-pyrazolo[3,4-b]pyridin-2-yl)-ethanone |
| 55. | 2-(5-Amino-3-methyl-pyrazolo[3,4-b]pyridin-1-yl)-1-[4-(4-chloro-3-methoxy-phenyl)-piperazin-1-yl]-ethanone |
| 56. | 1-[4-(4-Chloro-3-methoxy-phenyl)-piperazin-1-yl]-2-(3-methyl-5-nitro-pyrazolo[3,4-b]pyridin-1-yl)-ethanone |
| 57. | 2-(3-Amino-6-methyl-pyrazolo[3,4-b]pyridin-1-yl)-1-[4-(4-chloro-3-methoxy-phenyl)-piperazin-1-yl]-ethanone |
| 58. | 1-[4-(4-Chloro-2-fluoro-5-methoxy-phenyl)-2-methyl-piperazin-1-yl]-2-(3-[1,2,4]oxadiazol-3-yl-pyrazolo[3,4-b]pyridin-1-yl)-ethanone |
| 59. | 1-{2-[4-(4-Chloro-3-methoxy-phenyl)-piperazin-1-yl]-2-oxo-ethyl}-N-hydroxy-1H-pyrazolo[3,4-b]pyridine-3-carboxamidine |
| 60. | 1-[4-(4-Chloro-3-methoxy-phenyl)-piperazin-1-yl]-2-(3-[1,2,4]oxadiazol-3-yl-pyrazolo[3,4-b]pyridin-1-yl)-ethanone |
| 61. | 1-[4-(4-Chloro-3-methoxy-phenyl)-piperazin-1-yl]-2-[3-(5-methyl-[1,2,4]oxadiazol-3-yl)-pyrazolo[3,4-b]pyridin-1-yl]-ethanone |
| 62. | N-(1-{2-[4-(4-Chloro-3-methoxy-phenyl)-piperazin-1-yl]-2-oxo-ethyl}-1H-pyrazolo[3,4-b]pyridin-6-yl)-acetamide |
| 63. | 1-[4-(4-Chloro-3-methoxy-phenyl)-piperazin-1-yl]-2-(3-methanesulfonyl-pyrazolo[3,4-b]pyridin-1-yl)-ethanone |
| 64. | 2-(3-Aminomethyl-pyrazolo[3,4-b]pyridin-1-yl)-1-[4-(4-chloro-3-methoxy-phenyl)-piperazin-1-yl]-ethanone |
| 65. | 1-[4-(4-Chloro-3-methoxy-phenyl)-piperazin-1-yl]-2-(3-iodo-pyrazolo[3,4-b]pyridin-1-yl)-ethanone |
| 66. | 1-[4-(4-Chloro-2-fluoro-5-methoxy-phenyl)-2-methyl-piperazin-1-yl]-2-(3-iodo-pyrazolo[3,4-b]pyridin-1-yl)-ethanone |
| 67. | 1-[4-(4-Chloro-2-fluoro-5-methoxy-phenyl)-piperazin-1-yl]-2-(3-oxazol-2-yl-pyrazolo[3,4-b]pyridin-1-yl)-ethanone |
| 68. | 1-[4-(4-Chloro-3-methoxy-phenyl)-piperazin-1-yl]-2-[3-(1H-imidazol-2-yl)-pyrazolo[3,4-b]pyridin-1-yl]-ethanone |
| 69. | 1-[4-(4-Chloro-3-ethoxy-phenyl)-piperazin-1-yl]-2-[3-(1H-imidazol-2-yl)-pyrazolo[3,4-b]pyridin-1-yl]-ethanone |
| 70. | 1-{4-[4-Chloro-3-(2-fluoro-ethoxy)-phenyl+-piperazin-1-yl}-2-[3-(1H-imidazol-2-yl)-pyrazolo[3,4-b]pyridin-1-yl]-ethanone |
| 71. | 1-[4-(4-Chloro-3-methoxy-phenyl)-2-methybpiperazin-1-yl]-2-[3-(1H-imidazol-2-yl)-pyrazolo[3,4-b]pyridin-1-yl]-ethanone |
| 72. | 1-[4-(4-Chloro-3-methoxy-phenyl)-3-methylpiperazin-1-yl]-2-[3-(1H-imidazol-2-yl)-pyrazolo[3,4-b]pyridin-1-yl]-ethanone |
| 73. | 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone |
| 74. | 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone |
| 75. | 1-[4-(4-Chloro-2-fluoro-5-methoxy-phenyl)piperazin-1-yl]-2-[3-(1H-imidazol-2-yl)-pyrazolo[3,4-b]pyridin-1-yl]-ethanone |
| 76. | 1-{4-[4-Chloro-3-(2-fluoro-ethoxy)-phenyl]-2-methyl-piperazin-1-yl}-2-[3-(1H-imidazol-2-yl)-pyrazolo[3,4-b]pyridin-1-yl]-ethanone |
| 77. | 1-[4-(4-Chloro-3-methoxy-phenyl)-2-methylpiperazin-1-yl]-2-[3-(1H-imidazol-2-yl)-pyrazolo[3,4-b]pyridin-1-yl]-ethanone |
| 78. | 1-[4-(4-Chloro-5-ethoxy-2-fluoro-phenyl)-piperazin-1-yl]-2-[3-(1H-imidazol-2-yl)-pyrazolo[3,4-b]pyridin-1-yl]-ethanone |
| 79. | 1-[4-(4-Chloro-3-trifluoromethoxy-phenyl)-piperazin-1-yl]-2-[3-(1H-imidazol-2-yl)-pyrazolo[3,4-b]pyridin-1-yl]-ethanone |
| 80. | 1-[4-(4-Chloro-2-fluoro-5-methoxy-phenyl)-2-methyl-piperazin-1-yl]-2-[3-(1H-imidazol-2-yl)-pyrazolo[3,4b]pyridin-1-yl]-ethanone |

TABLE 1-continued

| | |
|---|---|
| 81. | 1-[4-(4-Chloro-3-ethoxy-phenyl)-2-methyl-piperazin-1-yl]-2-[3-(1H-imidazol-2-yl)-pyrazolo[3,4-b]pyridin-1-yl]-ethanone |
| 82. | 1-{4-[4-Chloro-2-fluoro-5-(2-fluoro-ethoxy)phenyl+-piperazin-1-yl}-2-[3-(1H-imidazol-2-yl)-pyrazolo[3,4-b]pyridin-1-yl]-ethanone |
| 83. | 1-[4-(4-Chloro-3-methoxy-phenyl)-3-methyl-piperazin-1-yl]-2-[3-(1H-imidazol-2-yl)-pyrazolo[3,4-b]pyridin-1-yl]-ethanone |
| 84. | 1-[4-(4-Chloro-3-methyl-phenyl)-piperazin-1-yl]-2-[3-(1H-imidazol-2-yl)-pyrazolo[3,4-b]pyridin-1-yl]-ethanone |
| 85. | 1-[4-(4-Chloro-2-fluoro-5-methoxy-phenyl)-2-methyl-piperazin-1-yl]-2-[3-(1H-imidazol-2-yl)-pyrazolo[3,4-b]pyridin-1-yl]-ethanone |
| 86. | 2-[4-Amino-3-(1H-imidazol-2-yl)-pyrazolo[3,4-d]pyrimidin-1-yl]-1-[4-(4-chloro-3-methoxy-phenyl)-piperazin-1-yl]-ethanone |
| 87. | 2-[5-Chloro-3-(1H-imidazol-2-yl)-indazol-1-yl]-1-[4-(4-chloro-3-methoxy-phenyl)-piperazin-1-yl]-ethanone |
| 88. | 2-[6-Chloro-3-(1H-imidazol-2-yl)-indazol-1-yl]-1-[4-(4-chloro-3-methoxy-phenyl)-piperazin-1-yl]-ethanone |

Another family of specific compounds of particular interest having formulae Ia and Ib consists of compounds, pharmaceutically acceptable salts, hydrates or N-oxides thereof as set forth in Table 2.

Preparation of Compounds

As provided in the examples below, the compounds and intermediates of the present invention can be prepared by one of skill in the art in a component assembly manner. Schemes 1A-1 M illustrate a variety of methods for the preparation of a variety of azaindazole-type derivatives. In each of these schemes, X is halogen; Nu is nucleophilic group; the symbol Ⓝ within an aryl ring indicate the replacement of one to two carbon(s) of said aryl ring vertex (vertices) with nitrogen atom(s); L is a ligand; and non-interfering substituents are provided as —R, —R', —R", and —R'".

Scheme 1A

Scheme 1A shows the synthesis of azaindazole derivatives from halo-pyridine-carbaldehyde or ketone.

Scheme 1B

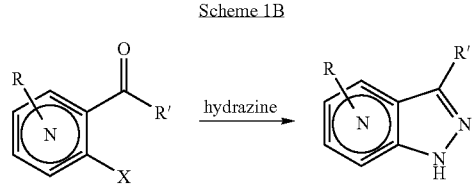

Scheme 1B shows the synthesis of azaindazole derivatives from halo-cyanopyridines.

Scheme 1C

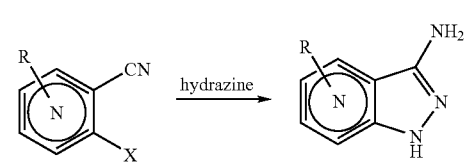

Scheme 1C shows the synthesis of azaindazole derivatives from amino-methyl-pyridine.

Scheme 1D

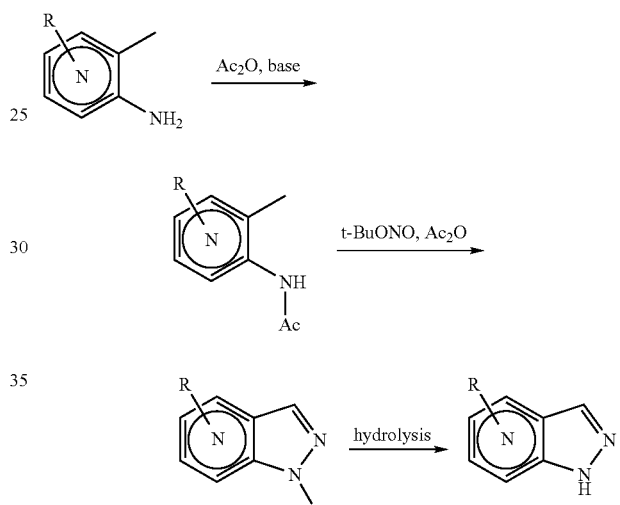

Scheme 1D shows the reaction of azaindazole derivatives with an α-haloacetate or α-haloacetamide.

Scheme 1E

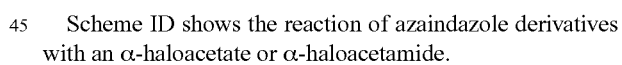

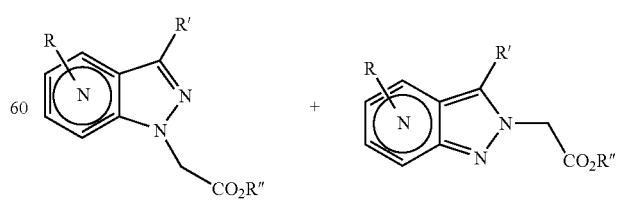

Scheme 1E shows the reaction of azaindazole derivatives with an electrophilic halogen source (X+).

Scheme 1F

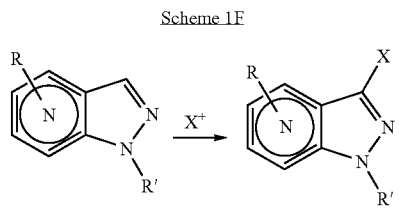

Scheme 1F shows a metal-assisted coupling reaction of a halo-azaindazole derivative.

Scheme 1G

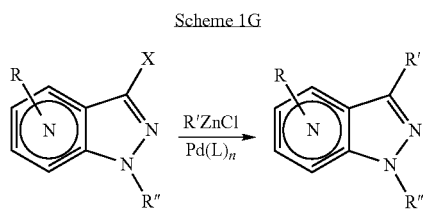

Scheme 1G shows a metal-assisted amination reaction of a halo-azaindazole derivative.

Scheme 1H

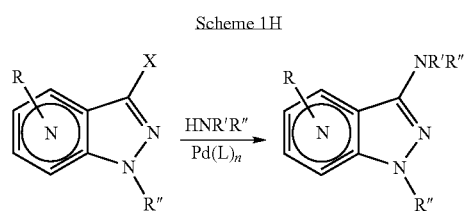

Scheme 1H shows the amination of an azaindazole derivative.

Scheme 1I

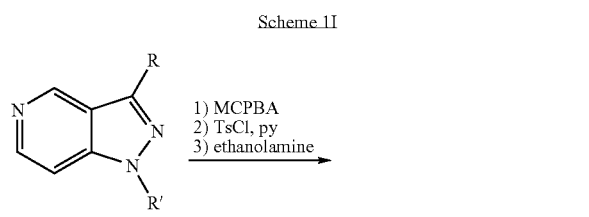

Scheme 1I shows the functionalization of an azaindazole derivative.

Scheme 1J

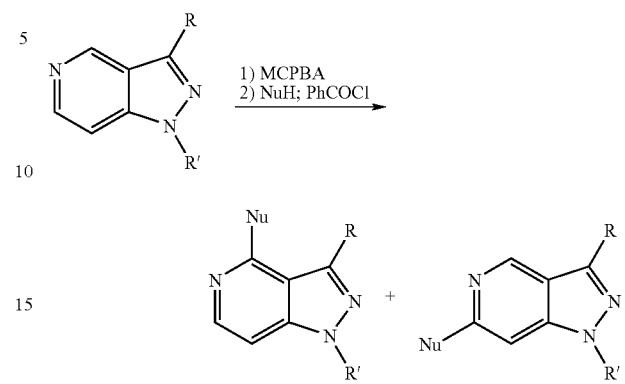

Scheme 1J shows the synthesis of a pyrazolopyrazine derivative.

Scheme 1K

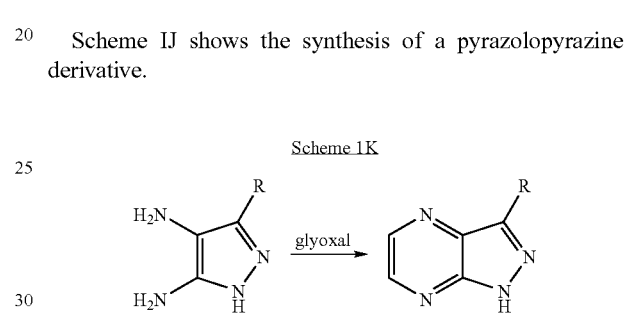

Scheme 1K shows the synthesis of a pyrazolopyrimidine derivative.

Scheme 1L

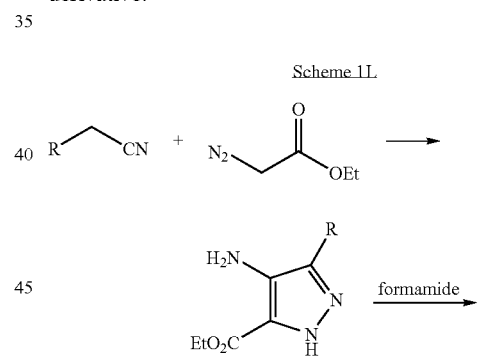

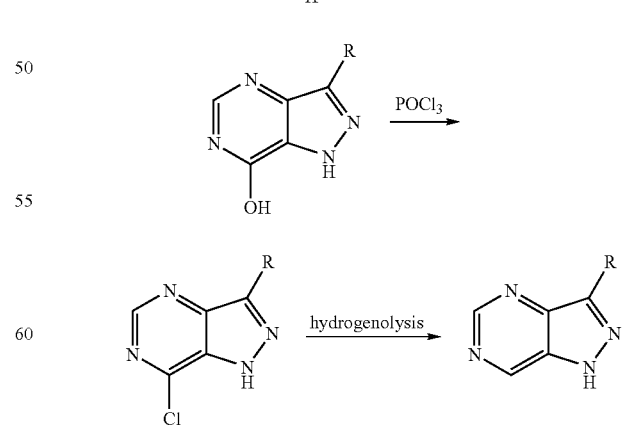

Scheme 1L shows the synthesis of a pyrazolopyrimidine derivative.

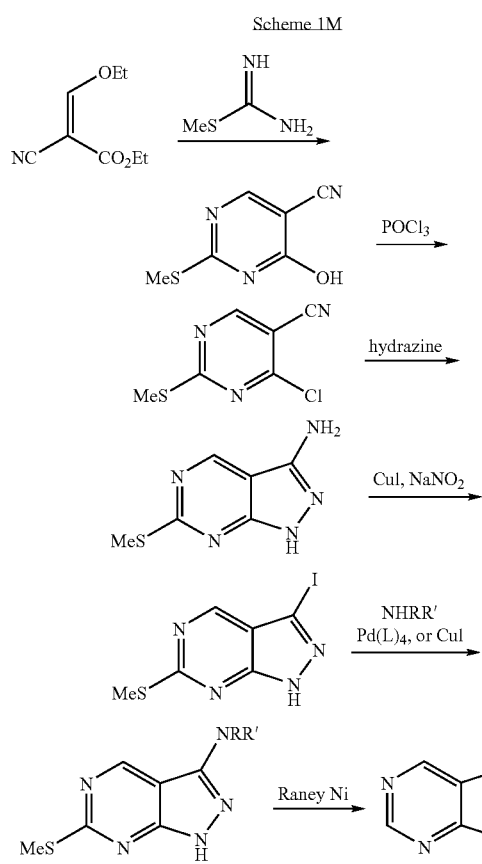

Scheme 1M shows the synthesis of N-oxide derivatives of the invention.

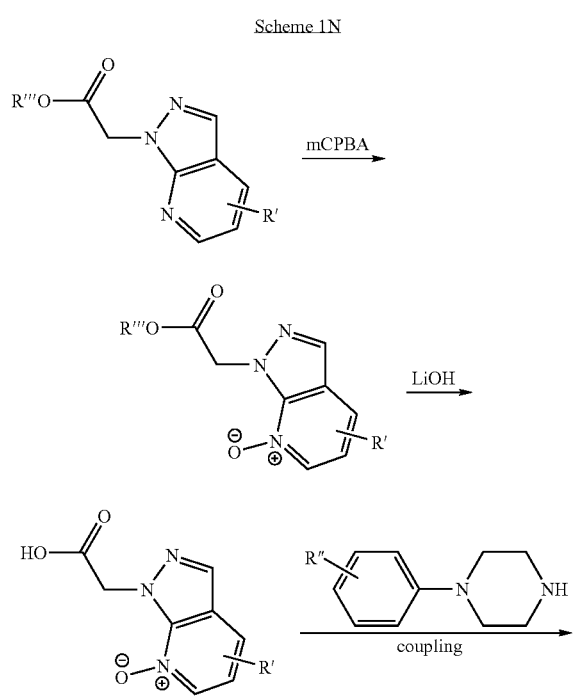

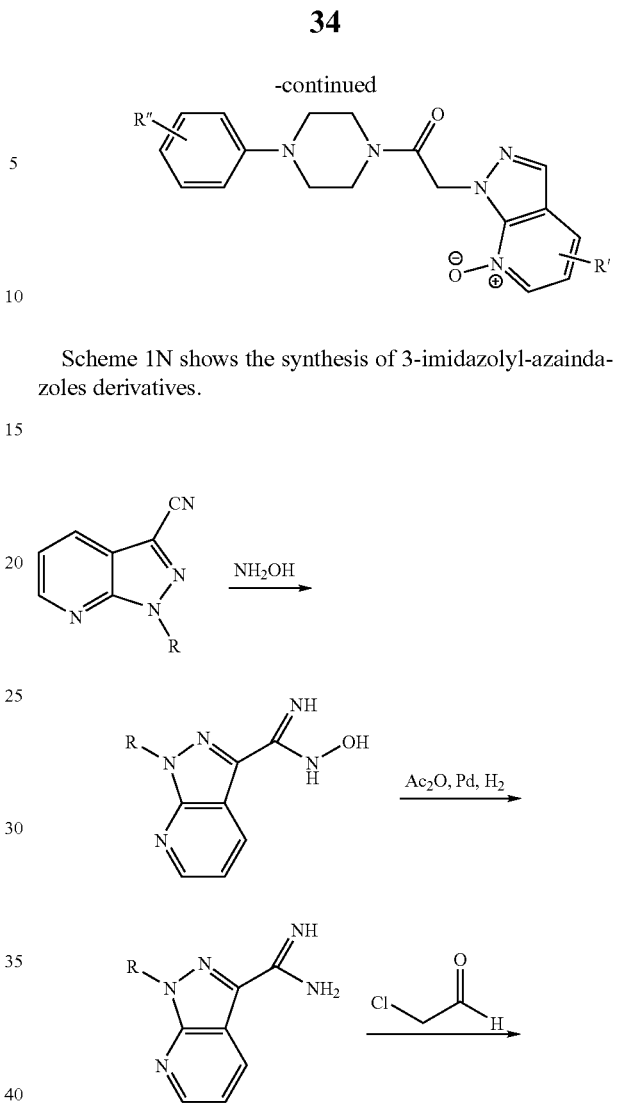

Scheme 1N shows the synthesis of 3-imidazolyl-azaindazoles derivatives.

Scheme 1N illustrates the synthesis of 3-imidazolyl substituted pyrazolo[3,4-b]pyridines wherein R represents a non-interfering substituent, such as, for example, a protecting group, a carboxy ester or the remainder of the compound of formula Ib. As shown in Scheme 1N, the reaction of $NH_2OH$ with 3-cyano pyrazolo[3,4-b]pyridine provides a hydroxylamidine compound, which upon reduction using hydrogen gas and a catalyst (e.g., Pd/C or $Pd(OH)_2$ produces an the amidine product. Cyclization of the amidine by treatment with chloroacetaldehyde will produce the imidazole product.

Scheme 1O

Scheme 1O shows the synthesis of 3-imidazolyl-azaindazoles derivatives.

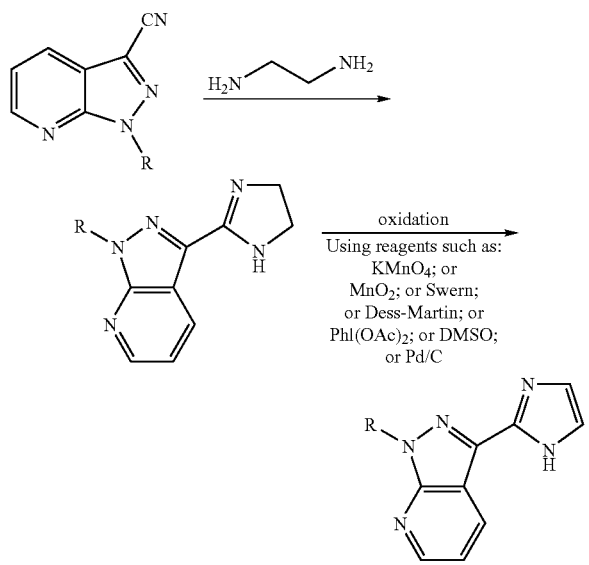

Scheme 1O illustrates the synthesis of 3-imidazolyl substituted pyrazolo[3,4-b]pyridines. R' represents a non-interfering substituent, such as, for example, a protecting group, a carboxy ester, or the remainder of the compound of formula Ib. As shown in Scheme 1O, the reaction of 3-cyano-pyrazolo[3,4-b]pyridine with ethylene diamine produces the cyclized imidazoline product, which upon oxidation produces the imidazole.

Scheme 1P

Scheme 1P shows the synthesis of 3-imidazolyl-azaindazoles derivatives. 3-imidazolyl-azaindazoles shown in Scheme 1P can be produced in kilogram scale using the outlined synthetic route.

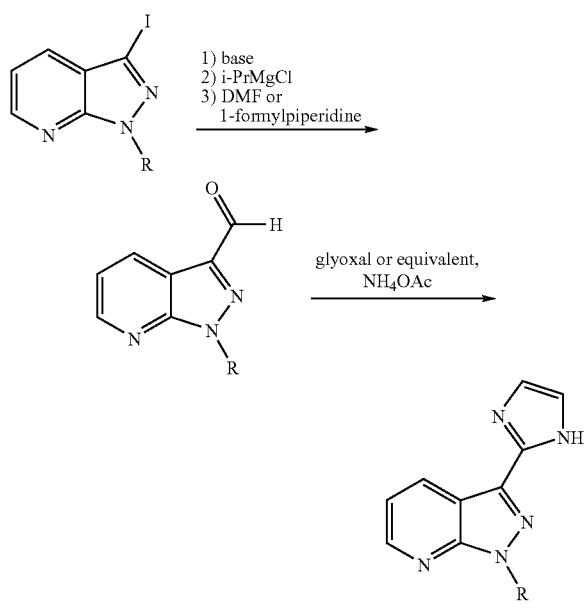

Scheme 1P illustrates the synthesis of 3-imidazolyl substituted pyrazolo[3,4-b]pyridines, wherein R' represents a non-interfering substituent, such as, for example, a protecting group, or a carboxy ester, or the remainder of the compound of formula I (see also the Examples). As shown in Scheme 1P, using a transmetallation process, a 3-iodo-pyrazolo[3,4-b]pyridine intermediate can be converted to a 3-formyl-pyrazolo[3,4-b]pyridine intermediate, which upon treatment with glyoxal, is cyclized to form 3-imidazolyl-pyrazolo[3,4]pyridine product.

IV. Pharmaceutical Compositions

In addition to the compounds provided above, compositions for modulating CCR1 activity in humans and animals will typically contain a pharmaceutical carrier or diluent.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. Nos. 4,733,655 (Palmaz), 4,800,882 (Gianturco), or 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars-Sanai Medical Center), U.S. Pat. Nos. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly (lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable popolymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1, the entire disclosure of which is incorporated in its entirety.

Moreover, as described for example in U.S. Pat. No. 6,770, 729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release a inhibitory agent in response to a decrease in the pH of the polymer composition. Alternatively, certain polymer compositions can be designed to release the inhibitory agent in response to the presence of hydrogen peroxide.

V. Methods of Treating Diseases Modulated by CCR1, CCR2 and/or CCR3

In yet another aspect, the present invention provides methods of treating CCR1, CCR2 and/or CCR3-mediated conditions or diseases by administering to a subject having such a disease or condition, a therapeutically effective amount of a compound of formula I above. The "subject" is defined herein to include animals such as mammals, including, but not limited to, primates (e.g., humans), cows, sheep, goats, horses, dogs, cats, rabbits, rats, mice and the like.

CCR1 provides a target for interfering with or promoting specific aspects of immune cell functions, or more generally, with functions associated with CCR1 expression on a wide range of cell types in a mammal, such as a human. Compounds that inhibit CCR1, are particularly useful for modulating monocyte, macrophage, lymphocyte, granulocyte, NK cell, mast cells, dendritic cell, neutrophils, and certain immune derived cell (for example, osteoclasts) function for therapeutic purposes. Accordingly, the present invention is directed to compounds which are useful in the prevention and/or treatment of a wide variety of inflammatory and immunoregulatory disorders and diseases (see Saeki, et al., *Current Pharmaceutical Design* 9:1201-1208 (2003)).

For example, an instant compound that inhibits one or more functions of CCR1 May be administered to inhibit (i.e., reduce or prevent) inflammation or cellular infiltration associated with an immune disorder. As a result, one or more inflammatory processes, such as leukocyte emigration or infiltration, chemotaxis, exocytosis (e.g., of enzymes, histamine) or inflammatory mediator release, can be inhibited. For example, monocyte infiltration to an inflammatory site (e.g., an affected joint in arthritis, or into the CNS in MS) can be inhibited according to the present method.

Similarly, an instant compound that promotes one or more functions of CCR1 is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, monocytes can be recruited to combat bacterial infections.

Diseases and conditions associated with inflammation, immune disorders and infection can be treated using the method of the present invention. In a preferred embodiment, the disease or condition is one in which the actions of immune cells such monocyte, macrophage, lymphocyte, granulocyte, NK cell, mast cell, dendritic cell, or certain immune derived cell (for example, osteoclasts) are to be inhibited or promoted, in order to modulate the inflammatory or autoimmune response.

In one group of embodiments, diseases or conditions, including chronic diseases, of humans or other species can treated with modulators of CCR1, CCR2 or CCR3 function. These diseases or conditions include: (1) allergic diseases such as systemic anaphylaxis or hypersensitivity responses, drug allergies, insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, hypersensitivity lung diseases and the like, (9) autoimmune diseases, such as fibromyalagia, scleroderma, ankylosing spondylitis, juvenile RA, Still's disease, polyarticular juvenile RA, pauciarticular juvenile RA, polymyalgia rheumatica, rheumatoid arthritis, psoriatic arthritis, osteoarthritis, polyarticular arthritis, multiple sclerosis, systemic lupus erythematosus, type I diabetes, type II diabetes, glomerulonephritis, and the like, (10) graft rejection (including allograft rejection and graft-v-host disease), and (11) other diseases in which undesired inflammatory responses or immune disorders are to be inhibited, such as cardiovascular disease including atherosclerosis and restenosis, myositis, neurodegenerative diseases (e.g., Alzheimer's disease), encephalitis, meningitis, hepatitis, nephritis, sepsis, sarcoidosis, allergic conjunctivitis, otitis, chronic obstructive pulmonary disease, sinusitis, Behcet's syndrome and gout and (12) immune mediated food allergies such as Celiac disease.

In another group of embodiments, diseases or conditions can be treated with modulators of CCR1 function. Examples of diseases to be treated with modulators of CCR1 function include cancers, cardiovascular diseases, diseases in which angiogenesis or neovascularization play a role (neoplastic diseases, retinopathy and macular degeneration), infectious diseases (viral infections, e.g., HIV infection, and bacterial infections) and immunosuppressive diseases such as organ transplant conditions and skin transplant conditions. The term "organ transplant conditions" is meant to include bone marrow transplant conditions and solid organ (e.g., kidney, liver, lung, heart, pancreas or combination thereof) transplant conditions.

The compounds of the present invention are accordingly useful in the prevention and treatment of a wide variety of inflammatory and immunoregulatory disorders and diseases.

Depending on the disease to be treated and the subject's condition, the compounds of the present invention may be administered by oral, parenteral (e.g., intramuscular, intraperitoneal, intravenous, ICV, intracisternal injection or infusion, subcutaneous injection, or implant), by implantation (e.g., as when the compound is coupled to a stent device), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

In the treatment or prevention of conditions which require chemokine receptor modulation an appropriate dosage level will generally be about 0.001 to 100 Mg per kg patient body weight per day which can be administered in single or multiple doses. Preferably, the dosage level will be about 0.01 to about 25 Mg/kg per day; more preferably about 0.05 to about 10 Mg/kg per day. A suitable dosage level may be about 0.01 to 25 mg/kg per day, about 0.05 to 10 Mg/kg per day, or about 0.1 to 5 Mg/kg per day. Within this range the dosage may be 0.005 to 0.05, 0.05 to 0.5 or 0.5 to 5.0 Mg/kg per day. For oral administration, the compositions are preferably provided in the form of tablets containing 1.0 to 1000 Milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, hereditary characteristics, general health, sex and diet of the subject, as well as the mode and time of administration, rate of excretion, drug combination, and the severity of the particular condition for the subject undergoing therapy.

Diseases and conditions associated with inflammation, immune disorder, infection and cancer can be treated or prevented with the present compounds, compositions, and methods.

The compounds and compositions of the present invention can be combined with other compounds and compositions having related utilities to prevent and treat the condition or disease of interest, such as inflammatory or autoimmune disorders, conditions and diseases, including inflammatory bowel disease, rheumatoid arthritis, osteoarthritis, psoriatic arthritis, polyarticular arthritis, multiple sclerosis, allergic diseases, psoriasis, atopic dermatitis and asthma, and those pathologies noted above.

For example, in the treatment or prevention of inflammation or autoimmunity or for example arthritis associated bone loss, the present compounds and compositions may be used in conjunction with an anti-inflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non steroidal anti-inflammatory agent, or a cytokine-suppressing anti-inflammatory agent, for example with a compound such as acetaminophen, aspirin, codeine, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds and compositions may be administered with an analgesic listed above; a potentiator such as caffeine, an H2 antagonist (e.g., ranitidine), simethicone, aluminum or magnesium hydroxide; a decongestant such as phenylephrine, phenylpropanolamine, pseudoephedrine, oxymetazoline, ephinephrine, naphazoline, xylometazoline, propylhexedrine, or levo desoxy ephedrine; an antitussive such as codeine, hydrocodone, caramiphen, carbetapentane, or dextromethorphan; a diuretic; and a sedating or non sedating antihistamine.

Likewise, compounds and compositions of the present invention may be used in combination with other drugs that are used in the treatment, prevention, suppression or amelioration of the diseases or conditions for which compounds and compositions of the present invention are useful. Such other drugs may be administered, by a route and in an amount commonly used therefor, contemporaneously or sequentially with a compound or composition of the present invention. When a compound or composition of the present invention is used contemporaneously with one or more other drugs, a pharmaceutical composition containing such other drugs in addition to the compound or composition of the present invention is preferred. Accordingly, the pharmaceutical compositions of the present invention include those that also contain one or more other active ingredients or therapeutic agents, in addition to a compound or composition of the present invention. Examples of other therapeutic agents that may be combined with a compound or composition of the present invention, either administered separately or in the same pharmaceutical compositions, include, but are not limited to: (a) VLA-4 antagonists, (b) corticosteroids, such as beclomethasone, methylprednisolone, betamethasone, prednisone, prednisolone, dexamethasone, fluticasone, hydrocortisone, budesonide, triamcinolone, salmeterol, salmeterol, salbutamol, formeterol; (c) immunosuppressants such as cyclosporine (cyclosporine A, Sandimmune®, Neoral®), tacrolirnus (FK-506, Prograf®), rapamycin (sirolimus, Rapamune®) and other FK-506 type immunosuppressants, and mycophenolate, e.g., mycophenolate mofetil (CellCept®); (d) antihistamines (H1-histamine antagonists) such as bromopheniramine, chlorpheniramine, dexchloipheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non steroidal anti asthmatics (e.g., terbutaline, metaproterenol, fenoterol, isoetharine, albuterol, bitolterol and pirbuterol), theophylline, cromolyn sodium, atropine, ipratropium bromide, leukotriene antagonists (e.g., zafmlukast, montelukast, pranlukast, iralukast, pobilukast and SKB-106,203), leukotriene biosynthesis inhibitors (zileuton, BAY-1005); (f) non steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone); (g) cyclooxygenase-2 (COX-2) inhibitors such as celecoxib (Celebrex®) and rofecoxib (Vioxx®); (h) inhibitors of phosphodiesterase type IV (PDE IV); (i) gold compounds such as auranofin and aurothioglucose, (j) etanercept (Enbrel®), (k) antibody therapies such as orthoclone (OKT3), daclizumab (Zenapax®), basiliximab (Simulect®) and infliximab (Remicade®), (l) other antagonists of the chemokine receptors, especially CCR5, CXCR2, CXCR3, CCR2, CCR3, CCR4, CCR7, $CX_3CR1$ and CXCR6; (m) lubricants or emollients such as petrolatum and lanolin, (n) keratolytic agents (e.g., tazarotene), (O) vitamin $D_3$ derivatives, e.g., calcipotriene or calcipotriol (Dovonex®), (p) PUVA, (q) anthralin (Drithrocreme®), (r) etretinate (Tegison®) and isotretinoin and (s) multiple sclerosis therapeutic agents such as interferon β-1β (Betaseron®), interferon (β-1α (Avonex®), azathioprine (Imurek®, Imuran®), glatiramer acetate (Capoxone®), a glucocorticoid (e.g., prednisolone) and cyclophosphamide (t) DMARDS such as methotrexate (u) other compounds such as 5-aminosalicylic acid and prodrugs thereof; hydroxychloroquine; D-penicillamine; antimetabolites such as azathioprine, 6-mercaptopurine and methotrexate; DNA synthesis inhibitors such as hydroxyurea and microtubule disrupters such as colchicine. The weight ratio of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

VI. EXAMPLES

The following examples are offered to illustrate, but not to limit the claimed invention.

Reagents and solvents used below can be obtained from commercial sources such as Aldrich Chemical Co. (Milwaukee, Wis., USA). $^1$H-NMR spectra were recorded on a Varian Mercury 400 MHz NMR spectrometer. Significant peaks are provided relative to TMS and are tabulated in the order: multiplicity (s, singlet; d, doublet; t, triplet; q, quartet; m, multiplet) and number of protons. Mass spectrometry results are reported as the ratio of mass over charge, followed by the relative abundance of each ion (in parenthesis). In the examples, a single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard MSD electrospray mass spectrometer using the HP1100 HPLC for sample delivery. Normally the analyte was dissolved in methanol at 0.1 Mg/mL and 1 Microlitre was infused with the delivery solvent into the mass spectrometer, which scanned from 100 to 1500 daltons. All compounds could be analyzed in the positive ESI mode, using acetonitrile/water with 1% formic acid as the delivery solvent. The compounds provided below could also be analyzed in the negative ESI mode, using 2 Mm NH$_4$OAc in acetonitrile/water as delivery system.

Compounds within the scope of this invention can be synthesized as described below, using a variety of reactions known to the skilled artisan. A sample of useful routes to the azaindazole derivatives and certain compounds of the invention are provided below or elsewhere within the present application. In the descriptions of the syntheses that follow, some of the arylpiperazine and heteroaromatic subunit precursors were obtained from commercial sources. These commercial sources include Aldrich Chemical Co., Acros Organics, Ryan Scientific Incorporated, Oakwood Products Incorporated, Lancaster Chemicals, Sigma Chemical Co., Lancaster Chemical Co., TCI-America, Alfa Aesar, Davos Chemicals, and GFS Chemicals. Certain relevant arylpiperazine compounds can be commercially obtained. Others could be prepared as described in U.S. patent application Ser. No. 11/008,774, the contents of which is hereby incorporated in its entirety for all purposes. Also, standard chemistries have been employed to link the arylpiperazine and heteroaromatic subunits (whether commercially obtained or prepared by the methods below) using a suitably optimized linker, such as the acetyl unit described in the body of this invention.

One skilled in the art will also recognize that alternative methods may be employed to synthesize the target compounds of this invention, and that the approaches described within the body of this document are not exhaustive, but do provide broadly applicable and practical routes to compounds of interest.

Certain molecules claimed in this patent can exist in different enantiomeric and diastereomeric forms and all such variants of these compounds are claimed.

Regioisomerism is a common property in organic chemistry, and is especially common with regards to certain structural types provided herein. Those skilled in the art will recognize, with respect to the compounds described herein, that the coupling reactions with the heteroaromatic ring systems can lead to either one of or a mixture of detectable regioisomers.

The detailed description of the experimental procedures used to synthesize key compounds in this text lead to molecules that are described by the physical data identifying them as well as by the structural depictions associated with them.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1

Synthesis of 1H-pyrazolo[3,4-b]pyridine

2-Chloro-3-formylpyridine (15.02 g, 106 Mmol, 1 equiv), hydrazine (10 mL, excess), and dioxane (90 mL) were combined in a sealed tube and heated at 150° C. for 16 hr. After cooling to room temperature, the solvent was evaporated in vacuo to provide a crude residue which was diluted with dichloromethane (600 mL). The organic solution was washed with water (50 mL), brine (50 mL) and dried over anhydrous sodium sulfate. The solvent was removed in vacuo to provide 1H-pyrazolo[3,4-b]pyridine as a yellow powder which was used without further purification: LCMS (ES) M+H 120.3, R$_f$ 0.20 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 2

Synthesis of 3-Thiazol-2-yl-1H-pyrazolo[3,4-b]pyridine

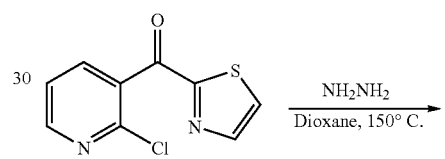

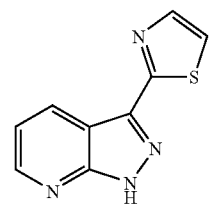

To a suspension of 2-chloro-3-[(2-thiazolyl)carbonyl]pyridine (257.5 Mg, 1.2 Mmol, 1 equiv) in dioxane (3 mL) in a sealed tube was added hydrazine (2 mL). The mixture was heated at 150° C. overnight, cooled to room temperature and concentrated in vacuo to provide a crude residue. The resultant residue was diluted with dichloromethane (300 mL), washed with water (50 mL) and brine (50 mL). The organic layer was separated, dried over sodium sulfate, filtered and concentrated in vacuo to provide 3-thiazol-2-yl-1H-pyrazolo[3,4-b]pyridine (212.3 Mg) as a yellow powder which used without further purification: LCMS (ES) M+H 203.5, R$_f$ 2.68 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 3

Synthesis of 1H-Pyrazolo[3,4-b]pyridin-3-ylamine

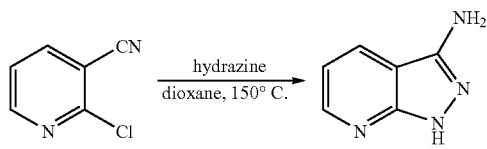

2-Chloro-3-cyanopyridine (2.77 g), hydrazine (5 mL), and dioxane (100 mL) were combined in a sealed tube and heated at 150° C. for 16 hr. The reaction mixture was cooled to room temperature and concentrated in vacuo to provide a crude residue. The resultant residue was dissolved in ethyl acetate (100 mL) and washed with saturated NaCl solution (50 mL). The organic layer was dried over sodium sulfate, filtered, and concentrated in vacuo to afford 1H-pyrazolo[3,4-b]pyridin-3-ylamine as a yellow solid which was used without further purification.

Example 4

Synthesis of 1H-pyrazolo[3,4-c]pyridine

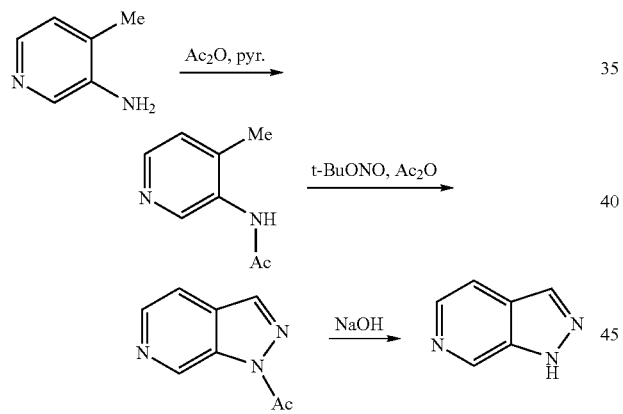

Preparation of 3-N-acetylamino-4-methylpyridine: To solution of 3-amino-4-methylpyridine (540.2 Mg, 5.0 Mmol, 1 equiv) in dichloromethane (20 mL) was added pyridine (0.8 mL, 10.0 Mmol, 2 equiv) and acetic anhydride (0.57 mL, 6.0 Mmol, 1.2 equiv). The resultant solution was stirred at room temperature for 16 h and concentrated in vacuo to provide a crude residue. The residue was diluted with dichloromethane (200 mL), and washed with saturated sodium bicarbonate aqueous solution (50 mL) and brine (50 mL). The organic layer was separated, dried over sodium sulfate, and concentrated in vacuo to yield 3-acetylamino-4-methylpyridine (400.2 Mg) as yellow solid which was used without further purification.

Preparation of 1-pyrazolo[3,4-c]pyridin-1-yl-ethanone: To a suspension of 3-acetylamino-4-methylpyridine (301.5 Mg, 2.0 Mmol, 1 equiv) in toluene (3 mL) was added tert-butyl nitrite (t-BuONO) (420 µL, 3.2 Mmol, 1.6 equiv), acetic anhydride (560 µL, 6.0 mmol, 3 equiv) and potassium acetate (235.2 Mg, 2.4 Mmol, 1.2 equiv). The resultant mixture was heated at 80° C. for 2 hours, cooled to room temperature, and diluted with ethyl acetate (200 mL). The mixture was washed with saturated sodium bicarbonate solution (50 mL), water (50 mL) and brine (50 mL). The organic layer was dried over sodium sulfate and concentrated in vacuo to provide a crude residue. The residue was purified by flash chromatography (silica, 15% ethyl acetate/hexane to 50% ethyl acetate/hexane) to give 1-pyrazolo[3,4-c]pyridin-1-yl-ethanone (20.2 Mg) which was used without further purification.

Synthesis of 1H-pyrazolo[3,4-c]pyridine: To a solution of 1-pyrazolo[3,4-c]pyridin-1-yl-ethanone (20.2 Mg, 0.17 Mmol, 1 equiv) in tetrahydrofuran (2 mL) and methanol (0.5 mL) was added sodium hydroxide aqueous solution (2 M, 0.25 mL). The reaction solution was stirred at room temperature for 1 hr and then concentrated in vacuo to provide a crude residue. The crude residue was diluted with water (20 mL) and extracted with dichloromethane (2×100 mL). The combined organic layers were washed with brine, dried over sodium sulfate, and concentrated in vacuo to provide 1H-pyrazolo[3,4-c]pyridine as white powder, which used without further purification: LCMS (ES) M+H 120.3, $R_f$ 0.22 min (Agilent Zorbax SB-$C_{18}$, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 5

Synthesis of 3-Iodo-1H-pyrazolo[3,4-b]pyridine

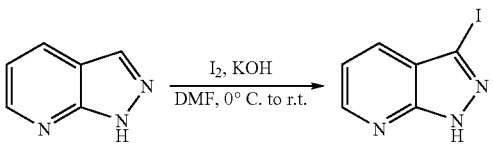

To a solution of 1H-pyrazolo[3,4-b]pyridine (500.0 Mg, 4.2 Mmol, 1 equiv) in DMF (10 mL) at 0° C., was added iodine (2.13 g, 8.4 Mmol, 2 equiv) and potassium hydroxide (943 mg, 16.8 Mmol, 4 equiv). The resultant mixture was allowed to warm to room temperature and stirred for 1 hour. The reaction solution was slowly quenched with saturated sodium thiosulfate ($Na_2S_2O_5$) solution (10 mL), and extracted with ethyl acetate (2×200 mL). The combined organic layers were washed with water (3×50 mL), brined (50 mL), dried over sodium sulfate and concentrated in vacuo to give 3-Iodo-1H-pyrazolo[3,4-b]pyridine (1.02 g) as a yellow powder which was used without further purification: LCMS (ES) M+H 246.2, $R_f$ 2.17 min (Agilent Zorbax SB-C18, 2.1× 50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 6

Synthesis of 1-[4-(4-Chloro-2-fluoro-5-methoxyphenyl)-2-(S)-methylpiperazin-1-yl]-2-pyrazolo[3,4-b]pyridine-1-ylethanone and 1-[4-(4-chloro-2-fluoro-5-methoxyphenyl)-2-(S)-methylpiperazin-1-yl]-2-pyrazolo[3,4-b]pyridine-2-ylethanone

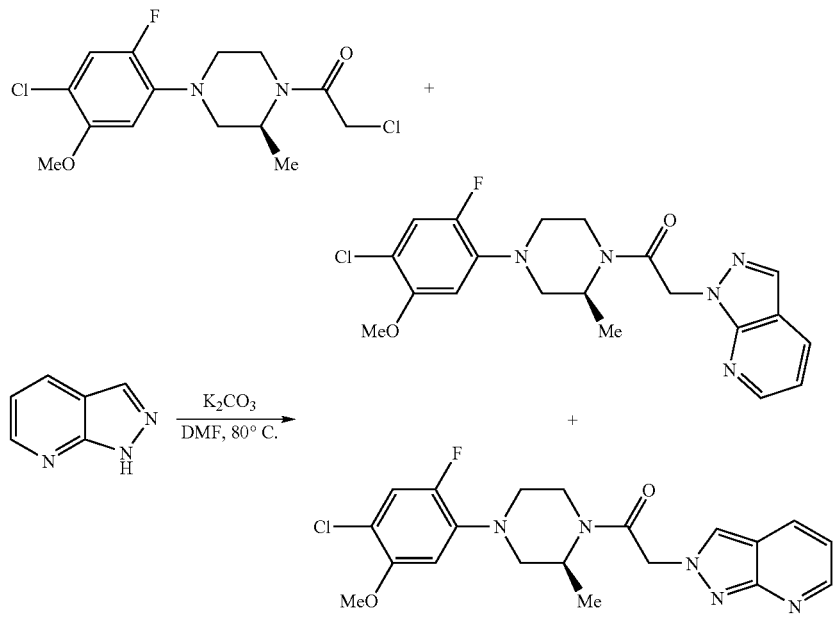

2-Chloro-1-[4-(4-chloro-2-fluoro-5-methoxyphenyl)-2-(S)-methylpiperazin-1-yl]ethanone (arylpiperazine) (4.81 g, 14.32 Mmol, 1 equiv), 1H-pyrazole[3,4-b]pyridine (2.27 g, 17.18 Mmol, 1.2 equiv), and potassium carbonate (20.00 g, 143.2 Mmol, 10 equiv) were dissolved in dimethylformamide (DMF) (10 mL) and heated at 80° C. for 1 hour, then cooled to room temperature. The resultant mixture was diluted with ethyl acetate (300 mL), and washed with water (3×150 mL) and brine (100 mL). The organic layer was dried ($Na_2SO_4$) and concentrated in vacuo to provide a crude residue. The crude residue was purified by flash chromatography (silica, 100% ethyl acetate with 1% triethylamine to 100% acetone with 1% triethylamine) provided 1-[4-(4-Chloro-2-fluoro-5-methoxyphenyl)-2-(S)-methylpiperazin-1-yl]-2-pyrazolo[3,4-b]pyridine-1-ylethanone (2.3 g) and 1-[4-(4-chloro-2-fluoro-5-methoxyphenyl)-2-(S)-methylpiperazin-1-yl]-2-pyrazolo[3,4-b]pyridine-2-ylethanone (2.5 g).

For 1-[4-(4-chloro-2-fluoro-5-methoxy-phenyl)-2-(S)-methyl-piperazin-1-yl]-2-pyrazolo[3,4-b]pyridine-1-yl-ethanone; LCMS (ES) M+H 418.5, $R_f$ 2.34 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile): For 1-[4-(4-chloro-2-fluoro-5-methoxyphenyl)-2-(S)-methylpiperazin-1-yl]-2-pyrazolo[3,4-b]pyridine-2-ylethanone; LCMS (ES) M+H 418.5, $R_f$ 2.00 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 7

Synthesis of 1-[4-(4-chloro-2-fluoro-5-methoxyphenyl)-2-(S)-methyl-piperazin-1-yl]-2-(3-oxazol-2-yl-pyrazolo[3,4-b]pyridin-1-yl)-ethanone

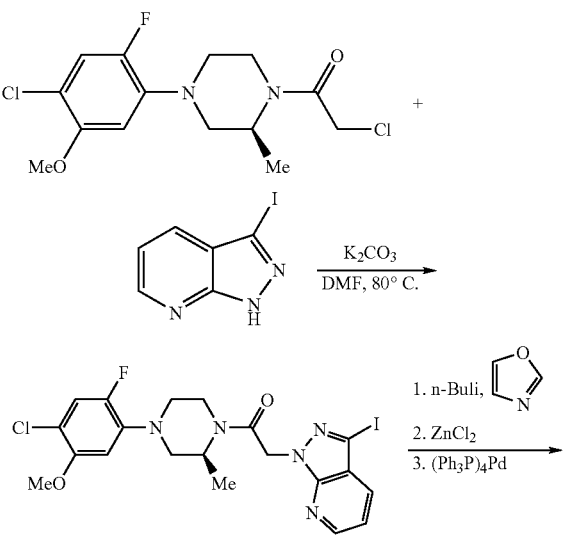

-continued

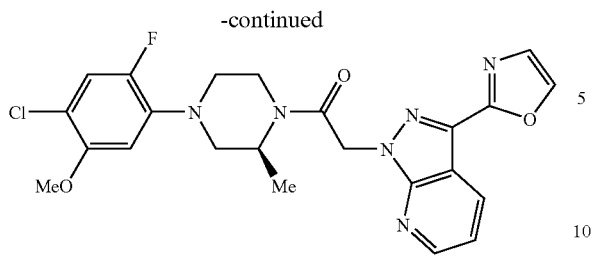

Preparation of 1-[4-(4-chloro-2-fluoro-5-methoxy-phenyl)-2-(S)-methyl-piperazin-1-yl]-2-(3-iodo-pyrazolo[3,4-b]pyridin-1-yl)-ethanone: This compound was synthesized according to the synthetic procedure outlined in Example 6.

Synthesis of 1-[4-(4-chloro-2-fluoro-5-methoxy-phenyl)-2-(S)-methyl-piperazin-1-yl]-2-(3-oxazol-2-yl-pyrazolo[3,4-b]pyridin-1-yl)-ethanone: To a solution of oxazole (40 µL, 0.54 Mmol, 3 equiv) in tetrahydrofuran (1 mL) under nitrogen atmosphere, was added dropwise n-butyl lithium (2.5 M in Hexane, 220 µL, 0.54 Mmol, 3 equiv.). The resultant mixture was stirred at −78° C. for an additional 30 min followed by the addition of ZnCl$_2$ (0.5 M in THF, 1.5 mL, 0.72 Mmol, 4 equiv.). The reaction solution was allowed to warm to 0° C. and stirred 1 hr followed by the addition of 1-[4-(4-chloro-2-fluoro-5-methoxy-phenyl)-2-(S)-methyl-piperazin-1-yl]-2-(3-iodo-pyrazolo[3,4-b]pyridin-1-yl)-ethanone (100.2 Mg, 0.18 Mmol, 1 equiv) and palladium tetrakis(triphenylphosphine) (22.3 Mg, 0.018, 0.1 equiv). The reaction mixture was then heated to reflux for 48 hr, cooled to room temperature and diluted with ethyl acetate (150 mL). The reaction mixture was washed with water (20 mL), brine (20 mL), dried over sodium sulfate, and concentrated in vacuo to provide the crude product. Purification by preparative HPLC provided the desired product 1-[4-(4-chloro-2-fluoro-5-methoxy-phenyl)-2-(S)-methyl-piperazin-1-yl]-2-(3-oxazol-2-yl-pyrazolo[3,4-b]pyridin-1-yl)-ethanone as a white powder (38.5 Mg): LCMS (ES) M+H 485.5, R$_f$ 2.56 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 8

Synthesis of 1-[4-(4-chloro-3-methoxyphenyl)piperazin-1-yl]-2-pyrazolo[3,4-b]pyridine-1-ylethanone and 1-[4-(4-chloro-3-methoxyphenyl)piperazin-1-yl]-2-pyrazolo[3,4-b]pyridine-2-ylethanone

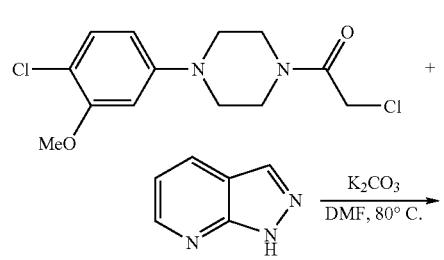

-continued

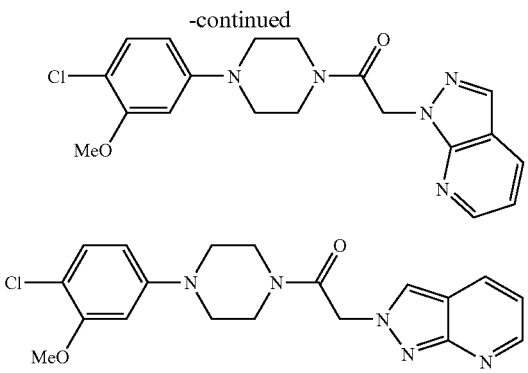

The two title compounds were synthesized according to the synthetic procedure as outlined in Example 6: For 1-[4-(4-Chloro-3-methoxyphenyl)piperazin-1-yl]-2-pyrazolo[3,4-b]pyridine-1-ylethanone; $^1$H NMR (400 MHz, CDCl$_3$) δ 8.57 (dd, 1H), 8.11 (s, 1H), 8.09 (dd, 1H), 7.22 (d, 1H), 7.17 (dd, 1H), 6.49 (d, 1H), 6.42 (dd, 1H), 5.44 (s, 2H), 3.92 (s, 3H), 3.79 (m, 4H), 3.18 (m, 4H); MS (M+H)$^+$: 386.5: For 1-[4-(4-Chloro-3-methoxyphenyl)piperazin-1-yl]-2-pyrazolo[3,4-b]pyridine-2-ylethanone; $^1$H NMR (400 MHz, CDCl$_3$) δ 8.65 (dd, 1H), 8.12 (s, 1H), 8.02 (dd, 1H), 7.20 (d, 1H), 7.03 (dd, 1H), 6.45 (d, 1H), 6.40 (dd, 1H), 5.35 (s, 2H), 3.88 (s, 3H), 3.87 (m, 2H), 3.79 (m, 2H), 3.15 (m, 4H); MS (M+H)$^+$: 386.5.

Example 9

Synthesis of 1H-Pyrazolo[4,3-c]pyridine

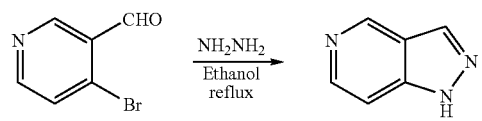

1H-Pyrazolo[4,3-c]pyridine was prepared according to the procedure outlined in Example 1.

Example 10

Synthesis of 1-[4-(4-chloro-2-fluoro-5-methoxyphenyl)-2-(S)-methylpiperazin-1-yl]-2-pyrazolo[4,3-c]pyridine-1-yl-ethanone and 1-[4-(4-chloro-2-fluoro-5-methoxyphenyl)-2-(S)-methylpiperazin-1-yl]-2-pyrazolo[4,3-c]pyridine-2-yl-ethanone

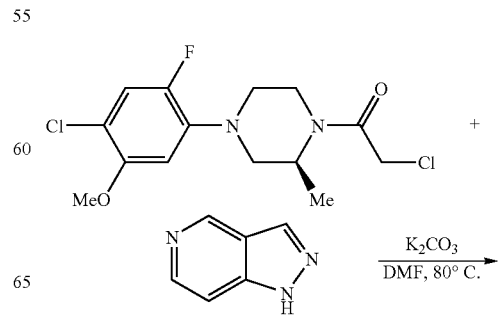

-continued

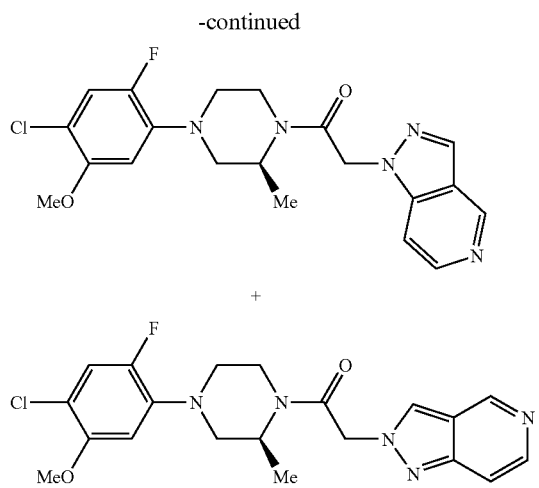

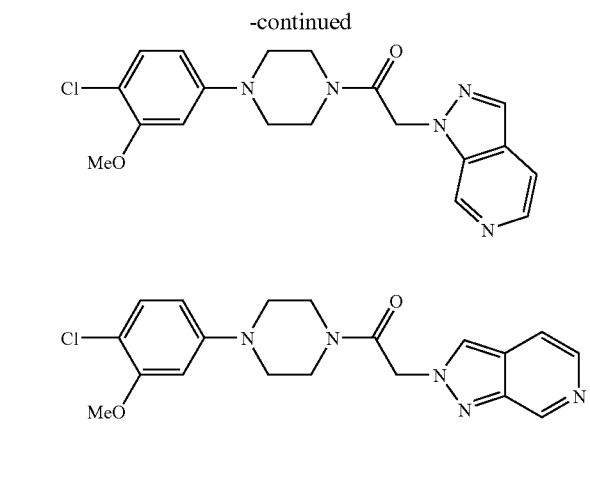

The two title compounds were synthesized according to the procedure as outlined in Example 6. For 1-[4-(4-Chloro-2-fluoro-5-methoxyphenyl)-2-(S)-methylpiperazin-1-yl]-2-pyrazolo[4,3-c]pyridine-1-yl-ethanone: LCMS (ES) M+H 418.5, $R_f$ 1.74 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile): For 1-[4-(4-Chloro-2-fluoro-5-methoxyphenyl)-2-(S)-methylpiperazin-1-yl]-2-pyrazolo[4,3-c]pyridine-2-yl-ethanone; LCMS (ES) M+H 418.5, $R_f$ 1.69 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

The two title compounds were synthesized according to the procedure outlined in Example 6: For 1-[4-(4-chloro-3-methoxy-phenyl)-piperazin-1-yl]-2-pyrazolo[3,4-c]pyridine-1-yl-ethanone; $^1$H NMR (400 MHz, CDCl$_3$) 9.02 (s, 1H), 8.34 (d, 1H), 8.09 (d, 1H), 7.63 (dd, 1H), 7.22 (d, 1H), 6.48 (d, 1H), 6.42 (dd, 1H), 5.38 (s, 2H), 3.88 (s, 3H), 3.79 (m, 4H), 3.14 (m, 4H) MS (M+H)$^+$, 386.5: For 1-[4-(4-chloro-3-methoxy-phenyl)-piperazin-1-yl]-2-pyrazolo[3,4-c]pyridine-2-yl-ethanone; $^1$H NMR (400 MHz, CDCl$_3$)) 9.22 (s, 1H), 8.13 (d, 1H), 8.10 (d, 1H), 7.50 (dd, 1H), 7.19 (d, 1H), 6.45 (d, 1H), 6.39 (dd, 1H), 5.37 (s, 2H), 3.85 (s, 3H), 3.76 (m, 4H), 3.14 (m, 4H). MS (M+H)$^+$, 386.5.

Example 11

Synthesis of 1-[4-(4-chloro-3-methoxy-phenyl)-piperazin-1-yl]-2-pyrazolo[3,4-c]pyridine-1-yl-ethanone and 1-[4-(4-chloro-3-methoxy-phenyl)-piperazin-1-yl]-2-pyrazolo[3,4-c]pyridine-2-yl-ethanone Example 12

Synthesis of 1-[4-(4-Chloro-2-fluoro-5-methoxy-phenyl)-piperazin-1-yl]-2-pyrazolo[3,4-b]pyridin-1-yl-ethanone and 1-[4-(4-Chloro-2-fluoro-5-methoxy-phenyl)-piperazin-1-yl]-2-pyrazolo[3,4-b]pyridin-2-yl-ethanone

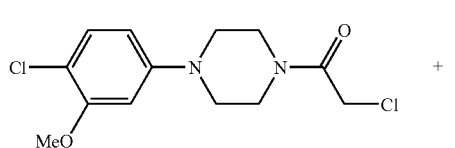

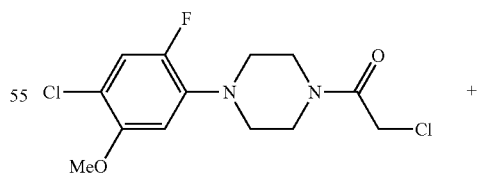

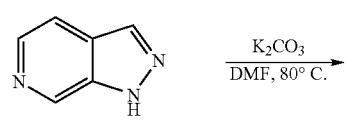
K$_2$CO$_3$ / DMF, 80° C. →

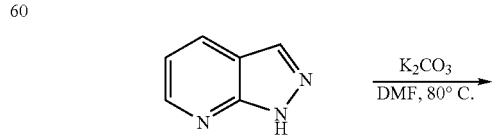
K$_2$CO$_3$ / DMF, 80° C. →

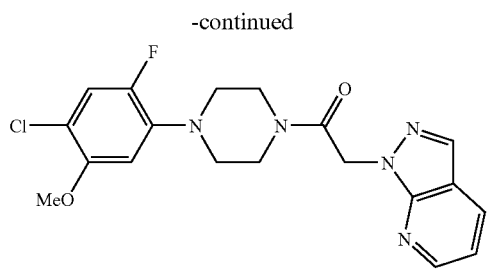

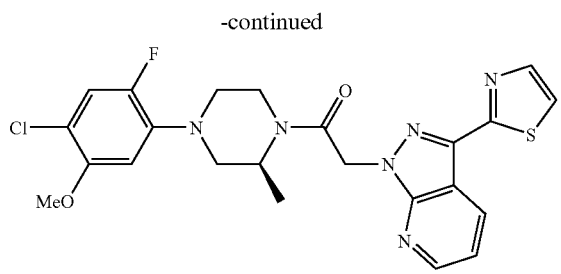

The title compound was synthesized according to the procedure outlined in Example 6: LCMS (ES) M+H 501.5, $R_f$ 2.82 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

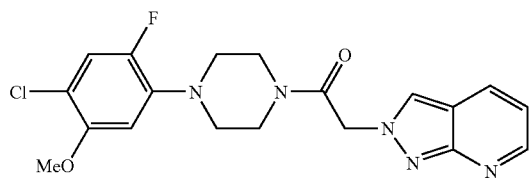

The two title compounds were synthesized according to the procedure outlined in Example 6. For 1-[4-(4-Chloro-2-fluoro-5-methoxy-phenyl)-piperazin-1-yl]-2-pyrazolo[3,4-b]pyridin-1-yl-ethanone: LCMS (ES) M+H, 404.5, $R_f$ 2.14 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile): For 1-[4-(4-Chloro-2-fluoro-5-methoxy-phenyl)-piperazin-1-yl]-2-pyrazolo[3,4-b]pyridin-2-yl-ethanone; LCMS (ES) M+H, 404.5, $R_f$ 1.76 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 14

Synthesis 3-pyrid-2-yl-1H-pyrazolo[3,4-b]pyridine

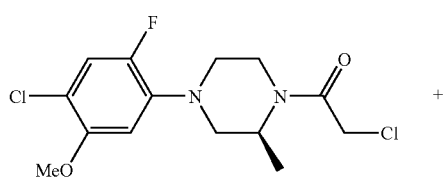

Example 13

Synthesis of 1-[4-(4-chloro-2-fluoro-5-methoxy-phenyl)-2-(S)-methyl-piperazin-1-yl]-2-(3-thiazol-2-yl-pyrazolo[3,4-b]pyridin-1-yl)-ethanone The title compound was synthesized according to the procedure outlined in Example 2.

Example 15

Synthesis of 1-[4-(4-Chloro-2-fluoro-5-methoxy-phenyl)-2-(S)-methyl-piperazin-1-yl]-2-(3-pyridin-2-yl-pyrazolo[3,4-b]pyridin-1-yl)-ethanone

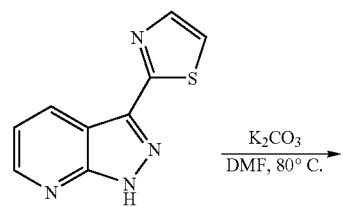

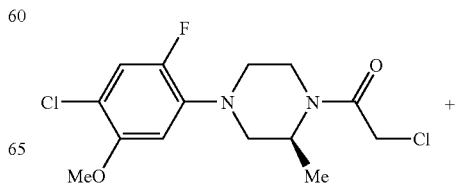

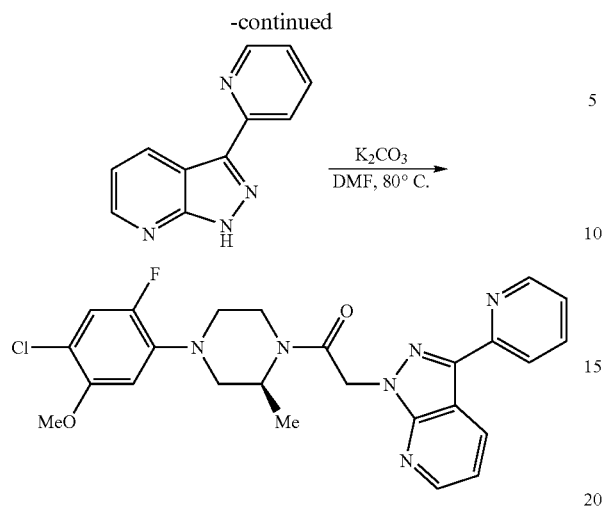

The title compound was synthesized according to the procedure outlined in Example 6: LCMS (ES) M+H 495.54, $R_f$ 2.73 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 16

Synthesis of 3-Chloro-1H-pyrazolo[3,4-b]pyridine

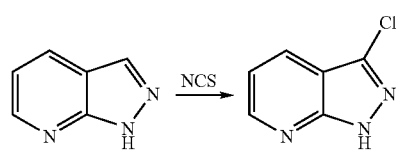

1H-pyrazolo[3,4-b]pyridine (89 Mg) and N-chlorosuccinimide (220 Mg) were combined in $CH_2Cl_2$ (4 mL) and heated at 45° C. for 16 hr, then cooled to room temperature. The resultant mixture was purified by flash chromatography (silica gel, 50% hexane/ethyl acetate) to afford 3-chloro-1H-pyrazolo[3,4-b]pyridine.

Example 17

Synthesis of 1-[4-(4-Chloro-3-methoxyphenyl)piperazin-1-yl]-2-(3-chloropyrazolo[3,4-b]pyridin-1-yl)ethanone

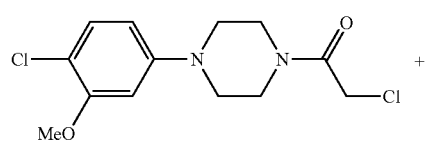

The title compound was synthesized according to the procedure outlined in Example 6: LCMS (ES) M+H 420.5, $R_f$ 2.37 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 18

Synthesis of 3-Methyl-1H-pyrazolo[3,4-b]pyridine

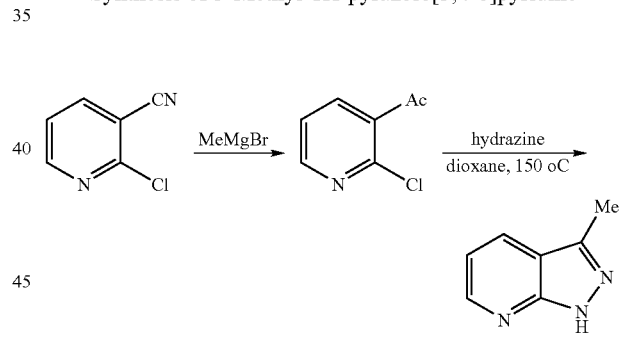

To a solution of 2-chloro-3-cyanopyridine (139 Mg) in tetrahydrofuran (5 mL) at 0° C. was added dropwise a solution of MeMgBr (3 M in ether, 0.67 mL). The resultant mixture was warmed to room temperature and stirred for 3 hr. The reaction solution was cooled to 0° C. and to it was added aqueous HCl solution (2 M, 5 mL). The reaction solution was then stirred an additional 16 hr at room temperature and then neutralized by the addition of saturated sodium bicarbonate ($NaHCO_3$) solution. The reaction solution was filtered to remove any precipitates and the filtrate was washed with ethyl acetate (3×10 mL) and aqueous brine (NaCl) solution (10 mL). The organic layer was dried over sodium sulfate ($Na_2SO_4$), filtered and concentrated in vacuo to give 3-acetyl-2-chloropyridine as a yellow powder which was used without further purification. The title compound (3-Methyl-1H-pyrazolo[3,4-b]pyridine) was synthesized from 3-acetyl-2-chloropyridine according to the procedure outlined in Example 2.

Example 19

Synthesis of 1-[4-(4-Chloro-3-methoxyphenyl)piperazin-1-yl]-2-(3-methylpyrazolo[3,4-b]pyridin-1-yl)ethanone

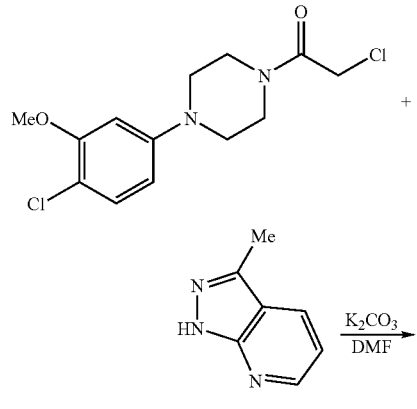

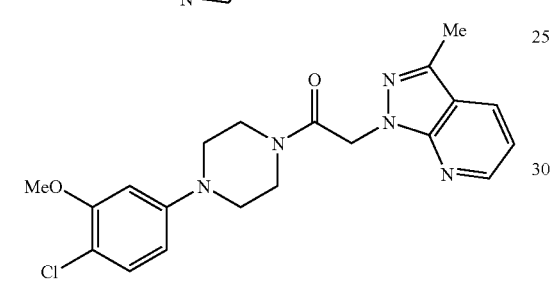

The title compound was synthesized according to the procedure outlined in Example 6: LCMS (ES) M+H 400.5, $R_f$ 2.12 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 20

Synthesis of 1-[4-(4-Chloro-2-fluoro-5-methoxyphenyl)-2-methylpiperazin-1-yl]-2-(3-methylpyrazolo[3,4-b]pyridin-1-yl)ethanone

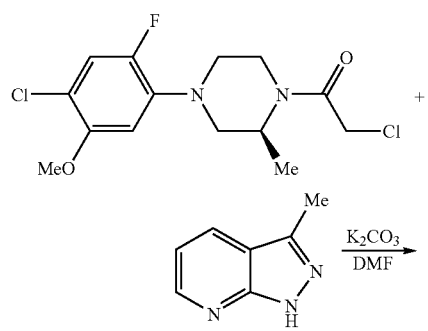

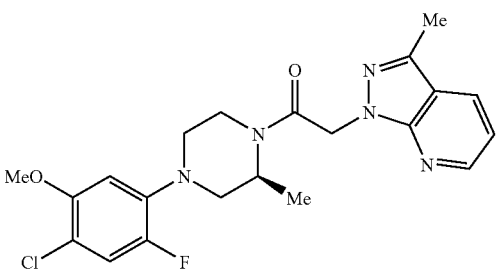

The title compound was synthesized according to the procedure outlined in Example 6: LCMS (ES) M+H 432.5, $R_f$ 2.42 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 21

Synthesis of 1-[4-(4-Chloro-3-methoxyphenyl)piperazin-1-yl]-2-(3-pyridin-2-yl-pyrazolo[3,4-b]pyridin-1-yl)ethanone

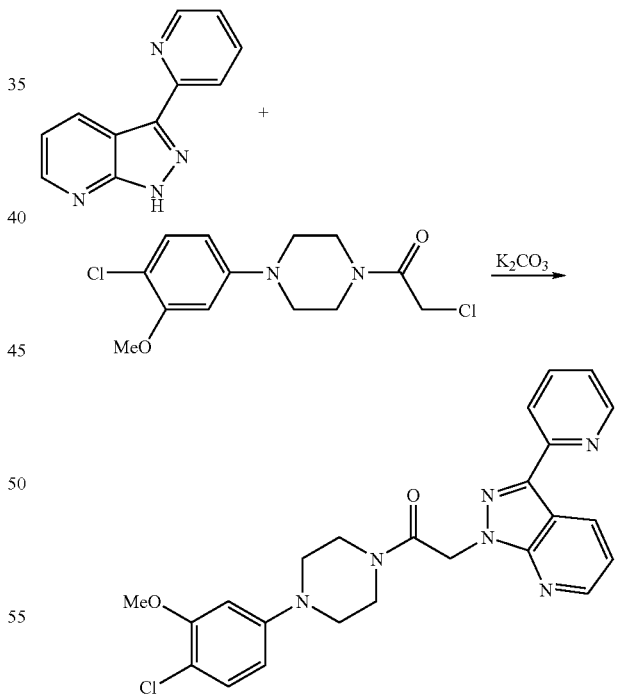

The title compound was synthesized according to the procedure outlined in Example 6: LCMS (ES) M+H 463.5, $R_f$ 2.32 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 22

Synthesis of 1-[4-(4-Chloro-3-methoxyphenyl)piperazin-1-yl]-2-(3-thiazol-2-yl-pyrazolo[3,4-b]pyridin-1-yl)ethanone

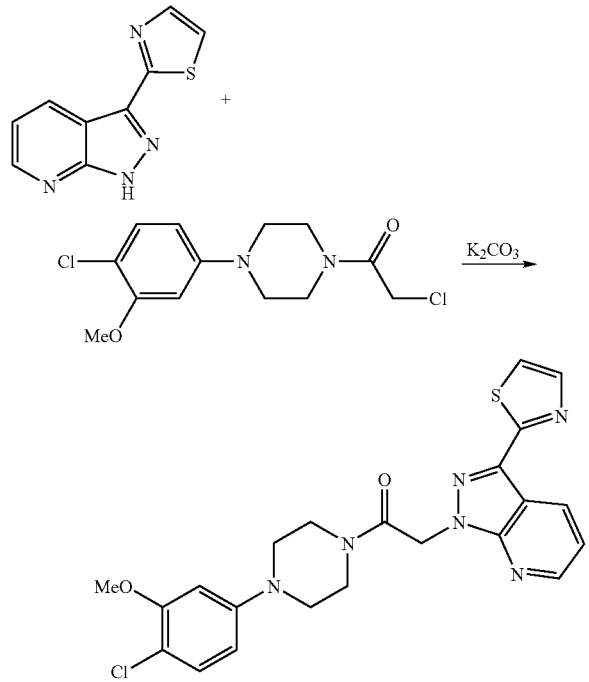

The title compound was synthesized according the procedure outlined in Example 6: LCMS (ES) M+H 469.5, $R_f$ 2.43 min (Agilent Zorbax SB-C18, 2.1 50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 23

Synthesis of 2-(3-Aminopyrazolo[3,4-b]pyridin-1-yl)-1-[4-(4-chloro-2-fluoro-5-methoxyphenyl)-2-methylpiperazin-1-yl]ethanone

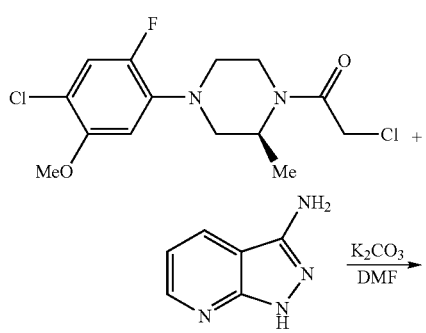

-continued

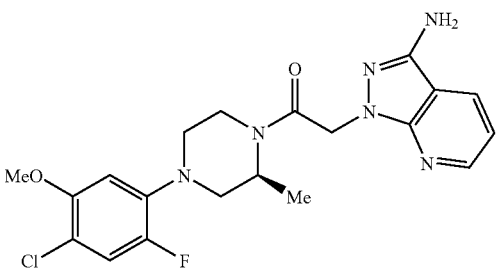

1H-Pyrazolo[3,4-b]pyridin-3-ylamine (67 Mg), 2-Chloro-1-[4-(4-chloro-2-fluoro-5-methoxy-phenyl)-2-methyl-piperazin-1-yl]-ethanone (167 Mg) and $K_2CO_3$ (414 Mg) were combined in DMF (1 mL) and heated at 80° C. for 2 hr, then cooled to room temperature. The resultant mixture was purified by preparative HPLC to provide 2-(3-Aminopyrazolo[3,4-b]pyridin-1-yl)-1-[4-(4-chloro-2-fluoro-5-methoxyphenyl)-2-methylpiperazin-1-yl]ethanone as a yellow powder. LCMS (ES) M+H 433.5, $R_f$ 2.06 min (Agilent Zorbax SB-C18, 2.1×50 mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 24

Synthesis of 1-[4-(4-Chloro-3-methoxy-phenyl)-piperazin-1-yl]-2-(3-oxazol-2-yl-pyrazolo[3,4-b]pyridin-1-yl)-ethanone

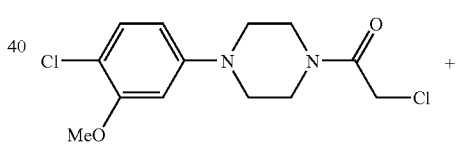

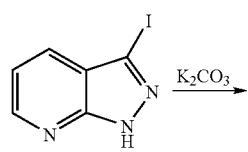

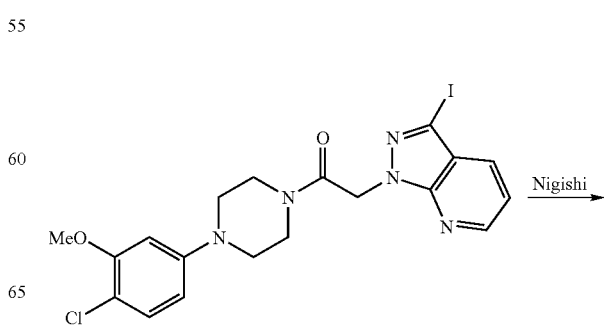

-continued

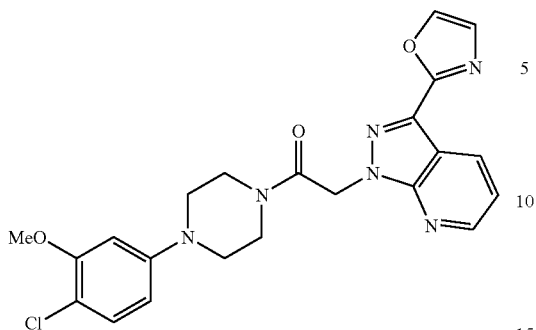

The title was synthesized according to the procedure outlined in Example 7: LCMS (ES) M+H 453.5, $R_f$ 2.20 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 25

Synthesis of 3-Fluoro-1H-pyrazolo[3,4-b]pyridine

The title was synthesized according to the procedure outlined in Example 5 using SelectFluor™ (1-Chloromethyl-4-fluoro-1,4-diazoniabicyclo[2.2.2]octane bis(tetrafluoroborate)) as the electrophile.

Example 26

Synthesis of 1-[4-(4-Chloro-3-methoxy-phenyl)-piperazin-1-yl]-2-(3-fluoro-pyrazolo[3,4-b]pyridin-1-yl)-ethanone

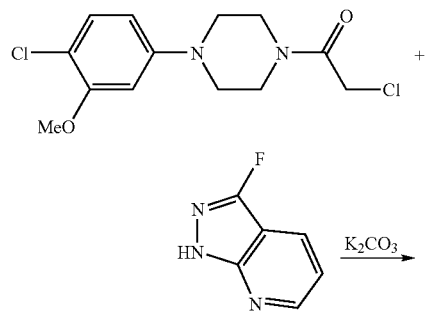

-continued

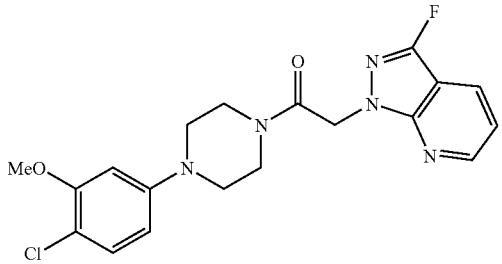

The title compound was synthesized according to the procedure outlined in Example 6: LCMS (ES) M+H 404.5, $R_f$ 2.27 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.08% formic acid/5% water/94.9% acetonitrile).

Example 27

Synthesis of 1-{2-[4-(4-Chloro-3-methoxy-phenyl)-piperazin-1-yl]-2-oxo-ethyl}1H-pyrazolo[3,4-b]pyridine-3-carbonitrile

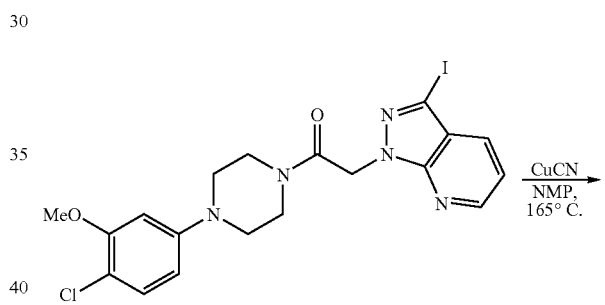

1-[4-(4-Chloro-3-methoxy-phenyl)-piperazin-1-yl]-2-(3-iodo-pyrazolo[3,4-b]pyridin-1-yl)-ethanone (128 Mg) and CuCN (112 Mg) were combined in N-methylpyridone (NMP) (1 mL) and heated at 165° C. for 16 hr, then cooled to room temperature. The reaction mixture was purified on preparative HPLC to afford 1-{2-[4-(4-Chloro-3-methoxy-phenyl)-piperazin-1-yl]-2-oxo-ethyl}-1H-pyrazolo[3,4-b]pyridine-3-carbonitrile as a white powder: LCMS (ES) M+H411.5, $R_f$ 2.33 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 28

Synthesis of 1H-pyrazolo[4,3-b]pyridine

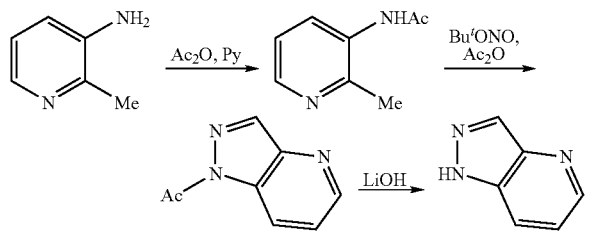

1H-pyrazolo[4,3-b]pyridine was synthesized according to the procedure outlined in Example 4 LCMS (ES) M+H 120.3.

Example 29

Synthesis of 1-[4-(4-chloro-3-methoxy-phenyl)piperazin-1-yl]-2-pyrazolo[4,3-b]pyridine-1-yl-ethanone and 1-[4-(4-chloro-3-methoxy-phenyl)piperazin-1-yl]-2-pyrazolo[4,3-b]pyridine-2-yl-ethanone

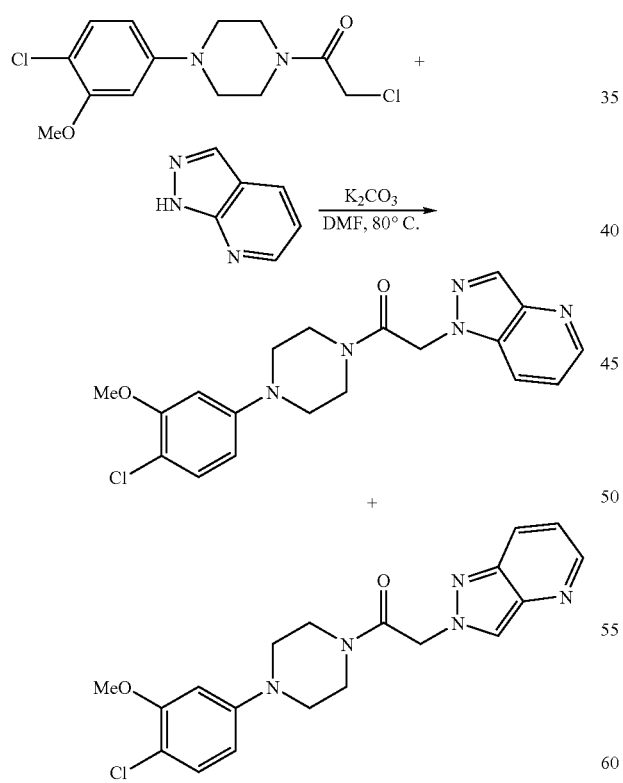

The two title compounds were synthesized according to the procedure outlined in Example 6: For 1-[4-(4-chloro-3-methoxy-phenyl)piperazin-1-yl]-2-pyrazolo[4,3-b]pyridine-1-yl-ethanone; $^1$H NMR (400 MHz, DMSO-$d_6$) δ 8.71 (dd, 1H), 8.26 (s, 1H), 8.04 (dd, 1H), 7.36 (dd, 1H), 7.20 (d, 1H), 6.69 (d, 1H), 6.51 (dd, 1H), 5.57 (s, 2H), 3.82 (s, 3H), 3.73 (m, 2H), 3.59 (m, 2H), 3.31 (m, 2H), 3.19 (m, 2H). LCMS (ES) M+H 386.5, $R_f$ 1.84 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile). For 1-[4-(4-chloro-3-methoxy-phenyl)piperazin-1-yl]-2-pyrazolo[4,3-b]pyridine-2-yl-ethanone; $^1$H NMR (400 MHz, CDCl$_3$) δ 8.55 (d, 1H), 8.34 (s, 1H), 7.99 (d, 1H), 7.19 (m, 2H), 6.44 (d, 1H), 6.40 (dd, 1H), 5.34 (s, 2H), 3.86 (s, 3H), 3.77 (m, 2H), 3.72 (m, 2H), 3.13 (m, 4H). LCMS (ES) M+H 386.5, $R_f$ 1.69 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 30

Synthesis of 2-(3-Chloro-pyrazolo[3,4-b]pyridine-2-yl)-acetic acid

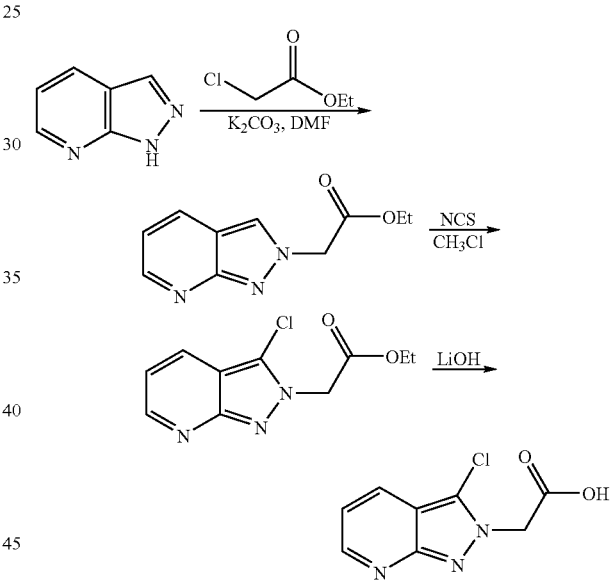

Preparation of pyrazolo[3,4-b]pyridin-2-yl-acetic acid ethyl ester: This compound was synthesized according to the procedure outlined in Example 6, using chloro-acetic acid ethyl ester in place of 2-Chloro-1-[4-(4-chloro-2-fluoro-5-methoxyphenyl)-2-(S)-methylpiperazin-1-yl]ethanone.

Preparation of (3-Chloro-pyrazolo[3,4-b]pyridin-2-yl)-acetic acid ethyl ester: To a solution of pyrazolo[3,4-b]pyridin-2-yl-acetic acid ethyl ester 57 (40.2 Mg, 0.2 Mmol, 1 equiv) in 1 mL of dichloromethane was added NCS (32.7 Mg, 1.2 Mmol, 1.2 equiv). The resultant mixture was heated at 70° C. for 30 min., cooled to room temperature, and diluted with 100 mL of dichloromethane. The organic solution was washed with 50 mL of saturated sodium bicarbonate aqueous solution, and 50 mL of brine. The organic layer was separated and dried over sodium sulfate. Evaporation of solvent in vacuo gave 46.7 Mg of (3-chloro-pyrazolo[3,4-b]pyridin-2-yl)-acetic acid ethyl ester as yellow solid.

Synthesis of 2-(3-Chloro-pyrazolo[3,4-b]pyridine-2-yl)-acetic acid: (3-Chloro-pyrazolo[3,4-b]pyridin-2-yl)-acetic acid ethyl ester was treated with 1N lithium hydroxide (LiOH) (1 equiv) in 1 mL of MeOH to provide 2-(3-Chloro-pyrazolo[3,4-b]pyridine-2-yl)-acetic acetic acid, which was used as directly in subsequent reactions without further purification: LCMS (ES) M+H 212.0, $R_f$ 0.34 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile).

Example 31

Synthesis of 1-[4-(4-chloro-3-methoxy-phenyl)piperazin-1-yl]-2-(3-chloro-pyrazolo[3,4-b]pyridine-2-yl)-ethanone

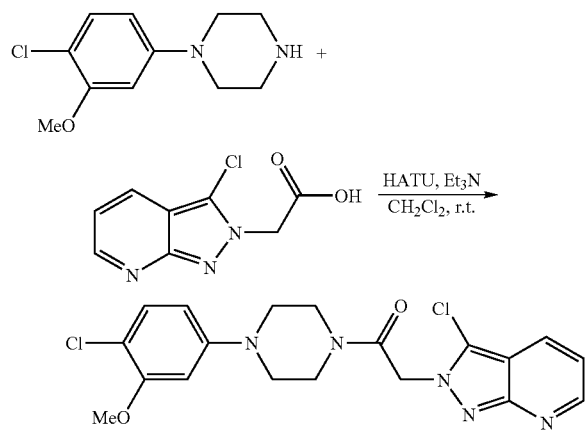

The title compound was synthesized according to standard amide formation conditions using 2-(7-Aza-1H-benzotriazole-1-yl)-1,1,3,3-tetramethyluronium hexafluorophosphate (HATU) as the coupling reagent: LCMS (ES) M+H 420.4, $R_f$ 2.17 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile.

Example 32

Synthesis of 2-(Pyrazolo[3,4-b]pyridin-1-yl-7-oxide)-acetic acid

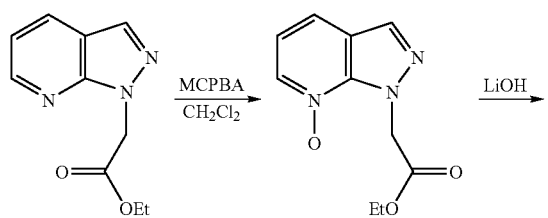

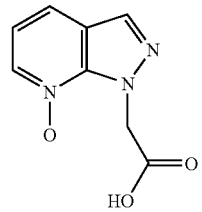

Preparation of 2-(Pyrazolo[3,4-b]pyridin-1-yl-7-oxide)-acetic acid ethyl ester: To a solution of pyrazolo[3,4-b]pyridin-1-yl-acetic acid ethyl ester (205.4 Mg, 1 Mmol, 1 equiv) in 10 mL of dichloromethane at 0° C., was added meta-chloroperoxybenzoic acid (mCPBA) (345.3 Mg, 1.5 Mmol, 1.5 equiv). The resultant mixture was allowed to warm to room temperature, and the reaction was stirred overnight. 1 mL of pyridine was added to the reaction mixture, and the mixture was stirred for another 30 min before the solvent was removed to provide a residue. The residue was diluted with 200 mL of dichloromethane, and washed with 1 N NaOH aqueous solution (10 mL×2), brine (20 mL). The organic layer was separated and dried over sodium sulfate. Evaporation in vacuo gave 2-(pyrazolo[3,4-b]pyridin-1-yl-7-oxide)-acetic acid ethyl ester as pale yellow solid, which was used without further purification: LCMS (ES) M+H 222.4, $R_f$ 1.48 min (Agilent Zorbax SB-C18, 2.1×50 mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile.

Synthesis of 2-(Pyrazolo[3,4-b]pyridin-1-yl-7-oxide)-acetic acid: 2-(pyrazolo[3,4-b]pyridin-1-yl-7-oxide)-acetic acid ethyl ester was treated with 1N LiOH (1 equiv) in 1 mL of methanol (MeOH) to provide 2-(Pyrazolo[3,4-b]pyridin-1-yl-7-oxide)-acetic acid: LCMS (ES) M+H 194.2, $R_f$ 0.22 min (Agilent Zorbax SB-C18, 2.1×50 Mm, 5µ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile Example 33

Synthesis of 1-[4-(4-Chloro-3-methoxy-phenyl)piperazin-1-yl]-2-(pyrazolo[3,4-b]pyridin-1-yl-7-oxide)-ethanone

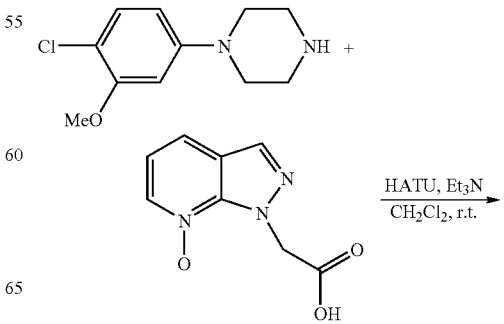

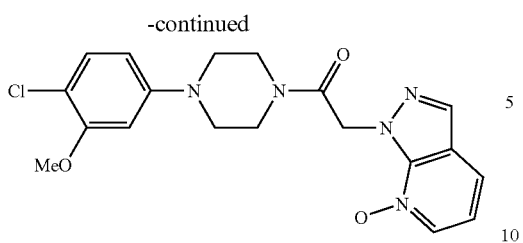

The title compound was prepared according to standard amide formation conditions as described in Example 43 using HATU as the coupling reagent: LCMS (ES) M+H 402.5, $R_f$ 1.54 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/94.9% acetonitrile.

Example 34

Synthesis of 1-[4-(4-Chloro-3-methoxy-phenyl)-piperazin-1-yl]-2-(6-methyl-pyrazolo[3,4-b]pyridin-1-yl)-ethanone

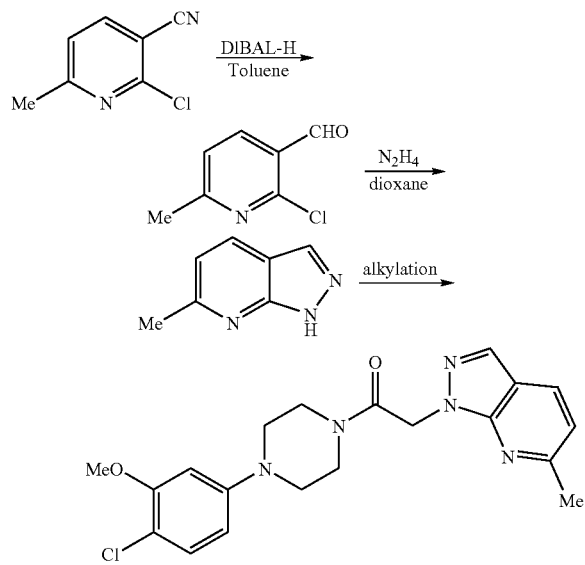

2-chloro-3-cyano-6-picoline was reduced by diisobutylaluminum hydride (DIBAL-H) following a literature procedure (Baker et. al., *J. Org. Chem.*, 1980, 45, 1354-1362.) followed by the hydrazine condensation protocol as described in Example 1 to provide the corresponding 6-Methyl-1H-pyrazolo[3,4-b]pyridine, which was then subjected to the alkylation protocol in described in Example 6 to provide title compound as a white powder: LCMS (ES) M+H 400.5, $R_f$ 2.161 min (Agilent Zorbax SB-C18, 2.1×50 Mm, 5μ, 35° C., 1 mL/min flow rate, a 2.5 min gradient of 20% to 100% B with a 1.1 min wash at 100% B, A=0.1% formic acid/5% acetonitrile/94.9% water, B=0.1% formic acid/5% water/94.9% acetonitrile).

Example 35

Synthesis of 1-[4-(4-chloro-3-methoxy-phenyl)-piperazin-1-yl]-2-(6-methyl-pyrazolo[3,4-b]pyridine-2-yl)-ethanone

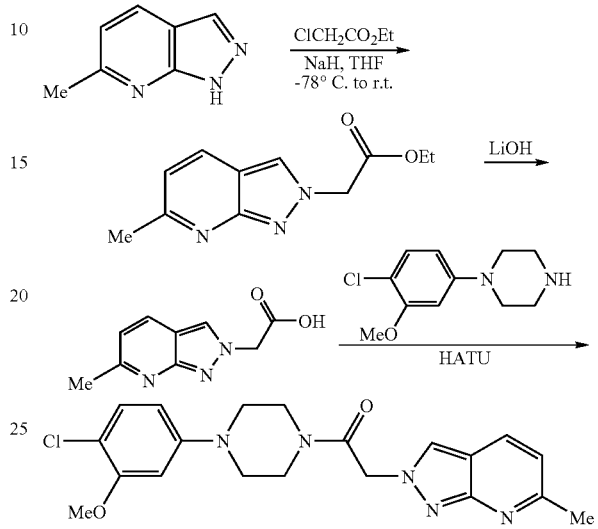

Preparation of (6-methyl-pyrazolo[3,4-b]pyridine-2-yl)-acetic acid ethyl ester: To a solution of 1H-6-methyl-pyrazolo[3,4-b]pyridine (1 Mmol, 1 eq.) in 3 mL of THF was added NaH (1.5 Mmol, 1.5 eq.) portion by portion at 0° C. under nitrogen. The resultant mixture was stirred at 0° C. for 10 minutes followed by the slow addition of 2-chloro ethyl acetate (excess) at 0° C. The resultant mixture was slowly to warmed to rt, and stirred for another 2 h. To the reaction mixture was added saturated NH$_4$Cl aq. solution, and aqueous mixture was extracted with 300 mL of EtOAc. The organic extract was separated and washed with sat. sodium bicarbonate aq. solution, brine solution, filtered and dried over sodium sulfate. The organic solvent was removed in vacuo, and the crude residue was purified by silica gel chromatography to provide 50.2 Mg desired product: HPLC retention time=0.78 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=220.1, found=220.4.

Preparation of (6-methyl-pyrazolo[3,4-b]pyridine-2-yl)-acetic acid: This compound was synthesized according to standard ester hydrolysis protocol as described in Example 30 using 1N LiOH as the base. The isolated product was used in the next step without purification.

Synthesis of 1-[4-(4-chloro-3-methoxy-phenyl)-piperazin-1-yl]-2-(6-methyl-pyrazolo[3,4-b]pyridine-2-yl)-ethanone: The title compound was synthesized according to standard peptide coupling protocol using HATU as the coupling reagent: $^1$H NMR (400 MHz, CDCl$_3$) δ 8.04 (s, 1H), 7.96 (d, 1H), 7.20 (d, 1H), 6.95 (d, 1H), 6.45 (d, 1H), 6.40 (dd, 1H), 5.29 (s, 2H), 3.92 (m, 2H), 3.88 (s, 3H), 3.78 (m, 2H), 3.13 (m, 4H). LCMS observed for (M+H)$^+$: 400.5.

Example 36

Synthesis of 1-[4-(4-Chloro-3-methoxy-phenyl)-piperazin-1-yl]-2-(3-morpholin-4-yl-pyrazolo[3,4-b]pyridin-1-yl)-ethanone

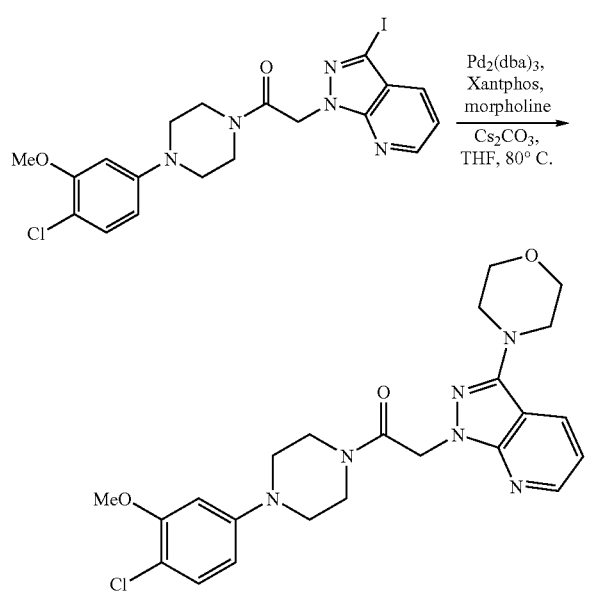

A mixture of 1-[4-(4-Chloro-3-methoxy-phenyl)-piperazin-1-yl]-2-(3-iodo-pyrazolo[3,4-b]pyridin-1-yl)-ethanone (102.4 Mg), morpholine (0.20 mL), Xantphos (35 Mg), Pd$_2$(dba)$_3$ (18.3 Mg) and Cs$_2$CO$_3$ (97 Mg) in THF (1 mL) was heated to 80° C. for 12 h. The reaction mixture was allowed to cool to room temperature, diluted by EtOAc (3 mL) and filtered. The filtrate was evaporated in vacuo. The crude residue was purified by flash chromatography (silica, Hexane/EtOAc) to provide the title compound as a white powder: LCMS (ES) M+H 471.6, R$_f$ 2.043 min (Agilent Zorbax SB-C18, 2.1×50 Mm, 5μ, 35° C., 1 mL/min flow rate, a 2.5 min gradient of 20% to 100% B with a 1.1 min wash at 100% B, A=0.1% formic acid/5% acetonitrile/94.9% water, B=0.1% formic acid/5% water/94.9% acetonitrile).

Example 37

Synthesis of 1-[4-(4-Chloro-2-fluoro-5-methoxy-phenyl)-2-(S)-methyl-piperazin-1-yl]-2-pyrazolo[3,4-c]pyridin-1-yl-ethanone

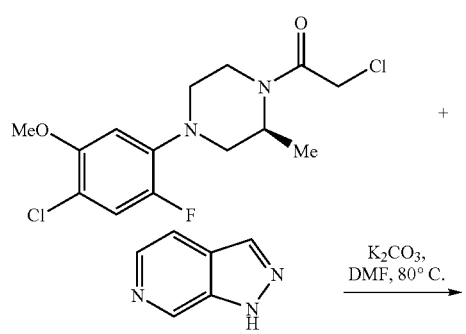

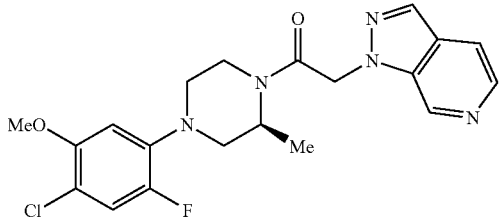

The title compound was synthesized following the alkylation protocol as described in Example 6: LCMS (ES) M+H 418.4, R$_f$ 2.055 min (Agilent Zorbax SB-C18, 2.1×50 Mm, 5μ, 35° C., 1 mL/min flow rate, a 2.5 min gradient of 20% to 100% B with a 1.1 min wash at 100% B, A=0.1% formic acid/5% acetonitrile/94.9% water, B=0.08% formic acid/5% water/94.9% acetonitrile).

Example 38

Synthesis of 1-[4-(4-Chloro-3-methoxy-phenyl)-piperazin-1-yl]-2-(6-oxy-pyrazolo[3,4-c]pyridin-1-yl)-ethanone

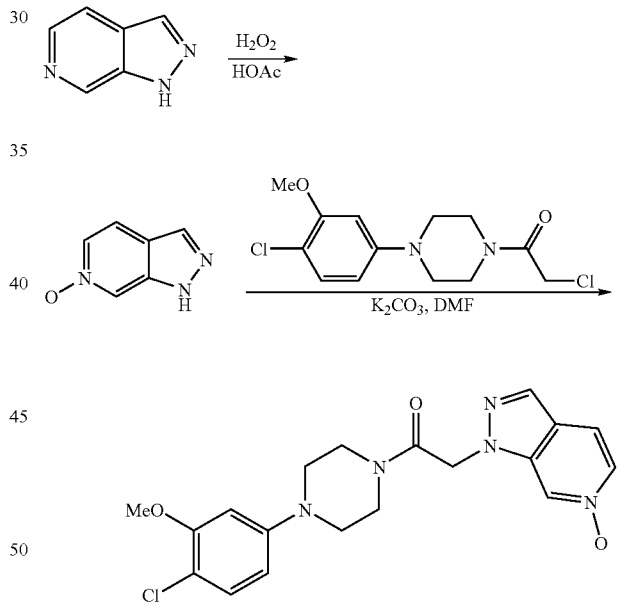

A mixture of 6-azaindazole (119 Mg), H$_2$O$_2$ (0.2 mL) in acetic acid (5 mL) was heated to 60° C. for 2 h. The resultant mixture was cooled to room temperature and concentrated in vacuo. The crude residue was dissolved in EtOAc (10 mL), washed with sat. aqueous NaHCO$_3$ solution (3 mL), dried (Na$_2$SO$_4$), filtered and evaporated in vacuo. The crude product (the N-oxide) was subjected to the alkylation protocol as described in Example 6 to provide the title compound as a white powder: LCMS (ES) M+H 402.4, R$_f$ 2.147 min (Agilent Zorbax SB-C18, 2.1×50 Mm, 5μ, 35° C., 1 mL/min flow rate, a 2.5 min gradient of 20% to 100% B with a 1.1 min wash at 100% B, A=0.1% formic acid/5% acetonitrile/94.9% water, B=0.1% formic acid/5% water/94.9% acetonitrile).

Example 39

Synthesis of 1-[4-(4-chloro-3-methoxy-phenyl)piperazin-1-yl]-2-(4-chloro-pyrazolo[4,3-c]pyridine-2-yl)-ethanone

Example 40

Synthesis of 1-[4-(4-chloro-3-methoxy-phenyl)-piperazin-1-yl]-2-(4-iodo-pyrazolo[4,3-c]pyridine-1-yl)-ethanone and 1-[4-(4-chloro-3-methoxy-phenyl)-piperazin-1-yl]-2-(4-iodo-pyrazolo[4,3-c]pyridine-2-yl)-ethanone

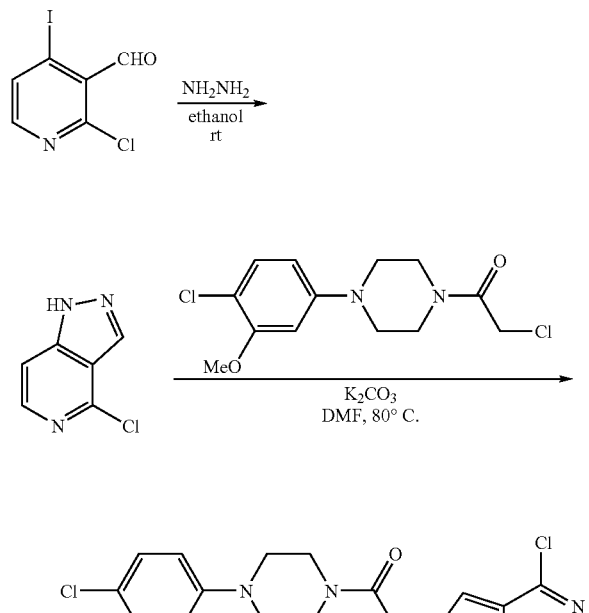

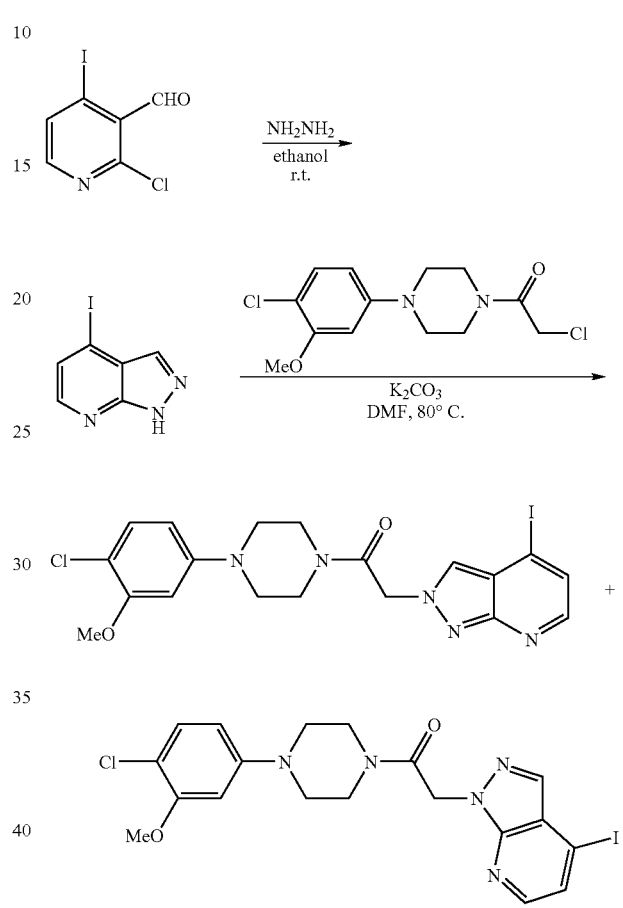

Preparation of 1H-4-chloro-pyrazolo[4,3-c]pyridine: To a mixture of 2-chloro-4-iodopyridine-3-carbaldehyde (6.24 Mmol, 1 eq.) and 5 mL of ethanol was added 4 mL of hydrazine (excess), the resultant mixture was stirred at rt for 6 h. The reaction solution was concentrated in vacuo, and the crude residue was diluted with 50 mL of water, and extracted with 500 mL of dichloromethane. The organic layer was then washed with brine, dried over anhydrous sodium sulfate, filtered and concentrated to provide a crude residue. To the crude residue was dissolved with 10 mL of dichloromethane and stirred for 5 minutes. The precipitated solids were isolated by filtration, washed with 2 mL of dichloromethane, and dried in vacuo to provided 350.2 Mg of 1H-4-chloro-pyrazolo[4,3,c]pyridine: HPLC retention time=0.44 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expected=154.0, found=154.3.

Synthesis of 1-[4-(4-chloro-3-methoxy-phenyl)-piperazin-1-yl]-2-(4-chloro-pyrazolo[4,3-c]pyridine-2-yl)-ethanone: Using 1H-4-chloro-pyrazolo[4,3-c]pyridine, the title compound was synthesized according to alkylation protocol in Example 6: $^1$H NMR (400 MHz, CDCl$_3$) δ 8.18 (d, 1H), 7.31 (dd, 1H), 7.21 (d, 1H), 6.47 (d, 1H), 6.42 (dd, 1H), 5.28 (s, 2H), 3.88 (s, 3H), 3.77 (m, 4H), 3.14 (m, 4H). LCMS observed for (M+H)$^+$: 420.4.

Preparation of 1H-4-iodo-pyrazolo[3,4,b]pyridine: To a mixture of 2-chloro-4-iodopyridine-3-carbaldehyde (6.24 Mmol, 1 eq.) and 5 mL of ethanol was added 4 mL of hydrazine (excess), the resultant mixture was stirred at rt for 6 h. The reaction mixture was concentrated in vacuo and crude residue was diluted with 50 mL of water, and extracted with 500 mL of dichloromethane. The organic layer was washed with brine, dried over anhydrous sodium sulfate and concentration in vacuo to provide a crude residue. To this residue was added 10 mL of dichloromethane, the resultant mixture was stirred for 5 minutes which resulted in the precipitation of the undesired cyclization isomer (1H-4-chloro-pyrazolo[4,3,c]pyridine) which was removed by filtration. The filtrate was concentrated in vacuo, and purified be by silica gel column (35% acetone in hexane to 50% acetone in hexane) to provide 250.0 Mg of 1H-4-iodo-pyrazolo[3,4,b]pyridine with a purity around 85%, which was used without further purification: HPLC retention time=1.22 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=246.0, found=246.1.

Synthesis of 1-[4-(4-chloro-3-methoxy-phenyl)-piperazin-1-yl]-2-(4-iodo-pyrazolo[4,3-c]pyridine-1-yl)-ethanone and 1-[4-(4-chloro-3-methoxy-phenyl)-piperazin-1-yl]-2-(4-iodo-pyrazolo[4,3-c]pyridine-2-yl)-ethanone: The title compounds were synthesized according to the standard alkylation procedure described in Example 6. For 1-[4-(4-chloro-3-methoxy-phenyl)-piperazin-1-yl]-2-(4-iodo-pyrazolo[4,3-c]pyridine-1-yl)-ethanone: HPLC retention time=2.50 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=512.0, found=512.4; For 1-[4-(4-chloro-3-methoxy-phenyl)-piperazin-1-yl]-2-(4-iodo-pyrazolo[4,3-c]pyridine-2-yl)-ethanone: HPLC retention time=2.23 minutes (Agilent Zorbax SB-C18, 2.1×50 Mm, 5μ, 35° C.) using 1 mL/min 2 h. The reaction solution was cooled to rt, and diluted with 20 mL of sat. NH$_4$Cl aq. solution and 200 mL of EtOAc. The diluted mixture was stirred vigorously for 2 h. The organic layer was then separated, washed with brine, dried over sodium sulfate, filtered and concentrated in vacuo to provide the crude product. Purification by HPLC provided 40.2 Mg desired product: $^1$H NMR (400 MHz, CDCl$_3$) δ 8.76 (d, 1H), 8.49 (d, 1H), 7.65 (d, 1H), 7.23 (d, 1H), 6.50 (d, 1H), 6.44 (dd, 1H), 5.53 (s, 2H), 3.89 (s, 3H), 3.79 (m, 4H), 3.22 (m+s, 4H+3H). LCMS observed for (M+H)$^+$: 464.4.

Example 42

Synthesis of 1-[4-(4-chloro-3-methoxy-phenyl)-piperazin-1-yl]-2-(3-amidomethyl-pyrazolo[3,4-b]pyridine-1-yl)-ethanone

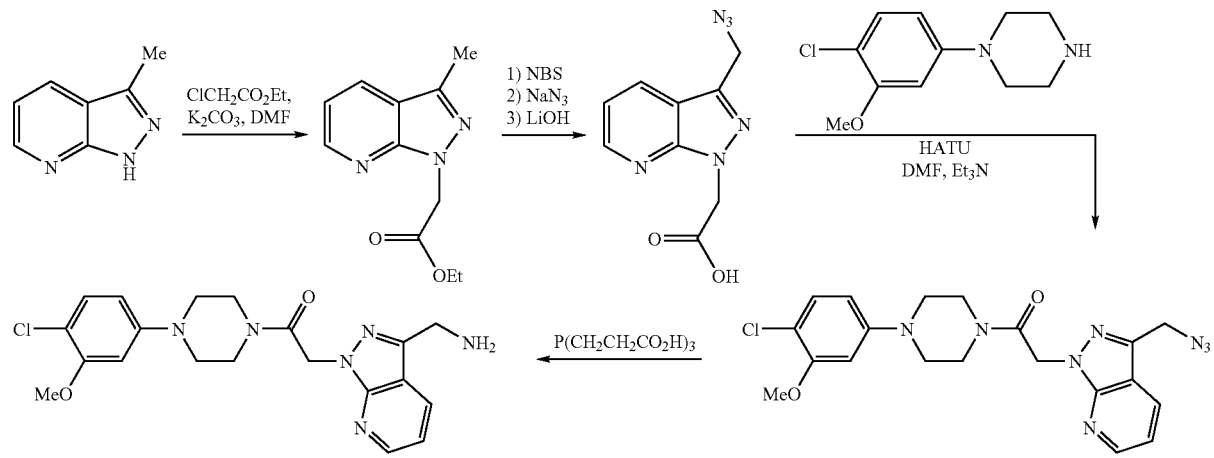

flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=512.0, found=512.4

Example 41

Synthesis of 1-[4-(4-chloro-3-methoxy-phenyl)-piperazin-1-yl]-2-(4-methylsulfonyl-pyrazolo[4,3-c]pyridine-1-yl)-ethanone

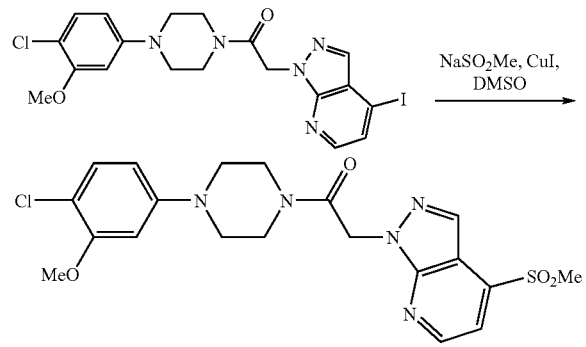

A mixture of 1-[4-(4-chloro-3-methoxy-phenyl)-piperazin-1-yl]-2-(4-iodo-pyrazolo[4,3-c]pyridine-1-yl)-ethanone (0.1 Mmol, 1 eq.), CuI (0.3 Mmol, 3 eq.) and NaSO$_2$Me (0.3 Mmol, 1 eq.) in 1 mL of DMSO was heated at 80° C. for Preparation of (3-methyl-pyrazolo[3,4-b]pyridine-1-yl) acetic acid ethyl ester: This compound was synthesized following the alkylation protocol similar to the one described in Example 6 HPLC retention time=2.06 minutes (Agilent Zorbax SB-C18, 2.1×50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=220.1, found=220.4.

Preparation of [3-(bromomethyl)-pyrazolo[3,4-b]pyridine-1-yl]acetic acid ethyl ester: A mixture of (3-methyl-pyrazolo[3,4-b]pyridine-1-yl)ethyl acetate (2.5 Mmol, 1 eq.), NBS (3.0 Mmol, 1.2 eq.), and benzoly peroxide (0.05 Mmol, 0.02 eq.) in 10 mL of CCl$_4$ was refluxed for 1.5 h. The resultant mixture was cooled to rt, and diluted with 500 mL of EtOAc. The resultant solution was then washed with 100 mL of sat. sodium bicarbonate aqueous solution, brine solution, dried over anhydrous sodium sulfate, filtered and concentrated in vacuo. The crude residue was purified by silica gel chromatography (20% EtOAc in hexane to 35% EtOAc in hexane) to provide 450.2 Mg of the desired product: HPLC retention time=2.50 minutes (Agilent Zorbax SB-C18, 2.1×50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=298.0, found=298.3.

Preparation of (3-azido-pyrazolo[3,4-b]pyridine-1-yl)acetic acid ethyl ester: A mixture of (3-(bromomethyl)-pyrazolo[3,4-b]pyridine-1-yl)acetic acid ethyl ester (0.5 Mmol, 1 eq.) and sodium azide (1 Mmol, 2 eq.) in 1 mL of DMF was heated at 80° C. for 1 h. The resultant mixture was cooled to rt, diluted with 150 mL of EtOAc, washed with water (40 mL×× 3), brine, dried over anhydrous sodium sulfate, filtered and concentrated in vacuo. The solvent was removed in vacuo to provide 135.2 Mg desired product: HPLC retention time=1.84 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=261.1, found=261.4.

Preparation of [3-(azidomethyl)-pyrazolo[3,4-b]pyridine-1-yl)acetic acid: This compound was synthesized according to standard hydrolysis protocol as described in Example 30 using 1 N LiOH: HPLC retention time=1.94 minutes (Agilent Zorbax SB-C18, 2.1×50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=233.1, found=233.4.

Preparation of 1-[4-(4-chloro-3-methoxy-phenyl)-piperazin-1-yl]-2-(3-azidomethyl-pyrazolo[3,4-b]pyridine-1-yl)-ethanone: This compound was synthesized according to standard peptide coupling procedure as described below in Example 43 using HATU as the coupling reagent: HPLC retention time=2.36 minutes (Agilent Zorbax SB-C18, 2.1× 50 Mm, 5μ, 35° C.) using 1 mL/min flow rate, a 2.5 minute gradient of 20% to 100% B with a 1.1 minute wash at 100% B (A=0.1% formic acid/5% acetonitrile 94.9% water, B=0.1% formic acid/5% water/94.9% acetonitrile); MS (ES) M+H expect=441.2, found=441.5.

Synthesis of 1-[4-(4-chloro-3-methoxy-phenyl)-piperazin-1-yl]-2-(3-amidomethyl-pyrazolo[3,4-b]pyridine-1-yl)-ethanone: To a solution of 1-[4-(4-chloro-3-methoxy-phenyl)-piperazin-1-yl]-2-(3-azidomethyl-pyrazolo[3,4-b]pyridine-1-yl)-ethanone (0.21 Mmol, 1 eq.) in 2 mL of THF was added dropwise at rt a solution of tris(2-carboxyethyl) phosphine HCl salt in 0.5 mL of water. The resultant mixture was stirred at rt for 30 min. The reaction solution was concentrated in vacuo, and the crude residue was diluted with 150 mL of dichloromethane, washed with 25 mL of water, brine, and dried over sodium sulfate. The solvent was removed in vacuo, and the crude residue was purified by HPLC to provide 26.2 mg final product: $^1$H NMR (400 MHz, CDCl$_3$) δ 8.17 (dd, 1H), 8.15 (dd, 1H), 7.22 (d, 1H), 7.12 (dd, 1H), 6.50 (d, 1H), 6.44 (dd, 1H), 5.40 (s, 2H), 4.25 (s, 2H), 3.89 (s, 3H), 3.77 (m, 4H), 3.19 (m, 4H). LCMS observed for (M+H)$^+$: 416.4.

Example 43

Synthesis of 1-[4-(4-chloro-3-methoxy-phenyl)-piperazin-1-yl]-2-(3-sulfonic acid-methyl-pyrazolo[3,4-b]pyridine-1-yl)-ethanone

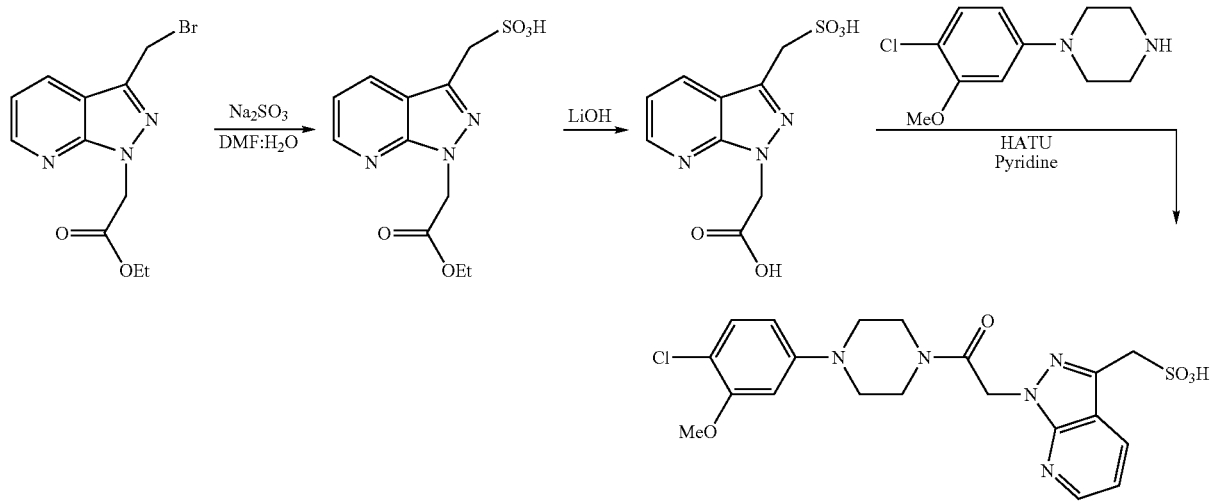

Preparation of [3-(sulfonic acid-methyl)-pyrazolo[3,4-b]pyridine-1-yl]acetic acid ethyl ester: A mixture of (3-(bromomethyl)-pyrazolo[3,4-b]pyridine-1-yl)acetic acid ethyl ester (0.13 Mmol, 1 eq.) and sodium sulfite (1.8 Mmol, excess) in a mixture of 1 mL of DMF and 0.5 mL of water was heated at 80° C. for one hour. The resultant solution was cooled to rt, and the solvent was removed in vacuo. The residue was extracted with 1:1 MeOH: CH$_2$Cl$_2$ (30 mL×3). The combined organic extracts were dried in vacuo, and the crude residue was used without further purification: HPLC retention time=1.63 minutes (Agilent Zorbax SB-C18, 2.1× 50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=300.1, found=300.5.

Preparation of [3-(sulfonic acid-methyl)-pyrazolo[3,4-b]pyridine-1-yl]acetic acid: This compound was synthesized according to standard hydrolysis protocol as described in Example 30 using 1 N LiOH as the base. The crude product was used without further purification.

Synthesis of 1-[4-(4-chloro-3-methoxy-phenyl)-piperazin-1-yl]-2-(3-sulfonic acid-methyl-pyrazolo[3,4-b]pyridine-1-yl)-ethanone: A mixture of sulfonic acid (100.2 Mg, contain lots of inorganic salt), 1H-4-(4-chloro-3-methoxyphenyl)piperazine 2×HCl salt (0.37 Mmol, excess), and HATU (0.37 excess) was suspended in 3 mL of pyridine, stirred at rt for 3 h. The pyridine solvent was removed in vacuo, and the crude residue was extracted with dichloromethane (10 mL×3). The organic extracts were removed, and the crude residue was purified by HPLC to provide 10 Mg of 1-[4-(4-chloro-3-methoxy-phenyl)-piperazin-1-yl]-2-(3-sulfonic acid-methyl-pyrazolo[3,4-b]pyridine-1-yl)-ethanone: HPLC retention time=0.28 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=480.1, found=480.5.

Example 44

Synthesis of 1-[4-(4-chloro-3-methoxy-phenyl)-piperazin-1-yl]-2-(5-chloro-pyrazolo[3,4-b]pyridine-1-yl)-ethanone Preparation of (3-iodo-5-chloro-pyrazolo[3,4-b]pyridine-1-yl)acetic acid: This compound was synthesized according to standard hydrolysis procedure as described in Example 30 using 1N LiOH: HPLC retention time=1.78 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=337.9, found=337.9.

Preparation of 1-[4-(4-chloro-3-methoxy-phenyl)-piperazin-1-yl]-2-(3-iodo-5-chloro-pyrazolo[3,4-b]pyridine-1-yl)-ethanone: The title compound was synthesized according to standard peptide coupling protocol as described in Example 43 using HATU as the coupling reagent: HPLC retention time=2.71 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=546.0, found=546.4.

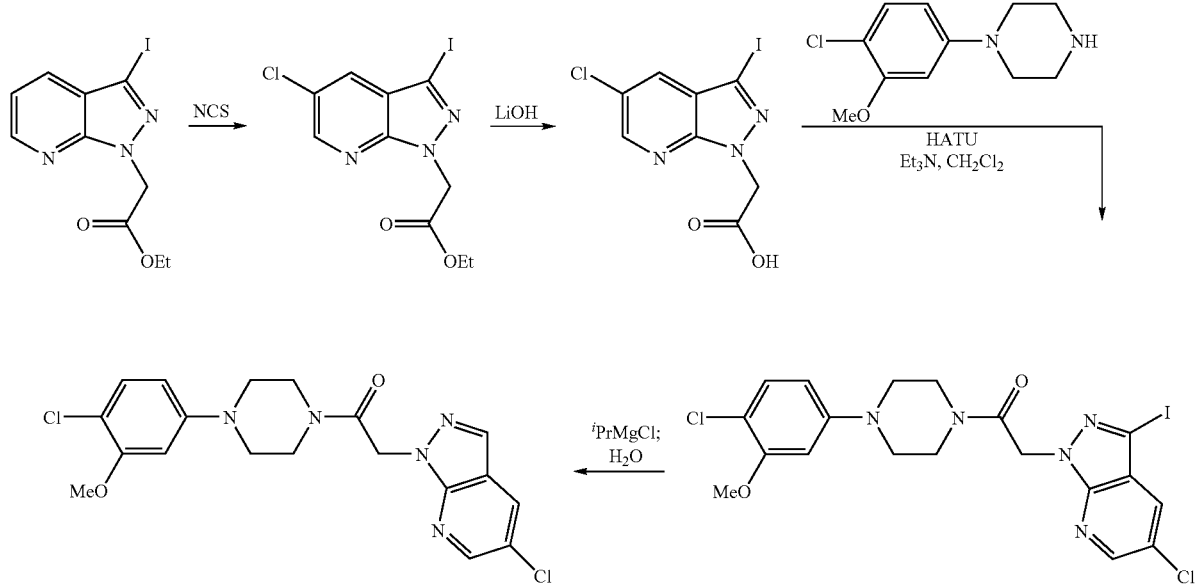

Preparation of (3-iodo-5-chloro-pyrazolo[3,4-b]pyridine-1-yl)acetic acid ethyl ester: To a solution of (3-iodo-5-pyrazolo[3,4-b]pyridine-1-yl)acetic acid ethyl ester (0.61, 1 eq.) in 2 mL of DMF was added N-chlorosuccinimide (NCS) (0.73, 1.2 eq.) as a solid. The resultant mixture was heated at 70° C. for 3 h. The reaction mixture was cooled to rt, and diluted with 250 mL of EtOAc. The diluted mixture was then washed with water (100 mL×3), brine, dried over sodium sulfate, filtered and concentrated in vacuo. The crude residue was purified by silica gel chromatography (15% EtOAc to 75% EtOAc in hexane) to provide 100.4 Mg white solid as final product: HPLC retention time=2.48 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=365.9, found=366.3.

Synthesis of 1-[4-(4-chloro-3-methoxy-phenyl)-piperazin-1-yl]-2-(5-chloro-pyrazolo[3,4-b]pyridine-1-yl)-ethanone: To a solution of 1-[4-(4-chloro-3-methoxy-phenyl)-piperazin-12426 -yl]-2-(3-iodo-5-chloro-pyrazolo[3,4-b]pyridine-1-yl)-ethanone (0.037 Mmol, 1 eq.) in 1.5 mL of dichloromethane under a nitrogen atmosphere cooled to −40° C., was added dropwise, 30 µl of 2.0 M solution of isopropyl magnesium chloride (0.056 Mmol, 1.5 eq.) in THF. The resultant mixture was for 30 minutes at −40° C. followed by dropwise addition of an ammonium chloride aqueous (aq) solution at low temperature. The reaction solution was warmed to rt, diluted with 200 mL of EtOAc, washed with 50 mL of water, brine, dried over sodium sulfate, filtered and concentrated in vacuo. The crude residue was purified by HPLC to provide 5 Mg final product: $^1$H NMR (400 MHz, CDCl$_3$) δ 8.44 (d, 1H), 8.05 (m, 1H), 7.23 (d, 1H), 6.50 (d, 1H), 6.43 (dd, 1H), 5.42 (s, 2H), 3.89 (s, 3H), 3.76 (m, 4H), 3.20 (m, 4H). LCMS observed for (M+H)$^+$: 421.1.

Example 45

Synthesis of 1-[4-(4-chloro-3-methoxy-phenyl)-piperazin-1-yl]-2-(4-chloro-pyrazolo[3,4-d]pyrimidine-1-yl)-ethanone and 1-[4-(4-chloro-3-methoxy-phenyl)-piperazin-1-yl]-2-(4-chloro-pyrazolo[3,4-d]pyrimidine-2-yl)-ethanone

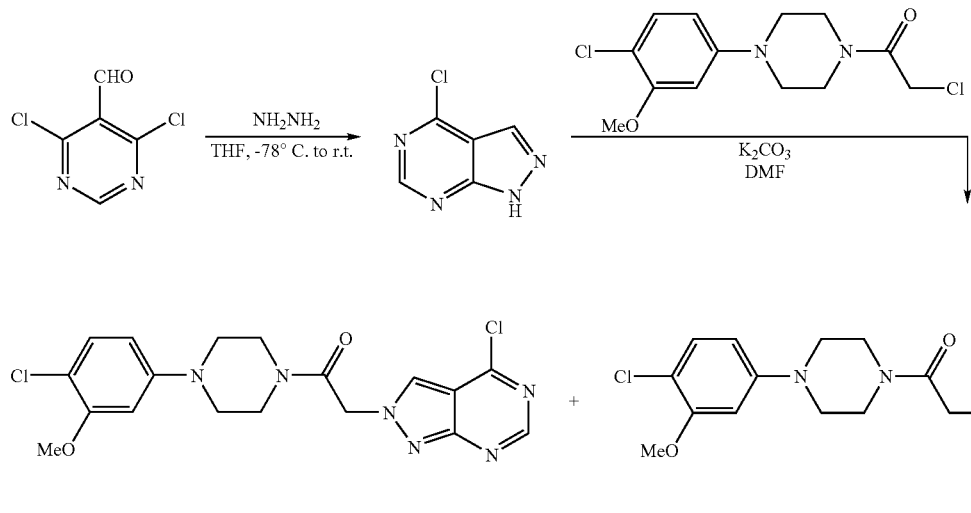

Preparation of 1H-4-chloro-pyrazolo[3,4-d]pyrimidine: This compound was synthesized according to standard hydrazine cyclization protocol as described in Example 1: HPLC retention time=0.36 minutes (Agilent Zorbax SB-C18, 2.1×50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=155.0, found=155.0.

Synthesis of 1-[4-(4-chloro-3-methoxy-phenyl)-piperazin-1-yl]-2-(4-chloro-pyrazolo[3,4-d]pyrimidine-1-yl)-ethanone and 1-[4-(4-chloro-3-methoxy-phenyl)-piperazin-1-yl]-2-(4-chloro-pyrazolo[3,4-d]pyrimidine-2-yl)-ethanone: These compounds were synthesized using 1H-4-chloro-pyrazolo[3,4-d]pyrimidine following the alkylation procedure as described in Example 6: For 1-[4-(4-chloro-3-methoxy-phenyl)-piperazin-1-yl]-2-(4-chloro-pyrazolo[3,4-d]pyrimidine-1-yl)-ethanone; $^1$H NMR (400 MHz, CDCl$_3$) δ 8.76 (s, 1H), 8.22 (s, 1H), 7.22 (d, 1H), 6.54 (d, 1H), 6.44 (dd, 1H), 5.41 (s, 2H), 3.88 (s, 3H), 3.77 (m, 4H), 3.23 (m, 4H), LCMS observed for (M+H)$^+$: 421.1: For 1-[4-(4-chloro-3-methoxy-phenyl)-piperazin-1-yl]-2-(4-chloro-pyrazolo[3,4-d]pyrimidine-2-yl)-ethanone; HPLC retention time=1.70 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=421.1, found=421.1.

Example 46

Synthesis of 1-[4-(4-chloro-3-methoxy-phenyl)-piperazin-1-yl]-2-(4-methoxy-pyrazolo[3,4-d]pyrimidine-1-yl)-ethanone

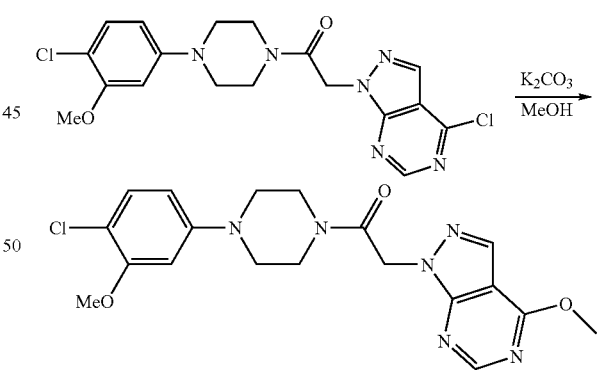

To a solution of 1-[4-(4-chloro-3-methoxy-phenyl)-piperazin-1-yl]-2-(4-chloro-pyrazolo[3,4-d]pyrimidine-1-yl)-ethanone (0.024 Mmol, 1 eq.) in 1 mL of MeOH was added solid potassium carbonate (excess), the resultant mixture was heated at 70° C. for 30 minutes, then filtered and dried under vacuum. The crude product was purified by HPLC to provide the desired product as a white powder: $^1$H NMR (400 MHz, CDCl$_3$) δ 8.90 (s, 1H), 8.07 (s, 1H), 7.22 (d, 1H), 6.50 (d, 1H), 6.44 (dd, 1H), 5.29 (s, 2H), 3.90 (s, 3H), 3.81 (m, 4H), 3.19 (m, 4H), 2.25 (s, 3H). LCMS observed for (M+H)$^+$: 418.9.

Example 47

Synthesis of 1-[4-(4-chloro-3-methoxy-phenyl)-piperazin-1-yl]-2-(6-chloro-pyrazolo[3,4-b]pyridine-1-yl)-ethanone and 1-[4-(4-chloro-3-methoxy-phenyl)-piperazin-1-yl]-2-(6-chloro-pyrazolo[3,4-b]pyridine-2-yl)-ethanone

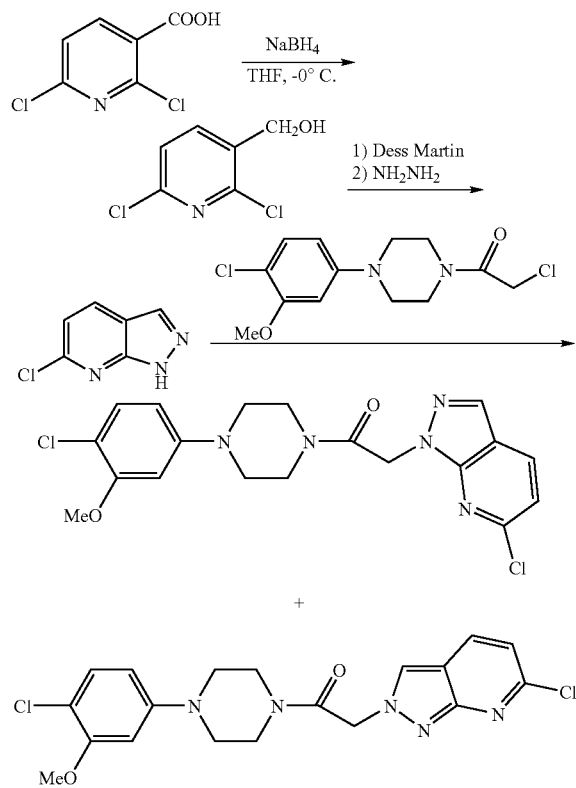

Preparation of (2,6-dichloro-3-pyridinyl)methanol: To a solution of 2,6-dichloro-3-nicotic acid (9 Mmol, 1 eq.) in 10 mL of dry THF at 0° C., was added NaBH$_4$ (27 Mmol, 3 eq.) portion by portion under nitrogen atmosphere. After the evolution of hydrogen gas subsided (which is observed as bubbling in the reaction mixture), BF$_3$·OMe$_2$ (27 Mmol, 3 eq.) was added dropwise to the reaction mixture at 0° C. The resultant mixture was stirred at 0° C. for 20 minutes followed by the slow addition of sat. NH$_4$Cl aq. solution. The reaction solution was then warmed to rt, and extracted with 300 mL of EtOAc, and the organic layer was washed with brine, dried over sodium sulfate, filtered and concentrated in vacuo to provide a white solid, which was used in subsequent reaction without further purification: HPLC retention time=0.71 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=178.0, found=178.0.

Preparation of 2,6-dichloro-3-formylpyridine: To a solution of the above alcohol (2 mmol, 1 eq.) in 10 mL of dichloromethane was added potassium carbonate (excess) as a solid, and Dess-Martin periodinate (2 Mmol, 1 eq.) at rt. The resultant mixture was stirred at rt for 30 minutes. A 5% sodium thiosulfate aq. solution was added to the reaction mixture and the resultant mixture was stirred for another 10 minutes. The reaction mixture was extracted with 300 mL of EtOAc, and the organic layer was washed with 50 mL of 5% sodium thiosulfate aq. solution, Sat. sodium bicarbonate aq. solution, brine, and dried over sodium sulfate. Evaporation of solvent in vacuo to provide 200.1 Mg of the desired product as a white solid: $^1$H NMR (400 MHz, CDCl$_3$) δ 10.37 (s, 1H), 8.17 (d, 1H), 7.42 (d, 1H).

Preparation of 6-choloro-pyrazolo[3,4-b]pyridine: To a solution of 2,6-dichloro-3-formylpyridine (0.89 Mmol, 1 eq.) in 3 mL THF was added hydrazine (1.06 Mmol, 1.2 eq.) at rt. The resultant solution was heated at 120° C. in sealed tube for overnight. The solvent was removed in vacuo, and the residue was dry loaded on silica gel column. Purification by silica gel chromatography provide 29.5 Mg final product: HPLC retention time=2.17 minutes (Agilent Zorbax SB-C18, 2.1×50 Mm, 5μ, 35° C.) using 1 mL/min flow rate, a 2.5 minute gradient of 0% to 100% B with a 1.1 minute wash at 100% B (A=0.1% formic acid/5% acetonitrile/94.9% water, B=0.1% formic acid/5% water/94.9% acetonitrile); MS (ES) M+H expect=154.0, found=154.0.

Synthesis of 1-[4-(4-chloro-3-methoxy-phenyl)-piperazin-1-yl]-2-(6-chloro-pyrazolo[3,4-b]pyridine-1-yl)-ethanone and 1-[4-(4-chloro-3-methoxy-phenyl)-piperazin-1-yl]-2-(6-chloro-pyrazolo[3,4-b]pyridine-2-yl)-ethanone:

The two title compounds were synthesized according to the standard coupling procedure described in Example 6: For 1-[4-(4-chloro-3-methoxy-phenyl)-piperazin-1-yl]-2-(6-chloro-pyrazolo[3,4-b]pyridine-1-yl)-ethanone; $^1$H NMR (400 MHz, CDCl$_3$) δ 8.08 (s, 1H), 8.01 (d, 1H), 7.25 (d, 1H), 7.16 (d, 1H), 6.50 (d, 1H), 6.45 (dd, 1H), 5.40 (s, 2H), 3.90 (s, 3H), 3.77 (m, 4H), 3.23 (m, 4H). LCMS observed for (M+H)$^+$: 420.5: For 1-[4-(4-chloro-3-methoxy-phenyl)-piperazin-1-yl]-2-(6-chloro-pyrazolo[3,4-b]pyridine-2-yl)-ethanone: HPLC retention time=1.66 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile). LCMS observed for (M+H)$^+$: 420.5.

Example 48

Synthesis of 1-[4-(4-chloro-3-methoxy-phenyl)-piperazin-1-yl]-2-(6-azido-pyrazolo[3,4-d]pyridine-1-yl)-ethanone

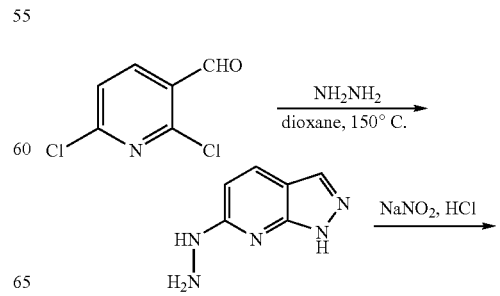

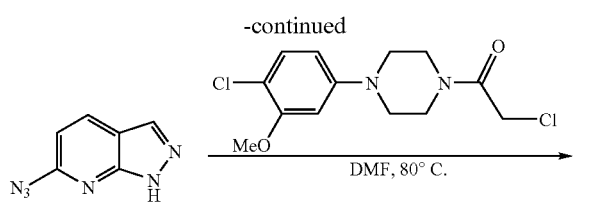

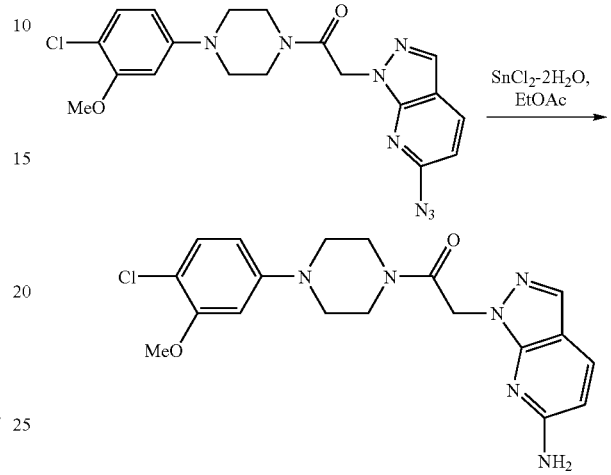

Example 49

Synthesis of 1-[4-(4-chloro-3-methoxy-phenyl)-piperazin-1-yl]-2-(6-amido-pyrazolo[3,4-b]pyridine-1-yl)-ethanone Preparation of 1H-6-hydrazo-pyrazolo[3,4-d]pyridine: To a solution of 2,6-dichloro-3-pyridinecarbaldehyde in 2 mL of dioxane was added excess amount of hydrazine. The resultant solution was heated at 150° C. overnight. Upon cooling to rt, the desired product precipitated out of solution as a white solid. The crude product was isolated by filtration, washed with a small amount of dioxane, and dried in vacuo. The crude product was used without further purification: HPLC retention time=1.78 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=337.9, found=337.9.

Preparation of 1H-6-azido-pyrazolo[3,4-d]pyridine: 1H-6-hydrazo-pyrazolo[3,4-d]pyridine was suspended into a mixture of 5 mL of concentrated HCl and 10 mL of water at 0° C., and to it was added dropwise a solution of sodium nitrate in 5 mL of water. The resultant mixture was stirred at 0° C. for 10 min and warmed to rt. The reaction mixture was neutralized to pH=7~8, and extracted with (200 mL×2) EtOAc. The combined organic extract was washed with brine, dried over sodium sulfate, filtered and concentrated in vacuo to provide the desired product which was used without further purification: HPLC retention time=0.50 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=161.0, found=160.8.

Synthesis of 1-[4-(4-chloro-3-methoxy-phenyl)-piperazin-1-yl]-2-(6-azido-pyrazolo[3,4-d]pyridine-1-yl)-ethanone: The title compound was synthesized according to alkylation protocol described in Example 6: HPLC retention time=2.22 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=427.1, found=427.1.

To a solution of 1-[4-(4-chloro-3-methoxy-phenyl)-piperazin-1-yl]-2-(6-azido-pyrazolo[3,4-b]pyridine-1-yl)-ethanone (0.071 Mmol, 1 eq.) in 1 mL of EtOAc was added SnCl$_2$·2H$_2$O as a solid. The resultant mixture was heated at 40° C. for 2 h. The resultant mixture was cooled to rt and diluted with 200 mL of EtOAc and 50 mL of Sat. sodium bicarbonate aq. solution. The diluted mixture was stirred for an additional 1 h, before the organic layer was separated, washed with brine, and dried over sodium sulfate. The solvent was removed in vacuo, and the residue was purified by HPLC to provide 10 Mg title compound: $^1$H NMR (400 MHz, CDCl$_3$) δ 7.86 (s, 1H), 7.74 (d, 1H), 7.24 (d, 1H), 7.20 (d, 1H), 6.45 (d, 1H), 6.39 (dd, 1H), 5.16 (s, 2H), 3.88 (s, 3H), 3.89 (m, 4H), 3.13 (m, 4H). LCMS observed for (M+H)$^+$: 401.1.

Example 50

Synthesis of 1-[4-(4-chloro-3-methoxy-phenyl)-piperazin-1-yl]-2-(7-amino-pyrazolo[3,4-c]pyridine-1-yl)-ethanone

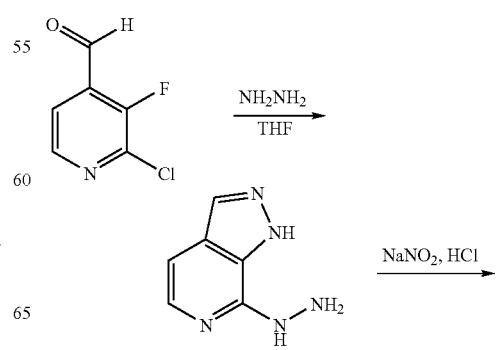

6.45 (d, 1H), 6.39 (dd, 1H), 5.16 (s, 2H), 3.88 (s, 3H), 3.89 (m, 4H), 3.13 (m, 4H). LCMS observed for (M+H)⁺: 401.1.

Example 51

Synthesis of 1-[4-(4-chloro-3-methoxy-phenyl)-piperazin-1-yl]-2-[3-(oxazole-2yl)-pyrazolo[3,4-b]pyridine-2-yl]-ethanone

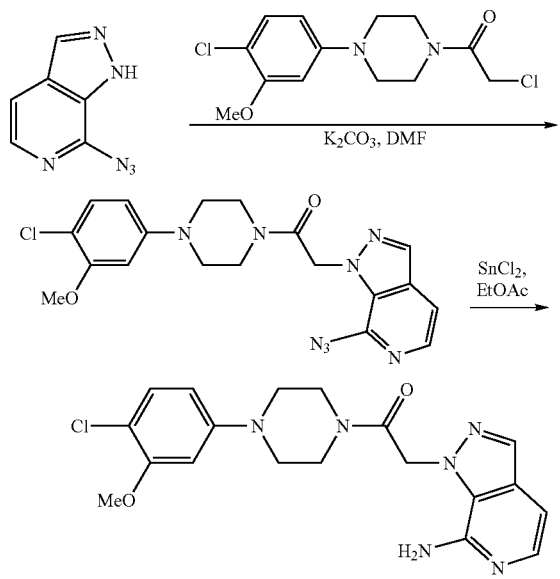

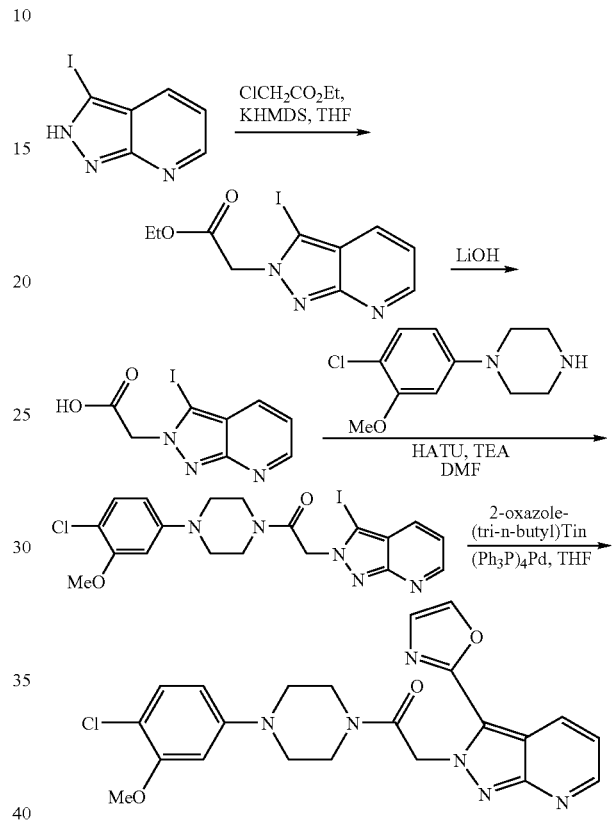

Preparation of 7-hydrazo-pyrazolo[3,4-c]pyridine: To a solution of 2-chloro-3-fluoro-4-formylpyridine (5.75 Mmol, 1 eq.) in 20 mL of THF was added 1 mL of hydrazine (excess). The resultant solution was heated at 110° C. in sealed tube for 5 h. The reaction was cooled to rt and solvent was removed in vacuo. The crude residue was washed several times with hexane, EtOAc, and dried in vacuo to provide a light yellow solid, which was used without further purification: HPLC retention time=0.20 minutes (Agilent Zorbax SB-C18, 2.1× 50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=150.1, found=150.0.

Preparation of 7-azido-pyrazolo[3,4-c]pyridine: This compound was synthesized according to protocol described in Example 48: HPLC retention time=0.26 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=161.0, found=160.9.

Preparation of 1-[4-(4-chloro-3-methoxy-phenyl)-piperazin-1-yl]-2-(7-azido-pyrazolo[3,4-c]pyridine-2-yl)-ethanone: This compound was synthesized according to protocol described in Example 6: HPLC retention time=2.43 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/ 94.9% acetonitrile); MS (ES) M+H expect=427.1, found=427.2.

Synthesis of 1-[4-(4-chloro-3-methoxy-phenyl)-piperazin-1-yl]-2-(7-amino-pyrazolo[3,4-c]pyridine-1-yl)-ethanone: The title compound was synthesized according to the procedure outlined in Example 49: ¹H NMR (400 MHz, CDCl₃) δ 7.86 (s, 1H), 7.74 (d, 1H), 7.24 (d, 1H), 7.20 (d, 1H), Preparation of (3-iodo-pyrazolo[3,4-b]pyridine-2-yl)acetic acid ethyl ester: To a solution of 3-Iodo-2H-pyrazolo[3,4-b]pyridine (4 Mmol, 1 eq.) in 10 mL of dry THF was added dropwise 0.5 M KHMDS (potassium hexamethyldisilazide) in toluene (4.4 Mmol, 1.1 eq.) at −78° C., under nitrogen atmosphere, and the resultant solution was stirred at for 30 minutes at −78° C. Chloro ethyl acetate (8 Mmol, 2 eq.) was added dropwise to the reaction solution and the reaction solution was warmed to rt over 1.5 hour and stirred overnight. Following an aqueous workup, the crude product was purified by silica gel chromatography (20% EtOAc in hexane to 70% EtOAc in hexane) to provide 70.2 Mg of (3-iodo-pyrazolo[3, 4-b]pyridine-2-yl)acetic acid ethyl ester: HPLC retention time=2.63 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expect=332.0, found=332.1.

Preparation of (3-iodo-pyrazolo[3,4-b]pyridine-2-yl)acetic acid: This compound was synthesized according to the standard ester hydrolysis protocol as described in Example 30 using 1N LiOH as the base. The crude product was used in the next step without purification: HPLC retention time=1.02 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expect=303.0, found=303.5.

Preparation of 1-[4-(4-chloro-3-methoxy-phenyl)-piperazin-1-yl]-2-(3-iodo-pyrazolo[3,4-b]pyridine-2-yl)-ethanone: This compound was synthesized according to standard peptide coupling protocol using HATU as the coupling reagent: HPLC retention time=297 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expect=512.0, found=512.5.

Synthesis of 1-[4-(4-chloro-3-methoxy-phenyl)-piperazin-1-yl]-2-[3-(oxazole-2-yl)-pyrazolo[3,4-b]pyridine-2-yl]-ethanone: To a mixture of 1-[4-(4-chloro-3-methoxy-phenyl)-piperazin-1-yl]-2-(3-iodo-pyrazolo[3,4-b]pyridine-2-yl)-ethanone (0.071 Mmol, 1 eq.) and tetrakis triphenylphosphine palladium (0.025 Mmol, 0.35 eq.) under nitrogen atmosphere was added 0.5 mL of THF and 2-oxazole-(tri-n-butyl)Tin (0.48 Mmol, 6.7 eq.). The resultant mixture was heated in a sealed tube at 80° C. for 48 h. The reaction solution was cooled to rt, diluted with 30 mL of NH$_4$Cl sat. aq. solution, and extracted with 300 mL of EtOAc. The organic layer was separated, washed with brine, dried over sodium sulfate, filtered and concentrated in vacuo. The crude residue was purified by silica gel chromatography (0% to 15% MeOH in EtOAc) to provide 12.3 Mg the title compound: $^1$H NMR (400 MHz, CDCl$_3$) δ 8.77 (dd, 1H), 8.51 (dd, 1H), 7.81 (d, 1H), 7.22 (m, 3H), 6.52 (d, 1H), 6.48 (dd, 1H), 6.01 (s, 2H), 3.90 (s, 3H), 3.80 (m, 4H), 3.27 (m, 4H). LCMS observed for (M+H)$^+$: 453.5.

Example 52

Synthesis of 1-[4-(4-chloro-3-methoxy-phenyl)-piperazin-1-yl]-2-(5-amino-pyrazolo[3,4-b]pyridine-1-yl]-ethanone

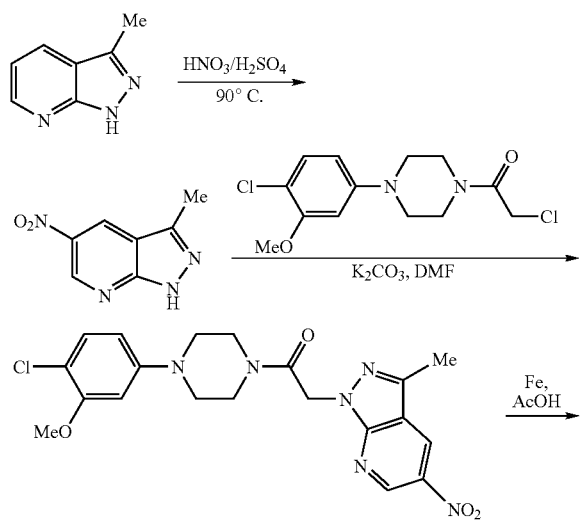

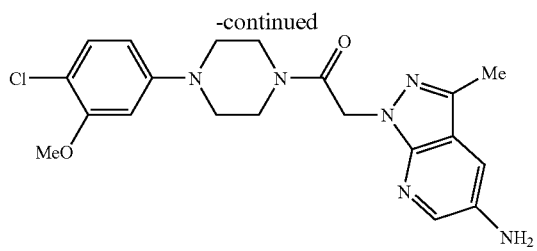

Preparation of 3-methyl-5-nitro-pyrazolo[3,4-b]pyridine: 3-Methyl-pyrazolo[3,4-b]pyridine (1 Mmol, 1 eq.) was suspended into a mixture of 1:1 fuming nitric acid and concentrated sulfuric acid (1 mL:1 mL), and the resultant mixture was heated at 90° C. for 30 minutes. The reaction mixture was then cooled to rt, and poured into a mixture of sodium bicarbonate and ice. The resultant solution was warmed up to rt and extracted with 300 mL of EtOAc. The organic extract was separated, washed with brine, dried over sodium sulfate, filtered, and concentrated in vacuo. The crude residue was purified by silica gel chromatography to provide 70.2 Mg of 3-methyl-5-nitro-pyrazolo[3,4-b]pyridine.

Preparation of 1-[4-(4-chloro-3-methoxy-phenyl)-piperazin-1-yl]-2-(5-nitro-pyrazolo[3,4-b]pyridine-1-yl]-ethanone: This compound was synthesized from 3-methyl-5-nitro-pyrazolo[3,4-b]pyridine according to the alkylation protocol described in Example 6: HPLC retention time=1.46 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=445.1, found=445.1.

Synthesis of 1-[4-(4-chloro-3-methoxy-phenyl)-piperazin-1-yl]-2-(5-amino-pyrazolo[3,4-b]pyridine-1-yl]-ethanone: 1-[4-(4-chloro-3-methoxy-phenyl)-piperazin-1-yl]-2-(5-nitro-pyrazolo[3,4-b]pyridine-1-yl]-ethanone (15 Mg) is combined with 200 Mg of iron powder in 2 mL of acetic acid at 100° C. for 30 min. After cooling to rt, the reaction solution was diluted with EtOAc and filtered. The filtrate was evaporated in vacuo and purified by HPLC to provide 1-[4-(4-chloro-3-methoxy-phenyl)-piperazin-1-yl]-2-(5-amino-pyrazolo[3,4-b]pyridine-1-yl]-ethanone: HPLC retention time=1.46 minutes (Agilent Zorbax SB-C18, 2.1×50 Mm, 5µ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=414.2, found=415.1.

Example 53

Synthesis of 1-[4-(4-chloro-3-methoxy-phenyl)-piperazin-1-yl]-2-[3-amino-6-methyl-pyrazolo[3,4-b]pyridine-1-yl]-ethanone

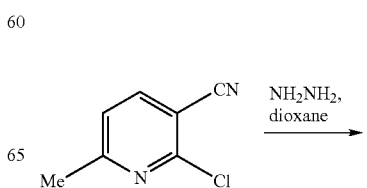

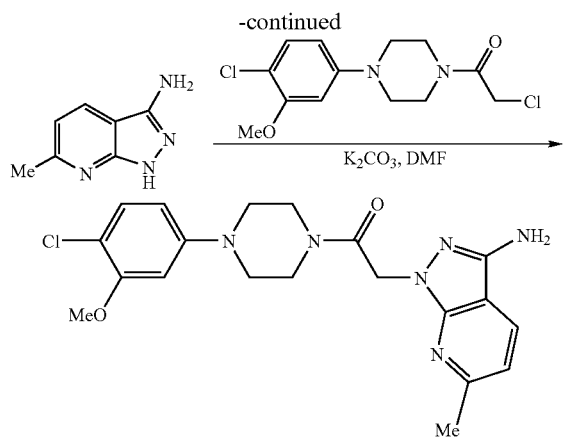

Preparation of 1H-3-amino-6-methyl-pyrazolo[3,4-d]pyridine: This compound was synthesized according to the cyclization procedure using hydrazine described in Example 3 and the crude product was used in the next step without further purification.

Synthesis of 1-[4-(4-chloro-3-methoxy-phenyl)-piperazin-1-yl]-2-[3-amino-6-methyl-pyrazolo[3,4-b]pyridine-1-yl]-ethanone: This compound was synthesized according to the standard coupling procedure described in Example 6: ¹H NMR (400 MHz, CDCl₃) 7.75 (d, 1H), 7.22 (d, 1H), 6.86 (d, 1H), 6.48 (d, 1H), 6.42 (dd, 1H), 5.18 (s, 2H), 3.89 (s, 3H), 3.75 (m, 4H), 3.16 (m, 4H), 2.62 (s, 3H). LCMS observed for (M+H)⁺: 415.5.

Example 54

Synthesis of 1-[(S)-4-(4-Chloro-2-fluoro-5-methoxy-phenyl)-2-methyl-piperazin-1-yl]-2-(3-[1,2,4]oxadiazol-3-yl-pyrazolo[3,4-b]pyridin-1-yl)ethanone

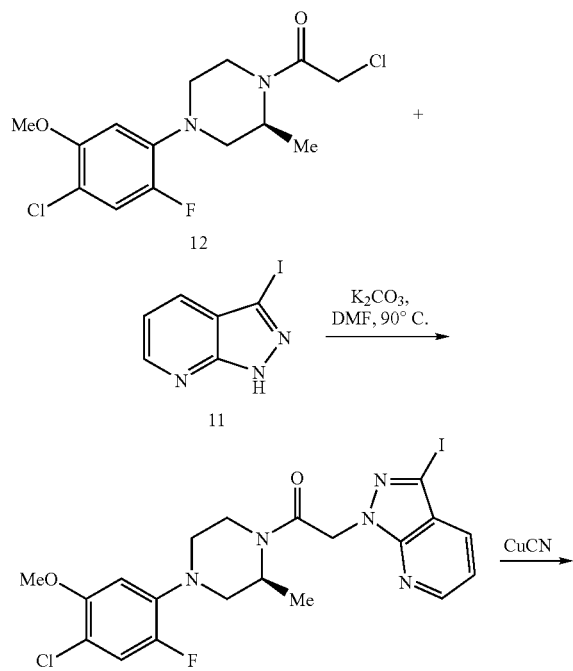

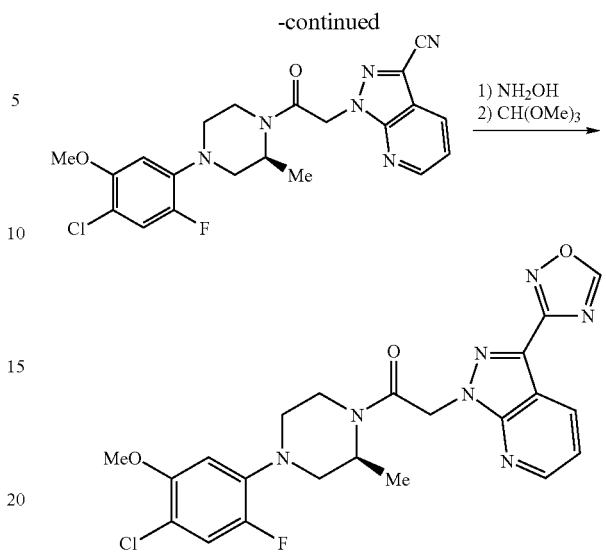

Preparation of 1-[(S)-4-(4-Chloro-2-fluoro-5-methoxy-phenyl)-2-methyl-piperazin-1-yl]-2-(3-iodo-pyrazolo[3,4-b]pyridin-1-yl)-ethanone: A mixture of 2-Chloro-1-[(S)-4-(4-chloro-2-fluoro-5-methoxy-phenyl)-2-methyl-piperazin-1-yl]-ethanone (1.37 g, 4.08 Mmol, 1 eq), 3-Iodo-1H-pyrazolo[3,4-b]pyridine (1.0 g, 4.08 Mmol, 1 eq), potassium carbonate (2.26 g, 16.4 Mmol, 4 eq), and DMF (15 mL) was stirred overnight at 90° C. The reaction solution was diluted with ethyl acetate, washed with saturated aqueous NaHCO₃, and concentrated in vacuo. The crude product was purified by flash chromatography to provide 1-[(S)-4-(4-Chloro-2-fluoro-5-methoxy-phenyl)-2-methyl-piperazin-1-yl]-2-(3-iodo-pyrazolo[3,4-b]pyridin-1-yl)-ethanone (2.2 g).

Preparation of 1-{2-[4-(4-Chloro-2-fluoro-5-methoxy-phenyl)-2-(S)-methyl-piperazin-1-yl]-2-oxo-ethyl}-1H-pyrazolo[3,4-b]pyridine-3-carbonitrile: A mixture of 1-[(S)-4-(4-Chloro-2-fluoro-5-methoxy-phenyl)-2-methyl-piperazin-1-yl]-2-(3-iodo-pyrazolo[3,4-b]pyridin-1-yl)-ethanone (2.2 g, 4.0 Mmol, 1 eq), CuCN (3.6 g, 40 Mmol, 10 eq), and DMF (25 mL) was stirred at 175° C. for 1 hrs. The reaction mixture was cooled to rt, diluted with ethyl acetate and filtered. The filtrate was washed with water, dried over Na₂SO₄, and purified by flash chromatography to provide 1-{2-[4-(4-Chloro-2-fluoro-5-methoxy-phenyl)-2-(S)-methyl-piperazin-1-yl]-2-oxo-ethyl}-1H-pyrazolo[3,4-b]pyridine-3-carbonitrile (1.6 g).

Preparation of 1-{2-[4-(4-Chloro-2-fluoro-5-methoxy-phenyl)-2-methyl-piperazin-1-yl]-2-oxo-ethyl}-N-hydroxy-1H-pyrazolo[3,4-b]pyridine-3-carboxamidine: A mixture of 1-{2-[4-(4-Chloro-2-fluoro-5-methoxy-phenyl)-2-(S)-methyl-piperazin-1-yl]-2-oxo-ethyl}-1H-pyrazolo[3,4-b]pyridine-3-carbonitrile (1.6 g, 3.6 Mmol, 1 eq), NH₂OH.HCl (0.84 g, 10.8 mmol, 3 eq), TEA (1.5 mL), and ethanol (10 mL) was stirred at 65° C. overnight. The reaction solution was concentrated in vacuo, and dissolved in ethyl acetate, washed with brine, and concentrated to provide 1-{2-[4-(4-Chloro-2-fluoro-5-methoxy-phenyl)-2-methyl-piperazin-1-yl]-2-oxo-ethyl}-N-hydroxy-1H-pyrazolo[3,4-b]pyridine-3-carboxamidine (1.2 g).

Preparation of 1-[(S)-4-(4-Chloro-2-fluoro-5-methoxy-phenyl)-2-methyl-piperazin-1-yl]-2-(3-[1,2,4]oxadiazol-3-yl-pyrazolo[3,4-b]pyridin-1-yl)-ethanone: A mixture of 1-{2-[4-(4-Chloro-2-fluoro-5-methoxy-phenyl)-2-methylpiperazin-1-yl]-2-oxo-ethyl}-N-hydroxy-1H-pyrazolo[3,4-b]pyridine-3-carboxamidine (1.2 g), trimethyl orthoformate (20 mL) and para-toluene sulfonic acid (PTSA) (0.1 g) was stirred at 100° C. overnight. The reaction mixture was concentrated in vacuo to provide a crude residue which was purified by flash chromatography to provide 1-[(S)-4-(4-Chloro-2-fluoro-5-methoxy-phenyl)-2-methyl-piperazin-1-yl]-2-(3-[1,2,4]oxadiazol-3-yl-pyrazolo[3,4-b]pyridin-1-yl)-ethanone (0.7 g). LCMS Retention time: 2.61 min (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile). LCMS observed for (M+H)$^+$: 486.

Example 55

Synthesis of 1-[4-(4-chloro-3-methoxy-phenyl)-piperazin-1-yl]-2-(3-cyano-pyrazolo[3,4-b]pyridine-1-yl)-ethanone

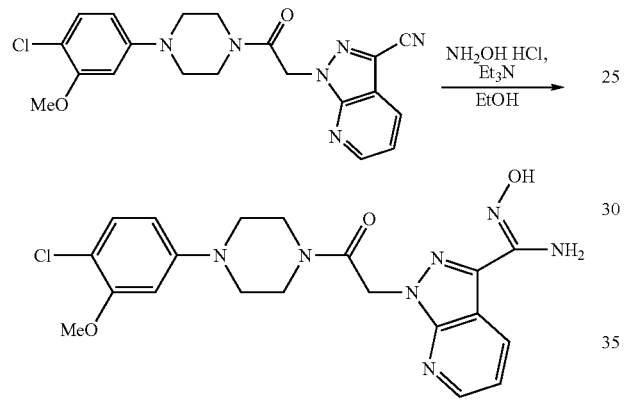

A solution of 1-[4-(4-chloro-3-methoxy-phenyl)-piperazin-1-yl]-2-(3-cyano-pyrazolo[3,4-b]pyridine-1-yl)-ethanone (0.15 Mmol, 1 eq.) and hydroxyl amine HCl salt (0.45 Mmol, 3 eq.) in 2.5 mL of EtOH was heated at 60° C. for 1 h. The reaction mixture was cooled to rt, and concentrated in vacuo. The crude residue was dissolved with 200 mL of dichloromethane, washed with 50 mL of 5% K$_2$CO$_3$ aq. solution, brine solution, dried over sodium sulfate, filtered and concentrated in vacuo to provide the desired product as a white solid: HPLC retention time=1.61 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.1% formic acid/5% water/94.9% acetonitrile); MS (ES) M+H expect=444.1, found=444.5.

Example 56

Synthesis of 1-[4-(4-chloro-3-methoxy-phenyl)-piperazin-1-yl]-2-[3-(oxadiazole-3-yl)-pyrazolo[3,4-b]pyridine-1-yl]-ethanone

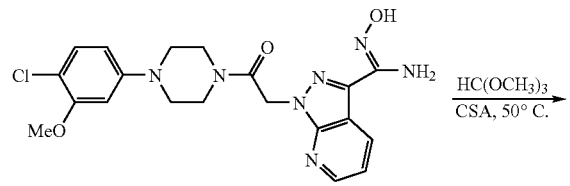

-continued

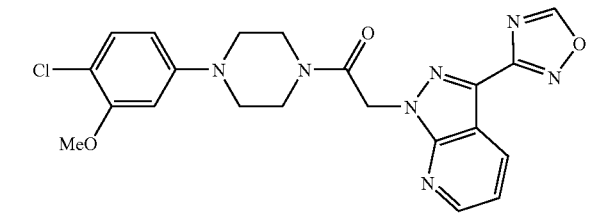

To a suspension of (0.067 Mmol, 1 eq.) of 1-[4-(4-chloro-3-methoxy-phenyl)-piperazin-1-yl]-2-(3-cyano-pyrazolo[3,4-b]pyridine-1-yl)-ethanone in 2 mL of trimethylorthoformate was added camphorsulfonic acid (CSA) (5.0 Mg, catalytic amount). The resultant mixture was heated at 50° C. for 10 minutes and cooled to rt. The reaction solution was concentration in vacuo to provide a crude residue which was purified by HPLC chromatography to provide 20.0 Mg of the title compound: $^1$H NMR (400 MHz, CDCl$_3$) δ 8.83 (s, 1H), 8.62 (dd, 1H), 7.35 (dd, 1H), 7.22 (d, 1H), 6.51 (d, 1H), 6.44 (dd, 1H), 5.59 (s, 2H), 3.89 (s, 3H), 3.79 (m, 4H), 3.23 (m, 4H). LCMS observed for (M+H)$^+$: 454.5.

Example 57

Synthesis of 1-[4-(4-chloro-3-methoxy-phenyl)-piperazin-1-yl]-2-[3-(5-methyl-oxadiazole-3-yl)-pyrazolo[3,4-b]pyridine-1-yl]-ethanone

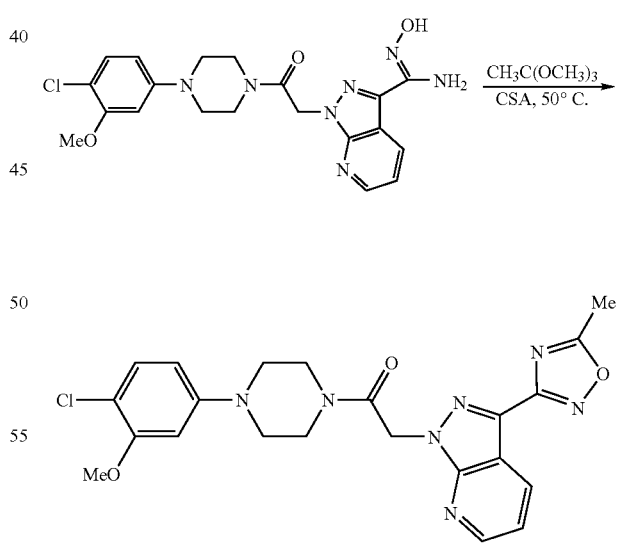

The title compound was synthesized according to the cyclization procedure using trimethylorthoacetate as described in Example 56: $^1$H NMR (400 MHz, CDCl$_3$) δ 8.61 (dd, 1H), 7.31 (dd, 1H), 7.22 (d, 1H), 6.54 (d, 1H), 6.42 (dd, 1H), 5.57 (s, 2H), 3.89 (s, 3H), 3.77 (m, 4H), 3.21 (m, 4H), 2.69 (s, 1H). LCMS observed for (M+H)$^+$: 468.5.

Example 58

Synthesis of 1-[4-(4-chloro-3-methoxy-phenyl)-piperazin-1-yl]-2-(6-acetimido-pyrazolo[3,4-b]pyridine-1-yl)-ethanone

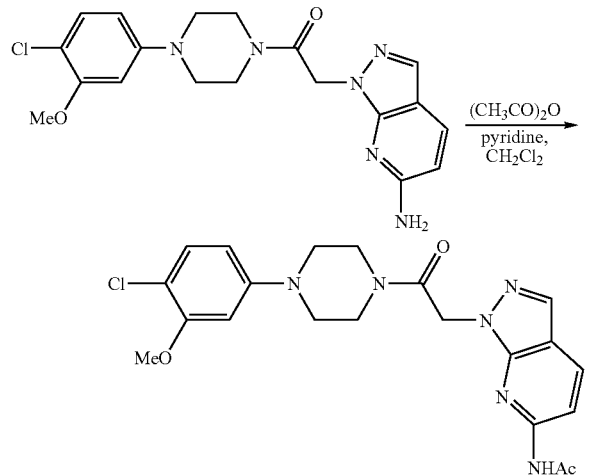

1-[4-(4-chloro-3-methoxy-phenyl)-piperazin-1-yl]-2-(6-amido-pyrazolo[3,4-b]pyridine-1-yl)-ethanone, acetic anhydride (1.2 equiv) and pyridine (3 equiv) was combined in DCM at rt for 30 min: HPLC retention time=1.82 minutes (Agilent Zorbax SB-C18, 2.1×50 Mm, 5μ, 35° C.) using 1 mL/min flow rate, a 2.5 minute gradient of 20% to 100% B with a 1.1 minute wash at 100% B (A=0.1% formic acid/5% acetonitrile/94.9% water, B=0.08% formic acid/5% water/94.9% acetonitrile); MS (ES) M+H expect=443.1, found = 442.8.

Example 59

Synthesis of 1-[4-(4-chloro-3-methoxy-phenyl)-piperazin-1-yl]-2-(3-methylsulfonyl-pyrazolo[4,3-c]pyridine-1-yl)-ethanone

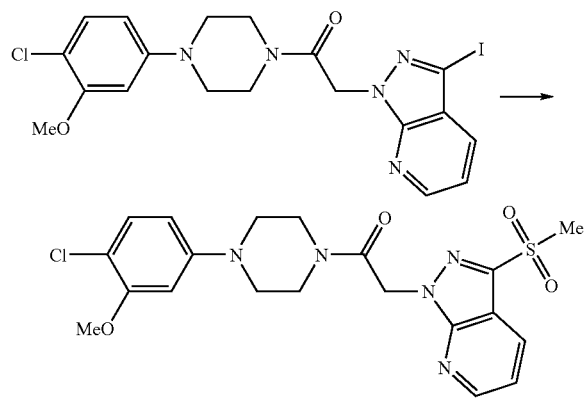

The title compound was synthesized from 1-[4-(4-Chloro-3-methoxy-phenyl)-piperazin-1-yl]-2-(3-iodo-pyrazolo[3,4-b]pyridin-1-yl)-ethanone according to the protocol described in Example 41: $^1$H NMR (400 MHz, CDCl$_3$) 8.65 (d, 1H), 8.48 (d, 1H), 7.39 (dd, 1H), 7.22 (d, 1H), 6.51 (s, 1H), 6.44 (d, 1H), 5.53 (s, 2H), 3.91 (s, 3H), 3.78 (m, 4H), 3.34 (s, 3H), 3.22 (m, 4H), LCMS observed for (M+H)$^+$: 415.0.

Example 60

Synthesis of 1-[4-(4-Chloro-2-fluoro-5-methoxy-phenyl)-piperazin-1-yl]-2-(3-oxazol-2-yl-pyrazolo[3,4-b]pyridin-1-yl)-ethanone

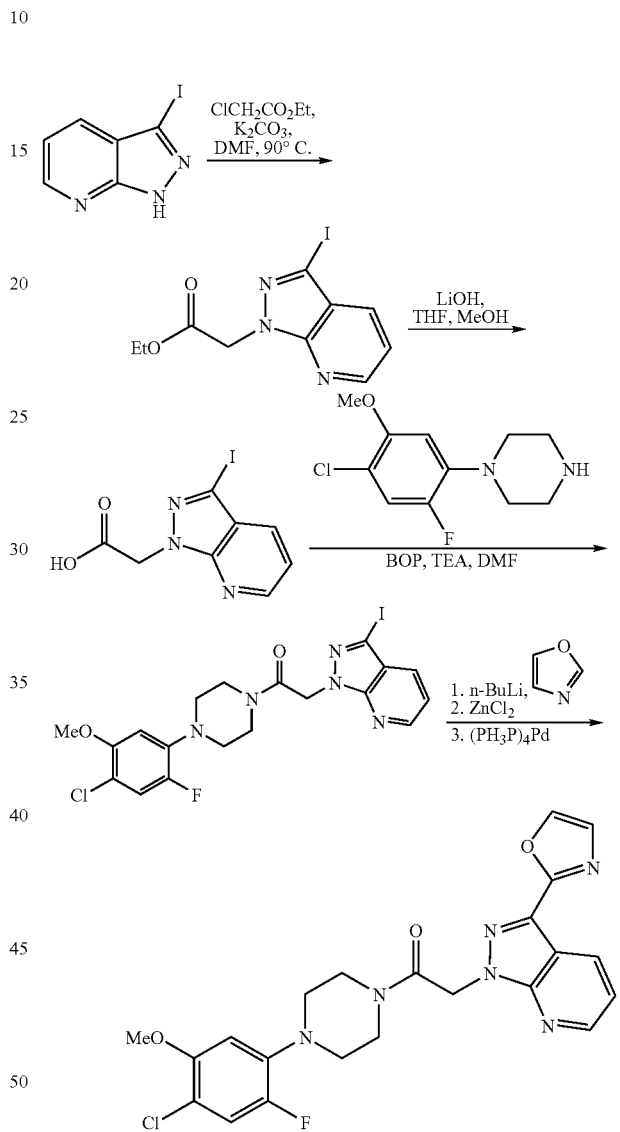

Preparation of Ethyl (3-Iodo-pyrazolo[3,4-b]pyridin-1-yl)-acetate: To a mixture of 3-iodo-1H-pyrazolo[3,4-b]pyridine (9.8 g, 40 Mmol, 1 equiv) and potassium carbonate (27.6 g, 5 equiv) in 15 mL of DMF at 90° C. was added ethyl chloroacetate (8.5 mL, 40 Mmol, 1 equiv). Two hours later, the reaction mixture was diluted with ethyl acetate followed by washing with saturated aqueous NaHCO$_3$. The organic layer was dried and concentrated to provide the crude product. Purification of the crude product by flash chromatography gave ethyl (3-Iodo-pyrazolo[3,4-b]pyridin-1-yl)-acetate (11 g).

Preparation of (3-iodo-pyrazolo[3,4-b]pyridin-1-yl)-acetic acid: Ethyl (3-Iodo-pyrazolo[3,4-b]pyridin-1-yl)-acetate (11 g, 33 Mmol, 1 equiv) was dissolved in 50 mL of THF and 50 mL of MeOH to the solution was added 40 mL of 1N LiOH for 3 h. The organic solvents were evaporated and the remaining aqueous phase was neutralized with 1N HCl to a pH of about 1 which resulted in the precipitation of the desired product as a white solid was filtered and air dried to give (3-iodo-pyrazolo[3,4-b]pyridin-1-yl)-acetic acid.

Preparation of 1-[4-(4-Chloro-2-fluoro-5-methoxy-phenyl)-piperazin-1-yl]-2-(3-iodo-2-yl-pyrazolo[3,4-b]pyridin-1-yl)-ethanone: A mixture of (3-iodo-pyrazolo[3,4-b]pyridin-1-yl)-acetic acid (3.03 g, 10 Mmol, 1 equiv), 1-(4-Chloro-2-fluoro-5-methoxy-phenyl)-piperazine (2.45 g, 1 equiv), BOP reagent (4.86 g, 1 equiv), triethylamine (4.2 mL, 3 equiv) in 10 mL of MF was stirred at rt overnight. To the reaction mixture was then added water and the solid precipitates were removed by filtration and air dried to give 1-[4-(4-Chloro-2-fluoro-5-methoxy-phenyl)-piperazin-1-yl]-2-(3-iodo-2-yl-pyrazolo[3,4-b]pyridin-1-yl)-ethanone. LCMS (ES) observed for M+H 530.0.

Synthesis of 1-[4-(4-Chloro-2-fluoro-5-methoxy-phenyl)-piperazin-1-yl]-2-(3-oxazol-2-yl-pyrazolo[3,4-b]pyridin-1-yl)-ethanone: To a solution of oxazole (690 Mg 10 mmol, 2.5 equiv) in tetrahydrofuran (5 mL) under nitrogen atmosphere, was added dropwise n-butyl lithium (2.5 M in Hexane, 4.8 mL, 3 equiv.). The resultant mixture was stirred at −78° C. for an additional 60 min followed by the addition of $ZnCl_2$ (0.5 M in THF, 32 mL, 4 equiv.). The reaction solution was allowed to warm to 0° C. and stirred 1 h followed by the addition of 1-[4-(4-Chloro-2-fluoro-5-methoxy-phenyl)-piperazin-1-yl]-2-(3-iodo-2-yl-pyrazolo[3,4-b]pyridin-1-yl)-ethanone (2.12 g, 4 Mmol, 1 equiv) and palladium tetrakis(triphenylphosphine) (462 Mg, 0.1 equiv). The reaction mixture was then heated to reflux for 12 hr, cooled to room temperature and diluted with ethyl acetate. The reaction mixture was washed with water, brine, dried over sodium sulfate, and concentrated in vacuo to provide the crude product. Purification by flash chromatography provided of the desired product 1-[4-(4-Chloro-2-fluoro-5-methoxy-phenyl)-piperazin-1-yl]-2-(3-oxazol-2-yl-pyrazolo[3,4-b]pyridin-1-yl)-ethanone as a white powder (1.03 g). LCMS (ES) observed for M+H 471.1. HPLC retention time=2.4 min (Agilent Zorbax SB-C18, 2.1×50 Mm, 5μ, 35° C., 1 mL/min flow rate, a 2.5 min gradient of 20% to 100% B with a 1.1 min wash at 100% B; A=0.1% formic acid/5% acetonitrile/94.9% water, B=0.1% formic acid/5% water/ 94.9% acetonitrile).

Example 61

Synthesis of 1-[4-(4-Chloro-5-ethoxy-2-fluorophenyl)piperazin-1-yl]-2-[3-(1H-imidazol-2-yl)-pyrazolo[3,4-b]pyridin-1-yl]ethanone

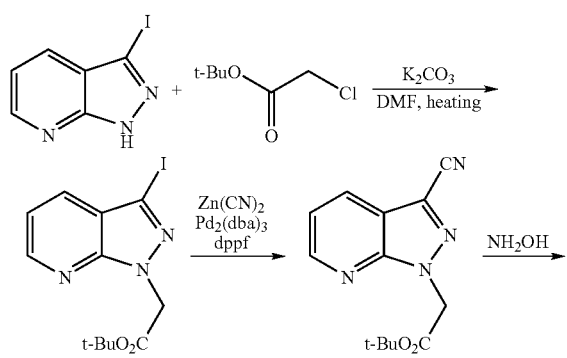

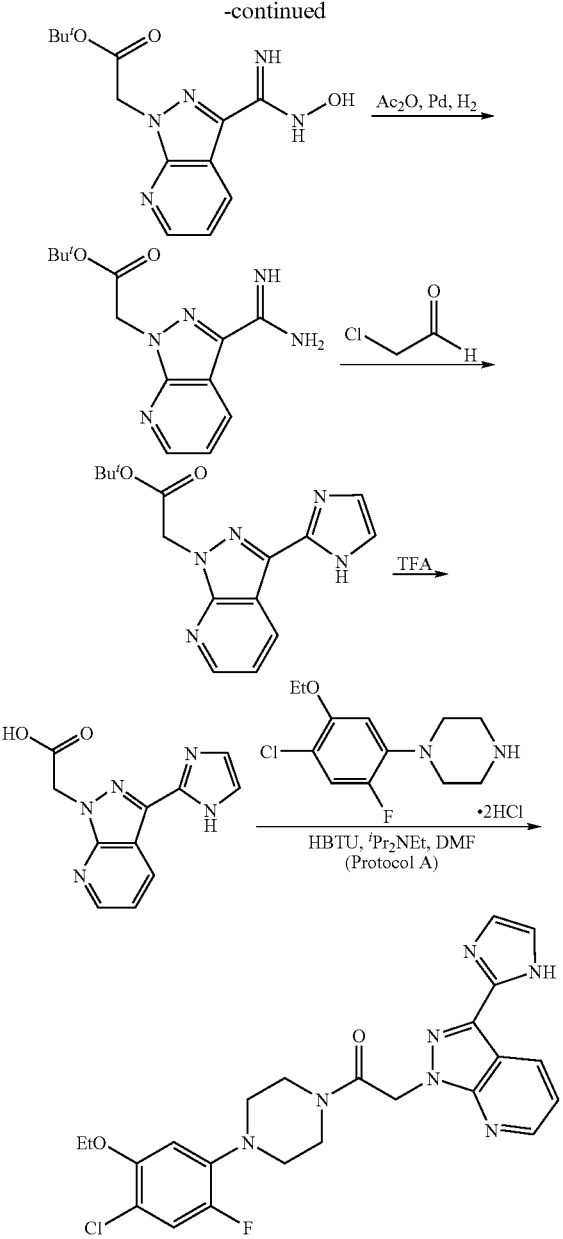

Step 1: A mixture of 3-iodo-7-azaindazole (25.50 g) and $K_2CO_3$ (41.4 g) in DMF (200 mL) was heated to 85° C. and t-butyl chloroacetate (14.3 mL) was slowly added. The mixture was stirred at this temperature for 1 hour (h), cooled to room temperature followed by the addition of water (300 mL). Filtration of the reaction mixture provided (3-iodo-pyrazolo[3,4-b]pyridin-1-yl)-acetic acid tert-butyl ester.

Step 2: A 250 mL flask was charged with (3-iodo-pyrazolo[3,4-b]pyridin-1-yl)-acetic acid tert-butyl ester (15.0 g), $PdCl_2$(dppf) (3.0 g), $Zn(CN)_2$ (4.96 g), DMF (200 mL) and $H_2O$ (14 mL). The flask containing the resultant suspension was degassed and backfilled with nitrogen gas repeatedly for 5 minutes, followed by addition of $Pd_2$(dba)$_3$ (3.85 g) to the reaction mixture. The reaction mixture was heated under $N_2$ at 90° C. for 16 h, cooled to room temperature, diluted with $H_2O$ (800 mL) and filtered. The collected solid was washed with toluene (10 mL) to provide (3-cyano-pyrazolo[3,4-b] pyridin-1-yl)-acetic acid tert-butyl ester as a yellow solid.

Step 3: A mixture of (3-cyano-pyrazolo[3,4-b]pyridin-1-yl)-acetic acid tert-butyl ester, hydroxylamine hydrochloride (8.28 g) and Et$_3$N (22.6 mL) in EtOH (120 mL) was heated over night under N$_2$ at 65° C. The mixture was cooled to room temperature, filtered and the collected solid was washed with H$_2$O (100 mL) and Et$_2$O (50 mL×2) to afforded [3-(N-hydroxycarbamimidoyl)-pyrazolo[3,4-b]pyridin-1-yl]-acetic acid tert-butyl ester.

Step 4: [3-(N-Hydroxycarbamimidoyl)-pyrazolo[3,4-b] pyridin-1-yl]-acetic acid tert-butyl ester (6.17 g) in a 100 mL vial was charged with AcOH (45 mL) and Ac$_2$O (4.3 mL). The resultant mixture was stirred at room temperature for 1 h at this time the initial suspension became a clear solution. To this solution was added Pd/C (10%, 900 Mg) and stirred under 1 atm H$_2$ balloon, and resultant mixture was stirred over night at room temperature. Filtration from celite washed with DCM/MeOH and evaporation gave (3-amidino-pyrazolo[3,4-b]pyridin-1-yl)-acetic acid tert-butyl ester which was used without further purification.

Step 5: (3-Amidino-pyrazolo[3,4-b]pyridin-1-yl)-acetic acid tert-butyl ester obtained above in a 100 mL vial was charged with chloroacetylaldehyde (5.72 mL), dioxane (50 mL) and K$_2$CO$_3$ (12.42 g). The resultant mixture was stirred at 80° C. for 4 h and more chloroacetylaldehyde (5.72 mL) and K$_2$CO$_3$ (12.42 g) were added. The mixture was stirred another 1 h at 80° C. and stirred at 120° C. for another 1 h, cooled to room temperature, diluted with dichloromethane (DCM), washed with brine, dried (Na$_2$SO$_4$), filtered and evaporated in vacuo. Purification by flash chromatography provided 2-(3-(1H-imidazol-2-yl)-1H-pyrazolo[3,4-b]pyridin-1-yl)acetic acid tert-butyl ester as a brown oil.

Step 6: 2-(3-(1H-imidazol-2-yl)-1H-pyrazolo[3,4-b]pyridin-1-yl)acetic acid tert-butyl ester (977 Mg) was dissolved in trifluoroacetic acid (TFA) (10 mL) and stirred at room temperature for 1 hr. The mixture was evaporated in vacuo to provide 2-(3-(1H-imidazol-2-yl)-1H-pyrazolo[3,4-b]pyridin-1-yl)acetic acid as a brown oil, which was used without further purification.

Step 7: (Protocol A—the HBTU coupling procedure) A solution of [3-(1H-imidazol-2-yl)-pyrazolo[3,4-b]pyridin-1-yl]acetic acid (0.30 M, 0.40 mL, 0.12 Mmol) was transferred to a vial. 1-(4-Chloro-5-ethoxy-2-fluorophenyl)piperazine dihydrochloride (48 mg, 0.14 Mmol), O-(benzotriazol-1-yl)-N,N,N',N'-tetramethyluronium hexafluorophosphate (HBTU) (55 Mg, 0.14 Mmol) and i-Pr$_2$NEt (0.30 mL) were added to the vial and the mixture was stirred at ambient temperature. After 30 minutes, LC/MS analysis indicated formation of desired product and complete consumption of the carboxylic acid starting material. The mixture was diluted with EtOAc, washed with water (1×) and brine (1×), dried over Na$_2$SO$_4$ and evaporated. The residue was purified by silica gel chromatography (1% to 8% MeOH in CH$_2$Cl$_2$) to provide 1-[4-(4-chloro-5-ethoxy-2-fluorophenyl)piperazin-1-yl]-2-[3-(1H-imidazol-2-yl)pyrazolo[3,4-b]pyridin-1-yl] ethanone as a tan solid: $^1$H NMR (CDCl$_3$, 400 MHz) δ 8.79 (dd, 0.6 H, J=8.4, 1.6 Hz), 8.66 (dd, 0.4 H, J=8.0, 1.6 Hz), 8.57-8.55 (m, 1H), 7.29-7.26 (m, 1H), 7.22-7.16 (m, 1H), 7.09-7.05 (m, 2H), 6.50-6.45 (m, 2H), 5.45 (s, 0.6H), 5.43 (s, 1.4H), 4.07-4.01 (m, 2H), 3.81-3.69 (m, 4H), 3.17-3.13 (m, 1.6H), 3.08-3.02 (m, 2.4H), 1.50-1.42 (m, 3H); LC/MS m/z (M+H)$^+$ 484.4.

Example 62

Synthesis of 1-{4-[4-Chloro-2-fluoro-5-(2-fluoroethoxy)-phenyl]piperazin-1-yl}-2-[3-(1H-imidazol-2-yl)-pyrazolo[3,4-b]pyridin-1-yl]ethanone

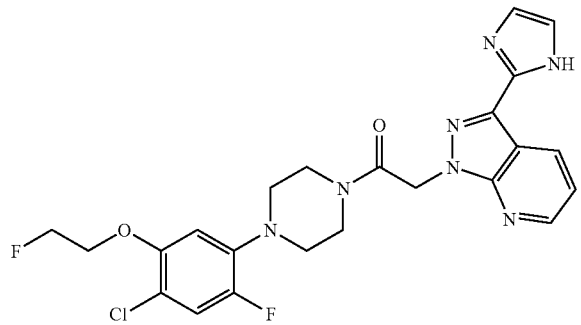

The title compound was prepared following Protocol A. 1-[4-Chloro-2-fluoro-5-(2-fluoroethoxy)phenyl]-piperazine dihydrochloride and [3-(1H-imidazol-2-yl)pyrazolo[3,4-b] pyridin-1-yl]acetic acid were used as the coupling components. The crude product was purified by silica gel chromatography (2% to 3.5% MeOH in CH$_2$Cl$_2$) to provide 1-{4-[4-chloro-2-fluoro-5-(2-fluoroethoxy)phenyl]piperazin-1-yl}-2-[3-(1H-imidazol-2-yl)pyrazolo[3,4-b]pyridin-1-yl] ethanone as a tan solid: $^1$H NMR (CDCl$_3$, 400 MHz) δ 8.79 (dd, 0.6H, J=8.0, 1.8 Hz), 8.67 (d, 0.4H, J=6.4 Hz), 8.57-8.55 (m, 1H), 7.30-7.25 (m, 1H), 7.11-7.06 (m, 2H), 6.63 (d, 0.6H, J=7.6 Hz), 6.57 (d, 0.4H, J=7.6 Hz), 6.54 (d, 1H, J=7.6 Hz), 5.45 (s, 0.7H), 5.43 (s, 1.3H), 4.83-4.80 (m, 1H), 4.71-4.68 (m, 1H), 4.31-4.18 (m, 2H), 3.82-3.76 (m, 3H), 3.50 (t, 1H, J=5.2 Hz), 3.23-3.04 (m, 4H); LC/MS m/z (M+H)$^+$ 502.4.

Example 63

Synthesis of 1-[4-(4-Chloro-3-ethoxyphenyl)piperazin-1-yl]-2-[3-(1H-imidazol-2-yl)pyrazolo[3,4-b]pyridin-1-yl]ethanone

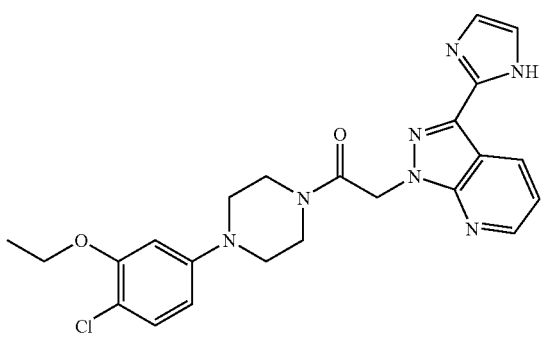

The title compound was prepared following Protocol A. 1-(4-Chloro-3-ethoxyphenyl)piperazine dihydrochloride and [3-(1H-imidazol-2-yl)pyrazolo[3,4-b]pyridin-1-yl]acetic acid were used as the coupling components. The crude product was purified by silica gel chromatography (4% to 15% MeOH in CH$_2$Cl$_2$) to provide 1-[4-(4-chloro-3-ethoxyphenyl)piperazin-1-yl]-2-[3-(1H-imidazol-2-yl)pyrazolo[3,4-b]pyridin-1-yl]ethanone as a tan solid (25 Mg): $^1$H NMR (CDCl$_3$, 400 MHz) δ 8.79 (dd, 0.6H), 8.66 (dd, 0.4H), 8.57-8.54 (m, 1H), 7.29-7.19 (m, 4H), 6.49-6.40 (m, 2H), 5.45 (s, 0.7H), 5.43 (s, 1.3H), 4.10-4.04 (m, 2H), 3.81-3.69 (m, 4H), 3.23-3.16 (m, 4H), 1.50-1.45 (m, 3H); LC/MS m/z (M+H)$^+$ 466.4.

Example 64

Synthesis of 1-[4-(4-Chloro-2-fluoro-5-methoxyphenyl)piperazin-1-yl]-2-[3-(1H-imidazol-2-yl)-pyrazolo[3,4-b]pyridin-1-yl]ethanone

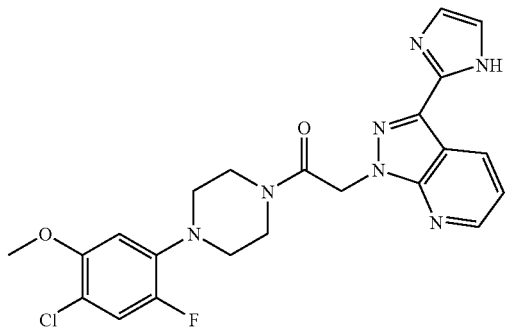

The title compound was prepared following Protocol A. 1-(4-Chloro-2-fluoro-5-methoxyphenyl)piperazine dihydrochloride and [3-(1H-imidazol-2-yl)-pyrazolo[3,4-b]pyridin-1-yl]-acetic acid were used as the coupling components. The crude product was purified by silica gel chromatography (1% to 10% MeOH in CH$_2$Cl$_2$) to provide 1-[4-(4-chloro-2-fluoro-5-methoxyphenyl)piperazin-1-yl]-2-[3-(1H-imidazol-2-yl)-pyrazolo[3,4-b]pyridin-1-yl]ethanone as a tan solid (27 Mg): $^1$H NMR (CDCl$_3$, 400 MHz) δ 8.79 (dd, 0.6H), 8.67 (dd, 0.4H), 8.57-8.55 (m, 1H), 7.31-7.20 (m, 2H), 7.12-7.06 (m, 2H), 6.49-6.45 (m, 1H), 5.45 (s, 0.6H), 5.43 (s, 1.4H), 3.86 (s, 0.9H), 3.85 (s, 2.1H), 3.81-3.75 (m, 4H), 3.15-3.08 (m, 4H); LC/MS m/z (M+H)$^+$ 470.4.

Example 65

Synthesis of 1-[(S)-4-(4-Chloro-3-methoxyphenyl)-2-methylpiperazin-1-yl]-2-[3-(1H-imidazol-2-yl)-pyrazolo[3,4-b]pyridin-1-yl]ethanone

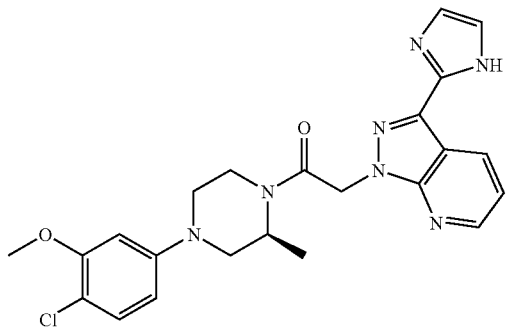

The title compound was prepared following Protocol A. (S)-1-(4-Chloro-3-methoxyphenyl)-3-methylpiperazine dihydrochloride and [3-(1H-imidazol-2-yl)pyrazolo[3,4-b]pyridin-1-yl]acetic acid were used as the coupling components. The crude product was purified by silica gel chromatography (1% to 8% MeOH in CH$_2$Cl$_2$) to provide 1-[(S)-4-(4-chloro-3-methoxyphenyl)-2-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.79 (dd, 0.6H), 8.66 (dd, 0.4H), 8.57-8.55 (m, 1H), 7.29-7.19 (m, 4H), 6.44-6.39 (m, 2H), 5.42 (br. s, 2H), 4.83 (br. s, 0.3H), 4.49 (br. s, 0.3H), 4.30 (br. s, 0.3H), 3.89 (s, 1.2H), 3.88 (s, 1.8H), 3.83 (br. s, 0.3H), 3.72-3.69 (m, 1H), 3.54-3.52 (m, 1H), 3.38 (br. s, 1H), 3.19-3.15 (m, 1H), 3.00 (br. s, 1H), 2.80 (br. s, 1H), 1.50-1.43 (m, 3H); LC/MS m/z (M+H)$^+$ 466.4.

Example 66

Synthesis of 1-[(S)-4-(4-Chloro-2-fluoro-5-methoxyphenyl)-2-methylpiperazin-1-yl]-2-[3-(1H-imidazol-2-yl)pyrazolo[3,4-b]pyridin-1-yl]ethanone

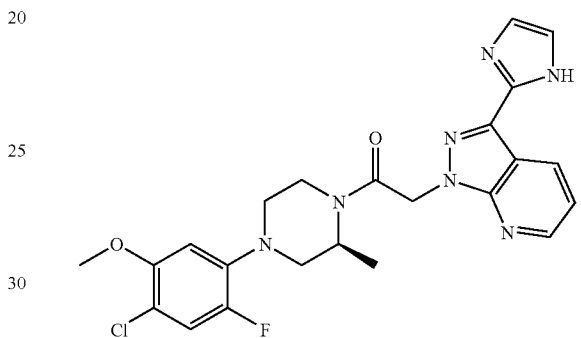

The title compound was prepared following protocol A. (S)-1-(4-Chloro-2-fluoro-5-methoxy-phenyl)-3-methylpiperazine dihydrochloride and [3-(1H-imidazol-2-yl)pyrazolo[3,4-b]pyridin-1-yl]acetic acid were used as the coupling components. The crude product was purified by silica gel chromatography (2% to 3% MeOH in CH$_2$Cl$_2$) to provide 1-[(S)-4-(4-chloro-2-fluoro-5-methoxyphenyl)-2-methylpiperazin-1-yl]-2-[3-(1H-imidazol-2-yl)pyrazolo[3,4-b]pyridin-1-yl]ethanone as a tan solid (29 Mg): $^1$H NMR (CDCl$_3$, 400 MHz) δ 8.79 (dd, 1H), 8.55 (dd, 1H), 7.27-7.21 (m, 3H), 7.07 (d, 1H), 6.43 (br. d, 1H), 5.46-5.37 (m, 2H), 4.83 (br. s, 0.3H), 4.51-4.48 (m, 0.6H), 4.28-4.21 (m, 0.6H), 3.86 (s, 0.9H), 3.85 (s, 2.1H), 3.79 (br. s, 0.3H), 3.67 (br. s, 0.3H), 3.33-3.21 (m, 2.5H), 2.95-2.93 (m, 0.9H), 2.83-2.76 (m, 1.6H), 1.48-1.40 (m, 3H); LC/MS m/z (M+H)$^+$ 484.4.

Example 67

Synthesis of 1-[(R)-4-(4-Chloro-3-methoxyphenyl)-3-methylpiperazin-1-yl]-2-[3-(1H-imidazol-2-yl)-pyrazolo[3,4-b]pyridin-1-yl]ethanone

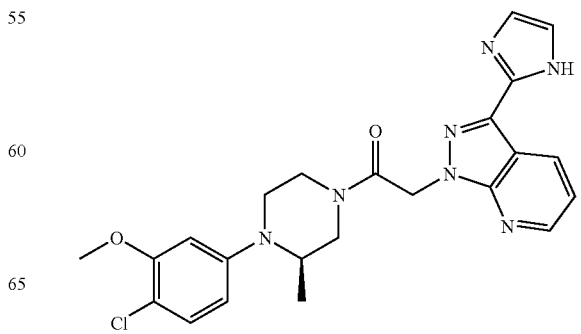

The title compound was prepared following Protocol A. (R)-1-(4-Chloro-3-methoxyphenyl)-2-methylpiperazine and [3-(1H-imidazol-2-yl)pyrazolo[3,4-b]pyridin-1-yl]acetic acid were used as the coupling components. The crude product was purified by silica gel chromatography (1% to 7.5% MeOH in CH$_2$Cl$_2$) to provide 1-[(R)-4-(4-chloro-3-methoxyphenyl)-3-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.76 (d, 0.6H), 8.66 (dd, 0.3H), 8.57-8.54 (m, 1H), 7.29-7.19 (m, 4H), 6.48-6.40 (m, 2H), 5.53-5.40 (m, 2H), 4.26 (br. d, 0.6H), 4.00 (br. d, 0.6H), 3.88 (s, 1.3H), 3.86 (s, 1.7H), 3.80-3.49 (m, 3.2H), 3.33 (br. s, 0.6H), 3.17-3.14 (m, 2H), 1.51-1.42 (m, 3H); LC/MS m/z (M+H)$^+$ 466.4.

Example 68

Synthesis of 1-[(S)-4-(4-Chloro-3-methoxyphenyl)-3-methylpiperazin-1-yl]-2-[3-(1H-imidazol-2-yl)-pyrazolo[3,4-b]pyridin-1-yl]ethanone

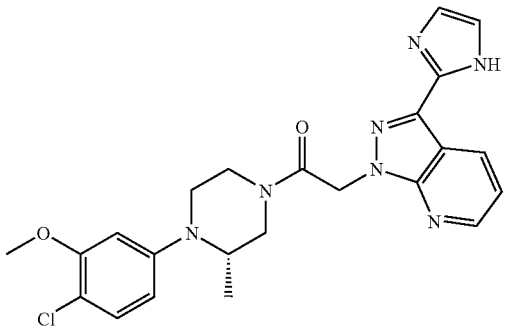

The title compound was prepared following protocol A. (S)-1-(4-Chloro-3-methoxyphenyl)-2-methylpiperazine and [3-(1H-imidazol-2-yl)pyrazolo[3,4-b]pyridin-1-yl]acetic acid were used as the coupling components. The crude product was purified by silica gel chromatography (1% to 7% MeOH in CH$_2$Cl$_2$) to provide 1-[(S)-4-(4-chloro-3-methoxyphenyl)-3-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.77 (d, 0.6H), 8.66 (d, 0.3H), 8.57-8.54 (m, 1H), 7.30-7.19 (m, 4H), 6.48-6.40 (m, 2H), 5.54-5.36 (m, 2H), 4.25 (br. d, 0.6H), 4.00 (br. d, 0.6H), 3.88 (s, 1.3H), 3.86 (s, 1.7H), 3.82-3.48 (m, 3.2H), 3.36-3.29 (m, 0.6H), 3.17-3.13 (m, 2H), 1.51-1.43 (m, 3H); LC/MS m/z (M+H)$^+$ 466.4.

Example 69

Synthesis of 1-[(R)-4-(4-Chloro-3-methoxyphenyl)-2-methylpiperazin-1-yl]-2-[3-(1H-imidazol-2-yl)-pyrazolo[3,4-b]pyridin-1-yl]ethanone

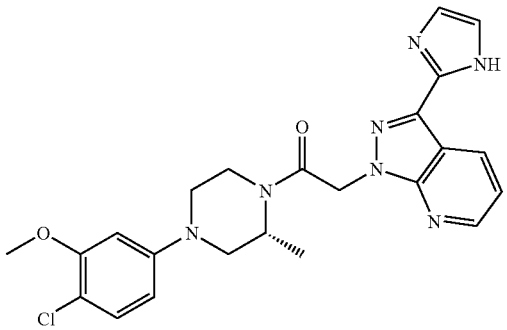

The title compound was prepared following Protocol A. (R)-1-(4-Chloro-3-methoxyphenyl)-3-methylpiperazine and [3-(1H-imidazol-2-yl)-pyrazolo[3,4-b]pyridin-1-yl]acetic acid were used as the coupling components. The crude product was purified by silica gel chromatography (1% to 7.5% MeOH in CH$_2$Cl$_2$) to provide 1-[(R)-4-(4-chloro-3-methoxyphenyl)-2-methylpiperazin-1-yl]-2-[3-(1H-imidazol-2-yl)-pyrazolo[3,4-b]pyridin-1-yl]ethanone as a tan solid: $^1$H NMR (CDCl$_3$, 400 MHz) δ 8.75 (d, 0.6H), 8.66 (dd, 0.4H), 8.57-8.54 (m, 1H), 7.29-7.18 (m, 4H), 6.44-6.39 (m, 2H), 5.42 (br. s, 2H), 4.82 (br. s, 0.3H), 4.45 (br. s, 0.3H), 4.33 (br. s, 0.3H), 3.88 (s, 1.2H), 3.87 (s, 1.8H), 3.83 (br. s, 0.3H), 3.73-3.67 (m, 1H), 3.54-3.52 (m, 1H), 3.38 (br. s, 1H), 3.17-3.13 (m, 1H), 2.99 (br. s, 1H), 2.80 (br. s, 1H), 1.50-1.42 (m, 3H); LC/MS m/z (M+H)$^+$ 466.4.

Example 70

Synthesis of 2-(3-(1H-imidazol-2-yl)-1H-pyrazolo[3,4-b]pyridin-1-yl)-1-((S)-4-(4-chloro-3-ethoxyphenyl)-2-methylpiperazin-1-yl)ethanone

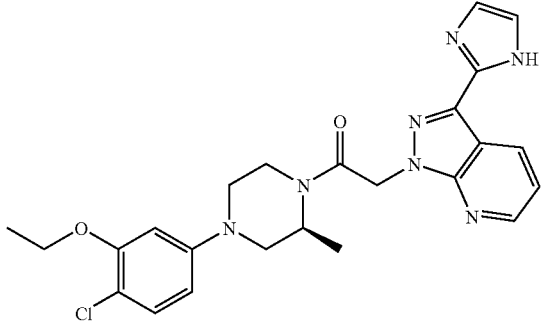

The title compound was prepared following Protocol A. To a vial containing (S)-1-(4-chloro-3-ethoxyphenyl)-3-methylpiperazine dihydrochloride (70 Mg, 0.21 Mmol) was added 2-(3-(1H-imidazol-2-yl)-1H-pyrazolo[3,4-b]pyridin-1-yl) acetic acid (51 Mg, 0.21 mmol), HBTU (81 Mg, 0.21 Mmol), DMF (0.7 mL), and DIPEA (0.15 mL, 0.87 Mmol). The reaction mixture was maintained at 30° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resulting residue was purified by preparative HPLC (20→95% gradient of MeCN—H$_2$O with 0.1% TFA) and the pure fractions lyophilized to afford the indicated compound (11 Mg, 11% yield): MS (ES) [M+H]$^+$ expected 480.2, found 480.5; $^1$H NMR (CDCl$_3$, 400 MHz) δ 9.94 (br s, 1H), 8.79 (dd, J=1.6, 8.0, 1H), 8.55 (dd, J=1.6, 4.4, 1H), 7.19-7.26 (m, 4H), 6.37-6.43 (m, 2H), 5.40 (br s, 2H), 2.78-4.81 (m, 10H), 4.07 (q, J=6.8, 2H), 1.46 (t, J=6.8, 3H).

Example 71

Synthesis of 2-(3-(1H-imidazol-2-yl)-1H-pyrazolo[3,4-b]pyridin-1-yl)-1-(4-(3-(2-fluoroethoxy)-4-chlorophenyl)piperazin-1-yl)ethanone

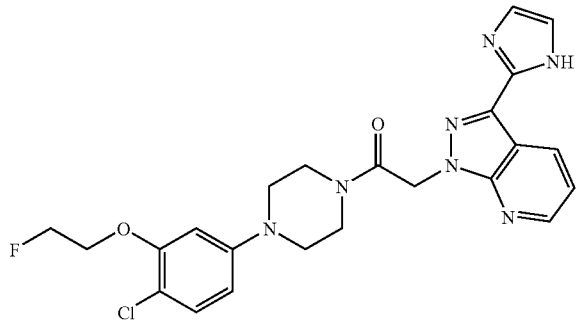

This compound was prepared by Protocol A. To a vial containing 1-(3-(2-fluoroethoxy)-4-chlorophenyl)piperazine dihydrochloride (70 Mg, 0.21 Mmol) was added 2-(3-(1H-imidazol-2-yl)-1H-pyrazolo[3,4-b]pyridin-1-yl)acetic acid (51 Mg, 0.21 Mmol), HBTU (83 Mg, 0.22 Mmol), DMF (0.7 mL), and DIPEA (0.20 mL, 1.2 Mmol). The reaction mixture was maintained at 20° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resultant residue was purified by preparative HPLC (20→95% gradient of MeCN—H$_2$O with 0.1% TFA) and the pure fractions lyophilized to afford the indicated compound (20 Mg, 20% yield): MS (ES) [M+H]$^+$ expected 484.2, found 484.4. $^1$H NMR (CDCl$_3$, 400 MHz) δ 9.94 (br s, 1H), 8.78 (dd, J=1.2, 8, 1H), 8.55 (dd, J=1.2, 4.6, 1H), 7.16-7.26 (m, 4H), 6.45-6.53 (m, 2H), 5.44 (s, 2H), 4.77 (dt, J=4.0, 46.8, 2H), 4.26 (dt, J=4.0, 26.8, 2H), 3.69-3.78 (m, 4H), 3.10-3.21 (m, 4H).

Example 72

Synthesis of 2-(3-(1H-imidazol-2-yl)-1H-pyrazolo[3,4-b]pyridin-1-yl)-1-((S)-4-(3-(2-fluoroethoxy)-4-chlorophenyl)-2-methylpiperazin-1-yl)ethanone

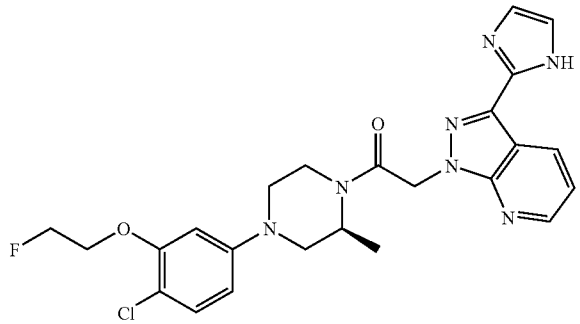

This compound was prepared by Protocol A. To a vial containing (S)-1-(3-(2-fluoroethoxy)-4-chlorophenyl)-3-methylpiperazine dihydrochloride (80 Mg, 0.23 Mmol) was added 2-(3-(1H-imidazol-2-yl)-1H-pyrazolo[3,4-b]pyridin-1-yl)acetic acid (51 Mg, 0.21 mmol), HBTU (81 Mg, 0.21 Mmol), DMF (0.7 mL), and DIPEA (0.2 mL, 1.2 Mmol). The reaction mixture was maintained at 30° C. for 24 h. The solution was diluted with EtOAc (30 mL) and washed with 1N HCl (2×10 mL) and sat. aq. NaCl (2×10 mL). The organic phase was dried over MgSO$_4$ and concentrated in vacuo. The resultant residue was purified by preparative HPLC (20→95% gradient of MeCN—H$_2$O with 0.1% TFA) and the pure fractions lyophilized to afford the indicated compound (14 Mg, 13% yield): MS (ES) [M+H]$^+$ expected 498.2, found 498.4. $^1$H NMR (CDCl$_3$, 400 MHz) δ 9.95 (br s, 1H), 8.79 (dd, J=1.6, 8.2, 1H), 8.55 (dd, J=1.6, 4.4, 1H), 7.19-7.26 (m, 4H), 6.44-6.50 (m, 2H), 5.40 (br s, 2H), 4.77 (dt, J=4.2, 47.2, 2H), 4.26 (dt, J=4.2, 27.2, 2H), 2.78-4.42 (m, 10H).

Example 73

Synthesis of 1-[4-(4-Chloro-3-methyl-phenyl)-piperazin-1-yl]-2-[3-(1H-imidazol-2-yl)-pyrazolo[3,4-b]pyridin-1-yl]-ethanone

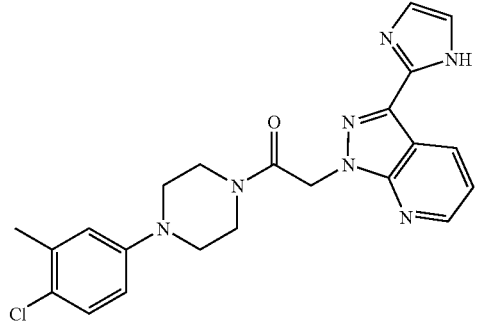

This compound was prepared by Protocol A. A vial was charged with 2-(3-(1H-imidazol-2-yl)-1H-pyrazolo[3,4-b]pyridin-1-yl)acetic acid (55 Mg, 0.226 Mmol), HBTU (125 mg, 0.33 Mmol), 1-(4-Chloro-3-methyl-phenyl)-piperazine dihydrochloride (142 Mg, 0.50 mmol), anhydrous DMF (2.0 mL), and DIPEA (0.5 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-methyl-phenyl)-piperazin-1-yl]-2-[3-(1H-imidazol-2-yl)-pyrazolo[3,4-b]pyridin-1-yl]-ethanone: MS (ES) [M+H]$^+$ found: 436.4

Example 74

Synthesis of 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone

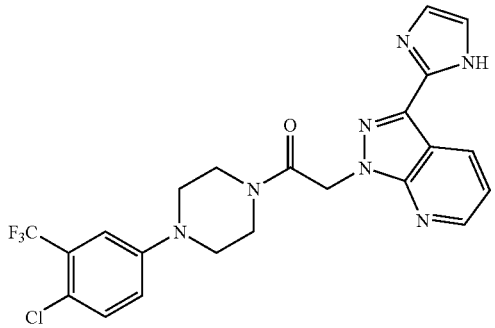

This compound was prepared by Protocol A. A vial was charged with 2-(3-(1H-imidazol-2-yl)-1H-pyrazolo[3,4-b]pyridin-1-yl)acetic acid (55 Mg, 0.226 Mmol), HBTU (125 Mg, 0.33 mmol), 1-(4-Chloro-3-trifluoromethyl-phenyl)-piperazine dihydrochloride (170 Mg, 0.50 mmol), anhydrous DMF (2.0 mL), and DIPEA (0.5 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-trifluoromethyl-phenyl)-piperazin-1-yl]-2-[3-(1H-imidazol-2-yl)-pyrazolo[3,4-b]pyridin-1-yl]-ethanone: MS (ES) [M+H]+ found: 490.4

Example 75

Synthesis of 1-[4-(4-Chloro-3-trifluoromethoxy-phenyl)-piperazin-1-yl]-2-[3-(1H-imidazol-2-yl)-pyrazolo[3,4-b]pyridin-1-yl]-ethanone

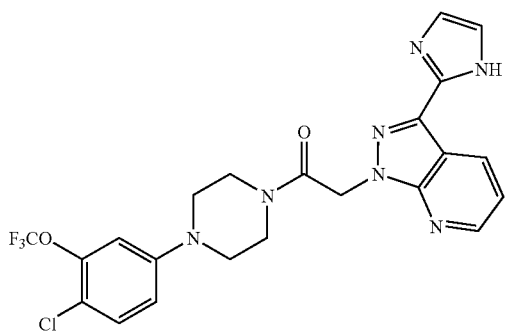

This compound was prepared by Protocol A. A vial was charged with 2-(3-(1H-imidazol-2-yl)-1H-pyrazolo[3,4-b]pyridin-1-yl)acetic acid (55 Mg, 0.226 Mmol), HBTU (125 mg, 0.33 Mmol), 1-(4-Chloro-3-trifluoromethoxy-phenyl)-piperazine dihydrochloride (177 mg, 0.50 Mmol), anhydrous DMF (2.0 mL), and DIPEA (0.4 mL). The vial was capped, heated to 45° C., and stirred overnight. The following day, the volatiles were removed in vacuo and separation by preparative hplc (reverse phase, acetonitrile-water gradient) gave 1-[4-(4-Chloro-3-trifluoromethoxy-phenyl)-piperazin-1-yl]-2-[3-(1H-imidazol-2-yl)-pyrazolo[3,4-b]pyridin-1-yl]-ethanone. MS (ES) [M+H]+ found: 506.4

Example 76

Synthesis of 1-[4-(4-Chloro-3-methoxy-phenyl)-piperazin-1-yl]-2-[3-(1H-imidazol-2-yl)-pyrazolo[3,4-b]pyridin-1-yl]-ethanone

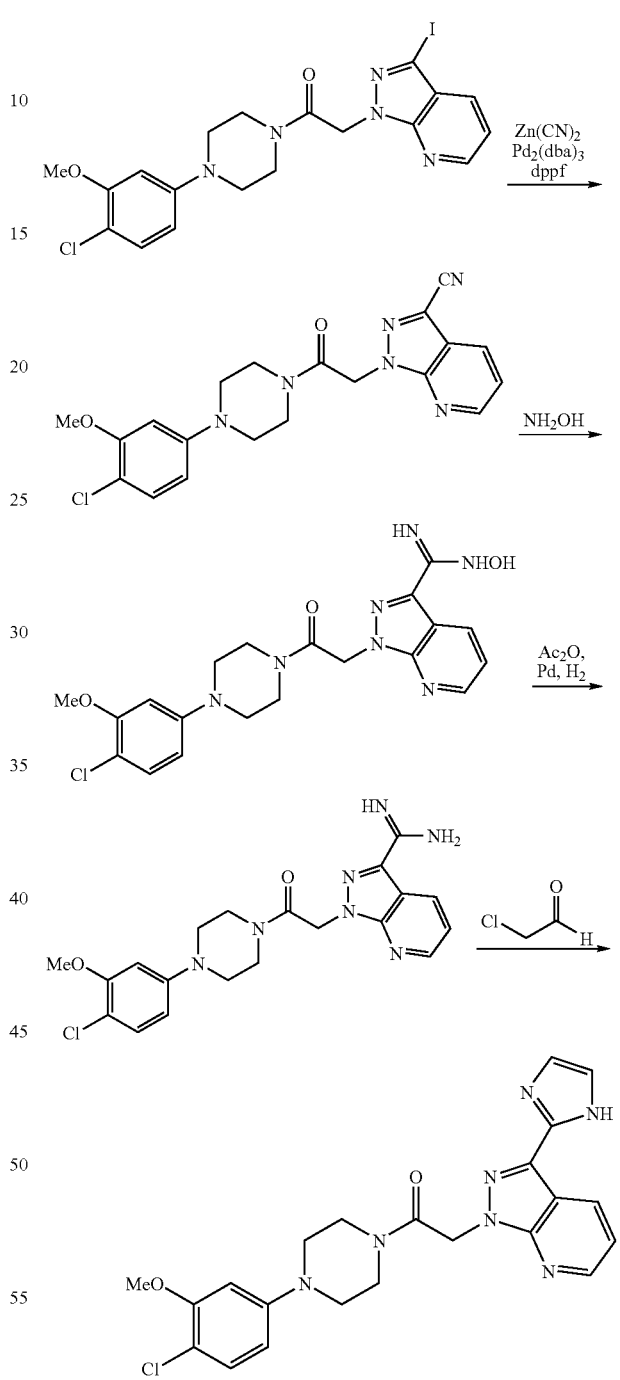

The title compound was prepared from 1-[4-(4-Chloro-3-methoxy-phenyl)-piperazin-1-yl]-2-[3-iodo-pyrazolo[3,4-b]pyridin-1-yl]-ethanone according to the procedure similar to those described from step 2 to step 5 in the synthesis of Example 61: $^1$H NMR (CDCl$_3$, 400 MHz) δ 10.22 (br, 1H), 8.82 (dd, 1H), 8.56 (dd, 1H), 7.20-7.30 (m, 3H), 7.11 (s, 1H), 6.47 (d, 1H), 6.42 (dd, 1H), 5.44 (s, 2H), 3.88 (s, 3H), 3.80 (m, 4H), 3.19 (m, 4H); MS (ES) M+H expect 452.2.

Example 77

Synthesis of 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone

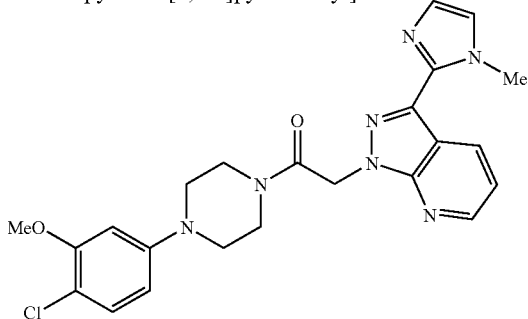

To the solution of 1-[4-(4-Chloro-3-methoxy-phenyl)-piperazin-1-yl]-2-[3-(1H-imidazol-2-yl)-pyrazolo[3,4-b]pyridin-1-yl]-ethanone (50 Mg, 0.11 Mmol, 1 eq) in THF was added 60% sodium hydride (5.7 Mg, 0.14 Mmol, 1.3 eq) and stirred for 1 hr, followed by the addition of iodomethane (25.8 Mg, 0.16 Mmol, 1.5 eq). 2 hrs later, LCMS indicated that the major peak is the desired product. preparative hplc (reverse phase, acetonitrile-water gradient) gave 1-[4-(4-Chloro-3-methoxy-phenyl)-piperazin-1-yl]-2-[3-(1-methyl-1H-imidazol-2-yl)-pyrazolo[3,4-b]pyridin-1-yl]-ethanone. MS (ES) [M+H]+ found: 465.2.

Example 78

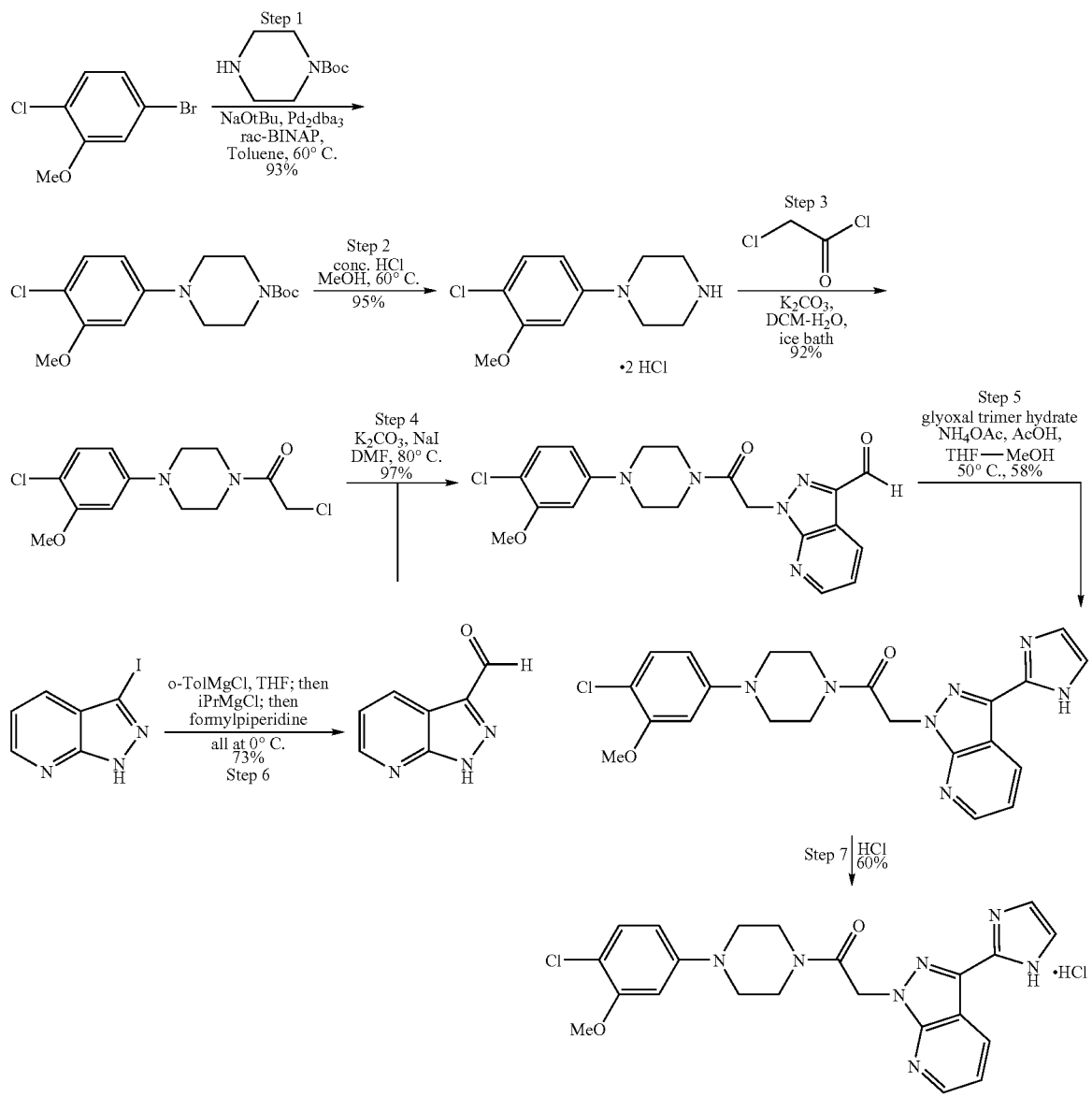

Step 1: Tert-butyl 4-(4-chloro-3-methoxyphenyl)piperazine-1-carboxylate

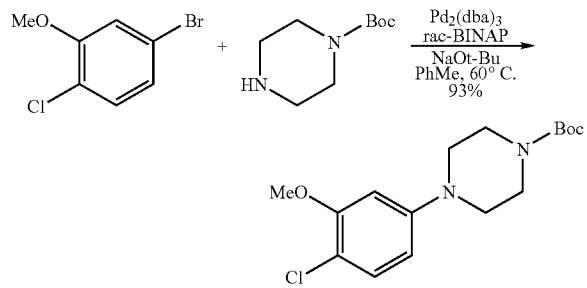

To a 3-necked, 5-L Morton flask equipped with a mechanical stirrer, gas adapter, heating mantle and thermometer was added rac-BINAP (4.24 g, 0.005 equiv) and Pd$_2$(dba)$_3$ (3.20 g, 0.0025 equiv). The flask was evacuated, and back-filled with nitrogen. Toluene (100 mL) was added by cannula. The mixture was stirred at room temperature for 15 min to give a purple solution. Toluene (2.0 L) was then added. 2-Chloro-5-bromoanisole (300.3 g, 1.356 mol, 1 equiv) was added in one portion. Boc-piperazine (252.4 g, 1 equiv) was added in one portion. Sodium tert-butoxide (183.0 g, 1.4 equiv) was added in one portion. The flask was evacuated and back-filled with nitrogen. The mixture was then heated to an internal temperature of 60° C. A heterogeneous light-orange slurry was obtained. After 1 h, the mixture becomes a homogeneous brown solution. After an additional 15 h, the mixture was cooled to room temperature. EtOAc (2.0 L) was added to the stirring mixture. The solid was filtered. The filtrate was washed with EtOAc (100 mL). The combined filtrate was washed with 10% aq. K$_2$CO$_3$ solution (1×1 L), water (1×1 L), and dried over MgSO$_4$. The solvent was removed in vacuo to afford the product as an orange solid (410.3 g, 93% yield).

Step 2: 1-(4-chloro-3-methoxyphenyl)piperazine dihydrochloride

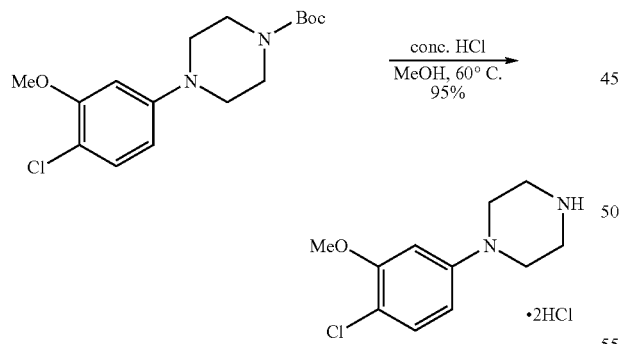

A 4-L beaker equipped with a mechanical stirrer was charged with tert-butyl 4-(4-chloro-3-methoxyphenyl)piperazine-1-carboxylate (500 g, 1.53 Mol, 1 equiv) and MeOH (1.50 L). While stirring at room temperature conc. 37% HCl (500 mL, 4 equiv) was added over 5 min. The internal temperature rose to 40° C., and the solution became thick with precipitate. After 15 min, the mixture was heated to an internal temperature of 60° C. on a hotplate. (Foaming begun at approximately 50° C. as the mixture warms.) After 2 h at 60° C., the solution was cooled to room temperature, and subsequently to 5° C. in a refrigerator. The product was collected by filtration in two batches. Each batch of the red-brown filtrate was washed with EtOAc (2×500 mL) to give a light yellow solid. The two batches were combined to afford the product (391.3 g). The filtrate was concentrated to a volume of 300 mL in vacuo and treated with hot (50° C.) MeOH (500 mL). The mixture was cooled to 5° C. in a refrigerator for 24 h. The resulting precipitate was collected by filtration and washed with EtOAc (2×200 mL) to afford an additional 44.3 g of product (total of 435.6 g, 95% yield).

Step 3: 2-chloro-1-(4-(4-chloro-3-methoxyphenyl)piperazin-1-yl)ethanone

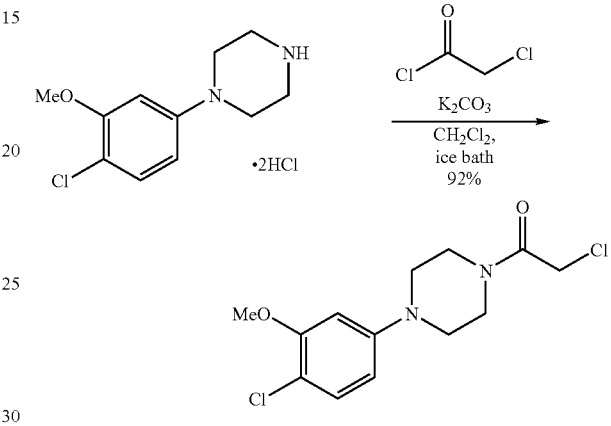

To a 3 L flask equipped with a mechanical stirrer was added 1-(4-chloro-3-methoxyphenyl)piperazine dihydrochloride (220 g, 0.73 Mol, 1 equiv), CH$_2$Cl$_2$ (1000 mL), and water (1000 mL). The biphasic mixture was cooled to 5° C. with an ice-water bath. K$_2$CO$_3$ (506 g, 5 equiv) was added to the vigorously stirring solution in portions to minimize foaming. A solution of chloroacetyl chloride (124.4 g, 1.5 equiv) in CH$_2$Cl$_2$ (100 mL) was added dropwise from an addition funnel, while maintaining an internal temperature below 8° C. After 1 h, the cooling bath was removed, and the reaction warmed to room temperature. After an additional 1 h, the layers were partitioned. The aqueous phase was extracted with CH$_2$Cl$_2$ (2×300 mL), and the combined organic layers dried over 3:1 Na$_2$SO$_4$/K$_2$CO$_3$ (addition of K$_2$CO$_3$ helps the solution phase to become clear). After filtration, the filtrate was concentrated in vacuo, and the residue was dried for 16 h under vacuum to afford the product as an off-white solid (410 g, 92% yield).

Step 6: 7-azaindazole-3-carboxaldehyde

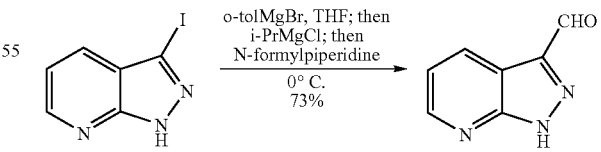

A 5 L 3-necked flask equipped with a digital thermometer, a 1 L addition funnel and mechanical stirrer (all glassware dried in oven and cooled in air for 30 min before use) was charged with 3-iodo-7-azaindaozle (196.0 g, 0.80 Mol) and 1 L of anhydrous THF (in SureSeal bottle from Aldrich and used as is). The solids completely dissolved in THF at room temperature to form a dark brown solution. The flask was then cooled to −5° C. with an ice/NaCl bath and moderate stirring and o-tolylmagnesium chloride (1 M solution in THF, 880 mL, 1.1 equiv) was added dropwise to keep the internal temperature between −5° C. to −3° C. (after ~820 mL of o-tolylmagnesium chloride solution was added, the temperature no longer rose). The whole addition process took 2 hr and 25 min. At the end of the addition, the mixture was a homogeneous dark brown solution.

After an additional 1 hr, isopropylmagnesium chloride solution (2 M in THF, 480 mL, 1.2 equiv) was added dropwise to keep internal temperature <4° C. After 25 min and about 200 mL isopropylmagnesium chloride solution was added, brown precipitate started to form. After a total of 380 mL of isopropylmagnesium chloride solution was added, the mixture became homogeneous again. The whole addition process was done in 45 min. After another 1 hr 25 min, a small amount of sample was taken out and quenched with $D_2O$. LCMS analysis of this sample indicated the complete Iodo-Mg exchange.

1-Formylpiperidine (120 mL, 1.3 equiv) was then added dropwise to keep the internal temperature between <2° C. After about 30 mL 1-formylpiperidine was added, the internal temperature did not go up anymore and rest of the 1-formylpiperidine was added relatively quickly. The whole addition process took 20 min. At the end of the addition, the mixture was still a dark homogeneous solution and was allowed to slowly warm up to room temperature and moderately stirred for 18 hr.

The mixture was re-cooled to 0° C. with an ice/NaCl bath and quenched by slow addition of a mixture of saturated $NH_4Cl$ solution (750 mL)/concentrated HCl solution (250 mL) to keep the internal temperature at <35° C. After the addition was complete, stirring was allowed to continue for 1 hr and a yellow precipitate appeared. The mixture was filtered and the solid was washed with THF (100 mL). The collected filtrate was transferred to a separation funnel and the pH of the aqueous layer was adjusted to between 5 and 6 with the addition of $NaHCO_3$ (around 5 g). The THF layer was separated and washed with sat. NaCl solution (2×100 mL). The combined aqueous layers (including the NaCl wash and quenched aqueous layer) was extracted with EtOAc (3×250 mL). The combined organic layers was dried ($Na_2SO_4$), filtered and evaporated in vacuo (bath temperature <30° C.) to give a brownish solid. This solid was triturated with $Et_2O$ (600 mL) and filtered. The collected solid was washed with $Et_2O$ (2×100 mL) to give 7-azaindazole-3-carboxaldehyde as a yellowish solid (86.6 g, 73%).

Step 4: 1-[4-(4-Chloro-5-ethoxy-2-fluorophenyl)piperazin-1-yl]-2-[3-formyl-pyrazolo[3,4-b]pyridin-1-yl]ethanone

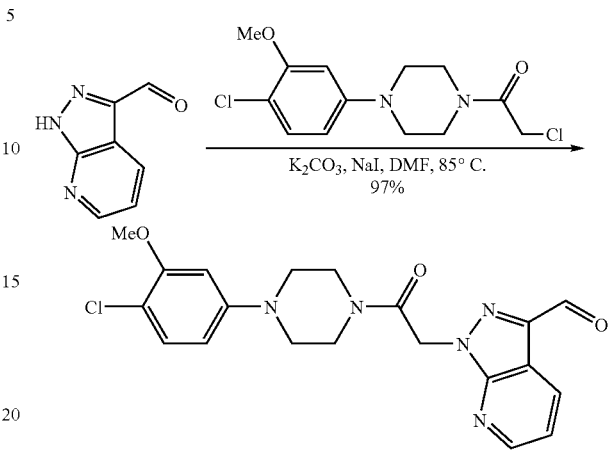

A mixture of 7-azaindazole-3-carboxaldehyde (86.6 g, 0.59 Mol, 1 equiv), NaI (8.8 g, 0.1 equiv) and $K_2CO_3$ (162.5 g, 2 equiv) in DMF (0.5 L) in a 5 L flask was heated to 85° C. (the heating process took around 1.5 h). 2-chloro-1-(4-(4-chloro-3-methoxyphenyl)piperazin-1-yl)ethanone (175 g, 1 equiv) was added in small portions to the reaction mixture. The whole addition process took about 30 min. The mixture was then stirred at 85° C. for 30 min and LCMS confirmed that the reaction was complete. After cooling down to room temperature, the mixture was transferred to a 4 L flask with 2 L ice. The reaction flask was rinsed with small amount of acetone (30 mL) and transferred to the DMF/ice mixture in the 4 L flask also. A lot of brownish solids precipitated out. After the ice completely melted, the mixture was filtered. The collected solid was washed with water (1 L), blended, and then washed with water (1 L) to get rid of some residual DMF. The collected solid contained a lot of water, so it was dissolved in $CH_2Cl_2$ (4 L) and the mixture was transferred to a 5 L separation funnel. The bottom $CH_2Cl_2$ layer was separated and the top aq. layer was washed with $CH_2Cl_2$ (2×100 mL). The combined $CH_2Cl_2$ layers were dried ($Na_2SO_4$), filtered and evaporated in vacuo to give 1-[4-(4-Chloro-5-ethoxy-2-fluorophenyl)piperazin-1-yl]-2-[3-formyl-pyrazolo[3,4-b]pyridin-1-yl]ethanone as a brownish solid (236.4 g, 97%) which was used without purification.

Step 5: 1-[4-(4-Chloro-5-ethoxy-2-fluorophenyl)piperazin-1-yl]-2-[3-(1H-imidazol-2-yl)-pyrazolo[3,4-b]pyridin-1-yl]ethanone

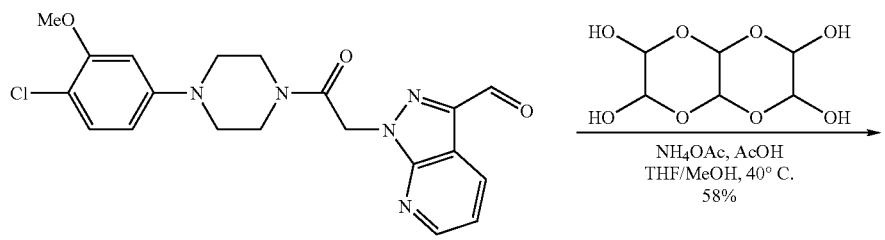

-continued

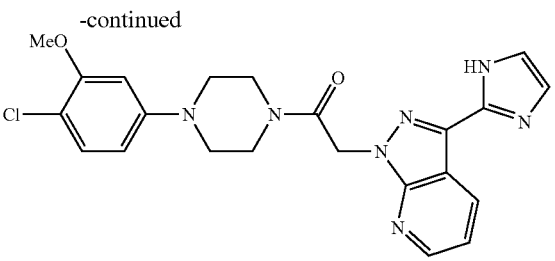

1-[4-(4-Chloro-5-ethoxy-2-fluorophenyl)piperazin-1-yl]-2-[3-formyl-pyrazolo[3,4-b]pyridin-1-yl]ethanone_(300 g, 723 Mmol, 1 equiv), glyoxal trimer dihydrate (60.6 g, 0.4 equiv), and ammonium acetate (222.9 g, 4 equiv) were suspended in a mixture of THF (720 mL) and MeOH (720 mL) in a 5 L round-bottomed flask fitted with a magnetic stir bar and nitrogen inlet. Acetic acid (84 mL, 2 equiv) was added and the mixture was heated in a 45° C. oil bath (solids dissolved upon heating). After 12 hours, LC/MS analysis indicated complete consumption of aldehyde starting material and formation of desired product (LC/MS m/z (M+H)$^+$ 452.1). The MeOH/THF were removed by rotary evaporation. The residue was dissolved in 10% MeOH in CH$_2$Cl$_2$ (ca. 1.5 L) and the mixture was shaken vigorously with aqueous potassium carbonate (ca. 210 g potassium carbonate in ca. 1.5 L water, pH of aqueous=8-9). The layers were separated, and the aqueous layer was extracted with 10% MeOH in CH$_2$Cl$_2$ (2×100 mL). The combined organic layers were concentrated to give a brown oily solid. The crude product was suspended in 10% MeOH in EtOAc (ca. 1 L). Anhydrous Na$_2$SO$_4$ (ca. 60 g) and silica gel (ca. 100 g) were added and the slurry was heated gently with a heat gun to dissolve the crude product. The slurry was transferred to a 2 L fritted glass filter funnel containing silica gel (ca. 100 g, pre-equilibrated with 10% MeOH in EtOAc), and the product was eluted through the silica gel plug with 10% MeOH in EtOAc (ca. 6 L) and 1% Et$_3$N, 10% MeOH in EtOAc (ca. 10 L). (Note: Incomplete dissolution of the product and/or precipitation of product in the presence of silica gel complicated the filtration). The solvents were removed by rotary evaporation. The residue was triturated with MeCN (1×300 mL) and dried (rotary evaporation followed by high vacuum) to provide 1-[4-(4-chloro-5-ethoxy-2-fluorophenyl)piperazin-1-yl]-2-[3-(1H-imidazol-2-yl)-pyrazolo[3,4-b]pyridin-1-yl]ethanone as an off-white solid (190 g, 58%, LC/MS purity >98%).

Step 7: 2-(3-1H-imidazol-2-yl)-1H-pyrazolo[3,4-b]pyridin-1-yl)-1-(4-(4-chloro-3-methoxyphenyl)piperazin-1-yl)ethanone hydrochloride salt

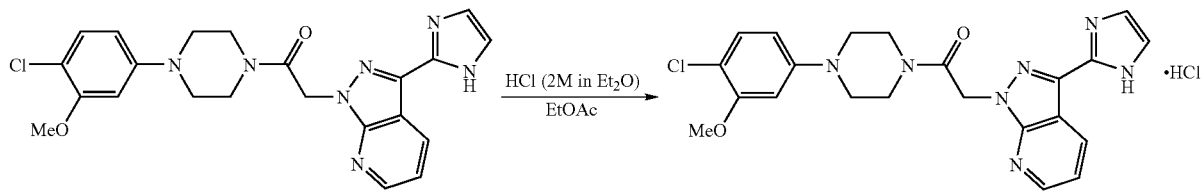

A 2 L flask with a magnetic stirrer was charged with the product of step 6 (5.1 g, 11.28 Mmol) and EtOAc (900 mL). The resulting suspension was heated to form a clear solution and cooled to room temperature under moderate stirring. HCl in Et$_2$O (2 M, 6.2 mL, 12.42 Mmol) was added dropwise to the resulting solution at room temperature over 5 min. After the addition, the resultant suspension was stirred at room temperature for another 1 h. The solid was collected by filtration and washed with Et$_2$O (150 mL×2) and dried in vacuo to afford 5.4 g of an off-white powder. A 250 mL flask with a magnetic stirrer was charged with the powder obtained above (5.4 g), acetone (100 mL) and deionized water (16 mL). The resulting suspension was heated to form a clear solution and stirred to cool. When the solution became cloudy (crystal seeds appeared), acetone (540 mL) was added slowly to the suspension over 20 min. The resulting suspension was heated to 50° C. and stirred for 2 h. Filtration while hot, washing with hot acetone (50 mL×2) and drying in vacuo gave 3.3 g (60%) of the product as an off-white solid: m.p. 164-165° C. The crystals appear as prisms under a polarizing microscope.

Example 79

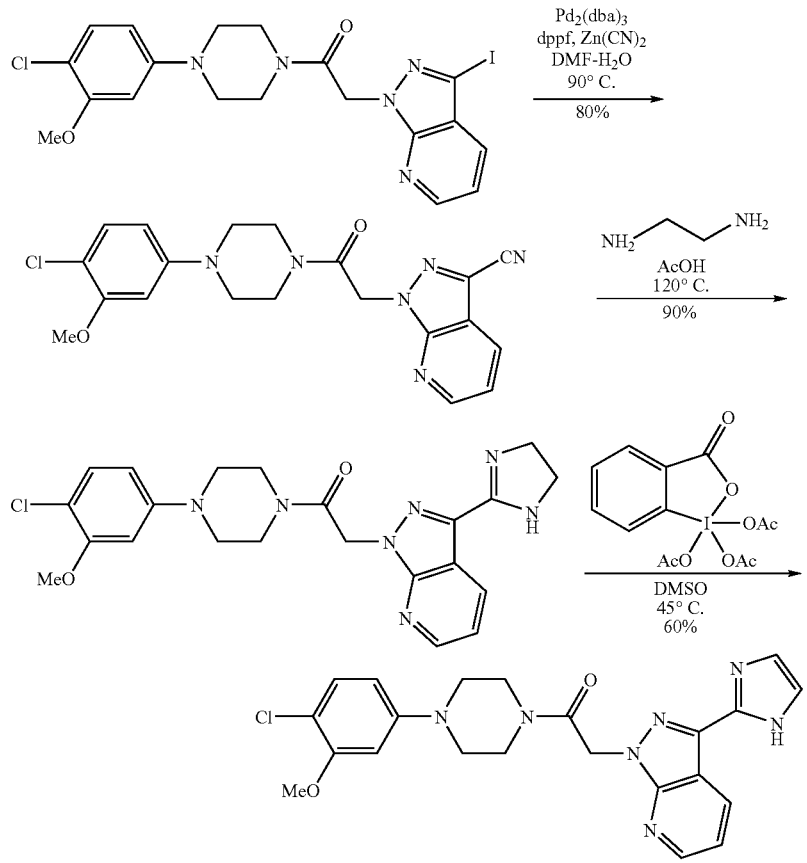

Step 1: Synthesis of 1-{2-[4-(4-Chloro-3-methoxy-phenyl)-piperazin-1-yl]-2-oxo-ethyl}-1H-pyrazolo[3,4-b]pyridine-3-carbonitrile

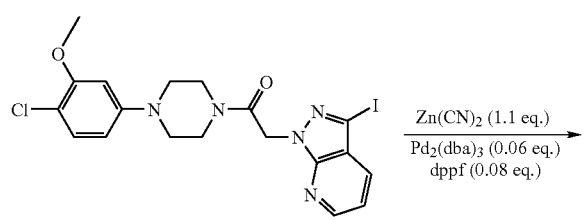

To a 2000 mL flask was charged with 1-[4-(4-Chloro-3-methoxy-phenyl)-piperazin-1-yl]-2-(3-iodo-pyrazolo[3,4-b]pyridin-1-yl)-ethanone (40 g, 78.1 Mmol), dppf (3.86 g, 6.96 mmol), Zn(CN)$_2$ (9.6 g, 81.6 Mmol), DMF (360 mL) and H$_2$O (20 mL). The resulting suspension was degassed using N$_2$ for 5 min, followed by addition of Pd$_2$(dba)$_3$ (4.24 g, 4.64 mmol). The reaction mixture was heated under N$_2$ at 90° C. for 2 h (monitor by TLC and LC-MS). After cooling to room temperature, diluted with EtOAc (1500 mL), filtered to remove the precipitate and washed with H$_2$O (1000×2 mL), saturated EDTA.4Na (800 mL×2), brine and dried over Na$_2$SO$_4$. After evaporation of the solvent, ether (150 mL) was added and stirred for 2 h. The resulting solid was filtered to give the desired product 30 g (93%) as light yellow powder. Recrystallization from refluxing CH$_3$CN (160 mL) afforded 26 g (80%) light yellow crystals: mp 183-185° C.; R$_t$=2.38 min; MS (ES) M+H expect 411.1, found 411.1.

Step 2: Synthesis of 1-(4-(4-chloro-3-methoxyphenyl)piperazin-1-yl)-2-(3-(4,5-dihydro-1H-imidazol-2-yl)-1H-pyrazolo[3,4-b]pyridin-1-yl)ethanone

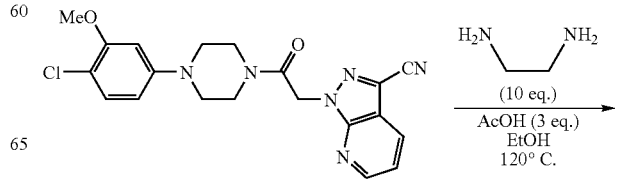

-continued

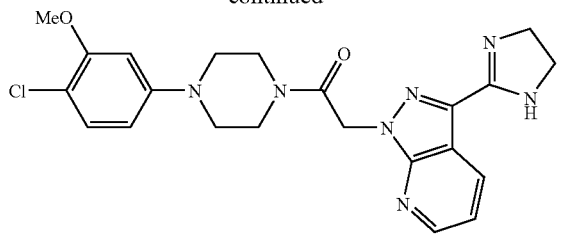

A 250 mL flask was charged with 1-(2-(4-chloro-3-methoxyphenyl)piperazin-1-yl)-2-oxoethyl)-1H-pyrazol[3,4-b]pyridine-3-carbonitrile (15.3 g, 37.2 Mmol), EtOH (40 mL, ~1 M). Under ice-bath and stirring, AcOH (6.75 mL, 112 Mmol) was added, followed by ethylenediamine (25 mL, 372 Mmol). The resulting mixture was heated at 120° C. (bath) under $N_2$ (observed mixture starting refluxing) for 1.5 h. TLC and LC-MS indicated the disappearance of starting material and formation of imidazoline. After cooling to room temperature, mixture was diluted with DCM (700 mL) and washed with $H_2O$ (350 mL). The $H_2O$ layer was back extracted with DCM (150 mL), and the combined organic layer was washed brine (350 mL) and dried over $MgSO_4$. After evaporating of the solvent under reduced pressure, the residue was suspended in hot EtOAc (80 mL). After cooling to room temperature, the solid was collected by filtration and washed with EtOAc (30 mL) to afford the title compound as white powders (16 g, 95%) which was used directly for next step: mp 133-135° C.; $R_t$=1.369 min. MS (ES) M+H expect 454.2, found 454.4.

Step 3: 2-(3-1H-imidazol-2-yl)-1H-pyrazolo[3,4-b]pyridin-1-yl)-O-(4-(4-chloro-3-methoxyphenyl)piperazin-1-yl)ethanone 2 h (monitor by TLC and LC-MS). After cooling to room temperature, quenching the reaction with sat $Na_2S_2O_3$ (100 mL) (ice-bath), followed 3 N NaOH (100 mL) (pH 12 to 13) and $H_2O$ (300 mL) and extracted with DCM (600 mL+300 mL). The combined organic layer was washed with sat $NaHCO_3$ (300 mL), brine (300 mL) and dried ($MgSO_4$, 120 g). After evaporation of the organic solvent, the residue yellow solid (~11 g) was dissolved in hot $CH_3CN$ (20 mL). After cooling to room temperature, the resulting solid was collected by filtration to afford 6.7 g (55%) of title compound as light tan crystals: mp 149-152° C.; $R_t$=1.309 min. MS (ES) M+H expect 452.2, found 452.4. Mother liquor was concentrated and afforded another 0.6 g (total isolated yield 60%).

Example 80

This example illustrates the evaluation of the biological activity associated with compounds of interest (candidate compounds) of the invention.

Materials and Methods
A. Cells
1. CCR1 Expressing Cells
a) THP-1 Cells

THP-1 cells were obtained from ATCC (TIB-202) and cultured as a suspension in RPMI-1640 Medium supplemented with 2 Mm L-glutamine, 1.5 g/L sodium bicarbonate, 4.5 g/L glucose, 10 Mm HEPES, 1 Mm sodium pyruvate, 0.05% 2-mercaptoethanol and 10% FBS. Cells were grown under 5% $CO_2$/95% air, 100% humidity at 37° C. and sub-cultured twice weekly at 1:5 (cells were cultured at a density range of $2\times10^5$ to $2\times10^6$ cells/mL) and harvested at $1\times10^6$ cells/mL. THP-1 cells express CCR1 and can be used in CCR1 binding and functional assays.

b) Isolated Human Monocytes

Monocytes were isolated from human buffy coats using the Miltenyi bead isolation system (Miltenyi, Auburn, Calif.).

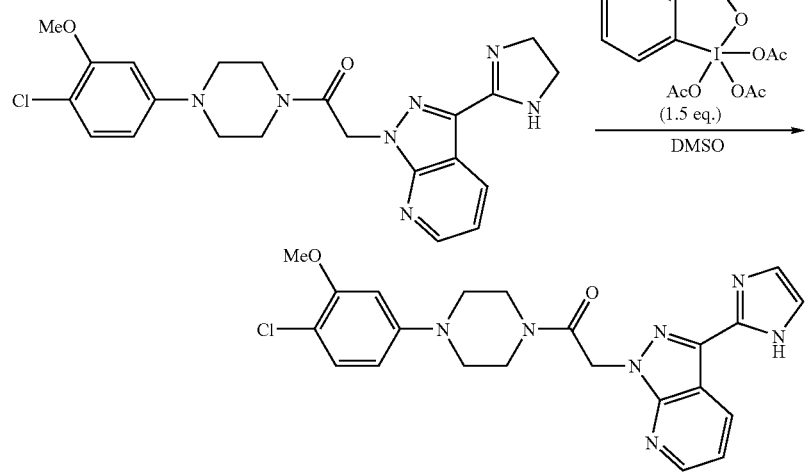

The above imidazoline (12.3 g, 27.1 Mmol) in a 500 mL flask was charged with anhydrous DMSO (108 mL, ~0.25 M). DMP (17.2 g, 40.6 Mmol) was added in portions under stirring. The resulting mixture was stirred at 45° C. under $N_2$ for Briefly, following a Ficoll gradient separation to isolate peripheral blood mononuclear cells, cells were washed with PBS and the red blood cells lysed using standard procedures. Remaining cells were labeled with anti-CD14 antibodies coupled to magnetic beads (Miltenyi Biotech, Auburn, Calif.). Labeled cells were passed through AutoMACS (Miltenyi, Auburn, Calif.) and positive fraction collected. Monocytes express CCR1 and can be used in CCR1 binding and functional assays.

B. Assays

1. Inhibition of CCR1 Ligand Binding

CCR1 expressing cells were centrifuged and resuspended in assay buffer (20 Mm HEPES pH 7.1, 140 Mm NaCl, 1 Mm $CaCl_2$, 5 Mm $MgCl_2$, and with 0.2% bovine serum albumin) to a concentration of $5 \times 10^6$ cells/mL for THP-1 cells and $5 \times 10^5$ for monocytes. Binding assays were set up as follows. 0.1 mL of cells ($5 \times 10^5$ THP-1 cells/well or $5 \times 10^4$ monocytes) was added to the assay plates containing the compounds, giving a final concentration of ~2-10 μM each compound for screening (or part of a dose response for compound $IC_{50}$ determinations). Then 0.1 mL of $^{125}I$ labeled MIP-1α (obtained from Perkin Elmer Life Sciences, Boston, Mass.) or 0.1 mL of $^{125}I$ labeled CCL15/leukotactin (obtained as a custom radiolabeling by Perkin Elmer Life Sciences, Boston, Mass.) diluted in assay buffer to a final concentration of ~50 pM, yielding ~30,000 cpm per well, was added (using $^{125}I$ labeled MIP-1α with THP-1 cells and $^{125}I$ labeled CCL15/leukotactin with monocytes), the plates sealed and incubated for approximately 3 hours at 4° C. on a shaker platform. Reactions were aspirated onto GF/B glass filters pre-soaked in 0.3% polyethyleneimine (PEI) solution, on a vacuum cell harvester (Packard Instruments; Meriden, Conn.). Scintillation fluid (40 μl; Microscint 20, Packard Instruments) was added to each well, the plates were sealed and radioactivity measured in a Topcount scintillation counter (Packard Instruments). Control wells containing either diluent only (for total counts) or excess MIP-1α or MIP-1β (1 μg/mL, for non-specific binding) were used to calculate the percent of total inhibition for compound. The computer program Prism from GraphPad, Inc. (San Diego, Calif.) was used to calculate $IC_{50}$ values. $IC_{50}$ values are those concentrations required to reduce the binding of labeled MIP-1α to the receptor by 50%. (For further descriptions of ligand binding and other functional assays, see Dairaghi, et al., *J. Biol. Chem.* 274:21569-21574 (1999), Penfold, et al., Proc. Natl. Acad. Sci. USA. 96:9839-9844 (1999), and Dairaghi, et al., *J. Biol. Chem.* 272:28206-28209 (1997)).

2. Calcium Mobilization

To detect the release of intracellular stores of calcium, cells (THP-1 or monocytes) were incubated with 3 μM of INDO-1 AM dye (Molecular Probes; Eugene, Oreg.) in cell media for 45 minutes at room temperature and washed with phosphate buffered saline (PBS). After INDO-1 AM loading, the cells were resuspended in flux buffer (Hank's balanced salt solution (HBSS) and 1% FBS). Calcium mobilization was measured using a Photon Technology International spectrophotometer (Photon Technology International; New Jersey) with excitation at 350 nm and dual simultaneous recording of fluorescence emission at 400 nm and 490 nm. Relative intracellular calcium levels were expressed as the 400 nm/490 nm emission ratio. Experiments were performed at 37° C. with constant mixing in cuvettes each containing $10^6$ cells in 2 mL of flux buffer. The chemokine ligands may be used over a range from 1 to 100 nM. The emission ratio was plotted over time (typically 2-3 minutes). Candidate ligand blocking compounds (up to 10 μM) were added at 10 seconds, followed by chemokines at 60 seconds (i.e., MIP-1α; R&D Systems; Minneapolis, Minn.) and control chemokine (i.e., SDF-1α; R&D Systems; Minneapolis, Minn.) at 150 seconds.

3. Chemotaxis Assays

Chemotaxis assays were performed using 5 [ m pore polycarbonate, polyvinylpyrrolidone-coated filters in 96-well chemotaxis chambers (Neuroprobe; Gaithersburg, Md.) using chemotaxis buffer (Hank's balanced salt solution (HBSS) and 1% FBS). CCR1 chemokine ligands (i.e., MIP-1α, CCL15/Leukotactin; R&D Systems; Minneapolis, Minn.) are use to evaluate compound mediated inhibition of CCR1 Mediated migration. Other chemokines (i.e., SDF-1α; R&D Systems; Minneapolis, Minn.) are used as specificity controls. The lower chamber was loaded with 29 μl of chemokine (i.e., 0.1 nM CCL15/Leukotactin) and varying amounts of compound; the top chamber contained 100,000 THP-1 or monocyte cells in 20 μl. The chambers were incubated 1-2 hours at 37° C., and the number of cells in the lower chamber quantified either by direct cell counts in five high powered fields per well or by the CyQuant assay (Molecular Probes), a fluorescent dye method that measures nucleic acid content and microscopic observation.

C. Identification of Inhibitors of CCR1

1. Assay

To evaluate small organic molecules that prevent the receptor CCR1 from binding ligand, an assay was employed that detected radioactive ligand (i.e, MIP-1α or CCL15/Leukotactin) binding to cells expressing CCR1 on the cell surface (for example, THP-1 cells or isolated human monocytes). For compounds that inhibited binding, whether competitive or not, fewer radioactive counts are observed when compared to uninhibited controls.

THP-1 cells and monocytes lack other chemokine receptors that bind the same set of chemokine ligands as CCR1 (i.e., MIP-1α, MPIF-1, Leukotactin, etc.). Equal numbers of cells were added to each well in the plate. The cells were then incubated with radiolabeled MIP-1α. Unbound ligand was removed by washing the cells, and bound ligand was determined by quantifying radioactive counts. Cells that were incubated without any organic compound gave total counts; non-specific binding was determined by incubating the cells with unlabeled ligand and labeled ligand. Percent inhibition was determined by the equation:

$$\% \text{ inhibition} = (1 - [(\text{sample } cpm) - (\text{nonspecific } cpm)] / [(\text{total } cpm) - (\text{nonspecific } cpm)]) \times 100.$$

2. Dose Response Curves

To ascertain a candidate compound's affinity for CCR1 as well as confirm its ability to inhibit ligand binding, inhibitory activity was titered over a $1 \times 10^{-10}$ to $1 \times 10^{-4}$ M range of compound concentrations. In the assay, the amount of compound was varied; while cell number and ligand concentration were held constant.

3. CCR1 Functional Assays

CCR1 is a seven transmembrane, G-protein linked receptor. A hallmark of signaling cascades induced by the ligation of some such receptors is the pulse-like release of calcium ions from intracellular stores. Calcium mobilization assays were performed to determine if the candidate CCR1 inhibitory compounds were able to also block aspects of CCR1 signaling. Candidate compounds able to inhibit ligand binding and signaling with an enhanced specificity over other chemokine and non-chemokine receptors were desired.

Calcium ion release in response to CCR1 chemokine ligands (i.e., MIP-1α, MPIF-1, Leukotactin, etc.) was measured using the calcium indicator INDO-1. THP-1 cells or monocytes were loaded with INDO-1/AM and assayed for calcium release in response to CCR1 chemokine ligand (i.e., MIP-1α) addition. To control for specificity, non-CCR1 ligands, specifically bradykinin, was added, which also signals via a seven transmembrane receptor. Without compound, a pulse of fluorescent signal will be seen upon MIP-1α addition. If a compound specifically inhibits CCR1-MIP-1α signaling, then little or no signal pulse will be seen upon MIP-1α addition, but a pulse will be observed upon bradykinin addition. However, if a compound non-specifically inhibits signaling, then no pulse will be seen upon both MIP-1α and bradykinin addition.

One of the primary functions of chemokines is their ability to mediate the migration of chemokine receptor-expressing cells, such as white blood cells. To confirm that a candidate compound inhibited not only CCR1 specific binding and signaling (at least as determined by calcium mobilization assays), but also CCR1 Mediated migration, a chemotaxis assay was employed. THP-1 Myelomonocytic leukemia cells, which resemble monocytes, as wells as freshly isolated monocytes, were used as targets for chemoattraction by CCR1 chemokine ligands (i.e., MIP-1α, CCL15/leukotactin). Cells were place in the top compartment of a microwell migration chamber, while MIP-1α(or other potent CCR1 chemokine ligand) and increasing concentrations of a candidate compound was loaded in the lower chamber. In the absence of inhibitor, cells will migrate to the lower chamber in response to the chemokine agonist; if a compound inhibited CCR1 function, then the majority of cells will remain in the upper chamber. To ascertain a candidate compound's affinity for CCR1 as well as to confirm its ability to inhibit CCR1 Mediated cell migration, inhibitory activity was titered over a $1\times10^{-10}$ to $1\times10^{-4}$ M range of compound concentrations in this chemotaxis assay. In this assay, the amount of compound was varied; while cell number and chemokine agonist concentrations were held constant. After the chemotaxis chambers were incubated 1-2 hours at 37° C., the responding cells in the lower chamber were quantified by labeling with the CyQuant assay (Molecular Probes), a fluorescent dye method that measures nucleic acid content, and by measuring with a Spectrafluor Plus (Tecan). The computer program Prism from GraphPad, Inc. (San Diego, Calif.) was used to calculate $IC_{50}$ values. $IC_{50}$ values are those compound concentrations required to inhibit the number of cells responding to a CCR1 agonist by 50%.

4. In Vivo Efficacy a) Rabbit Model of Destructive Joint Inflammation

To study the effects of candidate compounds on inhibiting the inflammatory response of rabbits to an intra-articular injection of the bacterial membrane component lipopolysaccharide (LPS), a rabbit model of destructive joint inflammation is used. This study design mimics the destructive joint inflammation seen in arthritis. Intra-articular injection of LPS causes an acute inflammatory response characterized by the release of cytokines and chemokines, many of which have been identified in rheumatoid arthritic joints. Marked increases in leukocytes occur in synovial fluid and in synovium in response to elevation of these chemotactic mediators. Selective antagonists of chemokine receptors have shown efficacy in this model (see Podolin, et al., *J. Immunol.* 169(11):6435-6444 (2002)).

A rabbit LPS study is conducted essentially as described in Podolin, et al. ibid., female New Zealand rabbits (approximately 2 kilograms) are treated intra-articularly in one knee with LPS (10 ng) together with either vehicle only (phosphate buffered saline with 1% DMSO) or with addition of CCX-105 (dose 1=50 μM or dose 2=100 μM) in a total volume of 1.0 mL. Sixteen hours after the LPS injection, knees are lavaged and cells counts are performed. Beneficial effects of treatment were determined by histopathologic evaluation of synovial inflammation. Inflammation scores are used for the histopathologic evaluation: 1—minimal, 2—mild, 3—moderate, 4—moderate-marked.

b) Evaluation of a Candidate Compound in a Rat Model of Collagen Induced Arthritis A 17 day developing type II collagen arthritis study is conducted to evaluate the effects of a candidate compound on arthritis induced clinical ankle swelling. Rat collagen arthritis is an experimental model of polyarthritis that has been widely used for preclinical testing of numerous anti-arthritic agents (see Trentham, et al., *J. Exp. Med.* 146(3):857-868 (1977), Bendele, et al., *Toxicologic Pathol.* 27:134-142 (1999), Bendele, et al., *Arthritis Rheum.* 42:498-506 (1999)). The hallmarks of this model are reliable onset and progression of robust, easily measurable polyarticular inflammation, marked cartilage destruction in association with pannus formation and mild to moderate bone resorption and periosteal bone proliferation.

Female Lewis rats (approximately 0.2 kilograms) are anesthetized with isoflurane and injected with Freund's Incomplete Adjuvant containing 2 Mg/mL bovine type II collagen at the base of the tail and two sites on the back on days 0 and 6 of this 17 day study. A candidate compound is dosed daily in a sub-cutaneous manner from day 0 till day 17 at a efficacious dose. Caliper measurements of the ankle joint diameter were taken, and reducing joint swelling is taken as a measure of efficacy.

In the table below, structures and activity are provided for representative compounds described herein. Activity is provided as follows for either the chemotaxis assay or binding assay as described above: +, $IC_{50}$>12.5 uM; ++, 2500 nM<$IC_{50}$<12.5 uM; +++, 1000 nM<$IC_{50}$<2500 nM; and ++++, $IC_{50}$<1000 nM.

TABLE 2

Structure

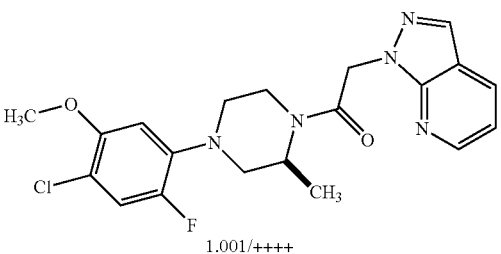

1.001/++++

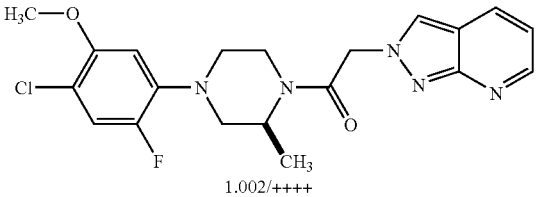

1.002/++++

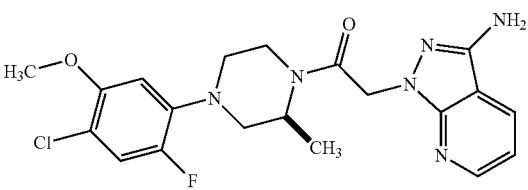

TABLE 2-continued
Structure
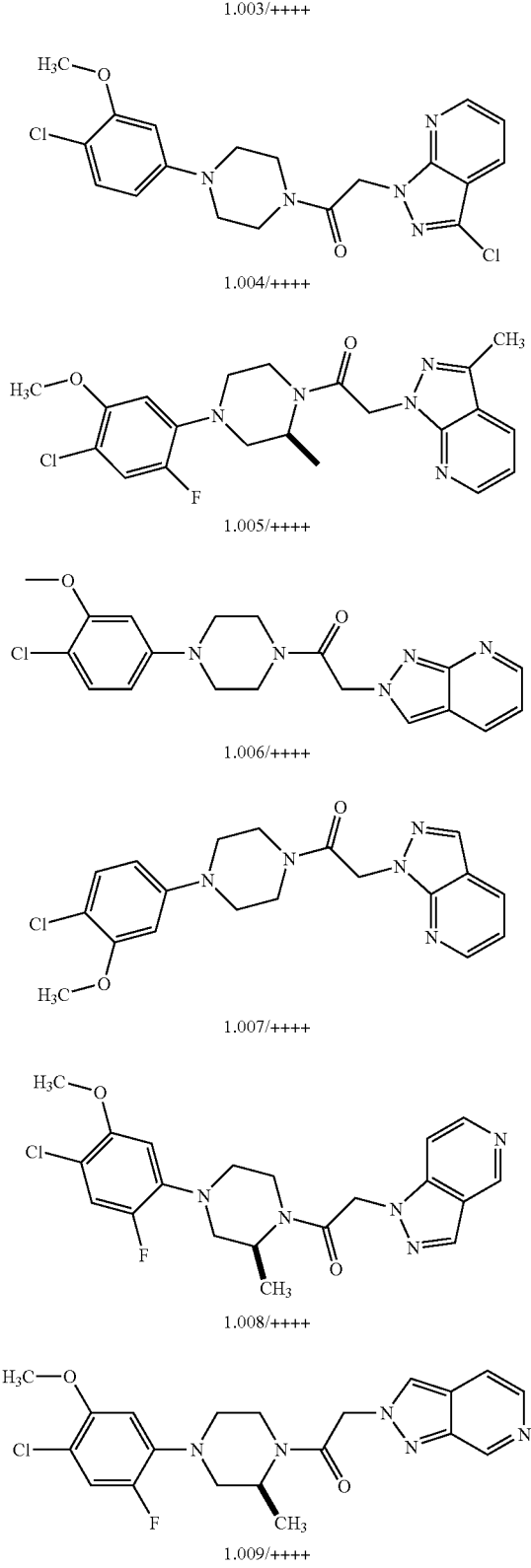
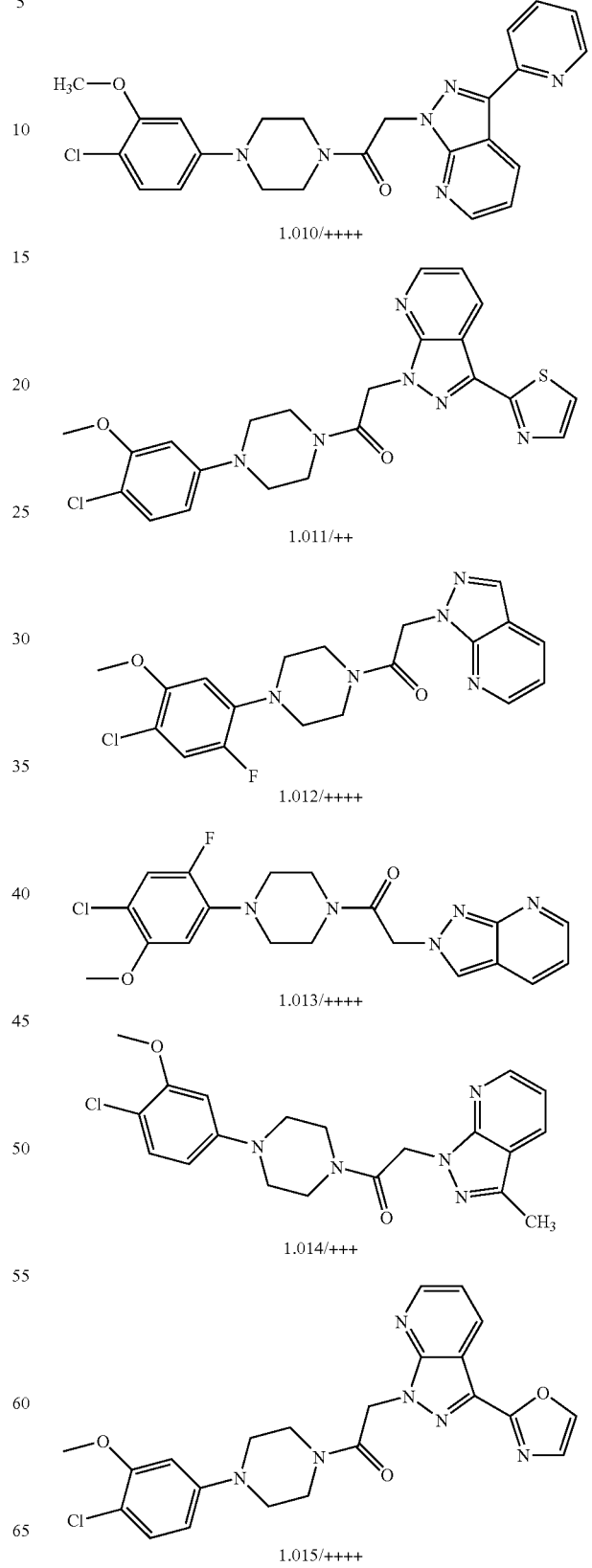

TABLE 2-continued
Structure
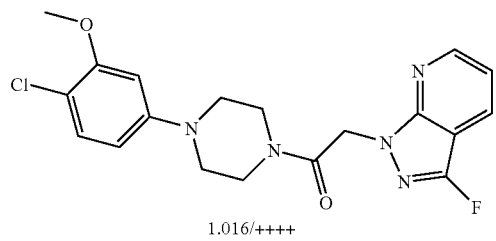
1.016/++++
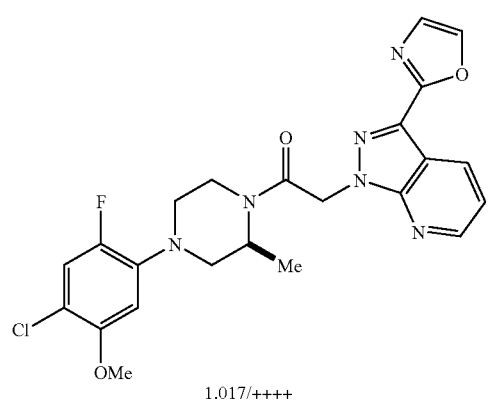
1.017/++++
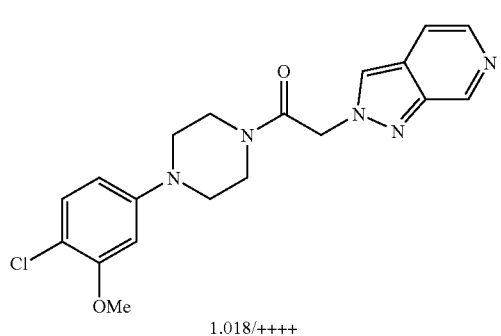
1.018/++++
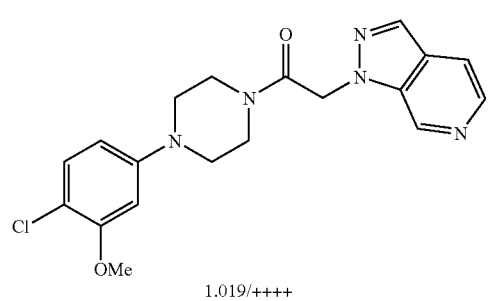
1.019/++++
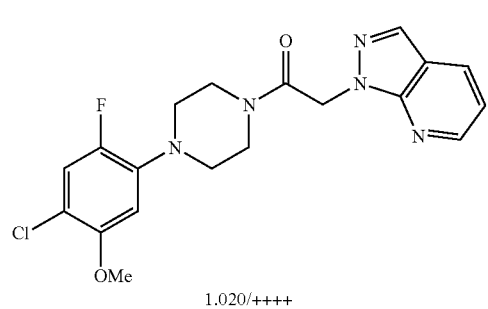
1.020/++++
TABLE 2-continued
Structure
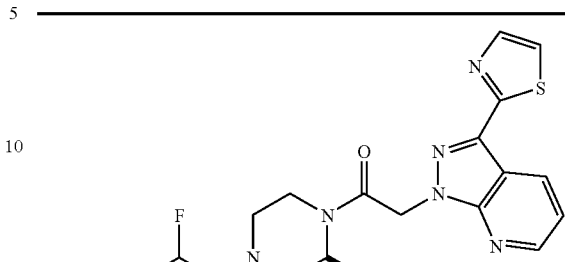
1.021/++++
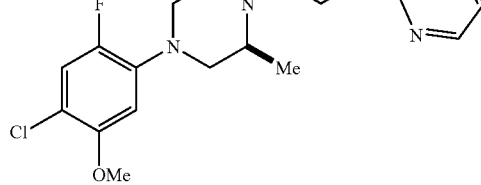
1.022/++++
1.023/++++
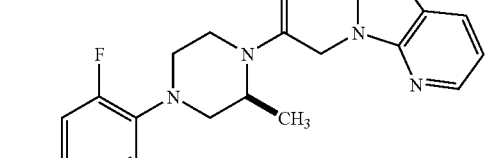
1.024/++++

TABLE 2-continued
Structure
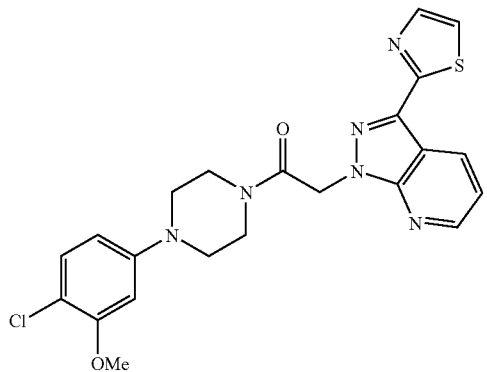
1.025/++++
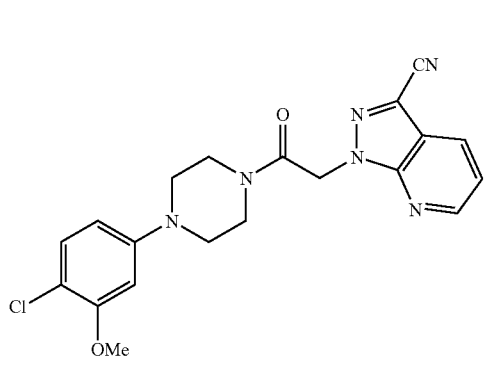
1.026/++++
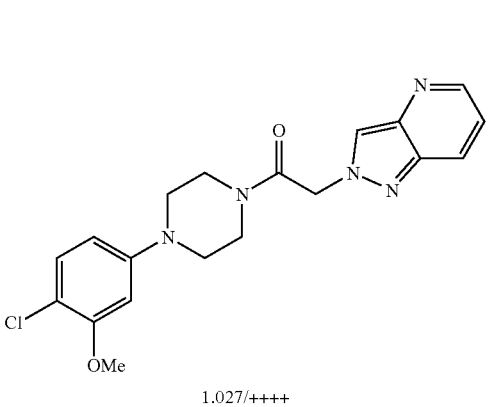
1.027/++++
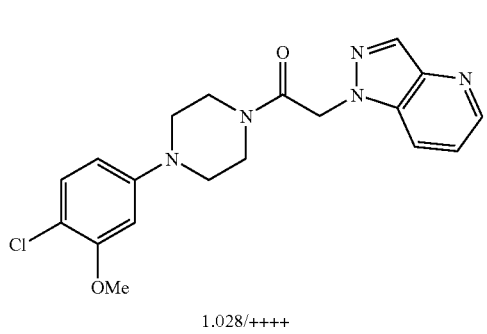
1.028/++++
TABLE 2-continued
Structure
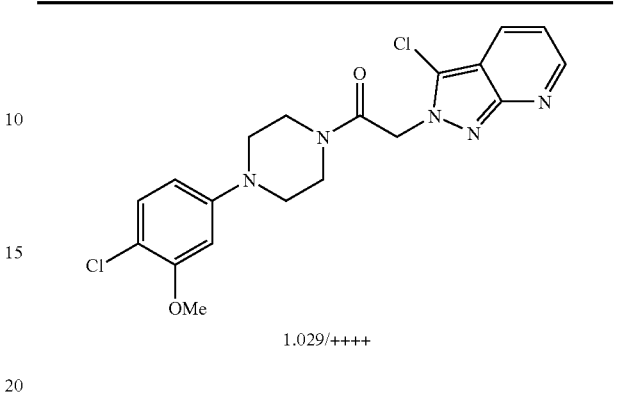
1.029/++++
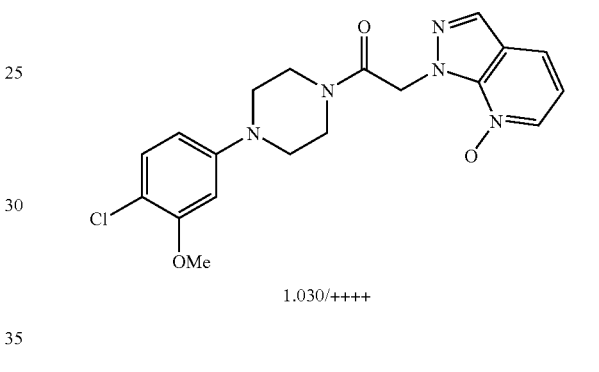
1.030/++++
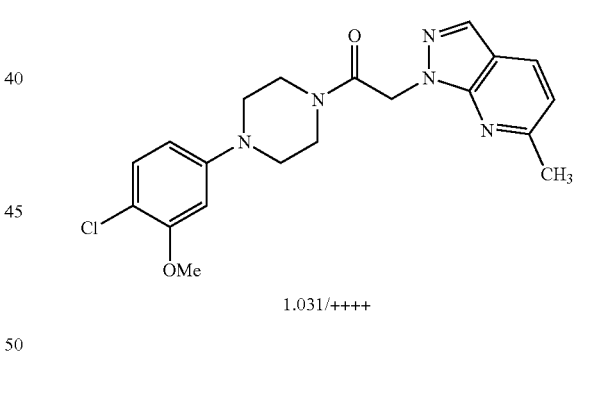
1.031/++++
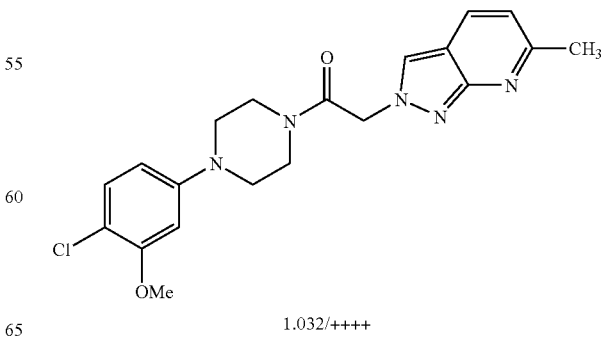
1.032/++++

TABLE 2-continued
| Structure |
|---|
| 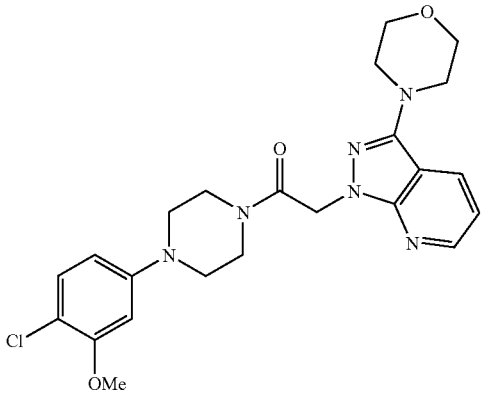 1.033/++++ |
| 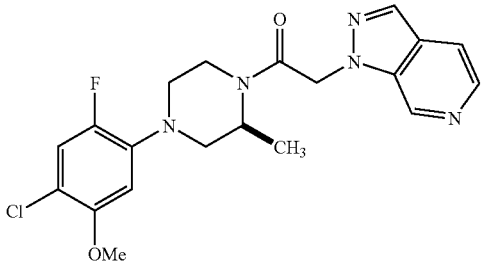 1.034/++++ |
| 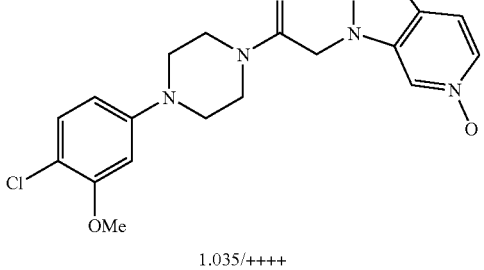 1.035/++++ |
| 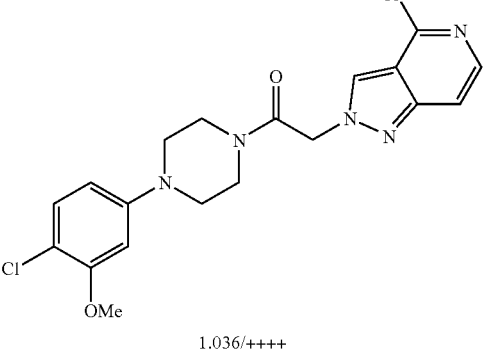 1.036/++++ |"
TABLE 2-continued
| Structure |
|---|
| 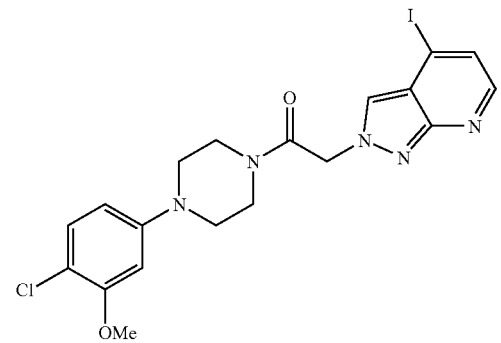 1.037/++++ |
| 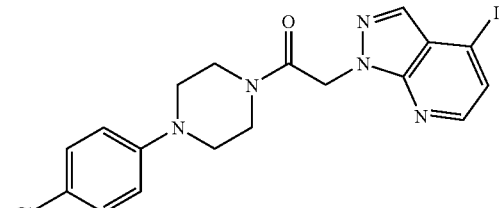 1.038/++++ |
| 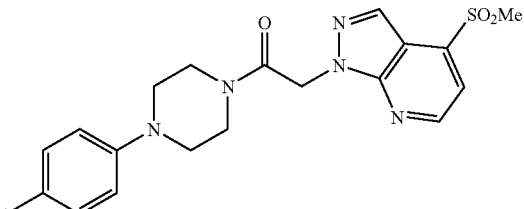 1.039/++++ |
| 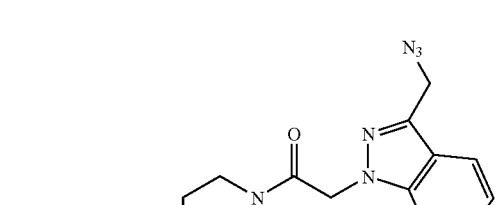 1.040/++++ |

TABLE 2-continued

| Structure |
|---|
| 1.041/+++ |
| 1.042/++++ |
| 1.043/++++ |
| 1.044/++++ |
| 1.045/++++ |

TABLE 2-continued

| Structure |
|---|
| 1.046/++++ |
| 1.047/++++ |
| 1.048/++++ |
| 1.049/++++ |
| 1.050/++++ |

TABLE 2-continued
Structure
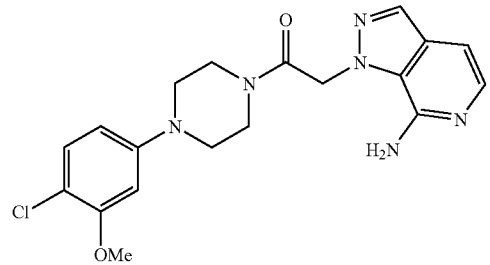
1.051/++++
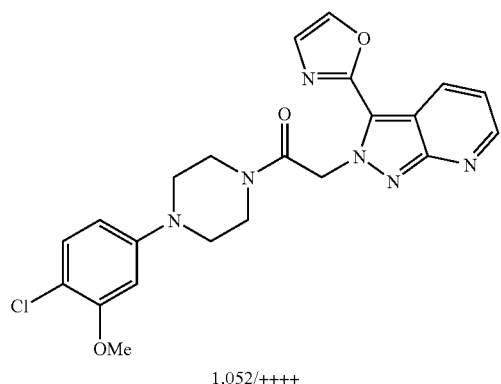
1.052/++++
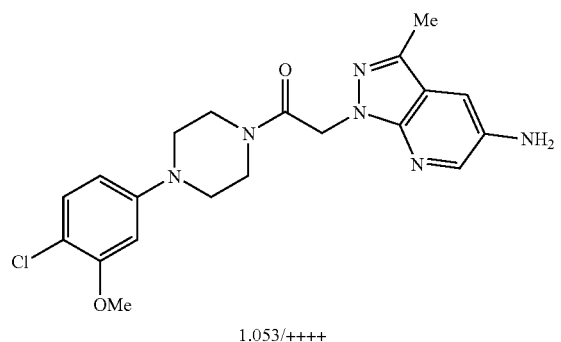
1.053/++++
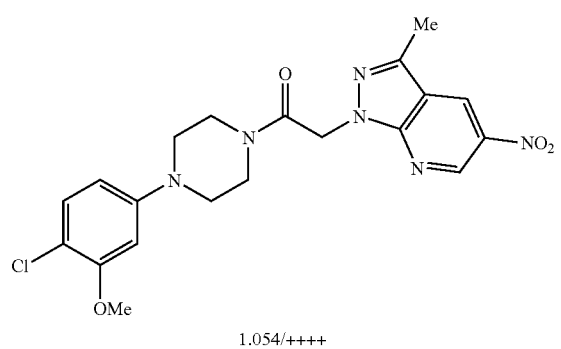
1.054/++++
TABLE 2-continued
Structure
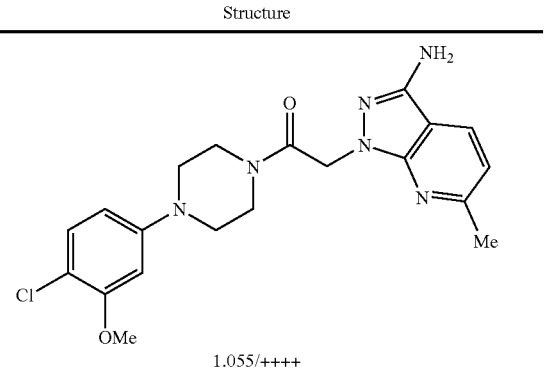
1.055/++++
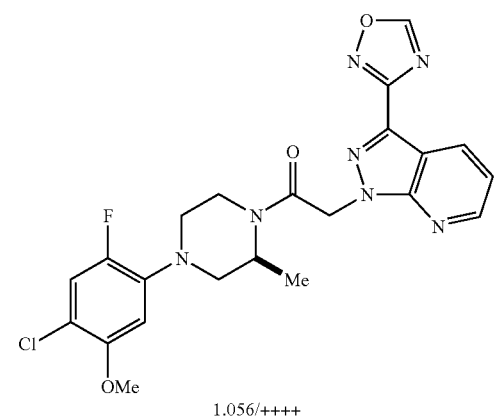
1.056/++++
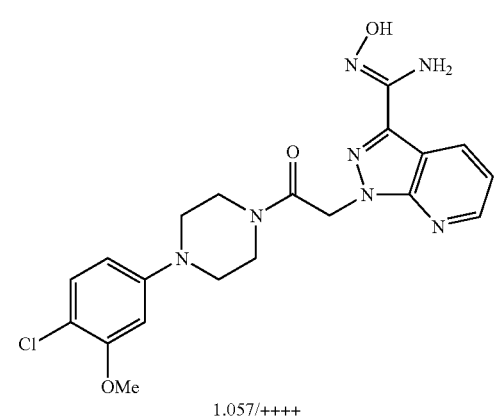
1.057/++++
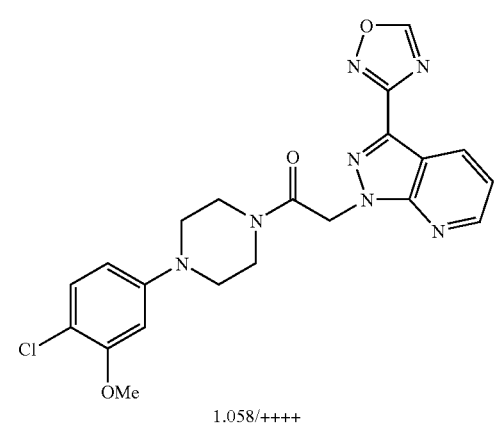
1.058/++++

TABLE 2-continued
Structure
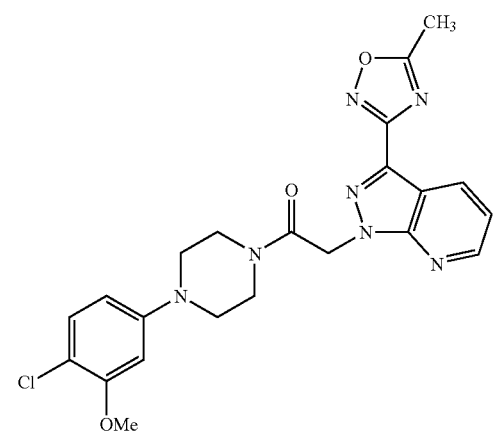
1.059/++++
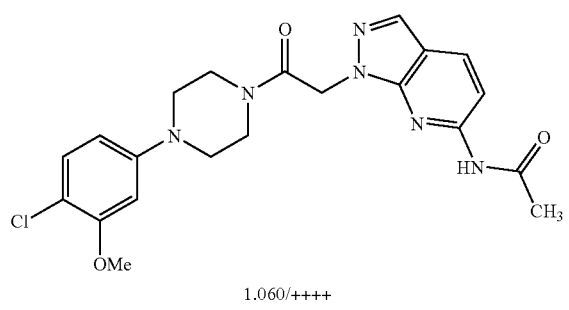
1.060/++++
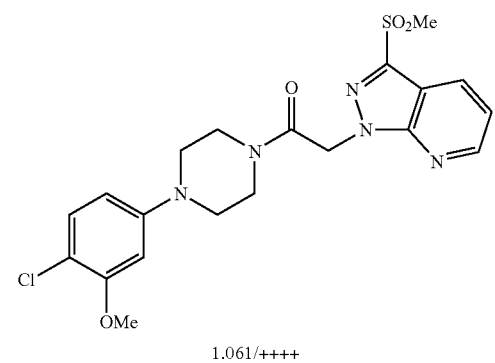
1.061/++++
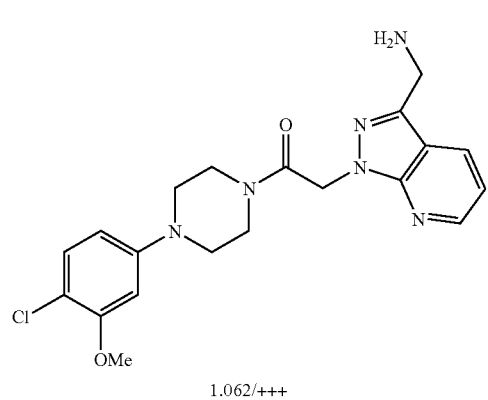
1.062/+++
TABLE 2-continued
Structure
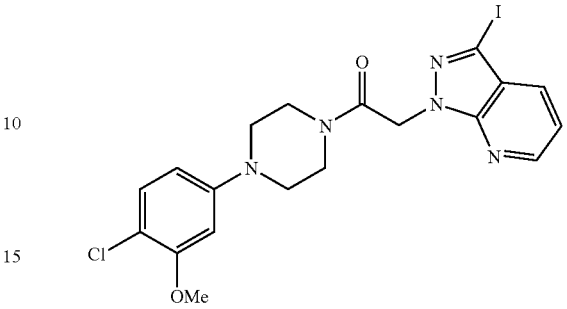
1.063/++++
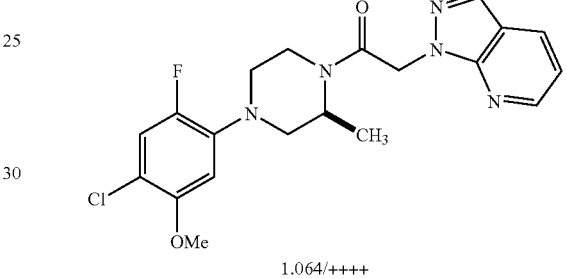
1.064/++++
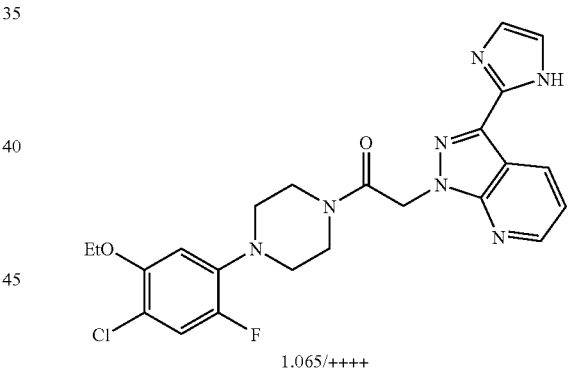
1.065/++++
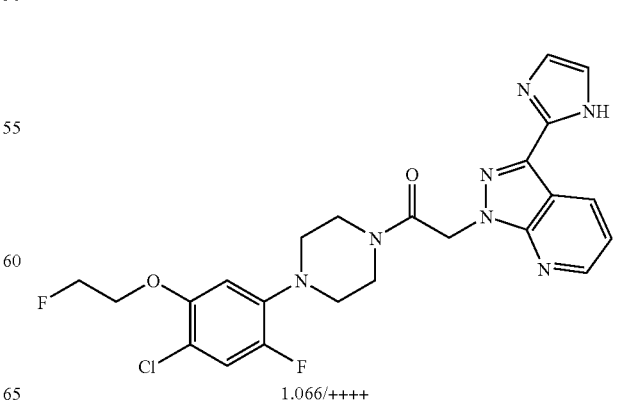
1.066/++++

TABLE 2-continued
Structure
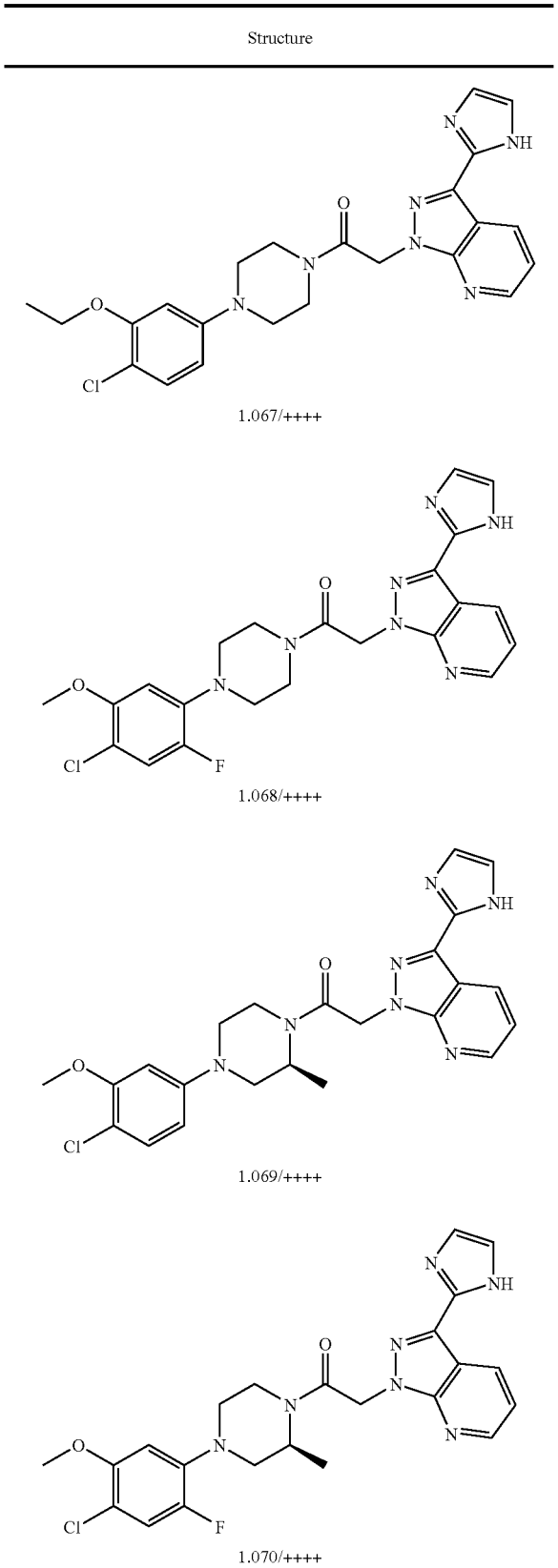
1.067/++++
1.068/++++
1.069/++++
1.070/++++
TABLE 2-continued
Structure
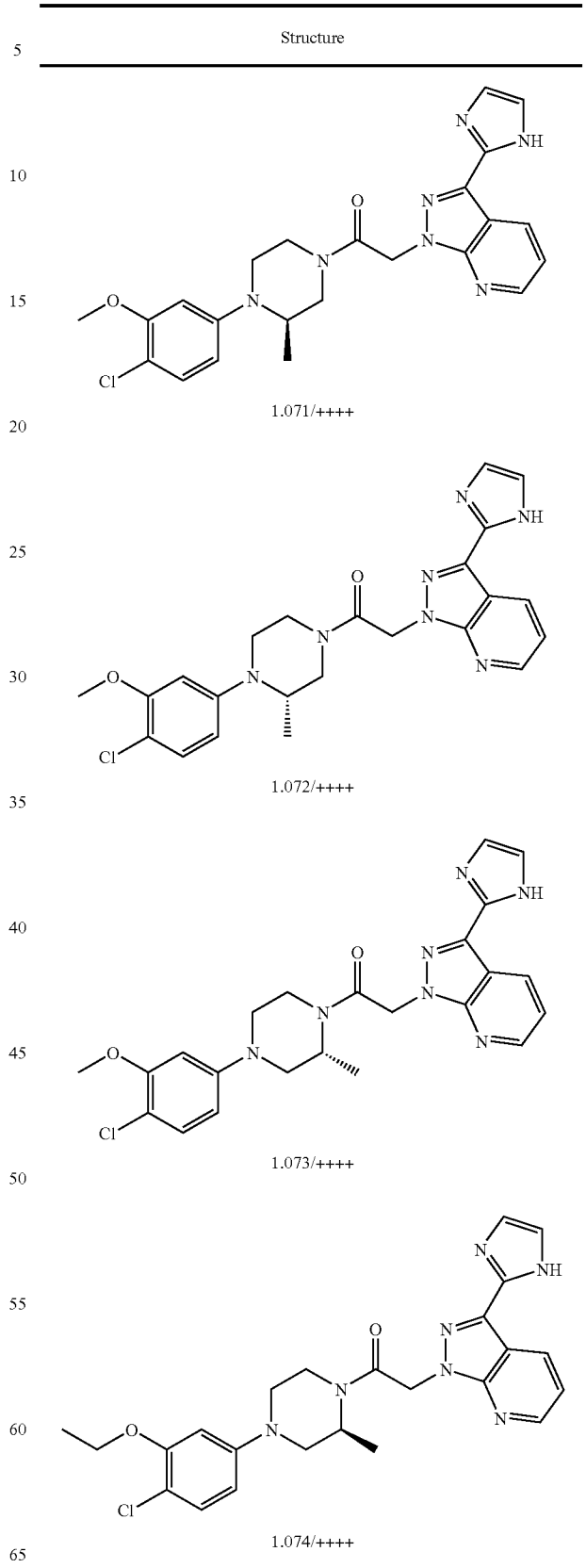
1.071/++++
1.072/++++
1.073/++++
1.074/++++

TABLE 2-continued

Structure 1.075/++++

1.076/++++

1.077/++++

1.078/++

1.079/++++

1.080/++++

1.081/++++

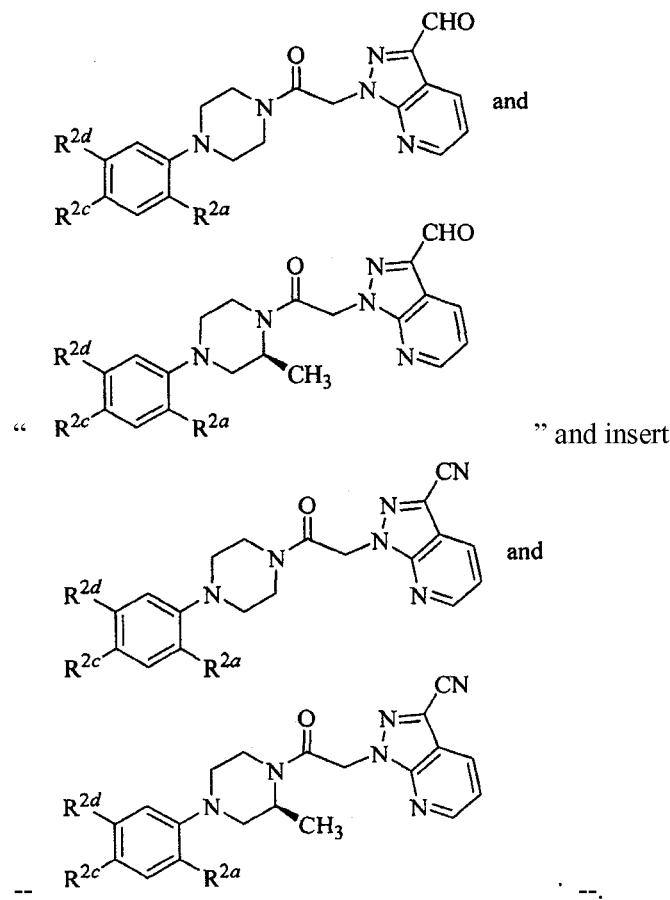

What is claimed is:
1. A method of preparing a compound having a formula selected from the group consisting of and

-continued

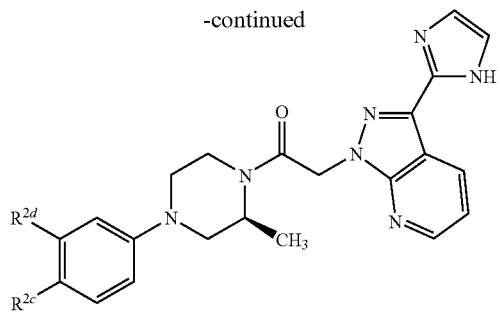

or a pharmaceutically acceptable salt, hydrate or N-oxide thereof;

wherein $R^{2c}$ and $R^{2d}$ are each independently selected from the group consisting of halogen, $C_{1-4}$ alkoxy, $C_{1-4}$ alkyl and $C_{1-4}$ haloalkyl; said method comprising:

(a) contacting an aldehyde selected from the group consisting of

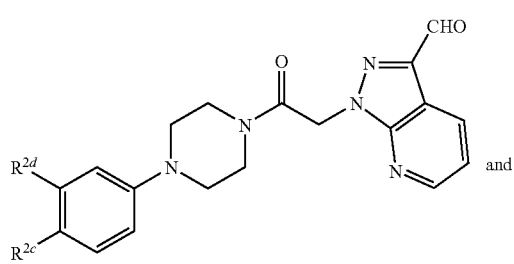 and

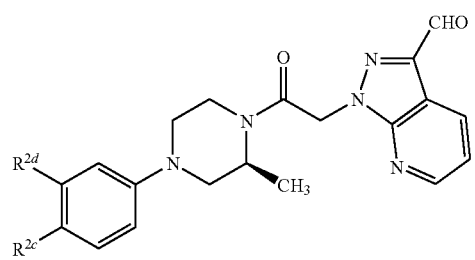

with an imidazole-forming reagent under conditions sufficient to form said compound.

2. A method in accordance with claim 1, wherein said imidazole-forming reagent is selected from the group consisting of glyoxal or a glyoxal equivalent.

3. A method in accordance with claim 1, wherein said imidazole-forming reagent is glyoxal and said contacting is in the presence of ammonium acetate.

4. A method of preparing a compound having a formula selected from the group consisting of

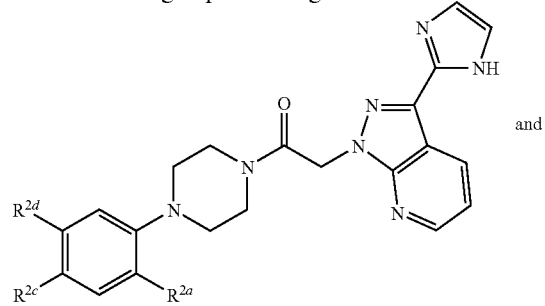 and

-continued

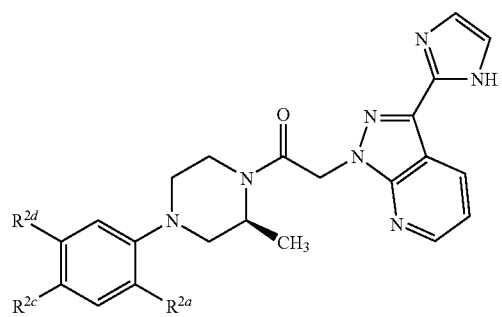

or a pharmaceutically acceptable salt, hydrate or N-oxide thereof; wherein $R^{2a}$, $R^{2c}$ and $R^{2d}$ are each independently selected from the group consisting of hydrogen, halogen, $C_{1-4}$ alkoxy, $C_{1-4}$ alkyl and $C_{1-4}$ haloalkyl, said method comprising:

(a) contacting an aldehyde selected from the group consisting of

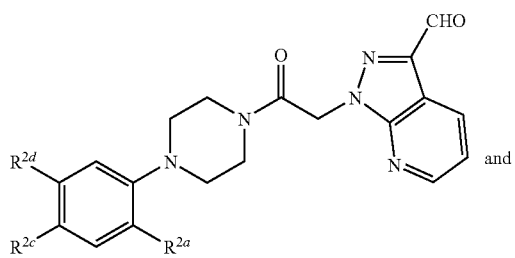 and

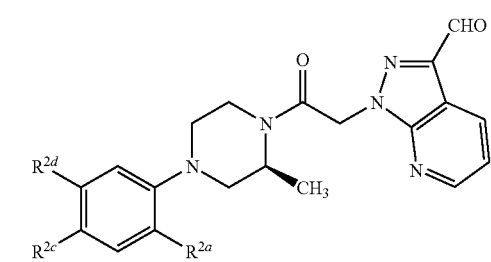

with an imidazole-forming reagent under conditions sufficient to form said compound.

5. A method in accordance with claim 4, wherein said imidazole-forming reagent is selected from the group consisting of glyoxal or a glyoxal equivalent.

6. A method in accordance with claim 4, wherein said imidazole-forming reagent is glyoxal and said contacting is in the presence of ammonium acetate.

7. A method of preparing a compound having a formula selected from the group consisting of

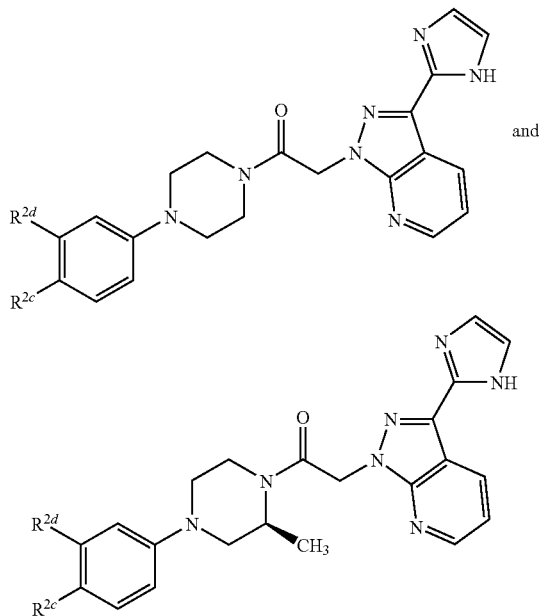

or a pharmaceutically acceptable salt, hydrate or N-oxide thereof; wherein $R^{2c}$ and $R^{2d}$ are each independently selected from the group consisting of halogen, $C_{1-4}$ alkoxy, $C_{1-4}$ alkyl and $C_{1-4}$ haloalkyl; said method comprising:
(a) contacting a nitrile selected from the group consisting of

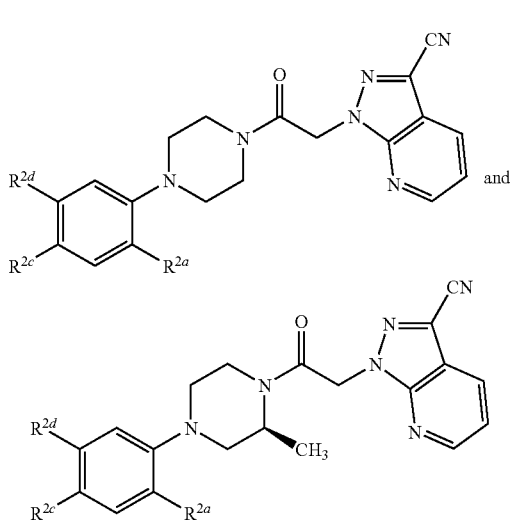

with ethylenediamine to form an imidazoline product; and
(b) oxidizing said imidazoline product to form said compound.

8. A method in accordance with claim 7, wherein said oxidizing is carried out with a reagent selected from the group consisting of $KMnO_4$, $MnO_2$, $PhI(OAc)_2$, Swern reagents and Dess-Martin periodane.

9. A method of preparing a compound having a formula selected from the group consisting of

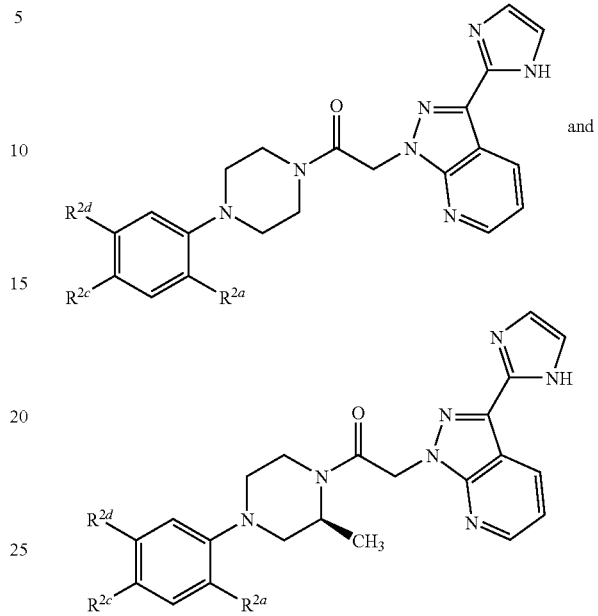

or a pharmaceutically acceptable salt, hydrate or N-oxide thereof;
wherein $R^{2a}$, $R^{2c}$ and $R^{2d}$ are each independently selected from the group consisting of hydrogen, halogen, $C_{1-4}$ alkoxy, $C_{1-4}$ alkyl and $C_{1-4}$ haloalkyl, said method comprising:
(a) contacting a nitrile selected from the group consisting of

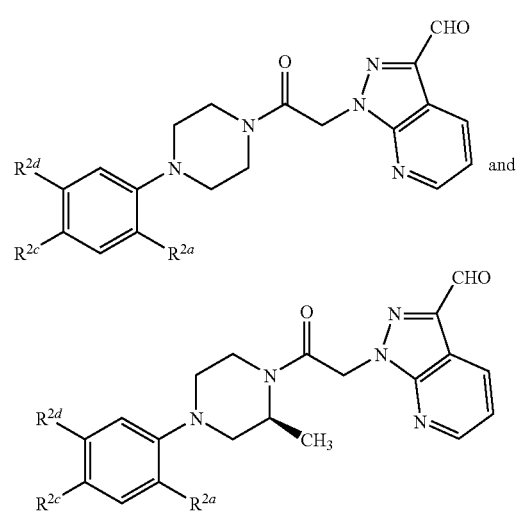

with ethylenediamine to form an imidazoline product; and
(b) oxidizing said imidazoline product to form said compound.

10. A method in accordance with claim 9, wherein said oxidizing is carried out with a reagent selected from the group consisting of $KMnO_4$, $MnO_2$, $PhI(OAc)_2$, Swern reagents and Dess-Martin periodane.

\* \* \* \* \*

UNITED STATES PATENT AND TRADEMARK OFFICE
CERTIFICATE OF CORRECTION

PATENT NO. : 7,777,035 B2  
APPLICATION NO. : 11/752201  
DATED : August 17, 2010  
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 375 days.

Signed and Sealed this  
Fifteenth Day of February, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,777,035 B2 | Page 1 of 2 |
| APPLICATION NO. | : 11/752201 | |
| DATED | : August 17, 2010 | |
| INVENTOR(S) | : Zhang et al. | |

It is certified that error appears in the above-identified patent and that said Letters Patent is hereby corrected as shown below:

In the Claims:

Claim 7, Column 145, Lines 39-59, please delete

" 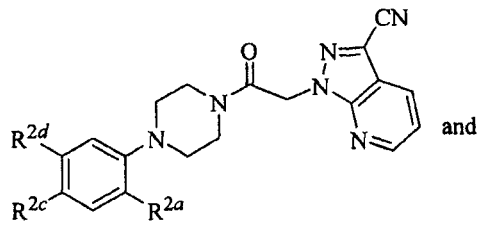 and

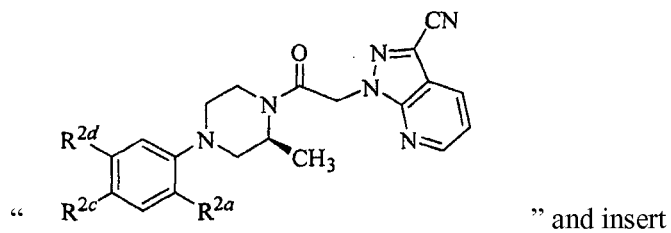 " and insert

-- 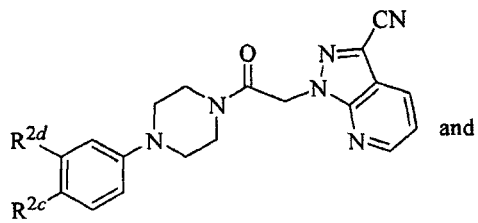 and

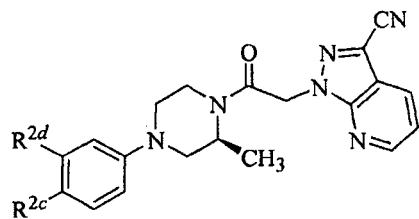 --.

Claim 8, Column 145, Line 66, please delete "Phl (OAc)₂" and insert -- PhI(OAc)$_2$ --.

Claim 9, Column 146, Lines 39-59, please delete

Signed and Sealed this
Seventeenth Day of May, 2011

David J. Kappos
*Director of the United States Patent and Trademark Office*

CERTIFICATE OF CORRECTION (continued)
U.S. Pat. No. 7,777,035 B2